US012590056B2

(12) United States Patent
Chen et al.

(10) Patent No.: US 12,590,056 B2
(45) Date of Patent: Mar. 31, 2026

(54) IGF2BP2 INHIBITORS AND USES THEREOF

(71) Applicant: CITY OF HOPE, Duarte, CA (US)

(72) Inventors: Jianjun Chen, Temple City, CA (US); Hengyou Weng, Duarte, CA (US); Huilin Huang, Duarte, CA (US); David Horne, Altadena, CA (US); Yuelong Ma, Glendora, CA (US); Hongzhi Li, Diamond Bar, CA (US); Xiaolan Deng, Temple City, CA (US)

(73) Assignee: CITY OF HOPE, Duarte, CA (US)

( * ) Notice: Subject to any disclaimer, the term of this patent is extended or adjusted under 35 U.S.C. 154(b) by 835 days.

(21) Appl. No.: 17/794,922

(22) PCT Filed: Jan. 27, 2021

(86) PCT No.: PCT/US2021/015311
§ 371 (c)(1),
(2) Date: Jul. 22, 2022

(87) PCT Pub. No.: WO2021/154870
PCT Pub. Date: Aug. 5, 2021

(65) Prior Publication Data

US 2023/0127630 A1 Apr. 27, 2023

Related U.S. Application Data

(60) Provisional application No. 62/966,827, filed on Jan. 28, 2020.

(51) Int. Cl.

| | |
|---|---|
| ***C07C 281/16*** | (2006.01) |
| ***C07C 211/26*** | (2006.01) |
| ***G01N 33/68*** | (2006.01) |

(52) U.S. Cl.
CPC .......... *C07C 281/16* (2013.01); *C07C 211/26* (2013.01); *G01N 33/6875* (2013.01); *G01N 2333/65* (2013.01)

(58) Field of Classification Search
None
See application file for complete search history.

(56) References Cited

U.S. PATENT DOCUMENTS

| | | | |
|---|---|---|---|
| 3,973,039 | A | 8/1976 | Livak et al. |
| 4,015,016 | A | 3/1977 | Livak et al. |
| 2010/0035940 | A1 | 2/2010 | Ostrov et al. |
| 2017/0095459 | A1 | 4/2017 | Habash et al. |

FOREIGN PATENT DOCUMENTS

| | | |
|---|---|---|
| WO | WO-2011/017106 A1 | 2/2011 |

OTHER PUBLICATIONS

Scott ("Polynitrogen systems from the Hydrazino-carbonic Acids. Part IX. The Synthesis and Bromination of Some 5-Tetrazolyl- and Related-hydrazones" J. Org. Chem. 1957, vol. 22, p. 692). (Year: 1957).*

(Continued)

*Primary Examiner* — Amy C Bonaparte
(74) *Attorney, Agent, or Firm* — Mintz, Levin, Cohn, Ferris, Glovsky and Popeo, P.C.

(57) ABSTRACT

Described herein, inter alia, are IGF2BP2 inhibitor compounds and methods of using the same.

17 Claims, 17 Drawing Sheets

Specification includes a Sequence Listing.

Adenosine (A)

$N^6$-methyladenosine ($m^6A$)

(56) References Cited

OTHER PUBLICATIONS

Kiss ("Identification of 8-Hydroxyquinoline Derivatives Active Against Somatic V658F Mutant JAK1-Dependent Cells", Arch. Pharm. Chem. Life Sci, 2016, p. 925). (Year: 2016).*
Topliss ("Utilization of Operational Schemes for Analog Synthesis in Drug Design", J. Med. Chem. 1972, p. 1006). (Year: 1972).*
Tzelepis ("Pharmacological Inhibition of the RNA m6a Write METTL3 as a Novel Therapeutic Strategy for Acute Myeloid Leukemia", Blood, Nov. 13, 2019, downloaded from http://doi.org/10.1182/blood-2019-127962) (Year: 2019).*
Weng ("N6-Methyladenosine Modification Regulates Cell Metabolism in Acute Myeloid Leukemia" Blood, Nov. 29, 2018, downloaded from: http://doi.org/10.1182/blood-2018-99-117455) (Year: 2018).*
He ("Functions of N6-methyladenosine and its role in cancer" Molecular Cancer, Dec. 4, 2019, p. 1-15). (Year: 2019).*
Abraham, M. L. et al. (Dec. 7, 2013). "Oxidant-induced intramolecular triazole formation," *Dalton Trans* 42(45):16066-16072.
Ion, A.E. et al. (Oct. 2007). "Triaminoguanidine derivatives as supports to construct magnetic assemblies: Synthesis and characterization of trinuclear nickel(II) complexes," *Inorganica Chimica Acta* 360(13):3925-3931.
Müller, I. M. et al. (Jan. 2005). "A New Ligand for the Formation of Triangular Building Blocks in Supramolecular Chemistry," *Eur J Inorg Chem* 2:257-263.
Müller, I. M. et al. (Jan. 7, 2005). "Rational design of tightly closed coordination tetrahedra that are stable in the solid state, in solution, and in the gas phase," *Angew Chem Int Ed Engl* 44(3):480-484.
Müller, I. M. et al. (May 2005). "Rational design of a coordination cage with a trigonal-bipyramidal shape constructed from 33 building units," *Angew. Chem. Int. Ed.* 44(19):2969-2973.
Müller, I. M. et al. (May 20, 2005). "From a Monomer to a Protein-Sized, Doughnut-Shaped Coordination Oligomer-The Influence of Side Chains of C3-Symmetric Ligands in Supramolecular Chemistry," *Chem Eur J* 11(11):3318-3324.
Oppel, I. M. et al. (2008). "Rational design of a double-walled tetrahedron containing two different C3-symmetric ligands," *Angew. Chem Int Ed Engl* 47(2):402-405.
Tahara, K. et al. (Jul. 21, 2014). "Porous molecular networks formed by the self-assembly of positively-charged trigonal building blocks at the liquid/solid interfaces," *Chem Commun* 50(57):7683-7685.
Zharkouskaya, A. et al. (2025). "A New Coordination Polymer Architecture with (10,3)-a Network Containing Chiral Hydrophilic 3-D Channels," *Eur J Inorg Chem* 24:4875-4879.
Hu, X. et al. (2020). "IGF2BP2 Regulates DANCR by Serving as an N6-Methyladenosine Reader," *Cell Death and Differentiation* 27(6):1782-1794.
International Search Report mailed on May 18, 2021 for PCT Application No. PCT/US2021/015311, filed Jan. 27, 2021, 3 pages.
Ji J. et al. (2019). "Synthesis of Novel N, N', N"-Tris[aryl(hetaryl)-methylideneamino]guanidine Derivatives as Efficient and Selective Colorimetric Sensors for Fluoride Ion," *Russian Journal of Organic Chemistry* 55(9):1399-1406.
Li, T. et al. (2019). "METTL3 Facilitates Tumor Progression via an $m^6$A-IGF2BP2-Dependent Mechanism in Colorectal Carcinoma," *Molecular Cancer* 18:112.
Written Opinion mailed on May 18, 2021 for PCT Application No. PCT/US2021/015311, filed Jan. 27, 2021, 10 pages.

* cited by examiner

Adenosine (A)

$N^6$-methyladenosine ($m^6A$)

IGF2BP2 INHIBITORS AND USES THEREOF

CROSS-REFERENCES TO RELATED APPLICATIONS

This application is the national stage filing under 35 U.S.C. § 371 of International Application No. PCT/US2021/015311 filed Jan. 27, 2021, which claims the benefit of U.S. Provisional Application No. 62/966,827, filed Jan. 28, 2020, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under Grant Numbers R01 CA214965 and R01 CA236399, awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-736N01US_Sequence_Listing_ST25.txt, created Jul. 14, 2022, 5,639 bytes, machine format IBM-PC, MS Windows operating system, is hereby incorporated by reference.

BACKGROUND $N^6$-methyladenosine ($m^6A$) is the most abundant internal modification in messenger RNAs and affects mRNA fate in different aspects. These effects rely on the recognition of $m^6A$ by specific RNA binding proteins ($m^6A$ readers). We recently identified the insulin-like growth factor 2 mRNA-binding proteins (IGF2BP1/2/3) as $m^6A$ readers that could bind and stabilize $m^6A$-modified mRNAs, and also promote the translation of target mRNAs. Among the three proteins in this family, IGF2BP2 is highly expressed and plays oncogenic roles in various types of cancers including colorectal cancer, hepatocellular carcinoma, breast cancer, lung cancer, gallbladder carcinoma, pancreatic cancer, glioblastoma, esophageal adenocarcinoma, and ovarian cancer, as well as in acute myeloid leukemia (AML). In addition, high level of IGF2BP2 expression is associated with poor prognosis in breast cancer, esophageal adenocarcinoma, gallbladder cancer, pancreatic cancer, lung cancer, ovarian cancer, glioma, liver cancer, and AML. Disclosed herein, inter alia, are solutions to these and other problems in the art.

BRIEF SUMMARY

In an aspect is provided a compound, or a pharmaceutically acceptable salt thereof, having the formula:

(I)

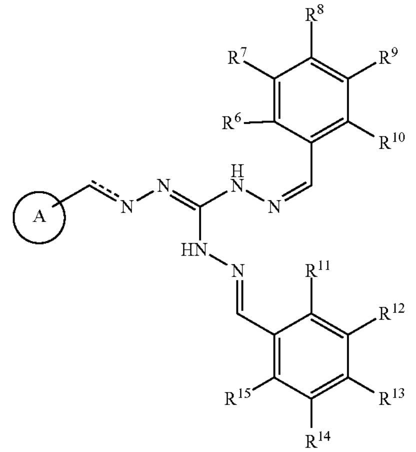

or (II)

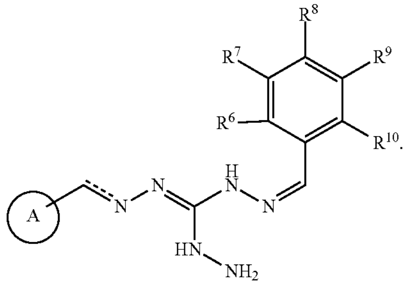

Ring A is a substituted or unsubstituted cycloalkyl, substituted or unsubstituted heterocycloalkyl, substituted or unsubstituted aryl, or substituted or unsubstituted heteroaryl.

is a single bond or a double bond.

$R^6$ is independently hydrogen, halogen, $—CX^6_3$, $—CHX^6_2$, $—CH_2X^6$, $—OCX^6_3$, $—OCH_2X^6$, $—OCHX^6_2$, —CN, $—SO_{n6}R^{6D}$, $—SO_{v6}NR^{6A}R^{6B}$, $—NHC(O)NR^{6A}R^{6B}$, $—NR^{6C}NR^{6A}R^{6B}$, $—ONR^{6A}R^{6B}$, $—NHC(O)NR^{6C}NR^{6A}R^{6B}$, $—N(O)_{m6}$, $—NR^{6A}R^{6B}$, $—C(O)R^{6C}$, $—C(O)OR^{6C}$, $—C(O)NR^{6A}R^{6B}$, $—OR^{6D}$, $—NR^{6A}SO_2R^{6D}$, $—NR^{6A}C(O)R^{6C}$, $—NR^{6A}C(O)OR^{6C}$, $—NR^{6A}OR^{6C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is independently hydrogen, halogen, $—CX^7_3$, $—CHX^7_2$, $—CH_2X^7$, $—OCX^7_3$, $—OCH_2X^7$, $—OCHX^7_2$, —CN, $—SO_{n7}R^{7D}$, $—SO_{v7}NR^{7A}R^{7B}$, $—NHC(O)NR^{7A}R^{7B}$, $—NR^{7C}NR^{7A}R^{7B}$, $—ONR^{7A}R^{7B}$, $—NHC(O)NR^{7C}NR^{7A}R^{7B}$, $—N(O)_{m7}$, $—NR^{7A}R^{7B}$, $—C(O)R^{7C}$, $—C(O)OR^{7C}$, $—C(O)NR^{7A}R^{7B}$, $—OR^{7D}$, $—NR^{7A}SO_2R^{7D}$, $—NR^{7A}C(O)R^{7C}$, $—NR^{7A}C(O)OR^{7C}$, $—NR^{7A}OR^{7C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ is independently hydrogen, halogen, $—CX^8_3$, $—CHX^8_2$, $—CH_2X^8$, $—OCX^8_3$, $—OCH_2X^8$, $—OCHX^8_2$, —CN, $—SO_{n8}R^{8D}$, $—SO_{v8}NR^{8A}R^{8B}$, $—NHC(O)NR^{8A}R^{8B}$, $—NR^{8C}NR^{8A}R^{8B}$, $—ONR^{8A}R^{8B}$, $—NHC(O)NR^{8C}NR^{8A}R^{8B}$, $—N(O)_{m8}$, $—NR^{8A}R^{8B}$, $—C(O)R^{8C}$, $—C(O)OR^{8C}$, $—C(O)NR^{8A}R^{8B}$, $—OR^{8D}$, $—NR^{8A}SO_2R^{8D}$, $—NR^{8A}C(O)R^{8C}$, $—NR^{8A}C(O)OR^{8C}$, $—NR^{8A}OR^{8C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is independently hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9D}$, —$SO_{v9}NR^{9A}R^{9B}$, —$NHC(O)NR^{9A}R^{9B}$, —$NR^{9C}NR^{9A}R^{9B}$, —$ONR^{9A}R^{9B}$, —$NHC(O)NR^{9C}NR^{9A}R^{9B}$, —$N(O)_{m9}$, —$NR^{9A}R^{9B}$, —$C(O)R^{9C}$, —$C(O)OR^{9C}$, —$C(O)NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ is independently hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10D}$, —$SO_{v10}NR^{10A}R^{10B}$, —$NHC(O)NR^{10A}R^{10B}$, —$NR^{10C}NR^{10A}R^{10B}$, —$ONR^{10A}R^{10B}$, —$NHC(O)NR^{10C}NR^{10A}R^{10B}$, —$N(O)_{m10}$, —$NR^{10A}R^{10B}$, —$C(O)R^{10C}$, —$C(O)OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{11}$ is independently hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —CN, —$SO_{n11}R^{11D}$, —$SO_{v11}NR^{11A}R^{11B}$, —$NHC(O)NR^{11A}R^{11B}$, —$NR^{11C}NR^{11A}R^{11B}$, —$ONR^{11A}R^{11B}$, —$NHC(O)NR^{11C}NR^{11A}R^{11B}$, —$N(O)_{m11}$, —$NR^{11A}R^{11B}$, —$C(O)R^{11C}$, —$C(O)OR^{11C}$, —$C(O)NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{12}$ is independently hydrogen, halogen, —$CX^{12}_3$, —$CHX^{12}_2$, —$CH_2X^{12}$, —$OCX^{12}_3$, —$OCH_2X^{12}$, —$OCHX^{12}_2$, —CN, —$SO_{n12}R^{12D}$, —$SO_{v12}NR^{12A}R^{12B}$, —$NHC(O)NR^{12A}R^{12B}$, —$NR^{12C}NR^{12A}R^{12B}$, —$ONR^{12A}R^{12B}$, —$NHC(O)NR^{12C}NR^{12A}R^{12B}$, —$N(O)_{m12}$, —$NR^{12A}R^{12B}$, —$C(O)R^{12C}$, —$C(O)OR^{12C}$, —$C(O)NR^{12A}R^{12B}$, —$OR^{12D}$, —$NR^{12A}SO_2R^{12D}$, —$NR^{12A}C(O)R^{12C}$, —$NR^{12A}C(O)OR^{12C}$, —$NR^{12A}OR^{12C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{13}$ is independently hydrogen, halogen, —$CX^{13}_3$, —$CHX^{13}_2$, —$CH_2X^{13}$, —$OCX^{13}_3$, —$OCH_2X^{13}$, —$OCHX^{13}_2$, —CN, —$SO_{n13}R^{13D}$, —$SO_{v13}NR^{13A}R^{13B}$, —$NHC(O)NR^{13A}R^{13B}$, —$NR^{13C}NR^{13A}R^{13B}$, —$ONR^{13A}R^{13B}$, —$NHC(O)NR^{13C}NR^{13A}R^{13B}$, —$N(O)_{m13}$, —$NR^{13A}R^{13B}$, —$C(O)R^{13C}$, —$C(O)OR^{13C}$, —$C(O)NR^{13A}R^{13B}$, —$OR^{13D}$, —$NR^{13A}SO_2R^{13D}$, —$NR^{13A}C(O)R^{13C}$, —$NR^{13A}C(O)OR^{13C}$, —$NR^{13A}OR^{13C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{14}$ is independently hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —CN, —$SO_{n4}R^{14D}$, —$SO_{v14}NR^{14A}R^{14B}$, —$NHC(O)NR^{14A}R^{14B}$, —$NR^{14C}NR^{14A}R^{14B}$, —$ONR^{14A}R^{14B}$, —$NHC(O)NR^{14C}NR^{14A}R^{14B}$, —$N(O)_{m14}$, —$NR^{14A}R^{14B}$, —$C(O)R^{14C}$, —$C(O)OR^{14C}$, —$C(O)NR^{14A}R^{14B}$, —$OR^{14D}$, —$NR^{14A}SO_2R^{14D}$, —$NR^{14A}C(O)R^{14C}$, —$NR^{14A}C(O)OR^{14C}$, —$NR^{14A}OR^{14C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{15}$ is independently hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —CN, —$SO_{n15}R^{15D}$, —$SO_{v15}NR^{15A}R^{15B}$, —$NHC(O)NR^{15A}R^{15B}$, —$NR^{15C}NR^{15A}R^{15B}$, —$ONR^{15A}R^{15B}$, —$NHC(O)NR^{15C}NR^{15A}R^{15B}$, —$N(O)_{m15}$, —$NR^{15A}R^{15B}$, —$C(O)R^{15C}$, —$C(O)OR^{15C}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ and $R^7$ substituents may be joined to form a substituted or unsubstituted cycloalkyl, substituted or unsubstituted heterocycloalkyl, substituted or unsubstituted aryl, or substituted or unsubstituted heteroaryl.

$R^7$ and $R^8$ substituents may be joined to form a substituted or unsubstituted cycloalkyl, substituted or unsubstituted heterocycloalkyl, substituted or unsubstituted aryl, or substituted or unsubstituted heteroaryl.

$R^8$ and $R^9$ substituents may be joined to form a substituted or unsubstituted cycloalkyl, substituted or unsubstituted heterocycloalkyl, substituted or unsubstituted aryl, or substituted or unsubstituted heteroaryl.

$R^9$ and $R^{10}$ substituents may be joined to form a substituted or unsubstituted cycloalkyl, substituted or unsubstituted heterocycloalkyl, substituted or unsubstituted aryl, or substituted or unsubstituted heteroaryl.

$R^{11}$ and $R^{12}$ substituents may be joined to form a substituted or unsubstituted cycloalkyl, substituted or unsubstituted heterocycloalkyl, substituted or unsubstituted aryl, or substituted or unsubstituted heteroaryl.

$R^{12}$ and $R^{13}$ substituents may be joined to form a substituted or unsubstituted cycloalkyl, substituted or unsubstituted heterocycloalkyl, substituted or unsubstituted aryl, or substituted or unsubstituted heteroaryl.

$R^{13}$ and $R^{14}$ substituents may be joined to form a substituted or unsubstituted cycloalkyl, substituted or unsubstituted heterocycloalkyl, substituted or unsubstituted aryl, or substituted or unsubstituted heteroaryl.

$R^{14}$ and $R^{15}$ substituents may be joined to form a substituted or unsubstituted cycloalkyl, substituted or unsubstituted heterocycloalkyl, substituted or unsubstituted aryl, or substituted or unsubstituted heteroaryl.

$R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, and $R^{15D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{7A}$ and $R^{7B}$ substituents bonded to the same nitrogen atom may be joined to form a substituted or unsubstituted heterocycloalkyl or substituted or unsubstituted heteroaryl; $R^{8A}$ and $R^{8B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{10A}$ and $R^{10B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{12A}$ and $R^{12B}$ substituents bonded to the same nitrogen atom may be joined to form a substituted or unsubstituted heterocycloalkyl or substituted or unsubstituted heteroaryl; $R^{13A}$ and $R^{13B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl; $R^{15A}$ and $R^{15B}$ substituents bonded to the same nitrogen atom may be joined to form a substituted or unsubstituted heterocycloalkyl or substituted or unsubstituted heteroaryl.

The symbols n6, n7, n8, n9, n10, n11, n12, n13, n14, and n15 are independently an integer from 0 to 4.

The symbols m6, m7, m8, m9, m10, m11, m12, m13, m14, m15, v6, v7, v8, v9, v10, v11, v12, v13, v14, and v15 are independently 1 or 2.

$X^6$, $X^7$, $X^8$, $X^9$, $X^{10}$, $X^{11}$, $X^{12}$, $X^{13}$, $X^{14}$, and $X^{15}$ are independently —F, —Cl, —Br, or —I.

In an aspect is provided a pharmaceutical composition including a compound described herein and a pharmaceutically acceptable excipient.

In an aspect is provided a method of treating a disease associated with a high level of IGF2BP2 in a subject in need thereof, the method including administering to the subject in need thereof a therapeutically effective amount of a compound described herein.

In an aspect is provided a method of treating a cancer in a subject in need thereof, the method including administering to the subject in need thereof a therapeutically effective amount of a compound described herein.

In an aspect is provided a method of treating a metabolic disorder in a subject in need thereof, the method including administering to the subject in need thereof a therapeutically effective amount of a compound described herein.

In an aspect is provided a method of treating aging in a subject in need thereof, the method including administering to the subject in need thereof a therapeutically effective amount of a compound described herein.

In an aspect is provided a method of modulating (e.g., decreasing) the level of activity of IGF2BP2 in a subject in need thereof, the method including administering to the subject in need thereof an effective amount of a compound described herein.

In an aspect is provided a method of decreasing the level of activity of IGF2BP2 in a cell, the method including contacting the cell with a compound described herein.

In an aspect is provided a method of treating a disease associated with a high level of IGF2BP2 in a subject in need thereof, the method including: i) determining the level of IGF2BP2 in the subject in need thereof; and ii) administering to the subject in need thereof an IGF2BP2 inhibitor, wherein the IGF2BP2 inhibitor decreases the ability of IGF2BP2 to bind to RNA $N^6$-methyladenosine ($m^6A$).

BRIEF DESCRIPTION OF THE DRAWINGS

FIG. 1A: IGF2BP2 reads $m^6A$. FIG. 1B: IGF2BP2 is overexpressed in AML patients with t(11q23)/MLL-rearrangements, inv(16), t(8;21) or t(15;17), relative to normal controls (NC) from healthy donors. FIG. 1C: IGF2BP2 knockdown (KD) results in reduced cell viability and growth in human MONOMAC6 (MM6) AML cells. FIG. 1D: IGF2BP2 KD inhibits MLL-AF9 mediated cell transformation/immortalization. FIG. 1E: IGF2BP2 KD inhibits maintenance of MLL-AF9-induced leukemia in vitro. FIG. 1F: IGF2BP2 KD significantly inhibited progression of MLL-AF9-induced AML in bone marrow transplantation (BMT) recipient mice and substantially prolonged survival. FIG. 1G: IGF2BP2 KD significantly inhibited engraftment of patient-derived AML cells in xenograft recipient mice and substantially prolonged survival.

FIG. 2A: Results of CETSA for IGF2BP2. FIG. 2B: Results of CETSA for IGF2BP1. FIG. 2C: Results of CETSA for IGF2BP3.

FIG. 4A: RNA pull-down assays demonstrated decreased binding of IGF2BP2 to $m^6A$-modified single strand RNA (SS-$m^6A$) in the presence of CWI1-2. FIG. 4B: CWI1-2 treatment reduces expression of IGF2BP2 target genes without affecting IGF2BP2 expression.

FIG. 5A: Relative viability vs. CWI1-2 concentration in healthy bone marrow #1. FIG. 5B: Relative viability vs. CWI1-2 concentration in healthy bone marrow #2. FIG. 5C: Relative viability vs. CWI1-2 concentration in AML blast cells collected from a primary AML patient. FIG. 5D: Relative survival vs. $\log_{10}$ concentration of CWI1-2 in IGF2BP2-high AML cell lines. FIG. 5E: Relative survival vs. $\log_{10}$ concentration of CWI1-2 in IGF2BP2-low AML cell lines.

Figure 1A:
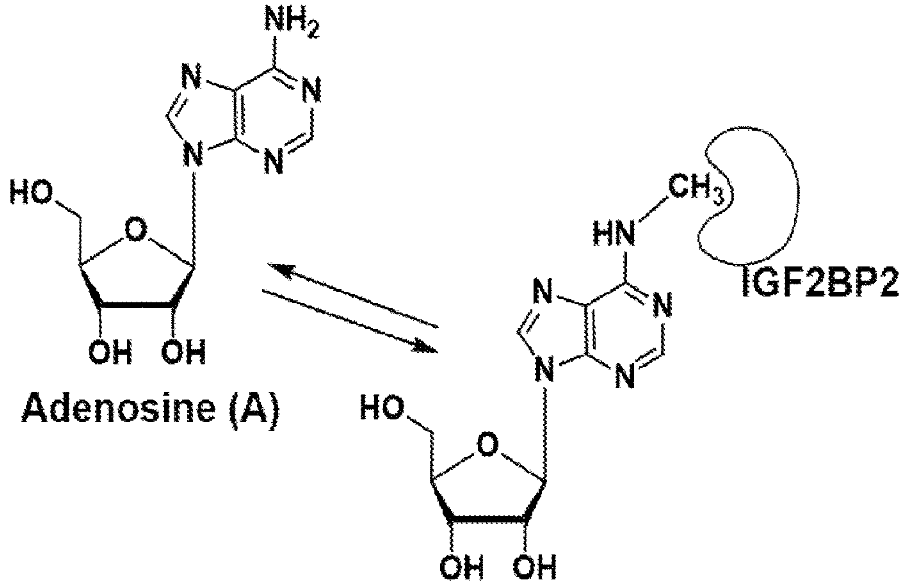
FIGS. 1A-1G. IGF2BP2, an RNA $N^6$-methyladenosine ($m^6A$) modification reader, is a promising target in AML and other cancers.
Figure 1B:
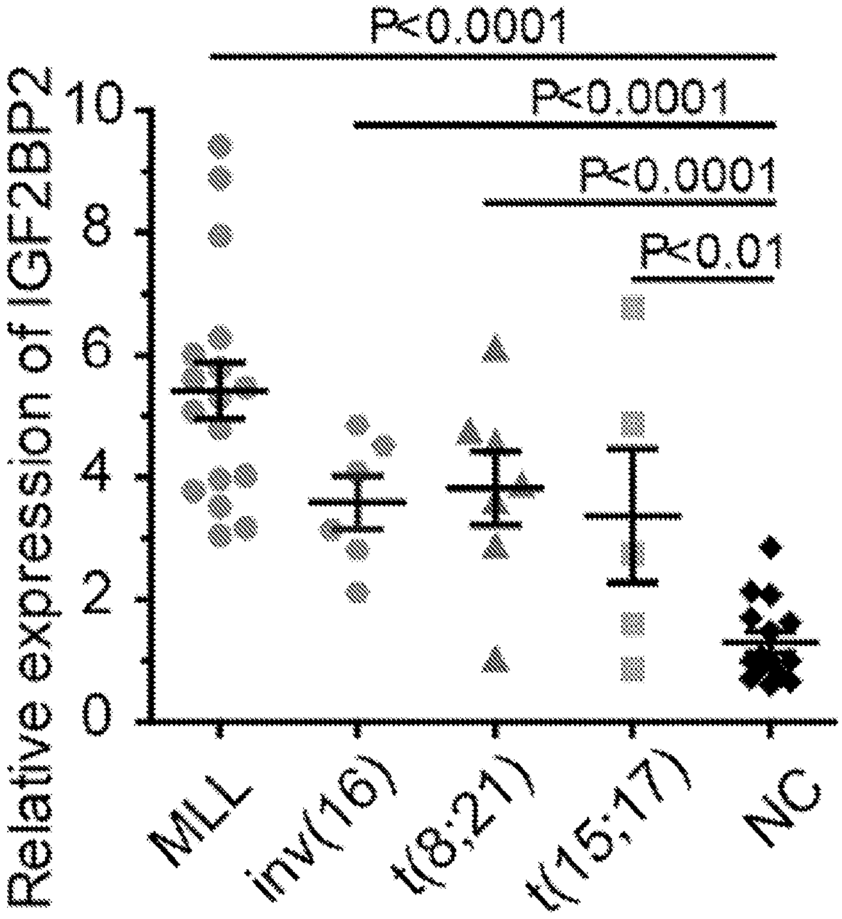
Figure 1C:
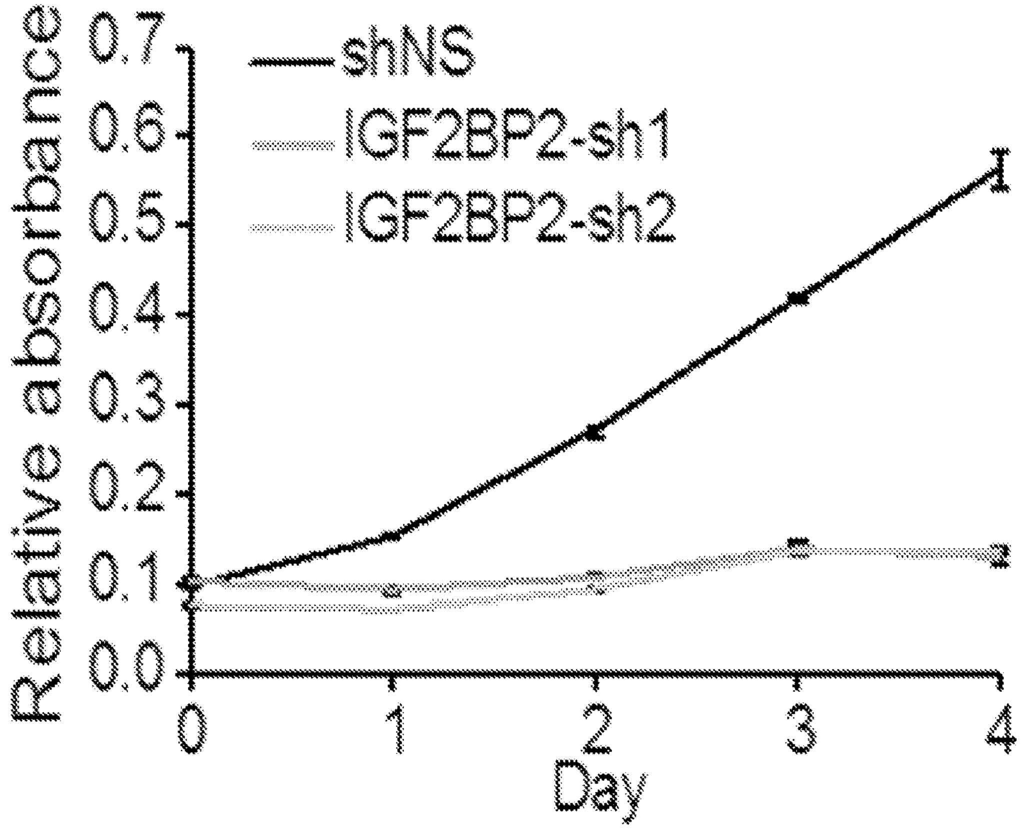
Figure 1D:
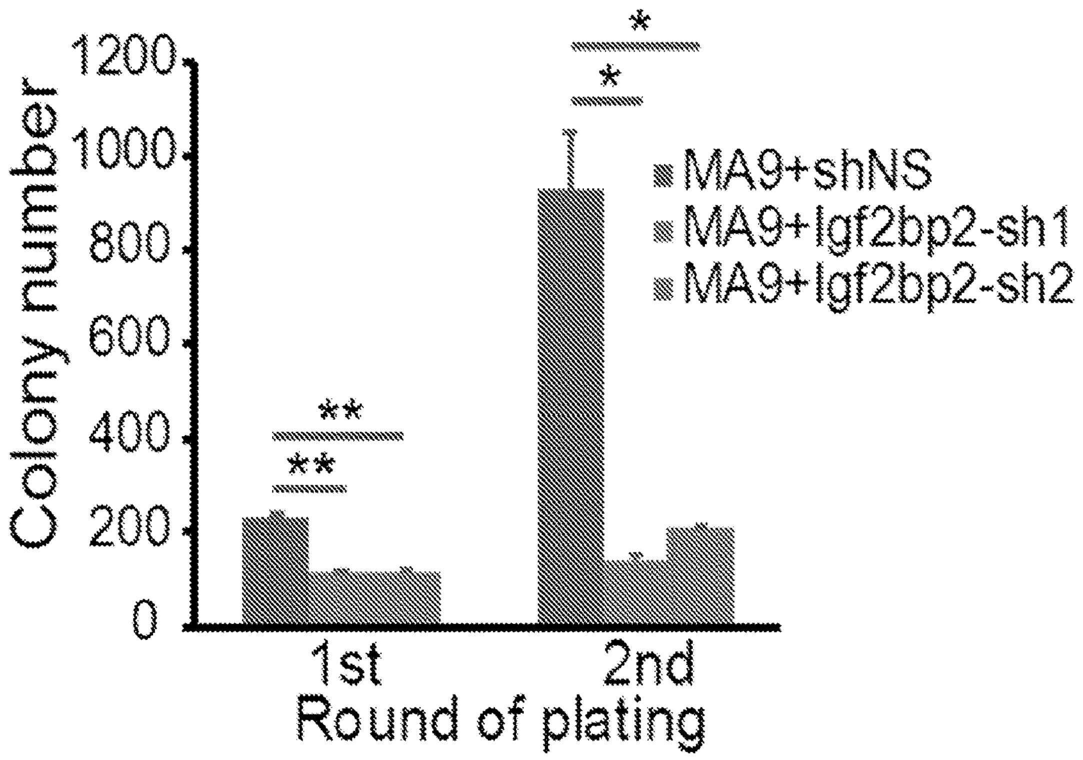
Figure 1E:
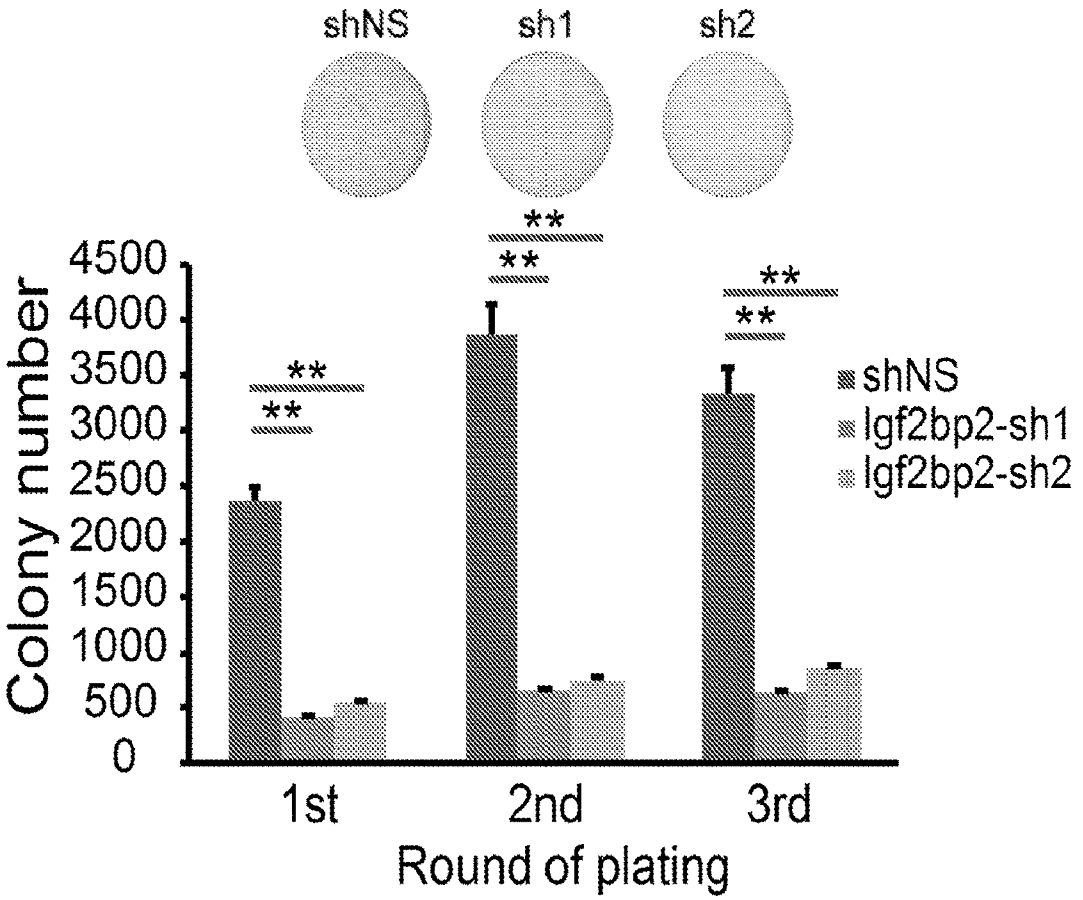
Figure 1F:
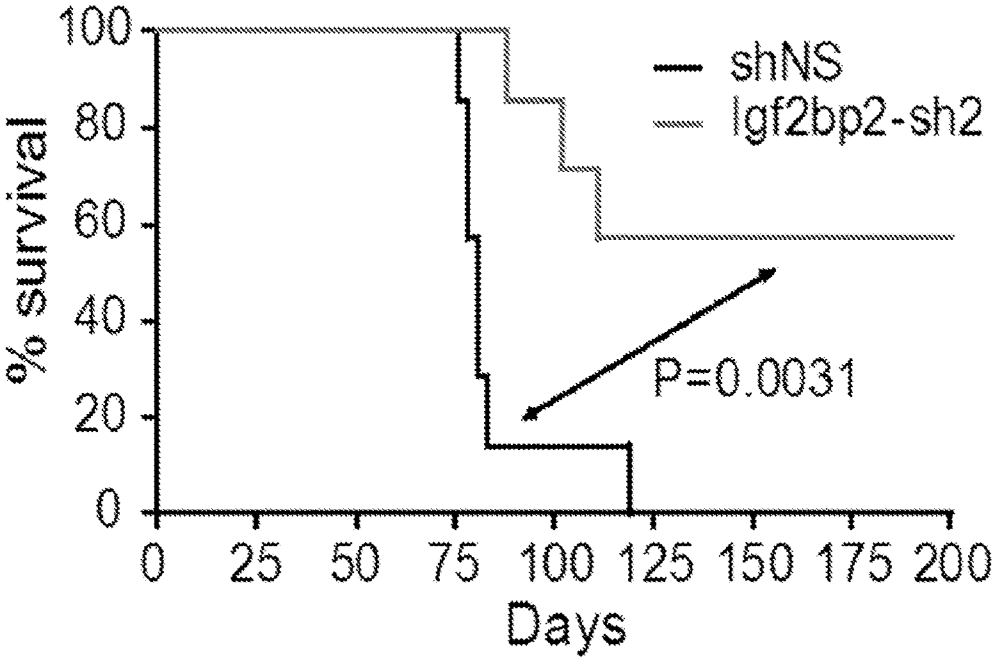
Figure 1G:
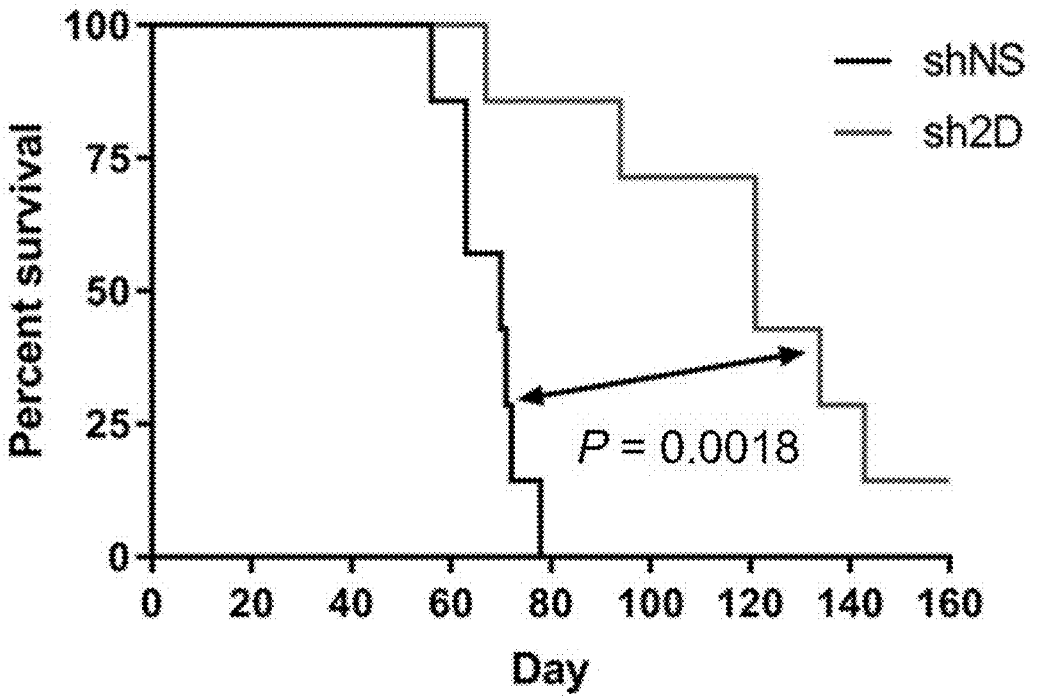
Figure 2A:
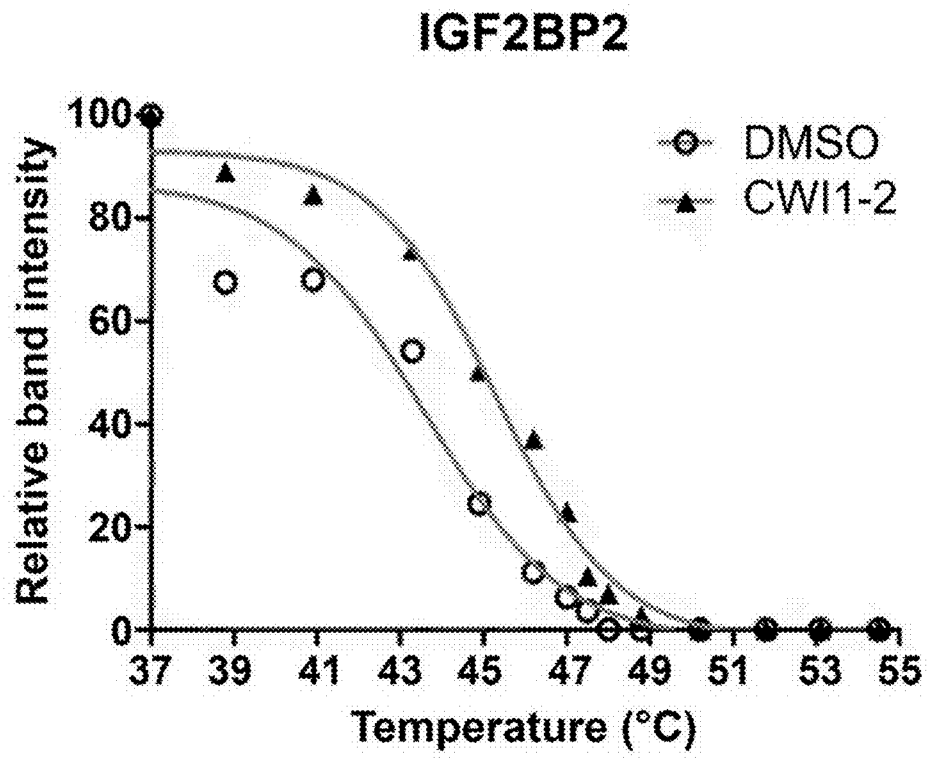
FIGS. 2A-2C. In vitro assays for direct and preferential binding of CWI1-2 to IGF2BP2. Cellular Thermal Shift Assay (CETSA) was conducted. The principle of the assay is unbound proteins denature and precipitate at elevated temperatures, while drug-bound proteins tend to remain in solution. Cells are seeded and treated. Cell pellets are washed, harvested, and heated. Cells are lysed and centrifuged. Western blot is performed.
Figure 2B:
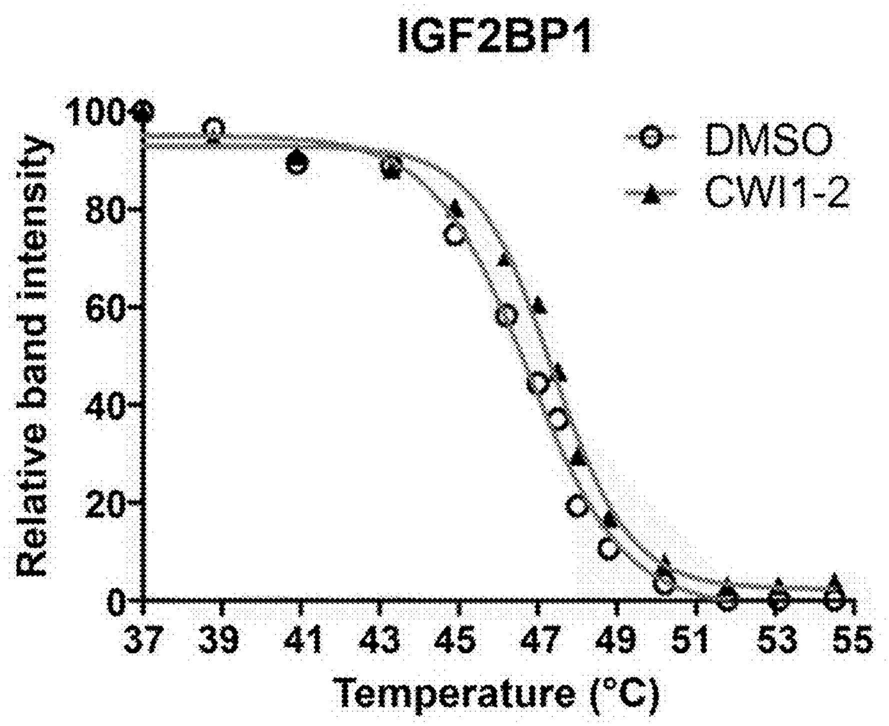
Figure 2C:
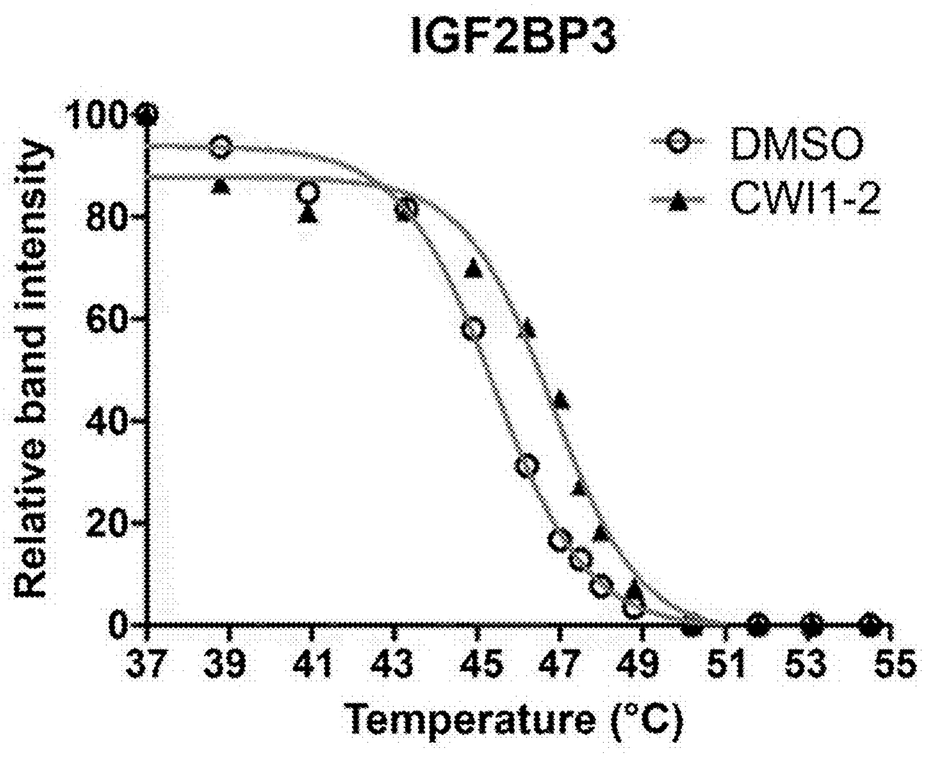
Figure 3:
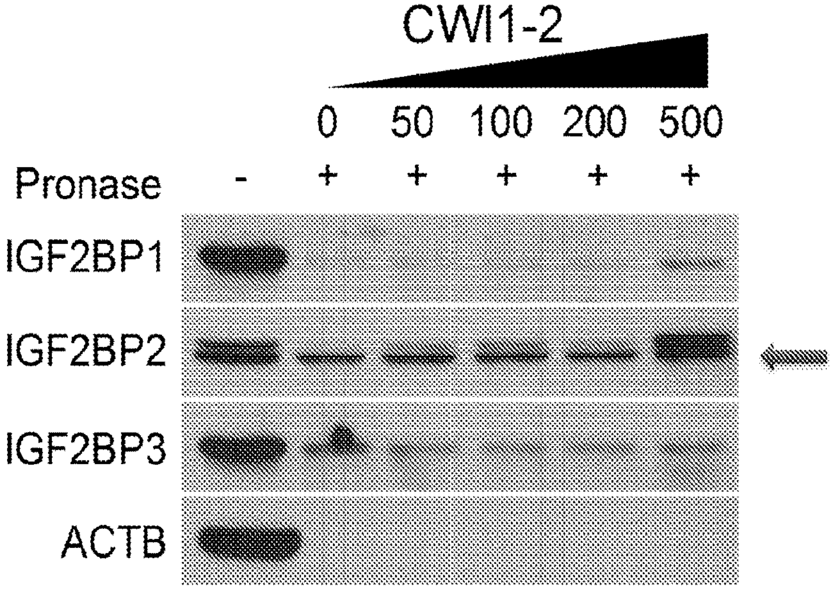
FIG. 3. In vitro assays for direct and preferential binding of CWI1-2 to IGF2BP2. Drug Affinity Responsive Target Stability (DARTS) assay was performed. The principle of the assay is binding of compound to proteins protects proteins from degradation by proteases.
Figure 4A:
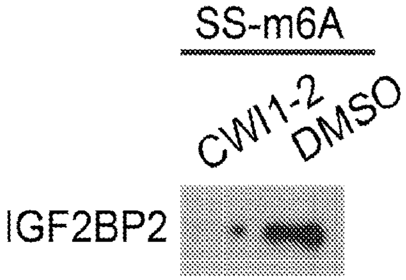
FIGS. 4A-4B. CWI1-2 inhibits binding of IGF2BP2 to $m^6A$-modified RNA and suppresses expression of the oncogenic targets of IGF2BP2.
Figure 4B:
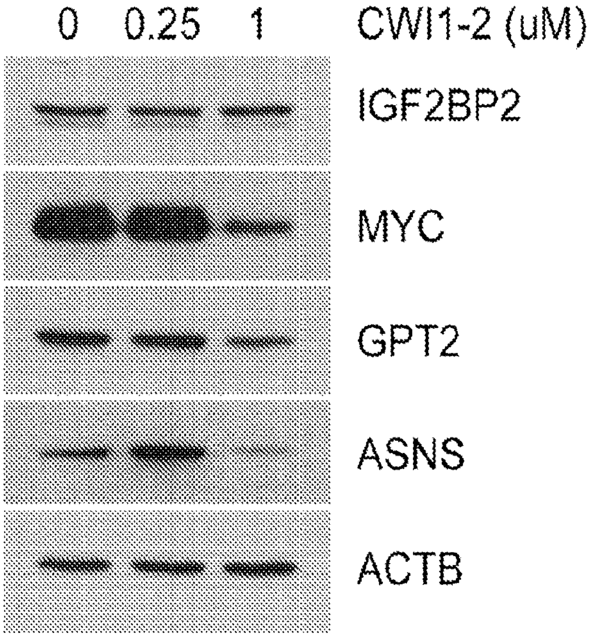
Figure 5A:
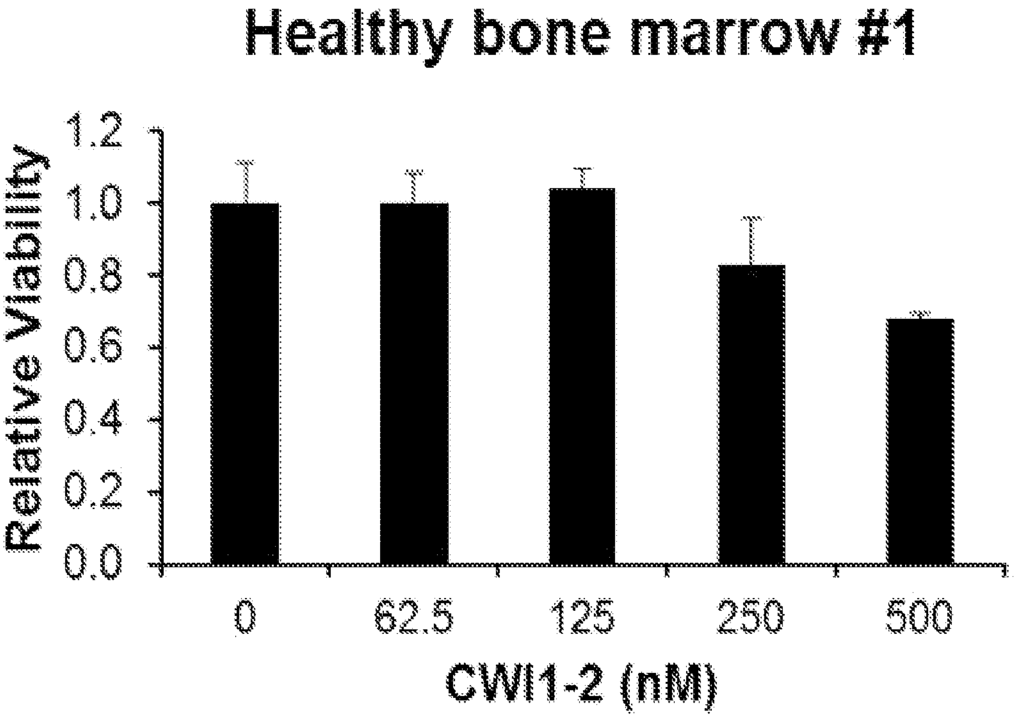
FIGS. 5A-5E. $IC_{50}$ of the lead compound CWI1-2 in human acute myeloid leukemia (AML) cells.
Figure 5B:
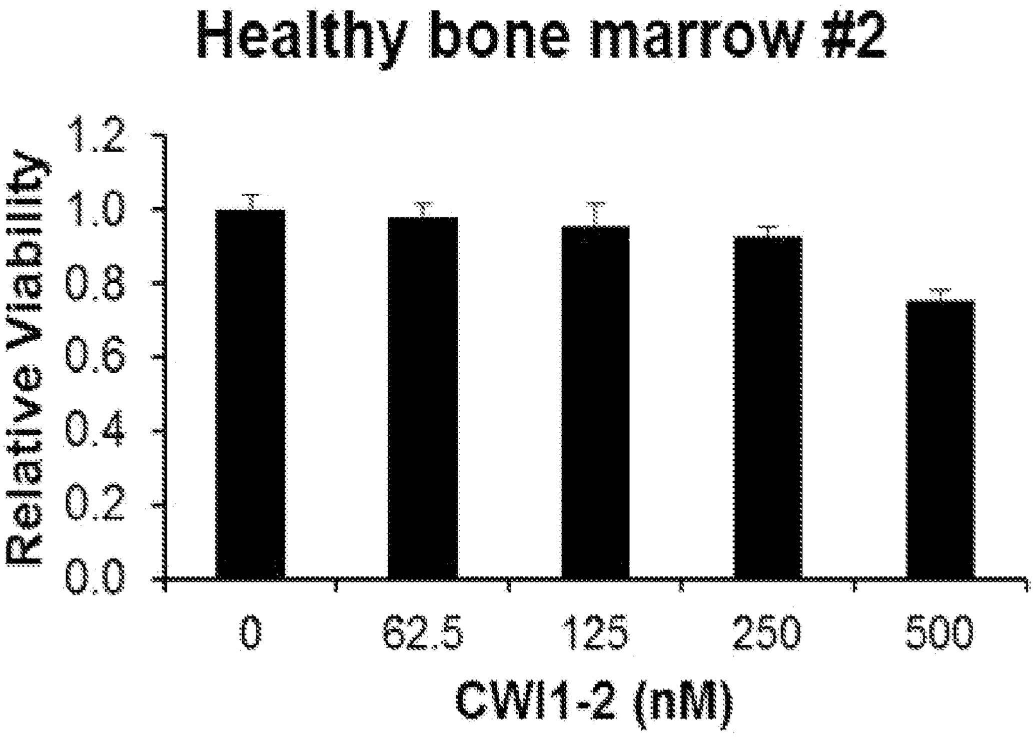
Figure 5C:
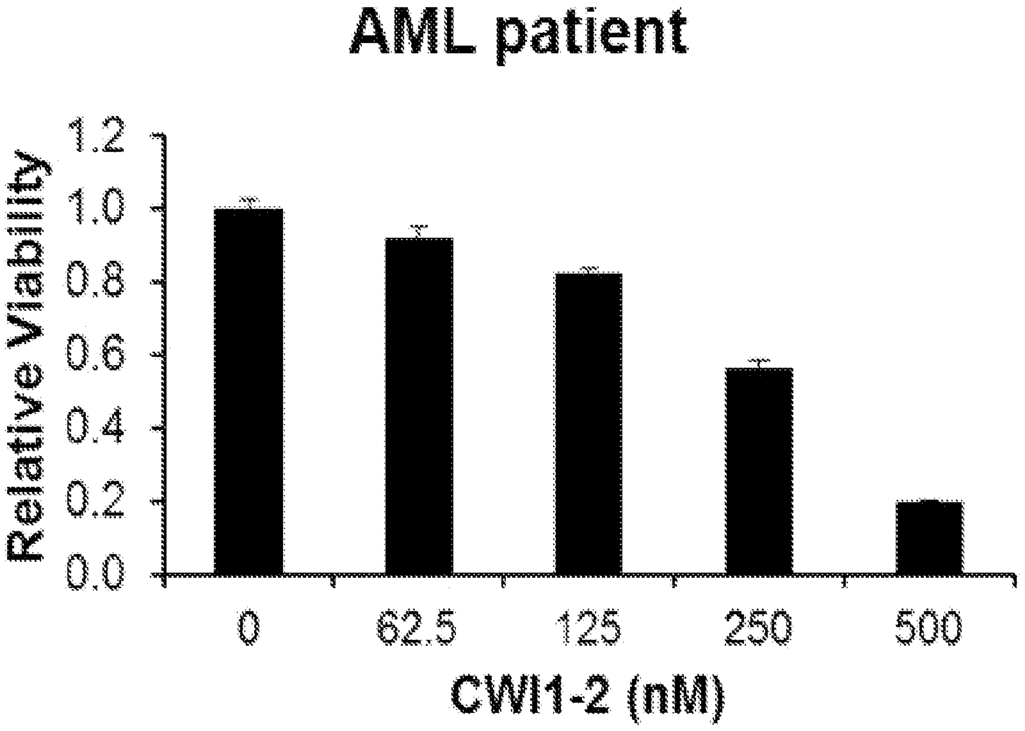
Figure 5D:
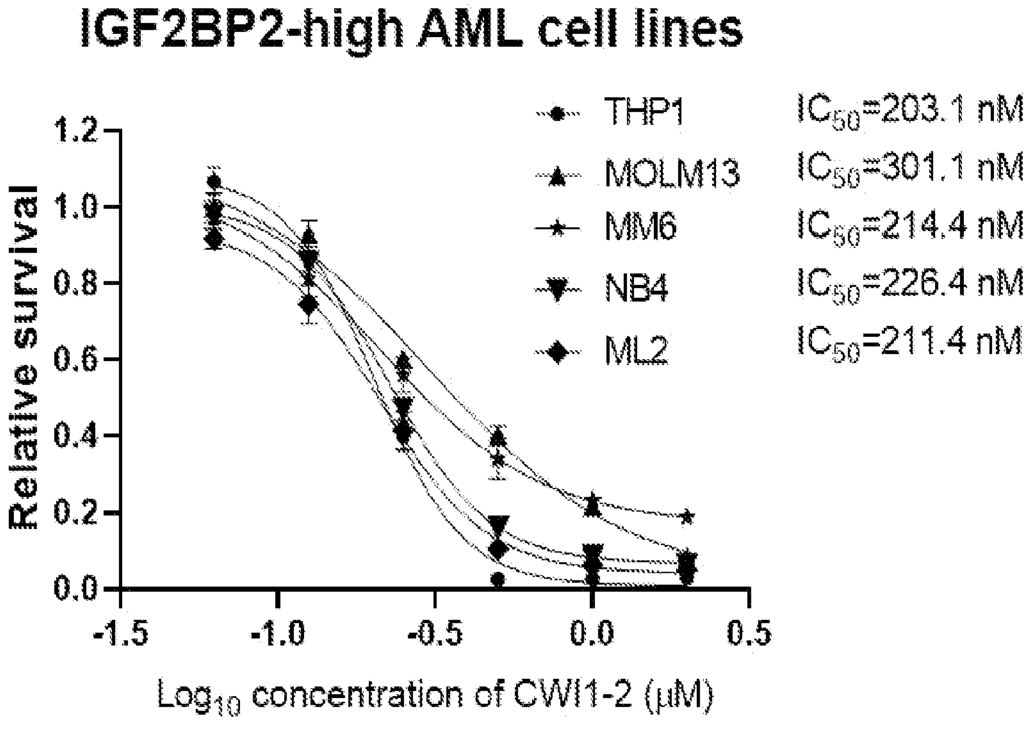
Figure 5E:
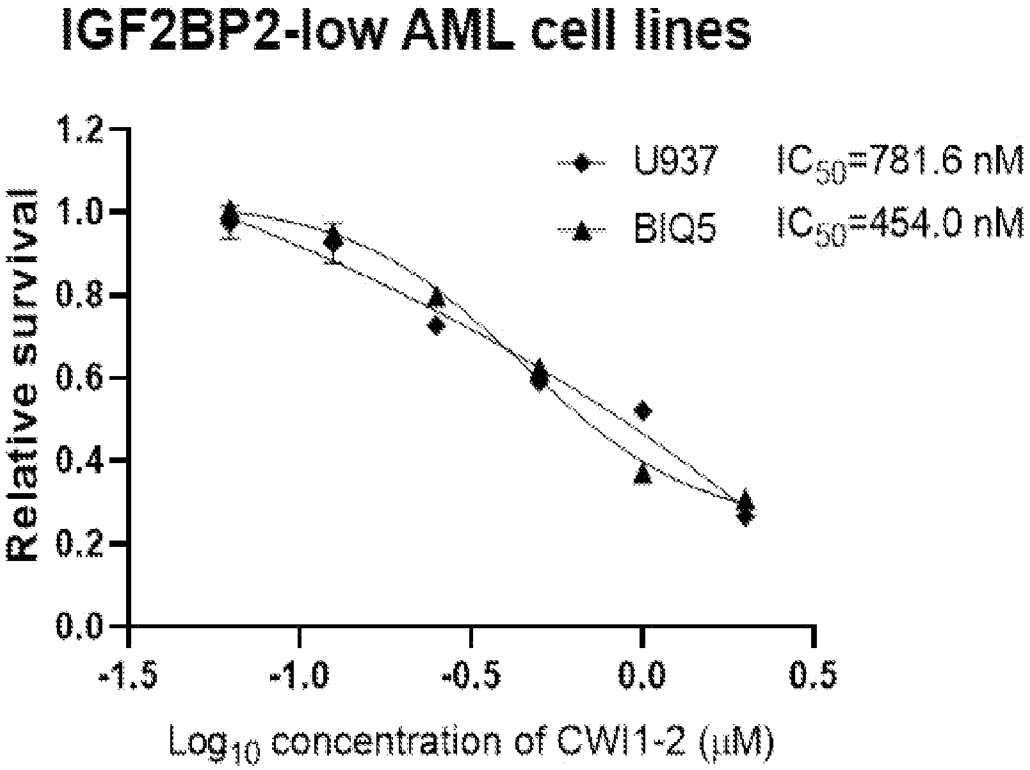
Figure 6A:
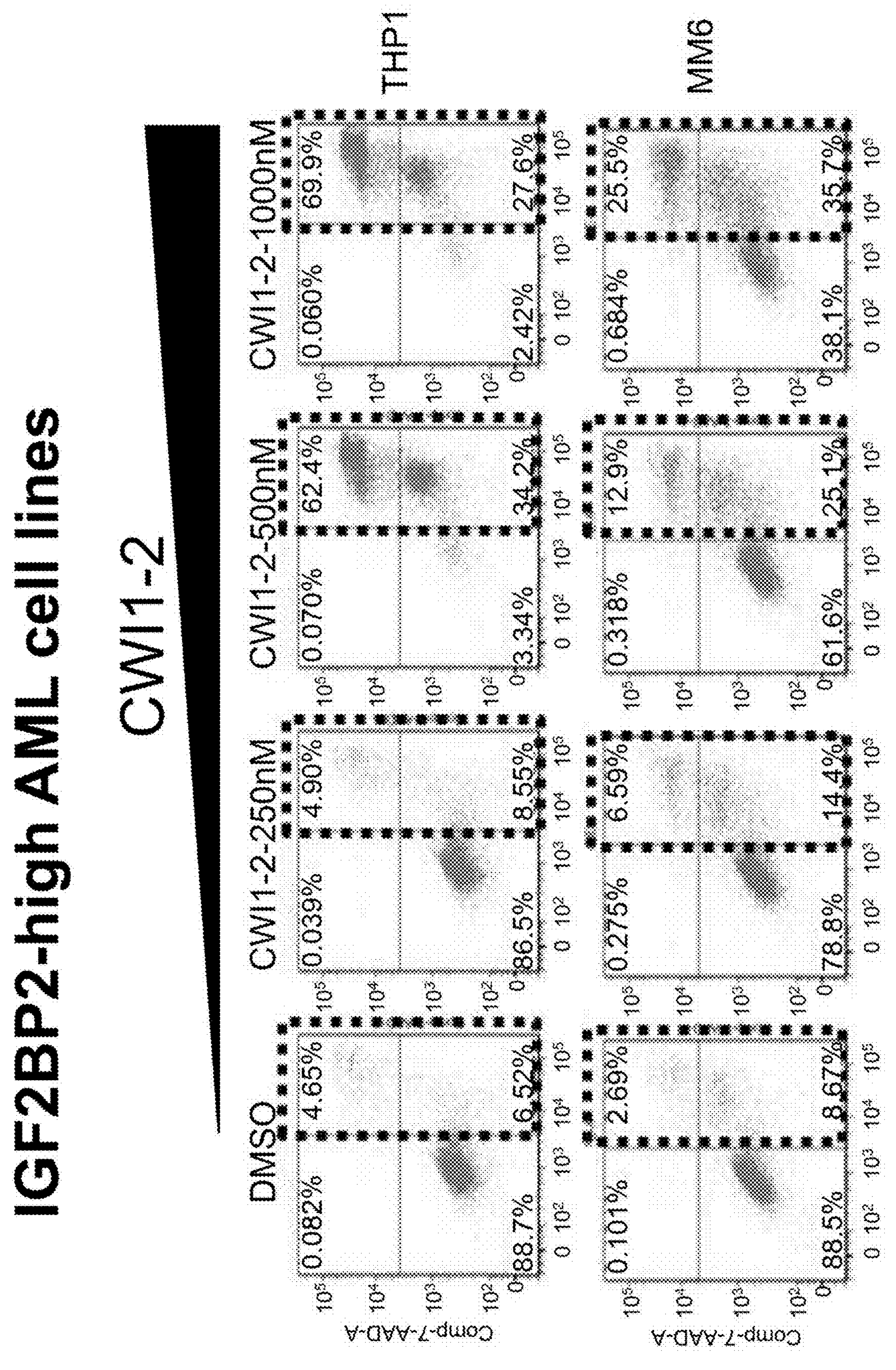
FIGS. 6A-6B. Effects of CWI1-2 on apoptosis in human acute myeloid leukemia (AML) cells. CWI1-2 induces remarkable apoptosis after 24-hour treatment in IGF2BP2- high AML cell lines (FIG. 6A) in a dose-dependent manner, but much less likely in IGF2BP2-low acute leukemia cell lines (FIG. 6B).
Figure 6A:
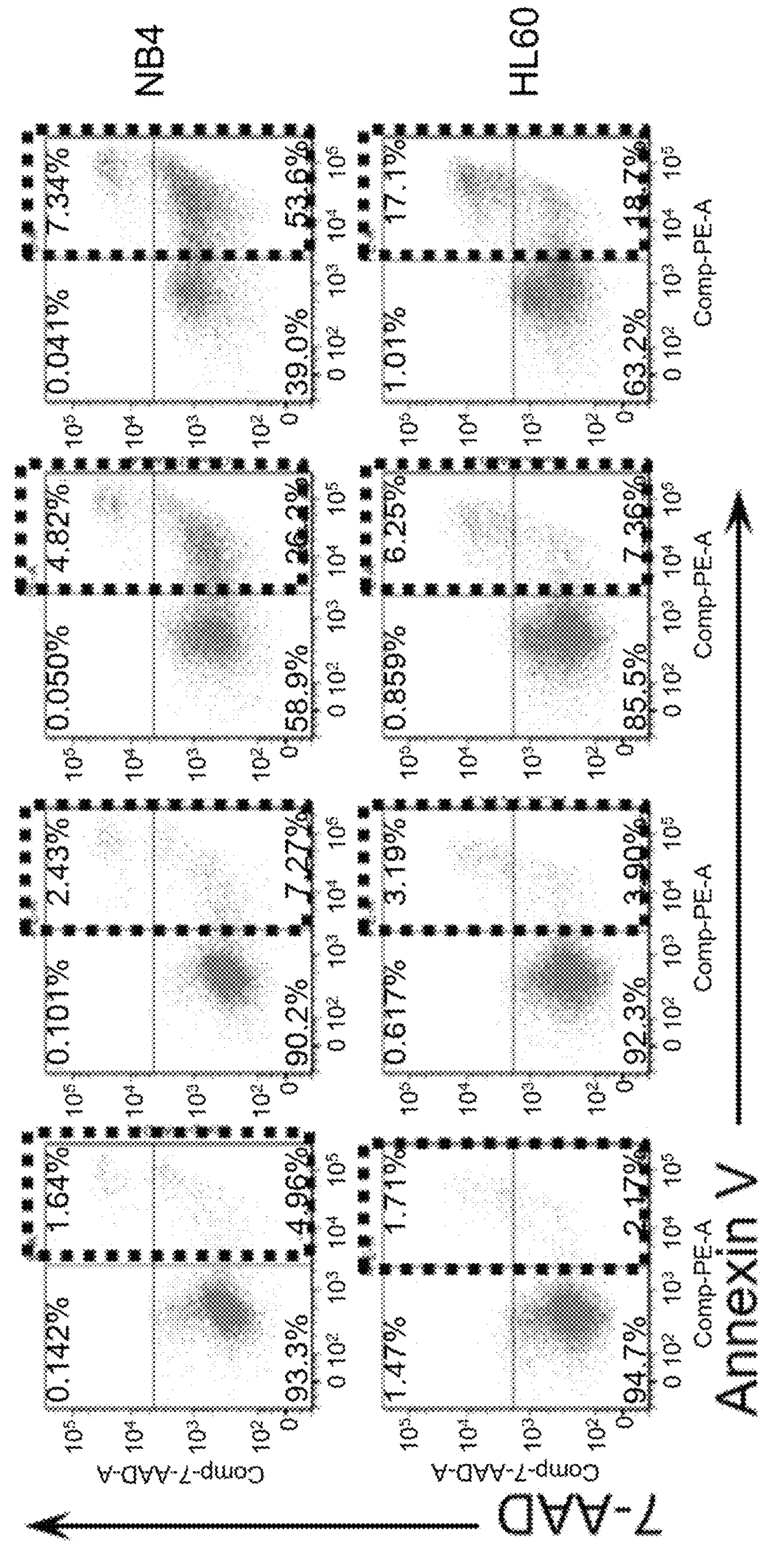
Figure 6B:
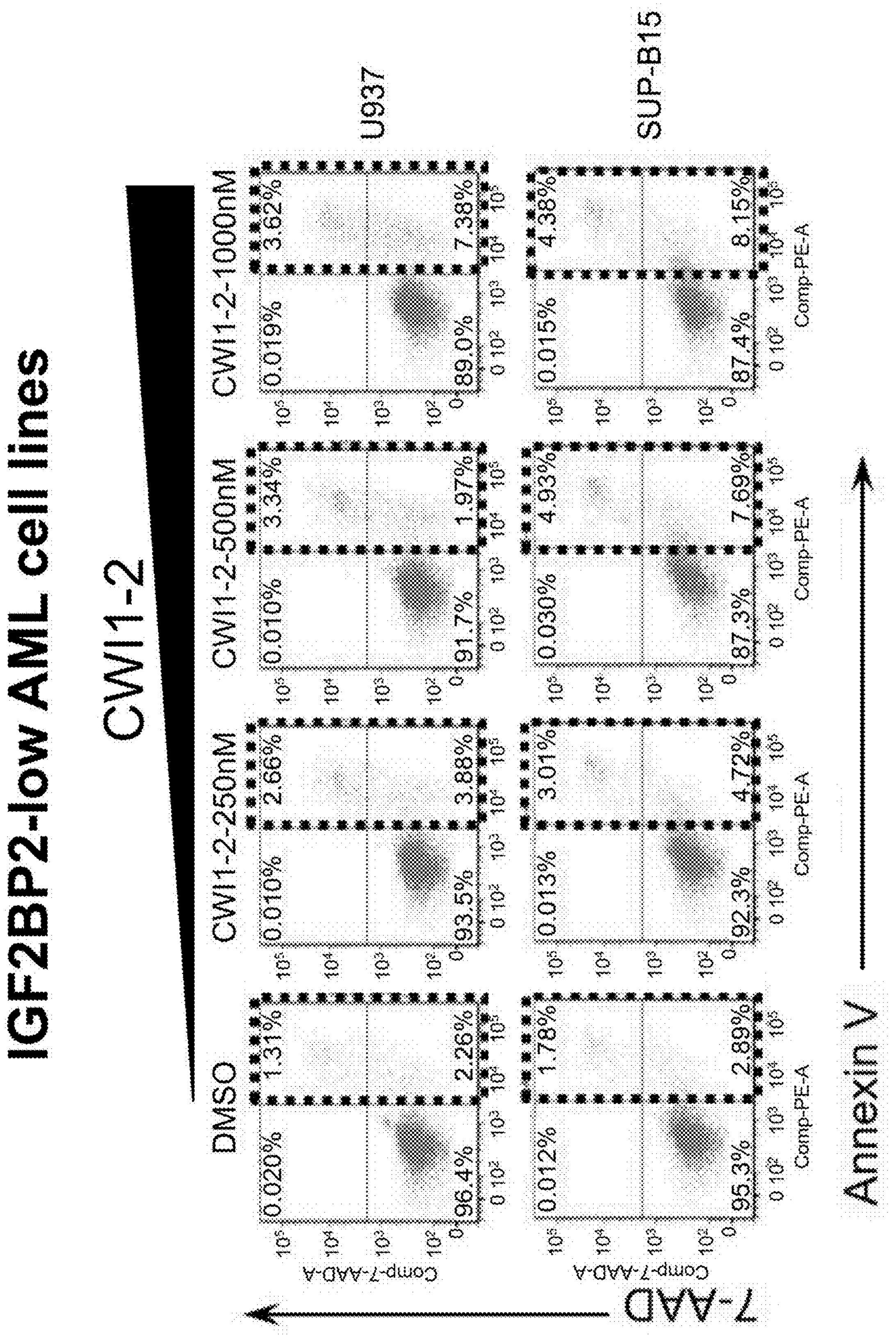
Figure 7A:
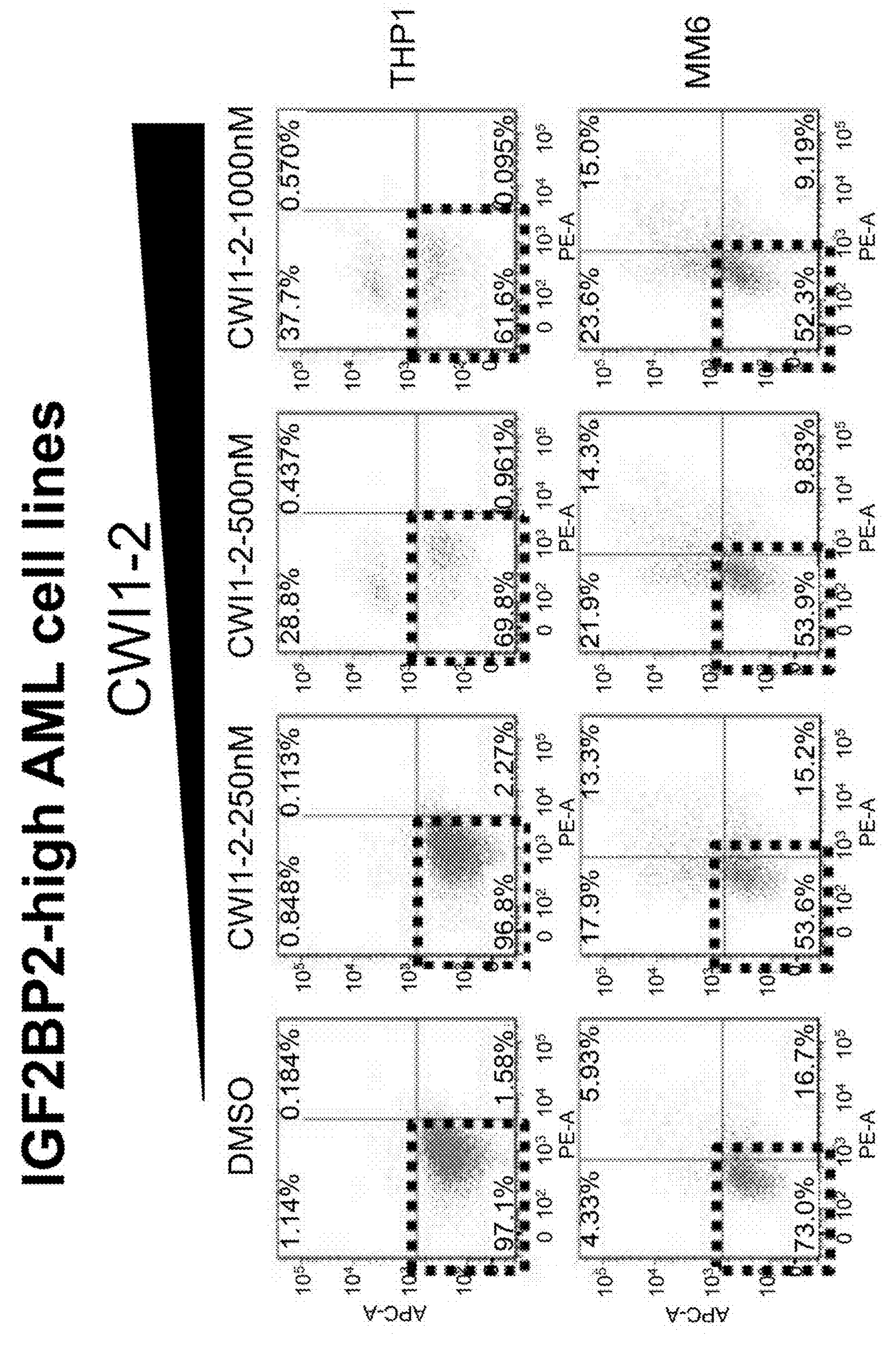
Figure 7A:
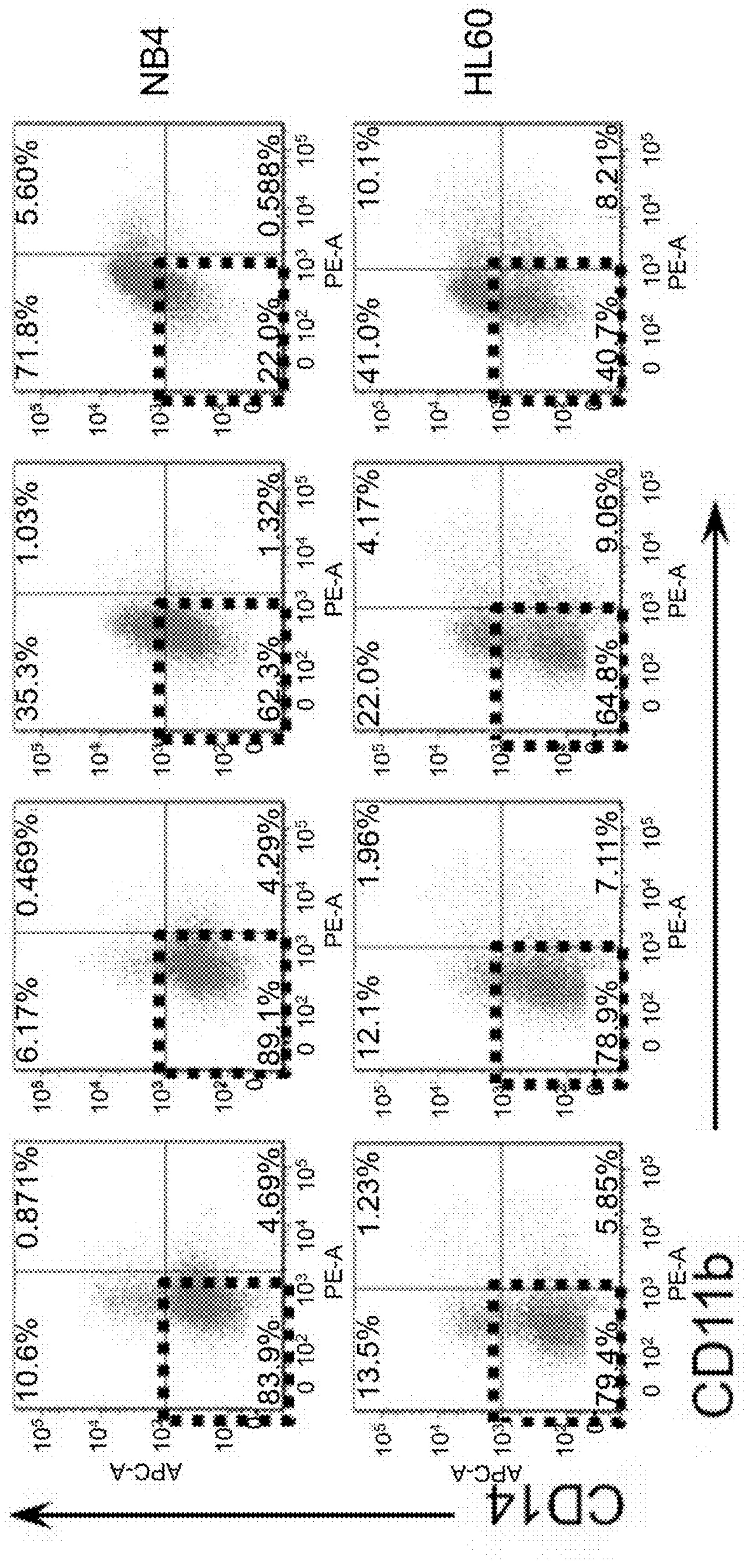
Figure 7B:
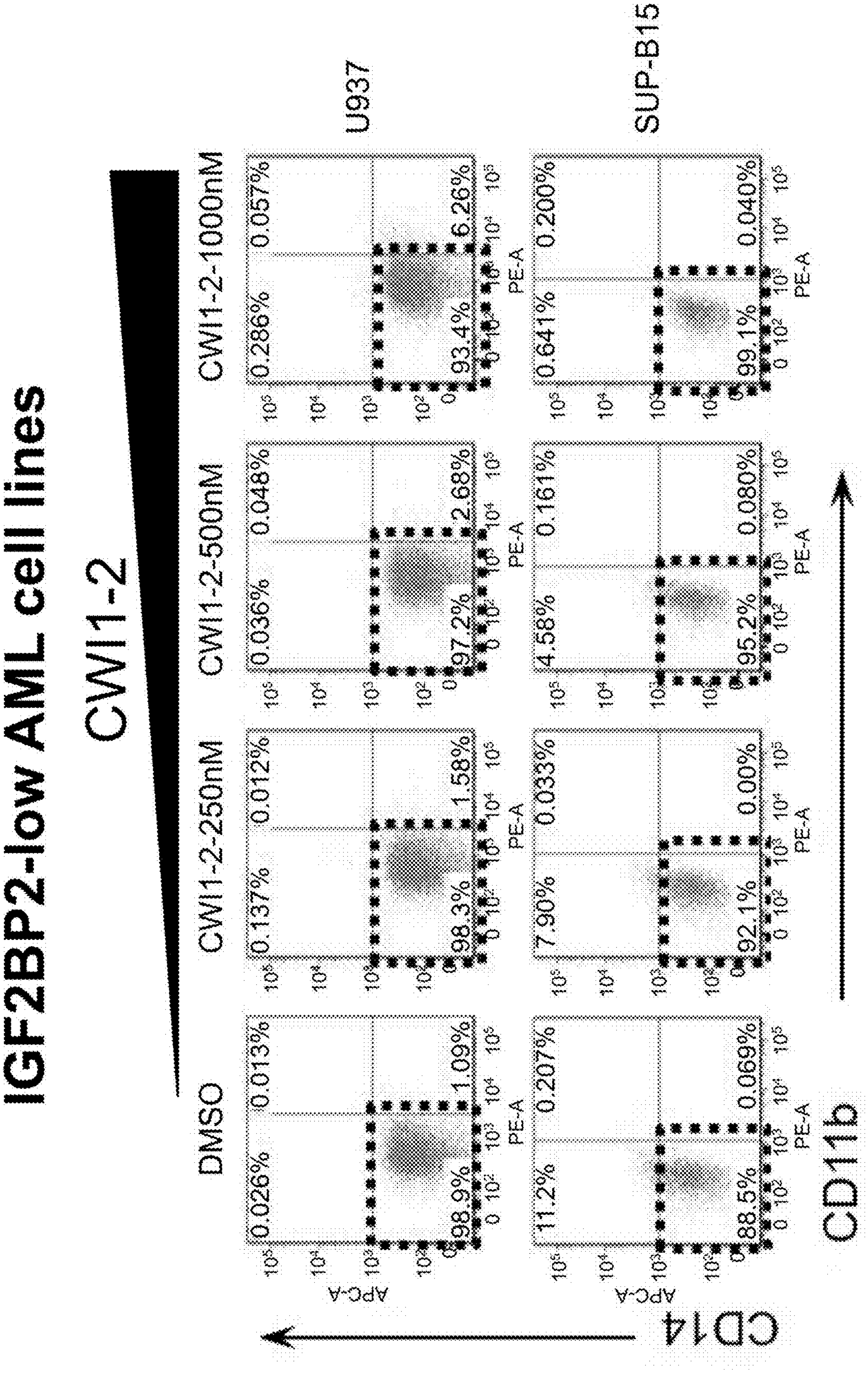

FIGS. 7A-7B. Effects of CWI1-2 on cell differentiation in acute myeloid leukemia (AML). CWI1-2 induces remarkable cell differentiation after 24-hour treatment in IGF2BP2-high AML cell lines (FIG. 7A) in a dose-dependent manner, but much less likely in IGF2BP2-low acute leukemia cell lines (FIG. 7B).

Figure 8A:
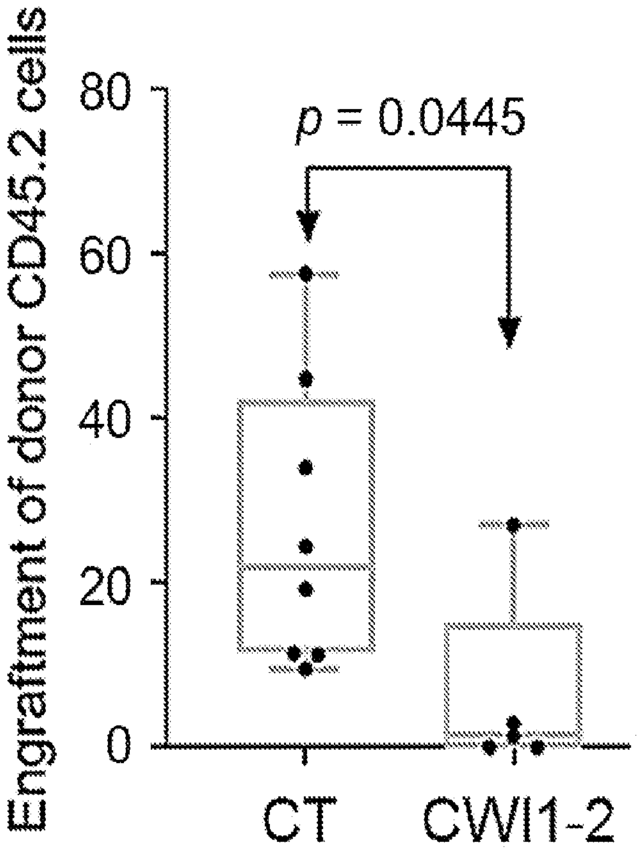
Figure 8B:
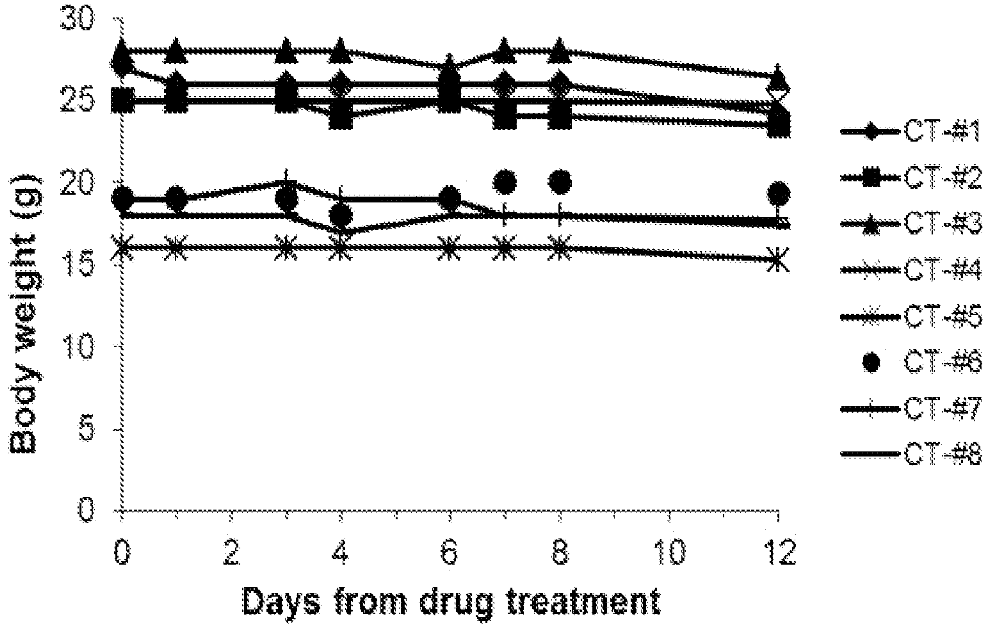
Figure 8B:
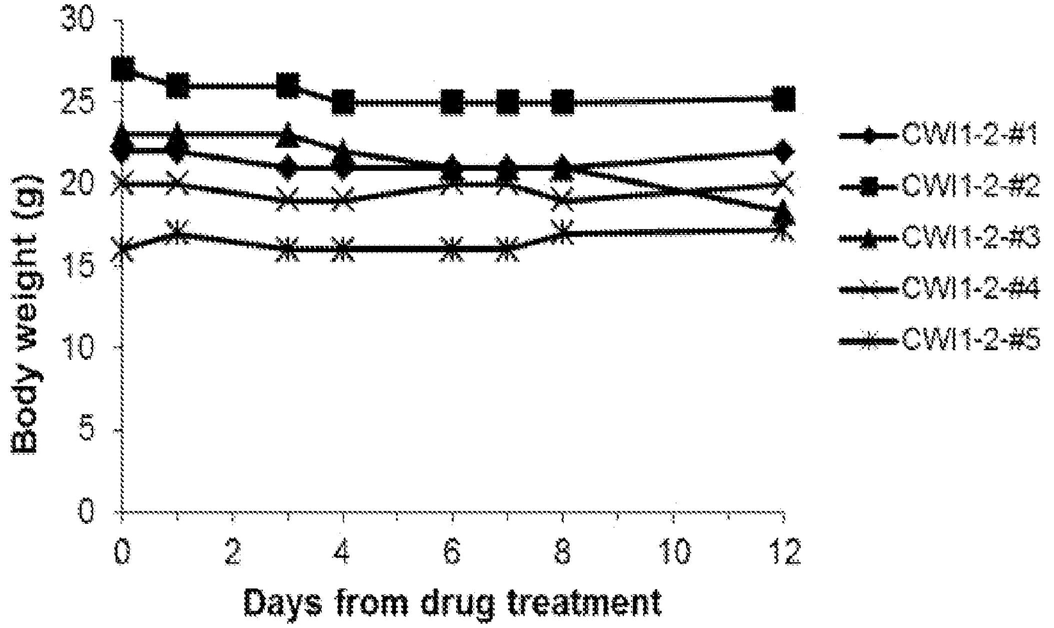

FIGS. 8A-8B. CWI1-2 inhibits engraftment of acute myelod leukemia (AML) cells in bone marrow transplant (BMT) recipient mice. FIG. 8A: Ten days after BMT with primary murine MLL-AF9 AML cells, recipient mice were given vehicle control (CT) or CWI1-2 daily for 7 days (5 mg/kg, i.v.). Peripheral blood was taken 3 days after the last treatment and assessed by flow cytometry. FIG. 8B: CWI1-2 treatment showed little effect on body weight of recipient mice.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. In embodiments, the alkyl is fully saturated. In embodiments, the alkyl is monounsaturated. In embodiments, the alkyl is polyunsaturated.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. In embodiments, an alkenylene includes one or more double bonds. In embodiments, an alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—S—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and $—CN$. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. In embodiments, a heteroalkenylene includes one or more double bonds. In embodiments, a heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. A bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. A bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In embodiments, the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). In embodiments, the multiple rings are attached to the parent molecular moiety through any atom contained within a heteroaromatic ring of the multiple rings. A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

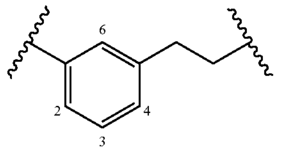

or

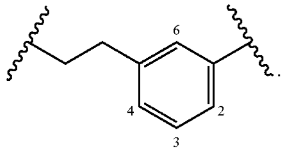

An alkylarylene moiety may be substituted (e.g., with a substituent group) on the alkylene moiety or the arylene linker (e.g., at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3$, $—SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR"", —NR—C(NR'R")=NR'", —S(O)R', $—S(O)_2R'$, $—S(O)_2NR'R"$, $—NRSO_2R'$, —NR'NR"R'", —ONR'R", —NR'C(O)NR"NR'"R"", —CN, $—NO_2$, $—NR'SO_2R"$, —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR'", —NR—C(NR'R")=NR'", —S(O)R', $—S(O)_2R'$, $—S(O)_2NR'R"$, $—NRSO_2R'$, —NR'NR"R'", —ONR'R", —NR'C(O)NR"NR'"R'", —CN, $—NO_2$, —R', $—N_3$, $—CH(Ph)_2$, fluoro($C_1$-$C_4$)alkoxy, and fluoro($C_1$-$C_4$)alkyl, $—NR'SO_2R"$, —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)-(CRR')_q-U-$, wherein T and U are independently $-NR-$, $-O-$, $-CRR'-$, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently $-CRR'-$, $-O-$, $-NR-$, $-S-$, $-S(O)-$, $-S(O)_2-$, $-S(O)_2NR'-$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s-X'-(C''R''R''')_d-$, where s and d are independently integers of from 0 to 3, and X' is $-O-$, $-NR'-$, $-S-$, $-S(O)-$, $-S(O)_2-$, or $-S(O)_2NR'-$. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$ $L^4$ may be substituted with one or more first substituent groups denoted by $R^{L4.1}$ $L^5$ may be substituted with one or more first substituent groups denoted by $R^{L5.1}$ and the like up to or exceeding an $L^{100}$ which may be substituted with one or more first substituent groups denoted by RL100.1 Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ . . . $R^{100.1}$; $R^{1A.1}$, $R^{2A.1}$, $R^{3A.1}$, $R^{4A.1}$, $R^{5A.1}$ . . . $R^{100A.1}$; $R^{L1.1}$, $R^{L2.1}$, $R^{L3.1}$, $R^{L4.1}$, $R^{L5.1}$ . . . $R^{L100.1}$) may be further substituted with one or more second substituent groups (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$) may be further substituted with one or more third substituent groups (e.g., $R^{1.3}$, $R^{2.3}$, $R^{3.3}$, $R^{4.3}$, $R^{5.3}$ . . . $R^{100.3}$; $R^{1A.3}$, $R^{2A.3}$, $R^{3A.3}$, $R^{4A.3}$, $R^{5A.3}$ . . . $R^{100A.3}$; $R^{L1.3}$, $R^{L2.3}$, $R^{L3.3}$, $R^{L4.3}$, $R^{L5.3}$ . . . $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

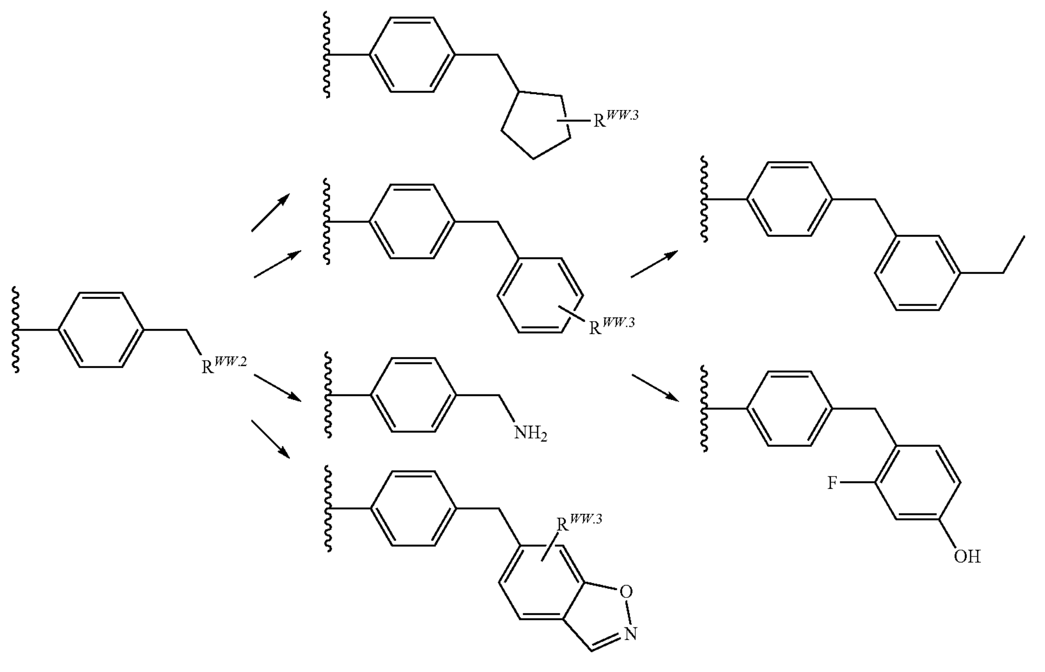

$R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, $-CX^{WW.2}_3$, $-CHX^{WW.2}_2$, $-CH_2X^{WW.2}$, $-OCX^{WW.2}_3$, $-OCH_2X^{WW.2}$, $-OCHX^{WW.2}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, $-CX^{WW.2}_3$, $-CHX^{WW.2}_2$, $-CH_2X^{WW.2}$, $-OCX^{WW.2}_3$, $-OCH_2X^{WW.2}$, $-OCHX^{WW.2}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X_{WW.2}$ is independently —F, —Cl, —Br, or —I.

$R^{WW.3}$ is independently oxo, halogen, $-CX^{WW.3}_3$, $-CHX^{WW.3}_2$, $-CH_2X^{WW.3}$, $-OCX^{WW.3}_3$, $-OCH_2X^{WW.3}$, $-OCHX^{WW.3}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g. substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, $-CX^{LWW.1}_3$, $-CHX^{LWW.1}_2$, $-CH_2X^{LWW.1}$, $-OCX^{LWW.1}_3$, $-OCH_2X^{LWW.1}$, $-OCHX^{LWW.1}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $-N_3$, $R^{LWW.2}$_substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$_substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, $-CX^{LWW.1}_3$, $-CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, —$CX^{LWW.2}_3$, —$CHX^{LWW.2}_2$, —$CH_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, —$CX^{LWW.2}_3$, —$CHX^{LWW.2}_2$, —$CH_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, —$CX^{LWW.3}_3$, —$CHX^{LWW.3}_2$, —$CH_2X^{LWW.3}$, —$OCX^{LWW.3}_3$, —$OCH_2X^{LWW.3}$, —$OCHX^{LWW.3}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, —$CX^{WW}_3$, —$CHX^{WW}_2$, —$CH_2X^{WW}$, —$OCX^{WW}_3$, —$OCH_2X^{WW}$, —$OCHX^{WW}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, —O—, —NH—, —C(O)—, —C(O)NH—, —NHC(O)—, —NHC(O)NH—, —C(O)O—, —OC(O)—, —S—, —$SO_2NH$—, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refer to the resulting association between atoms or molecules of bioconjugate reactive groups or bioconjugate reactive moieties. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

In this disclosure, "comprises," "comprising," "containing" and "having" and the like can have the meaning ascribed to them in U.S. Patent law and can mean "includes," "including," and the like. "Consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and/or appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), an additional number may be used to distinguish each appearance of that particular R group. For example, where multiple $R^{13}$ substituents are present, each $R^{13}$ substituent may be distinguished as $R^{13.A}$, $R^{13.B}$, $R^{13.C}$, $R^{13.D}$, etc., wherein each of $R^{13.A}$, $R^{13.B}$, $R^{13.C}$, $R^{13.D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Co-administer" is meant that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term "treating" and conjugations thereof, include prevention of an injury, pathology, condition, or disease. In embodiments, treating is preventing. In embodiments, treating does not include preventing. In embodiments, the treating or treatment is not prophylactic treatment.

An "effective amount" is an amount sufficient for a compound to accomplish a stated purpose relative to the absence of the compound (e.g., achieve the effect for which it is administered, treat a disease, reduce enzyme activity, increase enzyme activity, reduce signaling pathway, reduce one or more symptoms of a disease or condition. An example of an "effective amount" is an amount sufficient to contribute to the treatment, prevention, or reduction of a symptom or symptoms of a disease, which could also be referred to as a "therapeutically effective amount" when referred to in this context. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g., signaling pathway) of a protein in the absence of a compound as described herein (including embodiments, examples, figures, or Tables).

"Contacting" is used in accordance with its plain ordinary meaning and refers to the process of allowing at least two distinct species (e.g., chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a cellular component (e.g., protein, ion, lipid, nucleic acid, nucleotide, amino acid, protein, particle, organelle, cellular compartment, microorganism, virus, lipid droplet, small molecule, protein complex, protein aggregate, or macromolecule). In some embodiments contacting includes allowing a compound described herein to interact with a cellular component (e.g., protein, ion, lipid, nucleic acid, nucleotide, amino acid, protein, particle, virus, lipid droplet, organelle, cellular compartment, microorganism, small molecule, protein complex, protein aggregate, or macromolecule) that is involved in a signaling pathway.

As defined herein, the term "inhibition," "inhibit," "inhibiting" and the like in reference to a cellular component-inhibitor interaction means negatively affecting (e.g., decreasing) the activity or function of the cellular component (e.g., decreasing the signaling pathway stimulated by a cellular component (e.g., protein, ion, lipid, virus, lipid droplet, nucleic acid, nucleotide, amino acid, protein, particle, organelle, cellular compartment, microorganism, small molecule, protein complex, protein aggregate, or macromolecule)), relative to the activity or function of the cellular component in the absence of the inhibitor. In some embodiments inhibition refers to reduction of a disease or symptoms of disease. In some embodiments, inhibition refers to a reduction in the activity of a signal transduction pathway or signaling pathway (e.g., reduction of a pathway involving the cellular component). Thus, inhibition includes, at least in part, partially or totally blocking stimulation, decreasing, preventing, or delaying activation, or inactivating, desensitizing, or down-regulating the signaling pathway or enzymatic activity or the amount of a cellular component.

The term "modulator" refers to a composition that increases or decreases the level of a target molecule or the function of a target molecule or the physical state of the target of the molecule (e.g., a target may be a cellular component (e.g., protein, ion, lipid, virus, lipid droplet, nucleic acid, nucleotide, amino acid, protein, particle, organelle, cellular compartment, microorganism, small molecule, protein complex, protein aggregate, or macromolecule)) relative to the absence of the composition.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g., caused by) a cellular component (e.g., protein, ion, lipid, nucleic acid, nucleotide, amino acid, protein, particle, organelle, cellular compartment, microorganism, small molecule, protein complex, protein aggregate, or macromolecule). In embodiments, the disease is a cancer. In embodiments, the disease is a metabolic disorder. In embodiments, the disease is aging.

As used herein, the term "cancer" refers to all types of cancer, neoplasm or malignant tumors found in mammals (e.g., humans), including leukemia, lymphoma, carcinomas and sarcomas. Exemplary cancers that may be treated with a compound or method provided herein include cancer of the thyroid, endocrine system, brain, breast, cervix, colon, head and neck, liver, kidney, lung, non-small cell lung, melanoma, mesothelioma, ovary, sarcoma, stomach, uterus, medulloblastoma, colorectal cancer, or pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metabolic disorder" or "metabolic disease" refer to a disorder or a disease or condition in which a subject's metabolism or metabolic system (e.g., function of storing or utilizing energy) becomes impaired. In embodiments, a metabolic disorder may be associated with, related to, or may be diabetes (e.g., type 1 diabetes or type 2 diabetes), insulin resistance, metabolic syndrome, obesity, hyperlipidemia, hyperglycemia, high serum triglycerides, and/or high blood pressure. In embodiments, the metabolic disorder is diabetes. In embodiments, the metabolic disorder is type 1 diabetes (T1D). In embodiments, the metabolic disorder is type 2 diabetes (T2D). In embodiments, the metabolic disorder is obesity.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compounds described herein can be used in combination with one another, with other active agents known to be useful in treating a disease associated with cells expressing a disease associated cellular component, or with adjunctive agents that may not be effective alone, but may contribute to the efficacy of the active agent. The compounds described herein can be used in combination with other active agents known to be longevity agents or anti-aging agents.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As anon-limiting example, the compounds described herein can be co-administered with anti-cancer agents or conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., innotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The term "longevity" is used in accordance with its plain ordinary meaning and refers to a long life or the extension of life expectancy beyond an average life expectancy. A "longevity agent" is an agent (e.g., composition as described herein) capable of extending the life expectancy of a subject in comparison to the life expectancy of the subject in the absence of the agent (Lamming, D. W., et al. (2012). Science (New York, NY), 335(6076), 1638-1643., McCormick, M. A., et al. (2011). Philosophical Transactions of the Royal Society B: Biological Sciences, 366(1561)). A longevity agent may be capable of inducing one or more anti-aging effects in a subject wherein an aging effect is a condition or symptom of aging normally found in a similar subject.

In therapeutic use for the treatment of a disease, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer, or with adjunctive agents that may not be effective alone, but may contribute to the efficacy of the active agent.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

The term "associated" or "associated with" in the context of a substance or substance activity or function associated with a disease (e.g., a protein associated disease, disease associated with a cellular component) means that the disease (e.g., cancer) is caused by (in whole or in part), or a symptom of the disease is caused by (in whole or in part) the substance or substance activity or function or the disease or a symptom of the disease may be treated by modulating (e.g., inhibiting or activating) the substance (e.g., cellular component). As used herein, what is described as being associated with a disease, if a causative agent, could be a target for treatment of the disease.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

"Anti-cancer agent" is used in accordance with its plain ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. In embodiments, an anti-cancer agent is an agent with antineoplastic properties that has not (e.g., yet) been approved by the FDA or similar regulatory agency of a country other than the USA, for treating cancer. In embodiments, an anti-cancer agent is an inhibitor of K-Ras, RAF, MEK, Erk, PI3K, Akt, RTK, or mTOR. In embodiments, an anti-cancer agent is an MDM2 inhibitor or a genotoxic anti-cancer agent. In embodiments, an anti-cancer agent is nutlin-1, nutlin-2, nutlin-3, nutlin-3a, nutlin-3b, YH239-EE, MI-219, MI-773, MI-77301, MI-888, MX69, RG7112, RG7388, RITA, idasanutlin, DS-3032b, or AMG232. In embodiments, an anti-cancer agent is an alkylating agent, intercalating agent, or DNA replication inhibitor. Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g., U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irnnotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g., Taxol™ (i.e. paclitaxel), Taxotere™, compounds comprising the taxane skeleton, Erbulozole (i.e., R-55104), Dolastatin 10 (i.e., DLS-10 and NSC-376128), Mivobulin isethionate (i.e., as CI-980), Vincristine, NSC-639829, Discodermolide (i.e., as NVP-XX-A-296), ABT-751 (Abbott, i.e., E-7010), Altorhyrtins (e.g., Altorhyrtin A and Altorhyrtin C), Spongistatins (e.g., Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e., LU-103793 and NSC-D-669356), Epothilones (e.g., Epothilone A, Epothilone B, Epothilone C (i.e., desoxyepothilone A or dEpoA), Epothilone D (i.e., KOS-862, dEpoB, and desoxyepothilone B), Epothilone E, Epothilone F, Epothilone B N-oxide, Epothilone A N-oxide, 16-aza-epothilone B, 21-aminoepothilone B (i.e., BMS-310705), 21-hydroxyepothilone D (i.e., Desoxyepothilone F and dEpoF), 26-fluoroepothilone, Auristatin PE (i.e., NSC-654663), Soblidotin (i.e., TZT-1027), LS-4559-P (Pharmacia, i.e., LS-4577), LS-4578 (Pharmacia, i.e., LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e., ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e., LY-355703), AC-7739 (Ajinomoto, i.e., AVE-8063A and CS-39.HCl), AC-7700 (Ajinomoto, i.e., AVE-8062, AVE-8062A, CS-39-L-Ser-.HCl, and RPR-258062A), Vitilevuamide, Tubulysin A, Canadensol, Centaureidin (i.e., NSC-106969), T-138067 (Tularik, i.e., T-67, TL-138067 and TI-138067), COBRA-1 (Parker Hughes Institute, i.e., DDE-261 and WHI-261), H10 (Kansas State University), H16 (Kansas State University), Oncocidin A1 (i.e., BTO-956 and DIME), DDE-313 (Parker Hughes Institute), Fijianolide B, Laulimalide, SPA-2 (Parker Hughes Institute), SPA-1 (Parker Hughes Institute, i.e., SPIKET-P), 3-IAABU (Cytoskeleton/Mt. Sinai School of Medicine, i.e., MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e., MF-191), TMPN (Arizona State University), Vanadocene acetylacetonate, T-138026 (Tularik), Monsatrol, lnanocine (i.e., NSC-698666), 3-IAABE (Cytoskeleton/Mt. Sinai School of Medicine), A-204197 (Abbott), T-607 (Tuiarik, i.e., T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e., NSCL-96F037), D-68838 (Asta Medica), D-68836 (Asta Medica), Myoseverin B, D-43411 (Zentaris, i.e., D-81862), A-289099 (Abbott), A-318315 (Abbott), HTI-286 (i.e., SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™), erlotinib (Tarceva™), cetuximab (Erbitux™), lapatinib (Tykerb™) panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. A moiety of an anti-cancer agent is a monovalent anti-cancer agent (e.g., a monovalent form of an agent listed above).

"Chemotherapeutic" or "chemotherapeutic agent" is used in accordance with its plain ordinary meaning and refers to a chemical composition or compound having antineoplastic properties or the ability to inhibit the growth or proliferation of cells.

The term "electrophilic" as used herein refers to a chemical group that is capable of accepting electron density. An "electrophilic substituent," "electrophilic chemical moiety," or "electrophilic moiety" refers to an electron-poor chemical group, substituent, or moiety (monovalent chemical group), which may react with an electron-donating group, such as a nucleophile, by accepting an electron pair or electron density to form a bond.

"Nucleophilic" as used herein refers to a chemical group that is capable of donating electron density.

An amino acid residue in a protein "corresponds" to a given residue when it occupies the same essential structural position within the protein as the given residue. Instead of a primary sequence alignment, a three dimensional structural alignment can also be used, e.g., where the structure of the selected protein is aligned for maximum correspondence with the human protein and the overall structures compared. In this case, an amino acid that occupies the same essential position as a specified amino acid in the structural model is said to correspond to the specified residue.

The term "isolated," when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide," and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "$N^6$-methyladenosine" or "$m^6A$" is used in accordance with its plain ordinary meaning and refers to a modification (i.e., methylation of adenosine) in RNA (e.g., mRNA, tRNA, rRNA, and small nuclear RNA (snRNA)) and DNA.

The term "protein complex" is used in accordance with its plain ordinary meaning and refers to a protein which is associated with an additional substance (e.g., another protein, protein subunit, or a compound). Protein complexes typically have defined quaternary structure. The association between the protein and the additional substance may be a covalent bond. In embodiments, the association between the protein and the additional substance (e.g., compound) is via non-covalent interactions. In embodiments, a protein complex refers to a group of two or more polypeptide chains. Proteins in a protein complex are linked by non-covalent protein-protein interactions. A non-limiting example of a protein complex is the proteasome.

The term "insulin-like growth factor 2 mRNA-binding protein 2" or "IGF2BP2" refers to a protein that functions by binding to the 5' UTR of the insulin-like growth factor 2 (IGF2) mRNA and regulating IGF2 translation. In embodiments, the IGF2BP2 protein is the human IGF2BP2 protein. In embodiments, the IGF2BP2 protein encoded by the IGF2BP2 gene has the amino acid sequence set forth in or corresponding to Entrez 10644, UniProt Q9Y6M1, RefSeq (protein) NP_001007226.1, RefSeq (protein) NP_001278801.1, RefSeq (protein) NP_001278802.1, RefSeq (protein) NP_001278803.1, RefSeq (protein) NP_001278804.1, or RefSeq (protein) NP_006539.3. In embodiments, the amino acid sequence or nucleic acid sequence is the sequence known at the time of filing of the present application. In embodiments, IGF2BP2 has the sequence:

```
                                        (SEQ ID NO: 1)
MMNKLYIGNLSPAVTADDLRQLFGDRKLPLAGQVLLKSGYAFVDYPDQNW

AIRAIETLSGKVELHGKIMEVDYSVSKKLRSRKIQIRNIPPHLQWEVLDG

LLAQYGTVENVEQVNTDTETAVVNVTYATREEAKIAMEKLSGHQFENYSF

KISYIPDEEVSSPSPPQRAQRGDHSSREQGHAPGGTSQARQIDFPLRILV

PTQFVGAIIGKEGLTIKNITKQTQSRVDIHRKENSGAAEKPVTIHATPEG

TSEACRMILEIMQKEADETKLAEEIPLKILAHNGLVGRLIGKEGRNLKKI

EHETGTKITISSLQDLSIYNPERTITVKGTVEACASAEIEIMKKLREAFE

NDMLAVNQQANLIPGLNLSALGIFSTGLSVLSPPAGPRGAPPAAPYHPFT

THSGYFSSLYPHHQFGPFPHHHSYPEQEIVNLFIPTQAVGAIIGKKGAHI

KQLARFAGASIKIAPAEGPDVSERMVIITGPPEAQFKAQGRIFGKLKEEN

FFNPKEEVKLEAHIRVPSSTAGRVIGKGGKTVNELQNLTSAEVIVPRDQT

PDENEEVIVRIIGHFFASQTAQRKIREIVQQVKQQEQKYPQGVASQRSK.
```

II. Compounds

In an aspect is provided a compound, or a pharmaceutically acceptable salt thereof, having the formula:

(I)

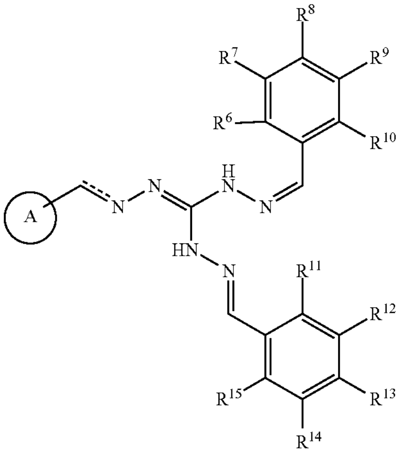

or (II)

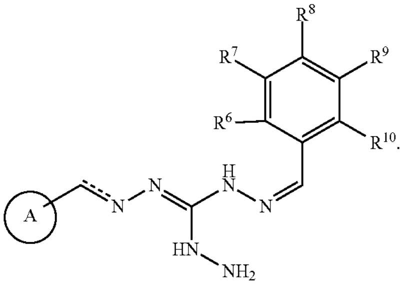

Ring A is a substituted or unsubstituted cycloalkyl, substituted or unsubstituted heterocycloalkyl, substituted or unsubstituted aryl, or substituted or unsubstituted heteroaryl.

⋰ is a single bond or a double bond.

$R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}R^{6D}$, —$SO_{v6}NR^{6A}R^{6B}$, —$NHC(O)NR^{6A}R^{6B}$, —$NR^{6C}NR^{6A}R^{6B}$, —$ONR^{6A}R^{6B}$, —$NHC(O)NR^{6C}NR^{6A}R^{6B}$, —$N(O)_{m6}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is independently hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —$NHC(O)NR^{7A}R^{7B}$, —$NR^{7C}NR^{7A}R^{7B}$, —$ONR^{7A}R^{7B}$, —$NHC(O)NR^{7C}NR^{7A}R^{7B}$, —$N(O)_{m7}$, —$NR^{7A}R^{7B}$, —$C(O)R^{7C}$, —$C(O)OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ is independently hydrogen, halogen, —$CX^8_3$, —$CHX^8_2$, —$CH_2X^8$, —$OCX^8_3$, —$OCH_2X^8$, —$OCHX^8_2$, —CN, —$SO_{n8}R^{8D}$, —$SO_{v8}NR^{8A}R^{8B}$, —$NHC(O)NR^{8A}R^{8B}$, —$NR^{8C}NR^{8A}R^{8B}$, —$ONR^{8A}R^{8B}$, —$NHC(O)NR^{8C}NR^{8A}R^{8B}$, —$N(O)_{m8}$, —$NR^{8A}R^{8B}$, —$C(O)R^{8C}$, —$C(O)OR^{8C}$, —$C(O)NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is independently hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9D}$, —$SO_{v9}NR^{9A}R^{9B}$, —$NHC(O)NR^{9A}R^{9B}$, —$NR^{9C}NR^{9A}R^{9B}$, —$ONR^{9A}R^{9B}$, —$NHC(O)NR^{9C}NR^{9A}R^{9B}$, —$N(O)_{m9}$, —$NR^{9A}R^{9B}$, —$C(O)R^{9C}$, —$C(O)OR^{9C}$, —$C(O)NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ is independently hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10D}$, —$SO_{v10}NR^{10A}R^{10B}$, —$NHC(O)NR^{10A}R^{10B}$, —$NR^{10C}NR^{10A}R^{10B}$, —$ONR^{10A}R^{10B}$, —$NHC(O)NR^{10C}NR^{10A}R^{10B}$, —$N(O)_{m10}$, —$NR^{10A}R^{10B}$, —$C(O)R^{10C}$, —$C(O)OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{11}$ is independently hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —CN, —$SO_{n11}R^{11D}$, —$SO_{v11}NR^{11A}R^{11B}$, —$NHC(O)NR^{11A}R^{11B}$, —$NR^{11C}NR^{11A}R^{11B}$, —$ONR^{11A}R^{11B}$, —$NHC(O)NR^{11C}NR^{11A}R^{11B}$, —$N(O)_{m11}$, —$NR^{11A}R^{11B}$, —$C(O)R^{11C}$, —$C(O)OR^{11C}$, —$C(O)NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{12}$ is independently hydrogen, halogen, —$CX^{12}_3$, —$CHX^{12}_2$, —$CH_2X^{12}$, —$OCX^{12}_3$, —$OCH_2X^{12}$, —$OCHX^{12}_2$, —CN, —$SO_{n12}R^{12D}$, —$SO_{v12}NR^{12A}R^{12B}$, —$NHC(O)NR^{12A}R^{12B}$, —$NR^{12C}NR^{12A}R^{12B}$, —$ONR^{12A}R^{12B}$, —$NHC(O)NR^{12C}NR^{12A}R^{12B}$, —$N(O)_{m12}$, —$NR^{12A}R^{12B}$, —$C(O)R^{12C}$, —$C(O)OR^{12C}$, —$C(O)NR^{12A}R^{12B}$, —$OR^{12D}$, —$NR^{12A}SO_2R^{12D}$, —$NR^{12A}C(O)R^{12C}$, —$NR^{12A}C(O)OR^{12C}$, —$NR^{12A}OR^{12C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{13}$ is independently hydrogen, halogen, —$CX^{13}_3$, —$CHX^{13}_2$, —$CH_2X^{13}$, —$OCX^{13}_3$, —$OCH_2X^{13}$, —$OCHX^{13}_2$, —CN, —$SO_{n13}R^{13D}$, —$SO_{v13}NR^{13A}R^{13B}$, —$NHC(O)NR^{13A}R^{13B}$, —$NR^{13C}NR^{13A}R^{13B}$, —$ONR^{13A}R^{13B}$, —$NHC(O)NR^{13C}NR^{13A}R^{13B}$, —$N(O)_{m13}$, —$NR^{13A}R^{13B}$, —$C(O)R^{13C}$, —$C(O)OR^{13C}$, —$C(O)NR^{13A}R^{13B}$, —$OR^{13D}$, —$NR^{13A}SO_2R^{13D}$, —$NR^{13A}C(O)R^{13C}$, —$NR^{13A}C(O)OR^{13C}$, —$NR^{13A}OR^{13C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{14}$ is independently hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —CN, —$SO_{n14}R^{14D}$, —$SO_{v14}NR^{14A}R^{14B}$, —$NHC(O)NR^{14A}R^{14B}$, —$NR^{14C}NR^{14A}R^{14B}$, —$ONR^{14A}R^{14B}$, —$NHC(O)NR^{14C}NR^{14A}R^{14B}$, —$N(O)_{m14}$, —$NR^{14A}R^{14B}$, —$C(O)R^{14C}$, —$C(O)OR^{14C}$, —$C(O)NR^{14A}R^{14B}$, —$OR^{14D}$, —$NR^{14A}SO_2R^{14D}$, —$NR^{14A}C(O)R^{14C}$, —$NR^{14A}C(O)OR^{14C}$, —$NR^{14A}OR^{14C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{15}$ is independently hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —CN, —$SO_{n15}R^{15D}$, —$SO_{v15}NR^{15A}R^{15B}$, —$NHC(O)NR^{15A}R^{15B}$, —$NR^{15C}NR^{15A}R^{15B}$, —$ONR^{15A}R^{15B}$, —$NHC(O)NR^{15C}NR^{15A}R^{15B}$, —$N(O)_{m15}$, —$NR^{15A}R^{15B}$, —$C(O)R^{15C}$, —$C(O)OR^{15C}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ and $R^7$ substituents may be joined to form a substituted or unsubstituted cycloalkyl, substituted or unsubstituted heterocycloalkyl, substituted or unsubstituted aryl, or substituted or unsubstituted heteroaryl.

$R^7$ and $R^8$ substituents may be joined to form a substituted or unsubstituted cycloalkyl, substituted or unsubstituted heterocycloalkyl, substituted or unsubstituted aryl, or substituted or unsubstituted heteroaryl.

$R^8$ and $R^9$ substituents may be joined to form a substituted or unsubstituted cycloalkyl, substituted or unsubstituted heterocycloalkyl, substituted or unsubstituted aryl, or substituted or unsubstituted heteroaryl.

$R^9$ and $R^{10}$ substituents may be joined to form a substituted or unsubstituted cycloalkyl, substituted or unsubstituted heterocycloalkyl, substituted or unsubstituted aryl, or substituted or unsubstituted heteroaryl.

$R^{11}$ and $R^{12}$ substituents may be joined to form a substituted or unsubstituted cycloalkyl, substituted or unsubstituted heterocycloalkyl, substituted or unsubstituted aryl, or substituted or unsubstituted heteroaryl.

$R^{12}$ and $R^{13}$ substituents may be joined to form a substituted or unsubstituted cycloalkyl, substituted or unsubstituted heterocycloalkyl, substituted or unsubstituted aryl, or substituted or unsubstituted heteroaryl.

$R^{13}$ and $R^{14}$ substituents may be joined to form a substituted or unsubstituted cycloalkyl, substituted or unsubstituted heterocycloalkyl, substituted or unsubstituted aryl, or substituted or unsubstituted heteroaryl.

$R^{14}$ and $R^{15}$ substituents may be joined to form a substituted or unsubstituted cycloalkyl, substituted or unsubstituted heterocycloalkyl, substituted or unsubstituted aryl, or substituted or unsubstituted heteroaryl.

$R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, and $R^{15D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{7A}$ and $R^{7B}$ substituents bonded to the same nitrogen atom may be joined to form a substituted or unsubstituted heterocycloalkyl or substituted or unsubstituted heteroaryl; $R^{8A}$ and $R^{8B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{10A}$ and $R^{10B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{12A}$ and $R^{12B}$ substituents bonded to the same nitrogen atom may be joined to form a substituted or unsubstituted heterocycloalkyl or substituted or unsubstituted heteroaryl; $R^{13A}$ and $R^{13B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl; $R^{15A}$ and $R^{15B}$ substituents bonded to the same nitrogen atom may be joined to form a substituted or unsubstituted heterocycloalkyl or substituted or unsubstituted heteroaryl.

The symbols n6, n7, n8, n9, n10, n11, n12, n13, n14, and n15 are independently an integer from 0 to 4.

The symbols m6, m7, m8, m9, m10, m11, m12, m13, m14, m15, v6, v7, v8, v9, v10, v11, v12, v13, v14, and v15 are independently 1 or 2.

$X^6$, $X^7$, $X^8$, $X^9$, $X^{10}$, $X^{11}$, $X^{12}$, $X^{13}$, $X^{14}$, and $X^{15}$ are independently —F, —Cl, —Br, or —I.

In embodiments, the compound has the formula (I)

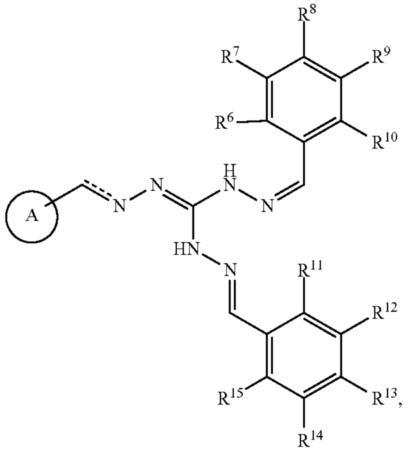

wherein Ring A, $R^6$, $R^7$, $R^8$, $R^9$, $R^{10}$, $R^{11}$, $R^{12}$, $R^{13}$, $R^{14}$, and $R^{15}$ are as described herein, including in embodiments; and ⋯ is a single bond or a double bond. In embodiments, the compound has the formula (II)

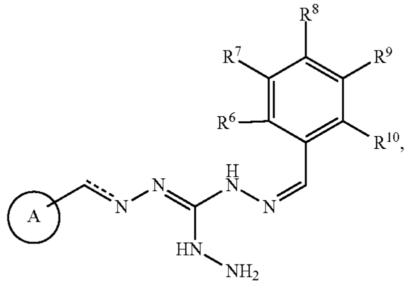

wherein Ring A, $R^6$, $R^7$, $R^8$, $R^9$, and $R^{10}$ are as described herein, including in embodiments; and  is a single bond or a double bond.

In embodiments, the compound has the formula:

(Ia)

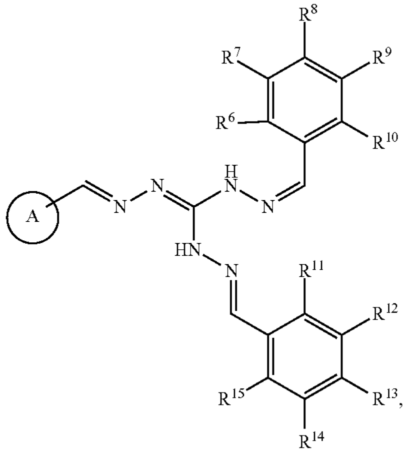

(Ib)

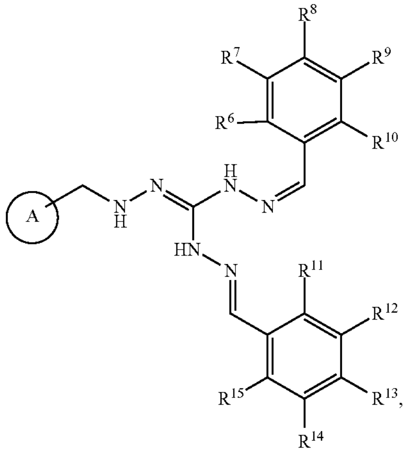

-continued (IIa)

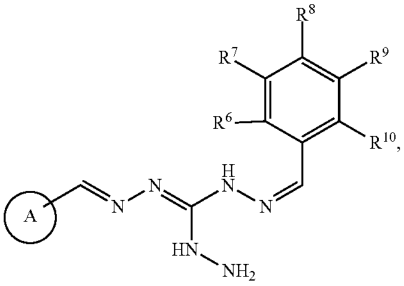

or (IIb)

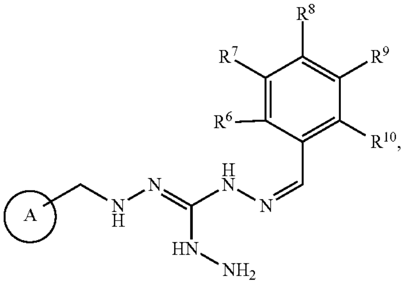

wherein Ring A, $R^6$, $R^7$, $R^8$, $R^9$, $R^{10}$, $R^{11}$, $R^{12}$, $R^{13}$, $R^{14}$, and $R^{15}$ are as described herein, including in embodiments. In embodiments, the compound has the formula (Ia)

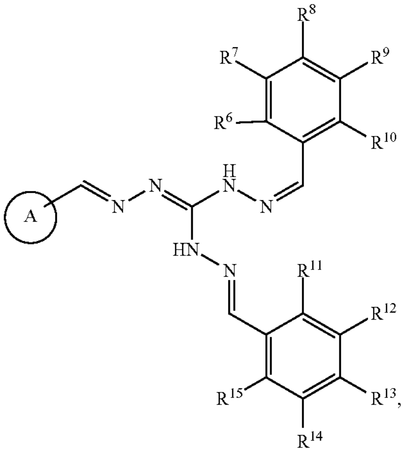

wherein Ring A, $R^6$, $R^7$, $R^8$, $R^9$, $R^{10}$, $R^{11}$, $R^{12}$, $R^{13}$, $R^{14}$, and $R^{15}$ are as described herein, including in embodiments. In embodiments, the compound has the formula:

(Ib)

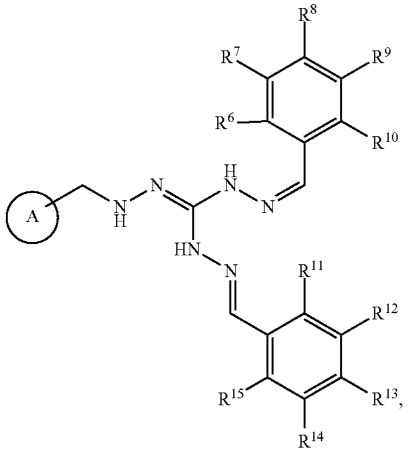

wherein Ring A, $R^6$, $R^7$, $R^8$, $R^9$, $R^{10}$, $R^{11}$, $R^{12}$, $R^{13}$, $R^{14}$, and $R^{15}$ are as described herein, including in embodiments. In embodiments, the compound has the formula:

(IIa)

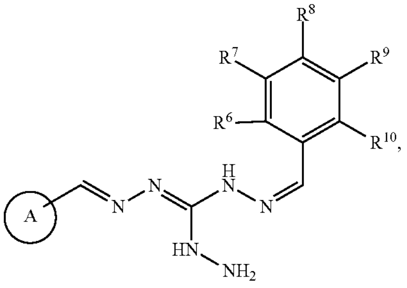

wherein Ring A, $R^6$, $R^7$, $R^8$, $R^9$, and $R^{10}$ are as described herein, including in embodiments. In embodiments, the compound has the formula (IIb)

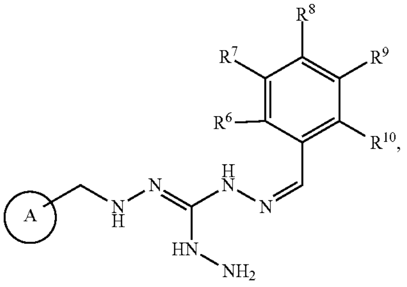

wherein Ring A, $R^6$, $R^7$, $R^8$, $R^9$, and $R^{10}$ are as described herein, including in embodiments.

In embodiments, the compound has the formula:

(Ic)

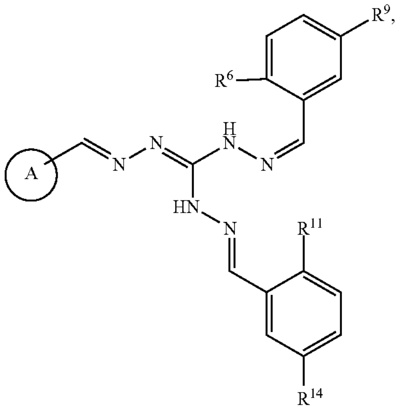

(Id)

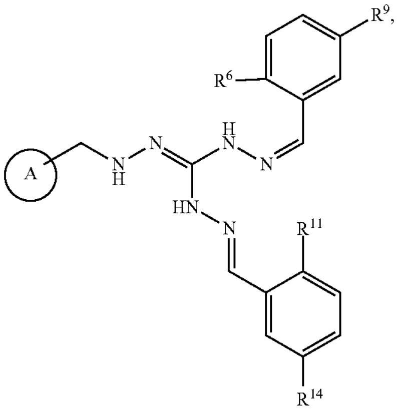

(IIc)

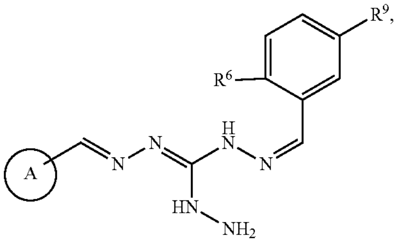

or (IId)

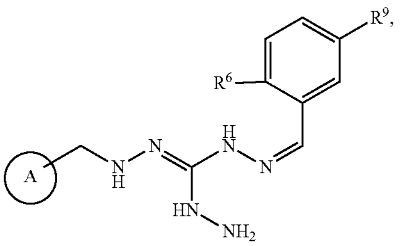

wherein Ring A, $R^6$, $R^9$, $R^{11}$, and $R^{14}$ are as described herein, including in embodiments. In embodiments, the compound has the formula (Ic)

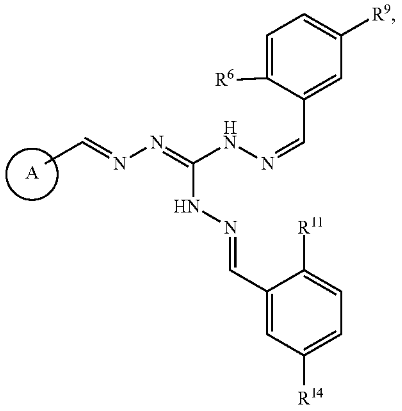

wherein Ring A, $R^6$, $R^9$, $R^{11}$, and $R^{14}$ are as described herein, including in embodiments. In embodiments, the compound has the formula:

(Id)

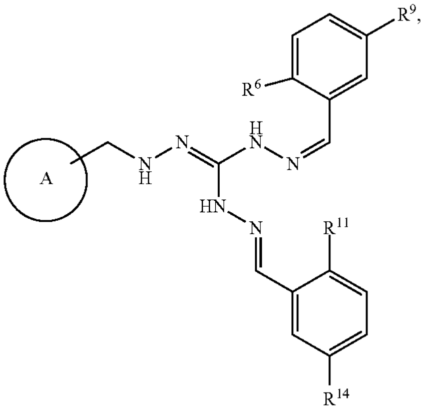

wherein Ring A, $R^6$, $R^9$, $R^{11}$, and $R^{14}$ are as described herein, including in embodiments. In embodiments, the compound has the formula:

(IIc)

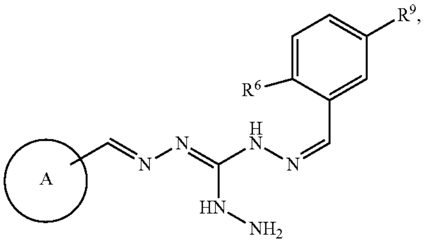

wherein Ring A, $R^6$, and $R^9$ are as described herein, including in embodiments. In embodiments, the compound has the formula (IId)

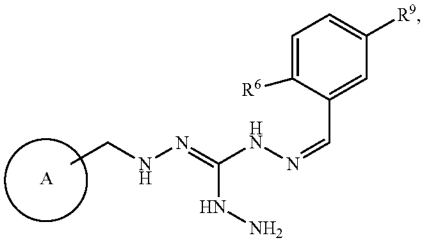

wherein Ring A, $R^6$, and $R^9$ are as described herein, including in embodiments. In embodiments, $R^6$, $R^9$, $R^{11}$, and $R^{14}$ are not hydrogen. In embodiments, $R^6$ and $R^9$ are not hydrogen.

In embodiments, the compound has the formula:

(III)

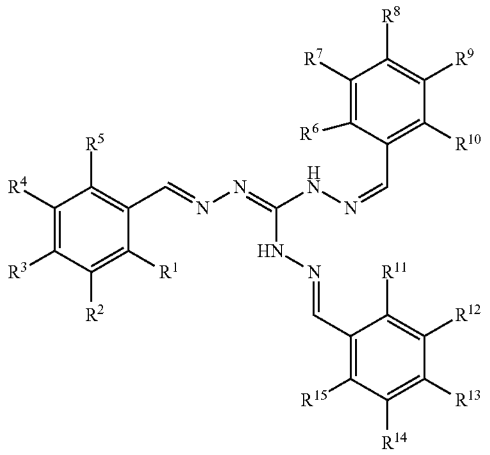

or (IV)

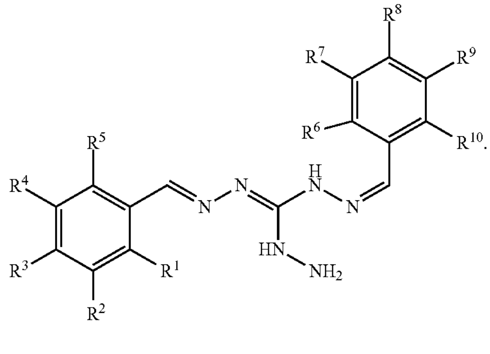

$R^6$, $R^7$, $R^8$, $R^9$, $R^{10}$, $R^{11}$, $R^{12}$, $R^{13}$, $R^{14}$, and $R^{15}$ are as described herein, including in embodiments.

$R^1$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NHC(O)NR^{1A}R^{1B}$, $—NR^{1C}NR^{1A}R^{1B}$, $—ONR^{1A}R^{1B}$, $—NHC(O)NR^{1C}NR^{1A}R^{1B}$, $—N(O)_{m1}$, $—NR^{1A}R^{1B}$, $—C(O)R^{1C}$, $—C(O)OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NHC(O)NR^{2A}R^{2B}$, $—NR^{2C}NR^{2A}R^{2B}$, $—ONR^{2A}R^{2B}$, $—NHC(O)NR^{2C}NR^{2A}R^{2B}$, $—N(O)_{m2}$, $—NR^{2A}R^{2B}$, $—C(O)R^{2C}$, $—C(O)OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NHC(O)NR^{3A}R^{3B}$, $—NR^3CNR^{3A}R^{3B}$, $—ONR^{3A}R^{3B}$, $—NHC(O)NR^3CNR^{3A}R^{3B}$, $—N(O)_{m3}$, $—NR^{3A}R^{3B}$, $—C(O)R^{3C}$, $—C(O)OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is independently hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{4D}$, $—SO_{v4}NR^{4A}R^{4B}$, $—NHC(O)NR^{4A}R^{4B}$, $—NR^4CNR^{4A}R^{4B}$, $—ONR^{4A}R^{4B}$, $—NHC(O)NR^4CNR^{4A}R^{4B}$, $—N(O)_{m4}$, $—NR^{4A}R^{4B}$, $—C(O)R^{4C}$, $—C(O)OR^{4C}$, $—C(O)NR^{4A}R^{4B}$, $—OR^{4D}$, $—NR^{4A}SO_2R^{4D}$, $—NR^{4A}C(O)R^{4C}$, $—NR^{4A}C(O)OR^{4C}$, $—NR^{4A}OR^{4C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is independently hydrogen, halogen, $—CX^5_3$, $—CHX^5_2$, $—CH_2X^5$, $—OCX^5_3$, $—OCH_2X^5$, $—OCHX^5_2$, —CN, $—SO_{n5}R^{5D}$, $—SO_{v5}NR^{5A}R^{5B}$, $—NHC(O)NR^{5A}R^{5B}$, $—NR^{5C}NR^{5A}R^{5B}$, $—ONR^{5A}R^{5B}$, $—NHC(O)NR^{5C}NR^{5A}R^{5B}$, $—N(O)_{m5}$, $—NR^{5A}R^{5B}$, $—C(O)R^{5C}$, $—C(O)OR^{5C}$, $—C(O)NR^{5A}R^{5B}$, $—OR^{5D}$, $—NR^{5A}SO_2R^{5D}$, $—NR^{5A}C(O)R^{5C}$, $—NR^{5A}C(O)OR^{5C}$, $—NR^{5A}OR^{5C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ and $R^2$ substituents may be joined to form a substituted or unsubstituted cycloalkyl, substituted or unsubstituted heterocycloalkyl, substituted or unsubstituted aryl, or substituted or unsubstituted heteroaryl.

$R^2$ and $R^3$ substituents may be joined to form a substituted or unsubstituted cycloalkyl, substituted or unsubstituted heterocycloalkyl, substituted or unsubstituted aryl, or substituted or unsubstituted heteroaryl.

$R^3$ and $R^4$ substituents may be joined to form a substituted or unsubstituted cycloalkyl, substituted or unsubstituted heterocycloalkyl, substituted or unsubstituted aryl, or substituted or unsubstituted heteroaryl.

$R^4$ and $R^5$ substituents may be joined to form a substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, and $R^{5D}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may be joined to form a substituted or unsubstituted heterocycloalkyl or substituted or unsubstituted heteroaryl; $R^{2A}$ and $R^{2B}$ substituents bonded to the same nitrogen atom may be joined to form a substituted or unsubstituted heterocycloalkyl or substituted or unsubstituted heteroaryl; $R^{3A}$ and $R^{3B}$ substituents bonded to the same nitrogen atom may be joined to form a substituted or unsubstituted heterocycloalkyl or substituted or unsubstituted heteroaryl; $R^{4A}$ and $R^{4B}$ substituents bonded to the same nitrogen atom may be joined to form a substituted or unsubstituted heterocycloalkyl or substituted or unsubstituted heteroaryl; $R^{5A}$ and $R^{5B}$ substituents bonded to the same nitrogen atom may be joined to form a substituted or unsubstituted heterocycloalkyl or substituted or unsubstituted heteroaryl.

The symbols n1, n2, n3, n4, and n5 are independently an integer from 0 to 4.

The symbols m1, m2, m3, m4, m5, v1, v2, v3, v4, and v5 are independently 1 or 2.

$X^1$, $X^2$, $X^3$, $X^4$, and $X^5$ are independently —F, —Cl, —Br, or —I.

In embodiments, the compound has the formula (III)

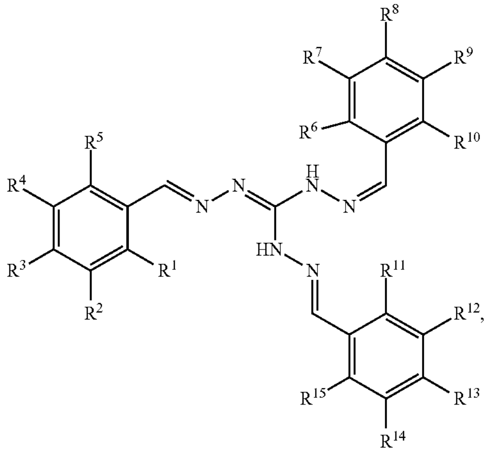

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as described herein, including in embodiments. In embodiments, the compound has the formula (IV)

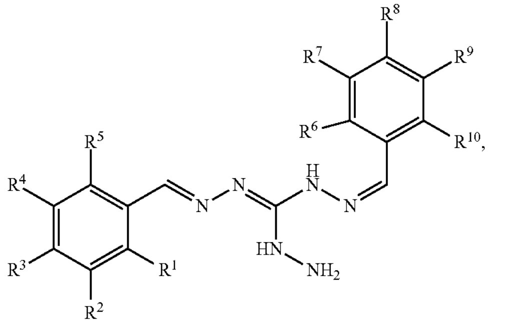

wherein $R^1$, $R^2$, $R^3$, $R^4$, $R^5$, $R^6$, $R^7$, $R^8$, $R^9$, and $R^{10}$ are as described herein, including in embodiments.

In embodiments, the compound has the formula:

(IIIa)

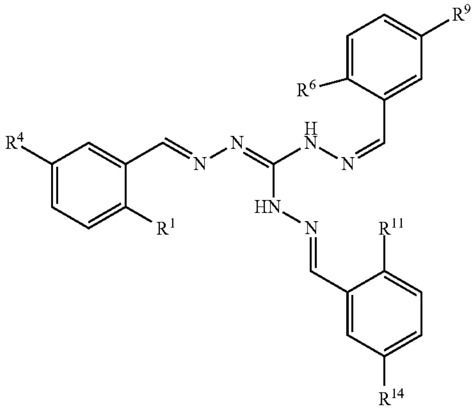

or (IVa)

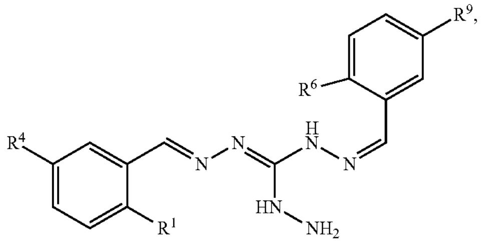

wherein $R^1$, $R^4$, $R^6$, $R^9$, $R^{11}$, and $R^{14}$ are as described herein, including in embodiments. In embodiments, the compound has the formula (IIIa)

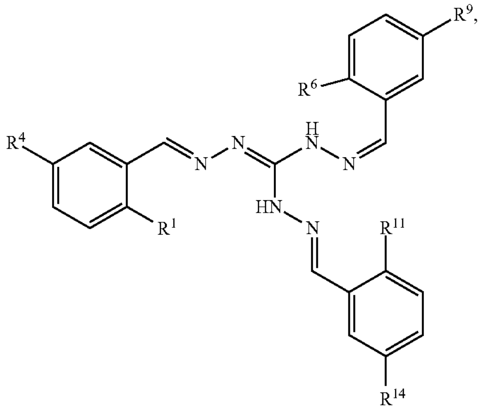

wherein $R^1$, $R^4$, $R^6$, $R^9$, $R^{11}$, and $R^{14}$ are as described herein, including in embodiments. In embodiments, the compound has the formula (IVa)

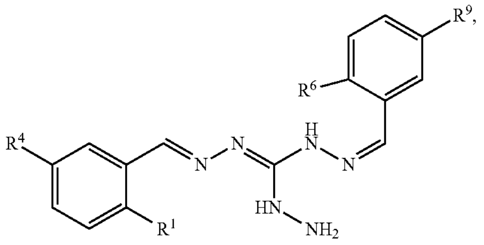

wherein $R^1$, $R^4$, $R^6$, and $R^9$ are as described herein, including in embodiments. In embodiments, $R^1$, $R^4$, $R^6$, $R^9$, $R^{11}$, and $R^{14}$ are not hydrogen. In embodiments, $R^1$, $R^4$, $R^6$, and $R^9$ are not hydrogen.

In embodiments, the compound has the formula (III)

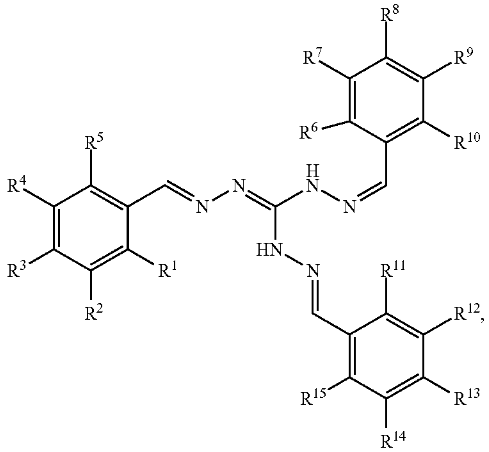

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as described herein, including in embodiments. In embodiments, the compound has the formula (IV)

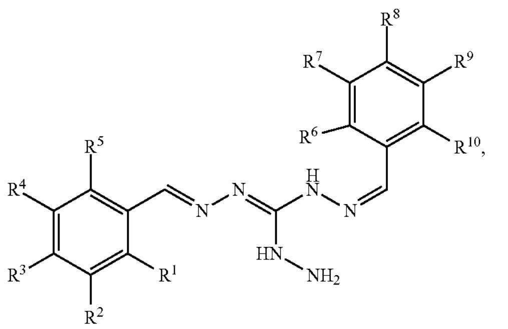

wherein $R^1$, $R^2$, $R^3$, $R^4$, $R^5$, $R^6$, $R^7$, $R^8$, $R^9$, and $R^{10}$ are as described herein, including in embodiments.

In embodiments, the compound has the formula:

(V)

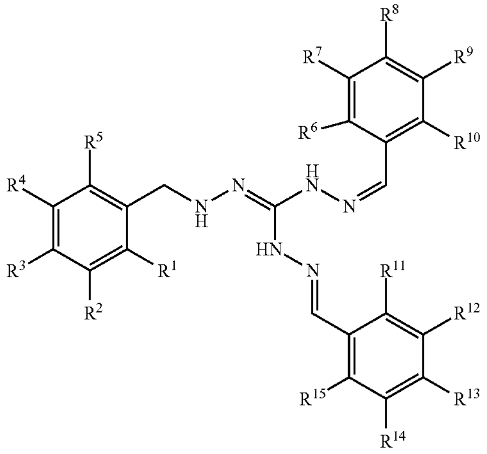

or (VI)

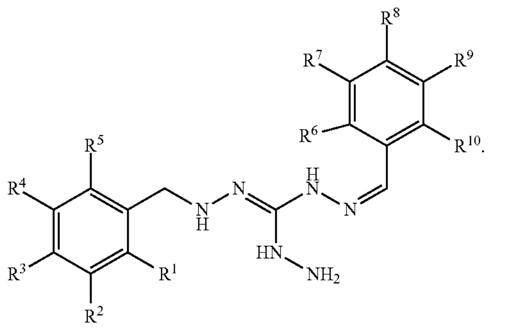

$R^6$, $R^7$, $R^8$, $R^9$, $R^{10}$, $R^{11}$, $R^{12}$, $R^{13}$, $R^{14}$, and $R^{15}$ are as described herein, including in embodiments. In embodiments, the compound has the formula (V)

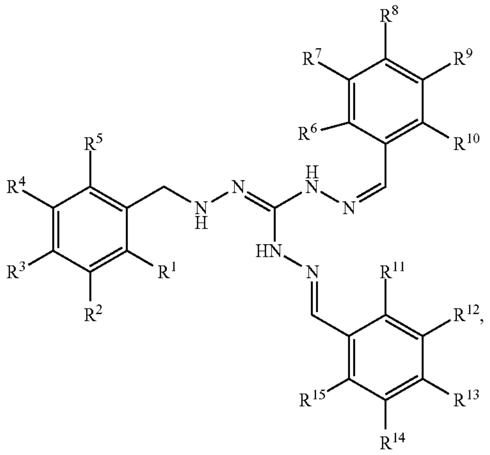

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as described herein, including in embodiments. In embodiments, the compound has the formula (VI)

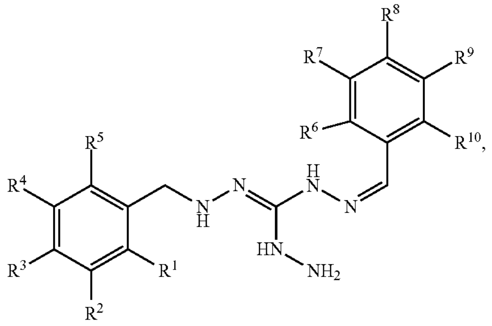

wherein $R^1$, $R^2$, $R^3$, $R^4$, $R^5$, $R^6$, $R^7$, $R^8$, $R^9$, and $R^{10}$ are as described herein, including in embodiments.

In an aspect is provided a compound, or a pharmaceutically acceptable salt thereof, having the formula:

(VII)

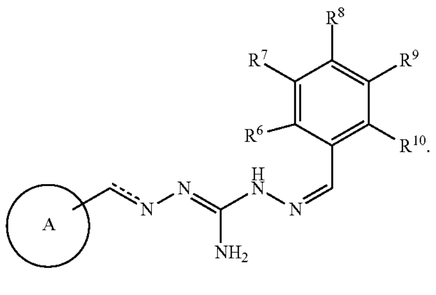

Ring A, $R^6$, $R^7$, $R^8$, $R^9$, and $R^{10}$ are as described herein, including in embodiments. is a single bond or a double bond.

In embodiments, the compound has the formula:

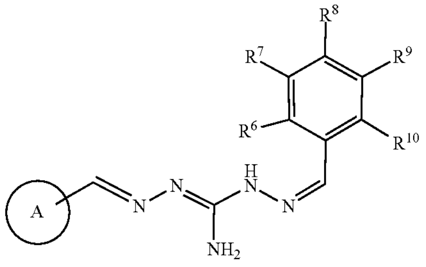

(VIIa), wherein Ring A, $R^6$, $R^7$, $R^8$, $R^9$, and $R^{10}$ are as described herein, including in embodiments. In embodiments, the compound has the formula (VIIb)

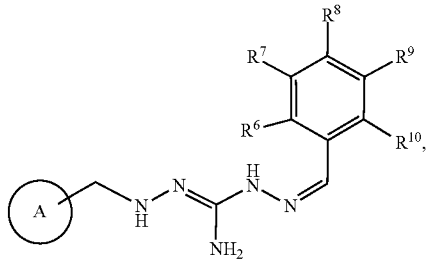

wherein Ring A, $R^6$, $R^7$, $R^8$, $R^9$, and $R^{10}$ are as described herein, including in embodiments.

In embodiments, the compound has the formula:

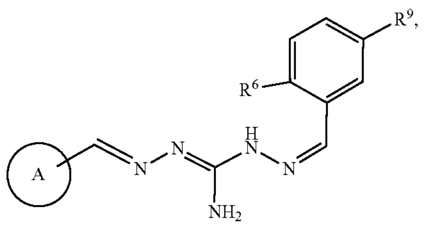

(VIIc), wherein Ring A, $R^6$, and $R^9$ are as described herein, including in embodiments. In embodiments, the compound has the formula (VIId)

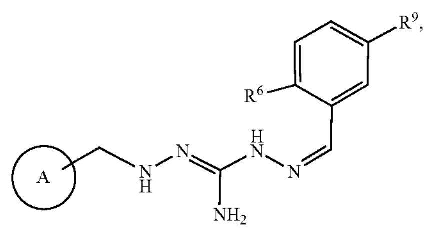

wherein Ring A, $R^6$, and $R^9$ are as described herein, including in embodiments. In embodiments, $R^6$ and $R^9$ are not hydrogen.

In embodiments, the compound has the formula:

(VIII)

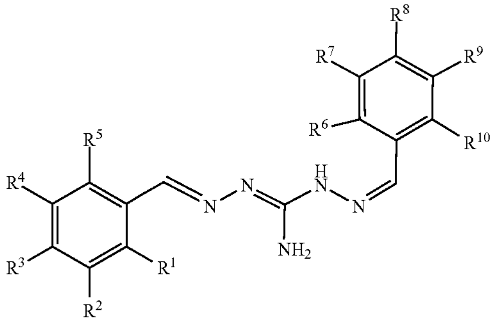

or (IX)

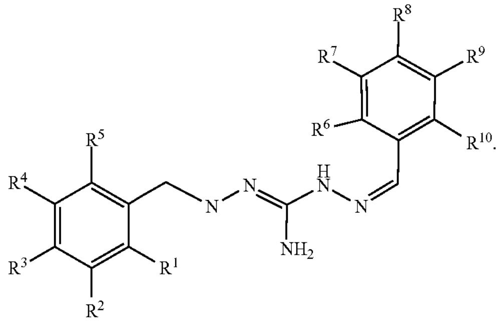

$R^1$, $R^2$, $R^3$, $R^4$, $R^5$, $R^6$, $R^7$, $R^8$, $R^9$, and $R^{10}$ are as described herein, including in embodiments. In embodiments, the compound has the formula:

(VIII)

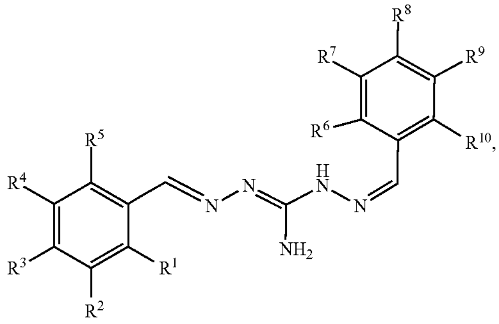

wherein $R^1$, $R^2$, $R^3$, $R^4$, $R^5$, $R^6$, $R^7$, $R^8$, $R^9$, and $R^{10}$ are as described herein, including in embodiments. In embodiments, the compound has the formula:

(IX)

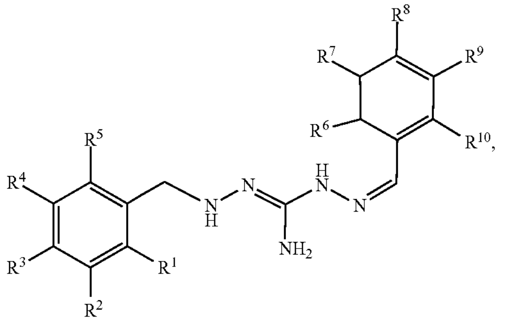

wherein $R^1$, $R^2$, $R^3$, $R^4$, $R^5$, $R^6$, $R^7$, $R^8$, $R^9$, and $R^{10}$ are as described herein, including in embodiments.

In embodiments, the compound has the formula:

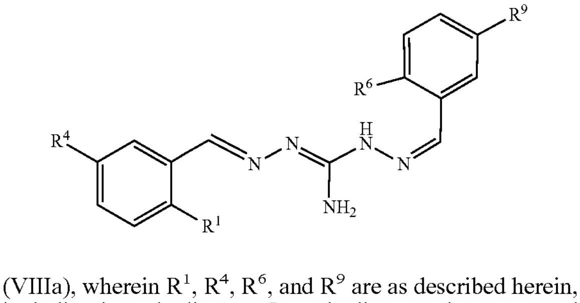

(VIIIa), wherein $R^1$, $R^4$, $R^6$, and $R^9$ are as described herein, including in embodiments. In embodiments, the compound has the formula:

(IXa)

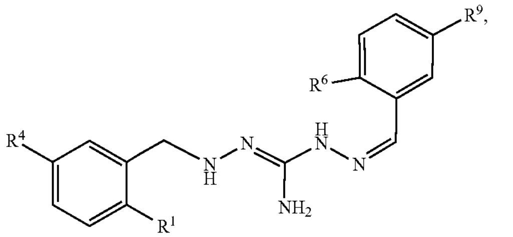

wherein $R^1$, $R^4$, $R^6$, and $R^9$ are as described herein, including in embodiments. In embodiments, $R^1$, $R^4$, $R^6$, and $R^9$ are not hydrogen.

In embodiments, Ring A is a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted Ring A (e.g., substituted cycloalkyl, substituted heterocycloalkyl, substituted aryl, and/or substituted heteroaryl) is substituted with at least one substituent group, size-limited substituent group, or lower substituent group; wherein if the substituted Ring A is substituted with a plurality of groups selected from substituent groups, size-limited substituent groups, and lower substituent groups; each substituent group, size-limited substituent group, and/or lower substituent group may optionally be different. In embodiments, when Ring A is substituted, it is substituted with at least one substituent group. In embodiments, when Ring A is substituted, it is substituted with at least one size-limited substituent group. In embodiments, when Ring A is substituted, it is substituted with at least one lower substituent group.

In embodiments, Ring A is an $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

$R^{20}$ is independently oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-SF_5$, $-N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{20}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{20}$ is substituted with a plurality of groups selected from substituent groups, size-limited substituent groups, and lower substituent groups; each substituent group, size-limited substituent group, and/or lower substituent group may optionally be different. In embodiments, when $R^{20}$ is substituted, it is substituted with at least one substituent group. In embodiments, when $R^{20}$ is substituted, it is substituted with at least one size-limited substituent group. In embodiments, when $R^{20}$ is substituted, it is substituted with at least one lower substituent group.

In embodiments, $R^{20}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$SF_5$, —$N_3$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{10}$ or phenyl), or $R^{21}$-substituted or unsubstituted heteroaryl (e.g., 5 to 10 membered, 5 to 9 membered, or 5 to 6 membered).

$R^{21}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$SF_5$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or or unsubstituted heteroaryl (e.g., 5 to 10 membered, 5 to 9 membered, or 5 to 6 membered).

In embodiments, Ring A is a substituted or unsubstituted cycloalkyl. In embodiments, Ring A is a substituted or unsubstituted $C_3$-$C_6$ cycloalkyl. In embodiments, Ring A is a substituted $C_3$-$C_6$ cycloalkyl. In embodiments, Ring A is an $R^{20}$-substituted $C_3$-$C_6$cycloalkyl. In embodiments, Ring A is an unsubstituted $C_3$-$C_6$ cycloalkyl. $R^{20}$ is as described herein, including in embodiments.

In embodiments, Ring A is a substituted or unsubstituted heterocycloalkyl. In embodiments, Ring A is a substituted or unsubstituted 3 to 6 membered heterocycloalkyl. In embodiments, Ring A is a substituted 3 to 6 membered heterocycloalkyl. In embodiments, Ring A is an $R^{20}$— substituted 3 to 6 membered heterocycloalkyl. In embodiments, Ring A is an unsubstituted 3 to 6 membered heterocycloalkyl. In embodiments, Ring A is an $R^{20}$-substituted 5 membered heterocycloalkyl. In embodiments, Ring A is an unsubstituted 5 membered heterocycloalkyl. In embodiments, Ring A is an $R^{20}$-substituted 6 membered heterocycloalkyl. In embodiments, Ring A is an unsubstituted 6 membered heterocycloalkyl.

In embodiments, Ring A is

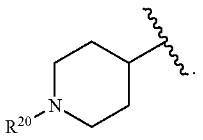

$R^{20}$ is as described herein, including in embodiments. In embodiments, Ring A is

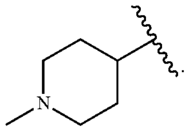 [SMILES: *C1CCN(C)CC1]

In embodiments, $R^{20}$ is independently a substituted or unsubstituted $C_1$-$C_4$ alkyl. In embodiments, $R^{20}$ is independently an $R^{21}$-substituted or unsubstituted $C_1$-$C_4$ alkyl, wherein $R^{21}$ is as described herein, including in embodiments. In embodiments, $R^{20}$ is independently an unsubstituted $C_1$-$C_4$ alkyl. In embodiments, $R^{20}$ is independently an unsubstituted methyl. In embodiments, $R^{20}$ is independently an unsubstituted ethyl. In embodiments, $R^{20}$ is independently an unsubstituted propyl. In embodiments, $R^{20}$ is independently an unsubstituted n-propyl. In embodiments, $R^{20}$ is independently an unsubstituted isopropyl. In embodiments, $R^{20}$ is independently an unsubstituted butyl. In embodiments, $R^{20}$ is independently an unsubstituted n-butyl. In embodiments, $R^{20}$ is independently an unsubstituted tert-butyl.

In embodiments, ⋯ is a single bond. In embodiments, ⋯ is a double bond.

In embodiments, $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC (O)$NR^{1A}R^{1B}$, —$NR^{1C}NR^{1A}R^{1B}$, —$ONR^{1A}R^{1B}$, —NHC(O) $NR^{1C}NR^{1A}R^{1B}$, —$N(O)_{m1}$, —$NR^{1A}R^{1B}$, —C(O)$R^{1C}$, —C(O)$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{1A}$, $R^{1B}$, $R^{1C}$, and $R^{1D}$ are as described herein, including in embodiments. $X^1$ is independently —F, —Cl, —Br, or —I. The symbol n1 is independently an integer from 0 to 4. The symbols m1 and v1 are independently 1 or 2.

In embodiments, $R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, $R^{1A}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1A}$ is substituted with a plurality of groups selected from substituent groups, size-limited substituent groups, and lower substituent groups; each substituent group, size-limited substituent group, and/or lower substituent group may optionally be different. In embodiments, when $R^{1A}$ is substituted, it is substituted with at least one substituent group. In embodiments, when $R^{1A}$ is substituted, it is substituted with at least one size-limited substituent group. In embodiments, when $R^{1A}$ is substituted, it is substituted with at least one lower substituent group.

In embodiments, $R^{1B}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, it is substituted with at least one substituent group. In embodiments, when $R^{1B}$ is substituted, it is substituted with at least one size-limited substituent group. In embodiments, when $R^{1B}$ is substituted, it is substituted with at least one lower substituent group.

In embodiments, $R^{1A}$ and $R^{1B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{1A}$ and $R^{1B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{1A}$ and $R^{1B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{1A}$ and $R^{1B}$ substituents bonded to the same nitrogen atom is substituted, it is substituted with at least one substituent group. In embodiments, when the moiety formed by joining $R^{1A}$ and $R^{1B}$ substituents bonded to the same nitrogen atom is substituted, it is substituted with at least one size-limited substituent group. In embodiments, when the moiety formed by joining $R^{1A}$ and $R^{1B}$ substituents bonded to the same nitrogen atom is substituted, it is substituted with at least one lower substituent group.

In embodiments, $R^{1C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{1C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1C}$ is substituted with a plurality of groups selected from substituent groups, size-limited substituent groups, and lower substituent groups; each substituent group, size-limited substituent group, and/or lower substituent group may optionally be different. In embodiments, when $R^{1C}$ is substituted, it is substituted with at least one substituent group. In embodiments, when $R^{1C}$ is substituted, it is substituted with at least one size-limited substituent group. In embodiments, when $R^{1C}$ is substituted, it is substituted with at least one lower substituent group.

In embodiments, $R^{1D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{1D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1D}$ is substituted with a plurality of groups selected from substituent groups, size-limited substituent groups, and lower substituent groups; each substituent group, size-limited substituent group, and/or lower substituent group may optionally be different. In embodiments, when $R^{1D}$ is substituted, it is substituted with at least one substituent group. In embodiments, when $R^{1D}$ is substituted, it is substituted with at least one size-limited substituent group. In embodiments, when $R^{1D}$ is substituted, it is substituted with at least one lower substituent group.

In embodiments, $R^1$ is independently hydrogen. In embodiments, $R^1$ is independently halogen. In embodiments, $R^1$ is independently $-F$. In embodiments, $R^1$ is independently $-Cl$. In embodiments, $R^1$ is independently $-Br$. In embodiments, $R^1$ is independently $-I$. In embodiments, $R^1$ is independently $-OH$.

In embodiments, $R^1$ is independently $-OR^{1D}$. In embodiments, $R^{1D}$ is independently hydrogen. In embodiments, $R^{1D}$ is independently unsubstituted $C_1$-$C_4$ alkyl. In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted n-propyl.

In embodiments, $R^{1D}$ is independently unsubstituted isopropyl. In embodiments, $R^{1D}$ is independently unsubstituted butyl. In embodiments, $R^{1D}$ is independently unsubstituted n-butyl. In embodiments, $R^{1D}$ is independently unsubstituted tert-butyl. In embodiments, $R^{1D}$ is independently substituted or unsubstituted aryl. In embodiments, $R^{1D}$ is independently substituted or unsubstituted phenyl.

In embodiments, $R^2$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NHC(O)NR^{2A}R^{2B}$, $—NR^{2C}NR^{2A}R^{2B}$, $—ONR^{2A}R^{2B}$, $—NHC(O)NR^{2C}NR^{2A}R^{2B}$, $—N(O)_{m2}$, $—NR^{2A}R^{2B}$, $—C(O)R^{2C}$, $—C(O)OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{2A}$, $R^{2B}$, $R^{2C}$, and $R^{2D}$ are as described herein, including in embodiments. $X^2$ is independently —F, —Cl, —Br, or —I. The symbol n2 is independently an integer from 0 to 4. The symbols m2 and v2 are independently 1 or 2.

In embodiments, $R^2$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^{2A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{2A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^{2A}$ is substituted, it is substituted with at least one substituent group. In embodiments, when $R^{2A}$ is substituted, it is substituted with at least one size-limited substituent group. In embodiments, when $R^{2A}$ is substituted, it is substituted with at least one lower substituent group.

In embodiments, $R^{2B}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{2B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2B}$ is substituted with a plurality of groups selected from substituent groups, size-limited substituent groups, and lower substituent groups; each substituent group, size-limited substituent group, and/or lower substituent group may optionally be different. In embodiments, when $R^{2B}$ is substituted, it is substituted with at least one substituent group. In embodiments, when $R^{2B}$ is substituted, it is substituted with at least one size-limited substituent group. In embodiments, when $R^{2B}$ is substituted, it is substituted with at least one lower substituent group.

In embodiments, $R^{2A}$ and $R^{2B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{2A}$ and $R^{2B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{2A}$ and $R^{2B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{2A}$ and $R^{2B}$ substituents bonded to the same nitrogen atom is substituted, it is substituted with at least one substituent group. In embodiments, when the moiety formed by joining $R^{2A}$ and $R^{2B}$ substituents bonded to the same nitrogen atom is substituted, it is substituted with at least one size-limited substituent group. In embodiments, when the moiety formed by joining $R^{2A}$ and $R^{2B}$ substituents bonded to the same nitrogen atom is substituted, it is substituted with at least one lower substituent group.

In embodiments, $R^{2C}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{2C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2C}$ is substituted with a plurality of groups selected from substituent groups, size-limited substituent groups, and lower substituent groups; each substituent group, size-limited substituent group, and/or lower substituent group may optionally be different. In embodiments, when $R^{2C}$ is substituted, it is substituted with at least one substituent group. In embodiments, when $R^{2C}$ is substituted, it is substituted with at least one size-limited substituent group. In embodiments, when $R^{2C}$ is substituted, it is substituted with at least one lower substituent group.

In embodiments, $R^{2D}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{2D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2D}$ is substituted with a plurality of groups selected from substituent groups, size-limited substituent groups, and lower substituent groups; each substituent group, size-limited substituent group, and/or lower substituent group may optionally be different. In embodiments, when $R^{2D}$ is substituted, it is substituted with at least one substituent group. In embodiments, when $R^{2D}$ is substituted, it is substituted with at least one size-limited substituent group. In embodiments, when $R^{2D}$ is substituted, it is substituted with at least one lower substituent group.

In embodiments, $R^2$ is independently hydrogen. In embodiments, $R^2$ is independently halogen. In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently —OH.

In embodiments, $R^2$ is independently $—OR^{2D}$. In embodiments, $R^{2D}$ is independently hydrogen. In embodiments, $R^{2D}$ is independently unsubstituted $C_1$-$C_4$ alkyl. In embodiments, $R^{2D}$ is independently unsubstituted methyl. In embodiments, $R^{2D}$ is independently unsubstituted ethyl. In embodiments, $R^{2D}$ is independently unsubstituted propyl. In embodiments, $R^{2D}$ is independently unsubstituted n-propyl. In embodiments, $R^{2D}$ is independently unsubstituted isopropyl. In embodiments, $R^{2D}$ is independently unsubstituted butyl. In embodiments, $R^{2D}$ is independently unsubstituted n-butyl. In embodiments, $R^{2D}$ is independently unsubstituted tert-butyl. In embodiments, $R^{2D}$ is independently substituted or unsubstituted aryl. In embodiments, $R^{2D}$ is independently substituted or unsubstituted phenyl.

In embodiments, $R^3$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NHC(O)NR^{3A}R^{3B}$, $—NR^{3C}NR^{3A}R^{3B}$, $—ONR^{3A}R^{3B}$, $—NHC(O)NR^{3C}NR^{3A}R^{3B}$, $—N(O)_{m3}$, $—NR^{3A}R^{3B}$, $—C(O)R^{3C}$, $—C(O)OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{3A}$, $R^{3B}$, $R^{3C}$, and $R^{3D}$ are as described herein, including in embodiments. $X^3$ is independently —F, —Cl, —Br, or —I. The symbol n3 is independently an integer from 0 to 4. The symbols m3 and v3 are independently 1 or 2.

In embodiments, $R^3$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^{3A}$ is independently hydrogen, halogen, $—CCl_3$, $—CBr_3$, $—CF_3$, $—CI_3$, $—CH_2Cl$, $—CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{3A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3A}$ is substituted with a plurality of groups selected from substituent groups, size-limited substituent groups, and lower substituent groups; each substituent group, size-limited substituent group, and/or lower substituent group may optionally be different. In embodiments, when $R^{3A}$ is substituted, it is substituted with at least one substituent group. In embodiments, when $R^{3A}$ is substituted, it is substituted with at least one size-limited substituent group. In embodiments, when $R^{3A}$ is substituted, it is substituted with at least one lower substituent group.

In embodiments, $R^{3B}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{3B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3B}$ is substituted with a plurality of groups selected from substituent groups, size-limited substituent groups, and lower substituent groups; each substituent group, size-limited substituent group, and/or lower substituent group may optionally be different. In embodiments, when $R^{3B}$ is substituted, it is substituted with at least one substituent group. In embodiments, when $R^{3B}$ is substituted, it is substituted with at least one size-limited substituent group. In embodiments, when $R^{3B}$ is substituted, it is substituted with at least one lower substituent group.

In embodiments, $R^{3A}$ and $R^{3B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{3A}$ and $R^{3B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{3A}$ and $R^{3B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{3A}$ and $R^{3B}$ substituents bonded to the same nitrogen atom is substituted, it is substituted with at least one substituent group. In embodiments, when the moiety formed by joining $R^{3A}$ and $R^{3B}$ substituents bonded to the same nitrogen atom is substituted, it is substituted with at least one size-limited substituent group. In embodiments, when the moiety formed by joining $R^{3A}$ and $R^{3B}$ substituents bonded to the same nitrogen atom is substituted, it is substituted with at least one lower substituent group.

In embodiments, $R^{3C}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{3C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3C}$ is substituted with a plurality of groups selected from substituent groups, size-limited substituent groups, and lower substituent groups; each substituent group, size-limited substituent group, and/or lower substituent group may optionally be different. In embodiments, when $R^{3C}$ is substituted, it is substituted with at least one substituent group. In embodiments, when $R^{3C}$ is substituted, it is substituted with at least one size-limited substituent group. In embodiments, when $R^{3C}$ is substituted, it is substituted with at least one lower substituent group.

In embodiments, $R^{3D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHOH, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{3D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3D}$ is substituted with a plurality of groups selected from substituent groups, size-limited substituent groups, and lower substituent groups; each substituent group, size-limited substituent group, and/or lower substituent group may optionally be different. In embodiments, when $R^{3D}$ is substituted, it is substituted with at least one substituent group. In embodiments, when $R^{3D}$ is substituted, it is substituted with at least one size-limited substituent group. In embodiments, when $R^{3D}$ is substituted, it is substituted with at least one lower substituent group.

In embodiments, $R^3$ is independently hydrogen. In embodiments, $R^3$ is independently halogen. In embodiments, $R^3$ is independently —F. In embodiments, $R^3$ is independently —Cl. In embodiments, $R^3$ is independently —Br. In embodiments, $R^3$ is independently —I. In embodiments, $R^3$ is independently —OH.

In embodiments, $R^3$ is independently $-OR^{3D}$. In embodiments, $R^{3D}$ is independently hydrogen. In embodiments, $R^{3D}$ is independently unsubstituted $C_1$-$C_4$ alkyl. In embodiments, $R^{3D}$ is independently unsubstituted methyl. In embodiments, $R^{3D}$ is independently unsubstituted ethyl. In embodiments, $R^{3D}$ is independently unsubstituted propyl. In embodiments, $R^{3D}$ is independently unsubstituted n-propyl. In embodiments, $R^{3D}$ is independently unsubstituted isopropyl. In embodiments, $R^{3D}$ is independently unsubstituted butyl. In embodiments, $R^{3D}$ is independently unsubstituted n-butyl. In embodiments, $R^{3D}$ is independently unsubstituted tert-butyl. In embodiments, $R^{3D}$ is independently substituted or unsubstituted aryl. In embodiments, $R^{3D}$ is independently substituted or unsubstituted phenyl.

In embodiments, $R^4$ is independently hydrogen, halogen, $-CX^4_3$, $-CHX^4_2$, $-CH_2X^4$, $-OCX^4_3$, $-OCH_2X^4$, $-OCHX^4_2$, —CN, $-SO_{n4}R^{4D}$, $-SO_{v4}NR^{4A}R^{4B}$, $-NHC(O)NR^{4A}R^{4B}$, $-NR^{4C}NR^{4A}R^{4B}$, $-ONR^{4A}R^{4B}$, $-NHC(O)NR^{4C}NR^{4A}R^{4B}$, $-N(O)_{m4}$, $-NR^{4A}R^{4B}$, $-C(O)R^{4C}$, $-C(O)OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, $-SF_5$, $-N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{4A}$, $R^{4B}$, $R^{4C}$, and $R^{4D}$ are as described herein, including in embodiments. $X^4$ is independently —F, —Cl, —Br, or —I. The symbol n4 is independently an integer from 0 to 4. The symbols m4 and v4 are independently 1 or 2.

In embodiments, $R^4$ is independently hydrogen, halogen, $-CCl_3$, $-CBr_3$, $-CF_3$, $-CI_3$, $-CHCl_2$, $-CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^{4A}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{4A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4A}$ is substituted with a plurality of groups selected from substituent groups, size-limited substituent groups, and lower substituent groups; each substituent group, size-limited substituent group, and/or lower substituent group may optionally be different. In embodiments, when $R^{4A}$ is substituted, it is substituted with at least one substituent group. In embodiments, when $R^{4A}$ is substituted, it is substituted with at least one size-limited substituent group. In embodiments, when $R^{4A}$ is substituted, it is substituted with at least one lower substituent group.

In embodiments, $R^{4B}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{4B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4B}$ is substituted with a plurality of groups selected from substituent groups, size-limited substituent groups, and lower substituent groups; each substituent group, size-limited substituent group, and/or lower substituent group may optionally be different. In embodiments, when $R^{4B}$ is substituted, it is substituted with at least one substituent group. In embodiments, when $R^{4B}$ is substituted, it is substituted with at least one size-limited substituent group. In embodiments, when $R^{4B}$ is substituted, it is substituted with at least one lower substituent group.

In embodiments, $R^{4A}$ and $R^{4B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{4A}$ and $R^{4B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{4A}$ and $R^{4B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{4A}$ and $R^{4B}$ substituents bonded to the same nitrogen atom is substituted, it is substituted with at least one substituent group. In embodiments, when the moiety formed by joining $R^{4A}$ and $R^{4B}$ substituents bonded to the same nitrogen atom is substituted, it is substituted with at least one size-limited substituent group. In embodiments, when the moiety formed by joining $R^{4A}$ and $R^{4B}$ substituents bonded to the same nitrogen atom is substituted, it is substituted with at least one lower substituent group.

In embodiments, $R^{4C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{4C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4C}$ is substituted with a plurality of groups selected from substituent groups, size-limited substituent groups, and lower substituent groups; each substituent group, size-limited substituent group, and/or lower substituent group may optionally be different. In embodiments, when $R^{4C}$ is substituted, it is substituted with at least one substituent group. In embodiments, when $R^{4C}$ is substituted, it is substituted with at least one size-limited substituent group. In embodiments, when $R^{4C}$ is substituted, it is substituted with at least one lower substituent group.

In embodiments, $R^{4D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{4D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4D}$ is substituted with a plurality of groups selected from substituent groups, size-limited substituent groups, and lower substituent groups; each substituent group, size-limited substituent group, and/or lower substituent group may optionally be different. In embodiments, when $R^{4D}$ is substituted, it is substituted with at least one substituent group. In embodiments, when $R^{4D}$ is substituted, it is substituted with at least one size-limited substituent group. In embodiments, when $R^{4D}$ is substituted, it is substituted with at least one lower substituent group.

In embodiments, $R^4$ is independently hydrogen. In embodiments, $R^4$ is independently halogen. In embodiments, $R^4$ is independently $-F$. In embodiments, $R^4$ is independently $-Cl$. In embodiments, $R^4$ is independently $-Br$. In embodiments, $R^4$ is independently $-I$. In embodiments, $R^4$ is independently $-OH$.

In embodiments, $R^4$ is independently $-OR^{4D}$. In embodiments, $R^{4D}$ is independently hydrogen. In embodiments, $R^{4D}$ is independently unsubstituted $C_1$-$C_4$ alkyl. In embodiments, $R^{4D}$ is independently unsubstituted methyl. In embodiments, $R^{4D}$ is independently unsubstituted ethyl. In embodiments, $R^{4D}$ is independently unsubstituted propyl. In embodiments, $R^{4D}$ is independently unsubstituted n-propyl. In embodiments, $R^{4D}$ is independently unsubstituted isopropyl. In embodiments, $R^{4D}$ is independently unsubstituted butyl. In embodiments, $R^{4D}$ is independently unsubstituted n-butyl. In embodiments, $R^{4D}$ is independently unsubstituted tert-butyl. In embodiments, $R^{4D}$ is independently substituted or unsubstituted aryl. In embodiments, $R^{4D}$ is independently substituted or unsubstituted phenyl.

In embodiments, $R^5$ is independently hydrogen, halogen, $—CX^5_3$, $—CHX^5_2$, $—CH_2X^5$, $—OCX^5_3$, $—OCH_2X^5$, $—OCHX^5_2$, —CN, $—SO_{n5}R^{5D}$, $—SO_{v5}NR^{5A}R^{5B}$, $—NHC(O)NR^{5A}R^{5B}$, $—NR^{5C}NR^{5A}R^{5B}$, $—ONR^{5A}R^{5B}$, $—NHC(O)NR^{5C}NR^{5A}R^{5B}$, $—N(O)_{m5}$, $—NR^{5A}R^{5B}$, $—C(O)R^{5C}$, $—C(O)OR^{5C}$, $—C(O)NR^{5A}R^{5B}$, $—OR^{5D}$, $—NR^{5A}SO_2R^{5D}$, $—NR^{5A}C(O)R^{5C}$, $—NR^{5A}C(O)OR^{5C}$, $—NR^{5A}OR^{5C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{5A}$, $R^{5B}$, $R^{5C}$, and $R^{5D}$ are as described herein, including in embodiments. $X^5$ is independently —F, —Cl, —Br, or —I. The symbol n5 is independently an integer from 0 to 4. The symbols m5 and v5 are independently 1 or 2.

In embodiments, $R^5$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^{5A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{5A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5A}$ is substituted with a plurality of groups selected from substituent groups, size-limited substituent groups, and lower substituent groups; each substituent group, size-limited substituent group, and/or lower substituent group may optionally be different. In embodiments, when $R^{5A}$ is substituted, it is substituted with at least one substituent group. In embodiments, when $R^{5A}$ is substituted, it is substituted with at least one size-limited substituent group. In embodiments, when $R^{5A}$ is substituted, it is substituted with at least one lower substituent group.

In embodiments, $R^{5B}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{5B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5B}$ is substituted with a plurality of groups selected from substituent groups, size-limited substituent groups, and lower substituent groups; each substituent group, size-limited substituent group, and/or lower substituent group may optionally be different. In embodiments, when $R^{5B}$ is substituted, it is substituted with at least one substituent group. In embodiments, when $R^{5B}$ is substituted, it is substituted with at least one size-limited substituent group. In embodiments, when $R^{5B}$ is substituted, it is substituted with at least one lower substituent group.

In embodiments, $R^{5A}$ and $R^{5B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{5A}$ and $R^{5B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{5A}$ and $R^{5B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{5A}$ and $R^{5B}$ substituents bonded to the same nitrogen atom is substituted, it is substituted with at least one substituent group. In embodiments, when the moiety formed by joining $R^{5A}$ and $R^{5B}$ substituents bonded to the same nitrogen atom is substituted, it is substituted with at least one size-limited substituent group. In embodiments, when the moiety formed by joining $R^{5A}$ and $R^{5B}$ substituents bonded to the same nitrogen atom is substituted, it is substituted with at least one lower substituent group.

In embodiments, $R^{5C}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{5C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5C}$ is substituted with a plurality of groups selected from substituent groups, size-limited substituent groups, and lower substituent groups; each substituent group, size-limited substituent group, and/or lower substituent group may optionally be different. In embodiments, when $R^{5C}$ is substituted, it is substituted with at least one substituent group. In embodiments, when $R^{5C}$ is substituted, it is substituted with at least one size-limited substituent group. In embodiments, when $R^{5C}$ is substituted, it is substituted with at least one lower substituent group.

In embodiments, $R^{5D}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{5D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5D}$ is substituted with a plurality of groups selected from substituent groups, size-limited substituent groups, and lower substituent groups; each substituent group, size-limited substituent group, and/or lower substituent group may optionally be different. In embodiments, when $R^{5D}$ is substituted, it is substituted with at least one substituent group. In embodiments, when $R^{5D}$ is substituted, it is substituted with at least one size-limited substituent group. In embodiments, when $R^{5D}$ is substituted, it is substituted with at least one lower substituent group.

In embodiments, $R^5$ is independently hydrogen. In embodiments, $R^5$ is independently halogen. In embodiments, $R^5$ is independently —F. In embodiments, $R^5$ is independently —Cl. In embodiments, $R^5$ is independently —Br. In embodiments, $R^5$ is independently —I. In embodiments, $R^5$ is independently —OH.

In embodiments, $R^5$ is independently —$OR^{5D}$. In embodiments, $R^{5D}$ is independently hydrogen. In embodiments, $R^{5D}$ is independently unsubstituted $C_1$-$C_4$ alkyl. In embodiments, $R^{5D}$ is independently unsubstituted methyl. In embodiments, $R^{5D}$ is independently unsubstituted ethyl. In embodiments, $R^{5D}$ is independently unsubstituted propyl. In embodiments, $R^{5D}$ is independently unsubstituted n-propyl. In embodiments, $R^{5D}$ is independently unsubstituted isopropyl. In embodiments, $R^{5D}$ is independently unsubstituted butyl. In embodiments, $R^{5D}$ is independently unsubstituted n-butyl. In embodiments, $R^{5D}$ is independently unsubstituted tert-butyl. In embodiments, $R^{5D}$ is independently substituted or unsubstituted aryl. In embodiments, $R^{5D}$ is independently substituted or unsubstituted phenyl.

In embodiments, $R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}R^{6D}$, —$SO_{v6}NR^{6A}R^{6B}$, —NHC(O)$NR^{6A}R^{6B}$, —$NR^{6C}NR^{6A}R^{6B}$, —$ONR^{6A}R^{6B}$, —NHC(O)$NR^{6C}NR^{6A}R^{6B}$, —$N(O)_{m6}$, —$NR^{6A}R^{6B}$, —C(O)$R^{6C}$, —C(O)$OR^{6C}$, —C(O)$NR^{6A}R^{6B}$, —$OR^{6D}$, —$NR^{6A}SO_2R^{6D}$, —$NR^{6A}$C(O)$R^{6C}$, —$NR^{6A}$C(O)$OR^{6C}$, —$NR^{6A}OR^{6C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{6A}$, $R^{6B}$, $R^{6C}$, and $R^{6D}$ are as described herein, including in embodiments. $X^6$ is independently —F, —Cl, —Br, or —I. The symbol n6 is independently an integer from 0 to 4. The symbols m6 and v6 are independently 1 or 2.

In embodiments, $R^6$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, $R^{6A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{6A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6A}$ is substituted with a plurality of groups selected from substituent groups, size-limited substituent groups, and lower substituent groups; each substituent group, size-limited substituent group, and/or lower substituent group may optionally be different. In embodiments, when $R^{6A}$ is substituted, it is substituted with at least one substituent group. In embodiments, when $R^{6A}$ is substituted, it is substituted with at least one size-limited substituent group. In embodiments, when $R^{6A}$ is substituted, it is substituted with at least one lower substituent group.

In embodiments, $R^{6B}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{6B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6B}$ is substituted with a plurality of groups selected from substituent groups, size-limited substituent groups, and lower substituent groups; each substituent group, size-limited substituent group, and/or lower substituent group may optionally be different. In embodiments, when $R^{6B}$ is substituted, it is substituted with at least one substituent group. In embodiments, when $R^{6B}$ is substituted, it is substituted with at least one size-limited substituent group. In embodiments, when $R^{6B}$ is substituted, it is substituted with at least one lower substituent group.

In embodiments, $R^{6A}$ and $R^{6B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{6A}$ and $R^{6B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{6A}$ and $R^{6B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{6A}$ and $R^{6B}$ substituents bonded to the same nitrogen atom is substituted, it is substituted with at least one substituent group. In embodiments, when the moiety formed by joining $R^{6A}$ and $R^{6B}$ substituents bonded to the same nitrogen atom is substituted, it is substituted with at least one size-limited substituent group. In embodiments, when the moiety formed by joining $R^{6A}$ and $R^{6B}$ substituents bonded to the same nitrogen atom is substituted, it is substituted with at least one lower substituent group.

In embodiments, $R^{6C}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{6C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6C}$ is substituted with a plurality of groups selected from substituent groups, size-limited substituent groups, and lower substituent groups; each substituent group, size-limited substituent group, and/or lower substituent group may optionally be different. In embodiments, when $R^{6C}$ is substituted, it is substituted with at least one substituent group. In embodiments, when $R^{6C}$ is substituted, it is substituted with at least one size-limited substituent group. In embodiments, when $R^{6C}$ is substituted, it is substituted with at least one lower substituent group.

In embodiments, $R^{6D}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{6D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6D}$ is substituted with a plurality of groups selected from substituent groups, size-limited substituent groups, and lower substituent groups; each substituent group, size-limited substituent group, and/or lower substituent group may optionally be different. In embodiments, when $R^{6D}$ is substituted, it is substituted with at least one substituent group. In embodiments, when $R^{6D}$ is substituted, it is substituted with at least one size-limited substituent group. In embodiments, when $R^{6D}$ is substituted, it is substituted with at least one lower substituent group.

In embodiments, $R^6$ is independently hydrogen. In embodiments, $R^6$ is independently halogen. In embodiments, $R^6$ is independently —F. In embodiments, $R^6$ is independently —Cl. In embodiments, $R^6$ is independently —Br. In embodiments, $R^6$ is independently —I. In embodiments, $R^6$ is independently —OH.

In embodiments, $R^6$ is independently $—OR^{6D}$. In embodiments, $R^{6D}$ is independently hydrogen. In embodiments, $R^{6D}$ is independently unsubstituted $C_1$-$C_4$ alkyl. In embodiments, $R^{6D}$ is independently unsubstituted methyl. In embodiments, $R^{6D}$ is independently unsubstituted ethyl. In embodiments, $R^{6D}$ is independently unsubstituted propyl. In embodiments, $R^{6D}$ is independently unsubstituted n-propyl. In embodiments, $R^{6D}$ is independently unsubstituted isopropyl. In embodiments, $R^{6D}$ is independently unsubstituted butyl. In embodiments, $R^{6D}$ is independently unsubstituted n-butyl. In embodiments, $R^{6D}$ is independently unsubstituted tert-butyl. In embodiments, $R^{6D}$ is independently substituted or unsubstituted aryl. In embodiments, $R^{6D}$ is independently substituted or unsubstituted phenyl.

In embodiments, $R^7$ is independently hydrogen, halogen, $—CX^7_3$, $—CHX^7_2$, $—CH_2X^7$, $—OCX^7_3$, $—OCH_2X^7$, $—OCHX^7_2$, —CN, $—SO_{n7}R^{7D}$, $—SO_{v7}NR^{7A}R^{7B}$, $—NHC(O)NR^{7A}R^{7B}$, $—NR^{7C}NR^{7A}R^{7B}$, $—ONR^{7A}R^{7B}$, $—NHC(O)NR^{7C}NR^{7A}R^{7B}$, $—N(O)_{m7}$, $—NR^{7A}R^{7B}$, $—C(O)R^{7C}$, $—C(O)OR^{7C}$, $—C(O)NR^{7A}R^{7B}$, $—OR^{7D}$, $—NR^{7A}SO_2R^{7D}$, $—NR^{7A}C(O)R^{7C}$, $—NR^{7A}C(O)OR^{7C}$, $—NR^{7A}OR^{7C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{7A}$, $R^{7B}$, $R^{7C}$, and $R^{7D}$ are as described herein, including in embodiments. $X^7$ is independently —F, —Cl, —Br, or —I. The symbol n7 is independently an integer from 0 to 4. The symbols m7 and v7 are independently 1 or 2.

In embodiments, $R^7$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^7$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments, $R^{7A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{7A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{7A}$ is substituted with a plurality of groups selected from substituent groups, size-limited substituent groups, and lower substituent groups; each substituent group, size-limited substituent group, and/or lower substituent group may optionally be different. In embodiments, when $R^{7A}$ is substituted, it is substituted with at least one substituent group. In embodiments, when $R^{7A}$ is substituted, it is substituted with at least one size-limited substituent group. In embodiments, when $R^{7A}$ is substituted, it is substituted with at least one lower substituent group.

In embodiments, $R^{7B}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{7B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{7B}$ is substituted with a plurality of groups selected from substituent groups, size-limited substituent groups, and lower substituent groups; each substituent group, size-limited substituent group, and/or lower substituent group may optionally be different. In embodiments, when $R^{7B}$ is substituted, it is substituted with at least one substituent group. In embodiments, when $R^{7B}$ is substituted, it is substituted with at least one size-limited substituent group. In embodiments, when $R^{7B}$ is substituted, it is substituted with at least one lower substituent group.

In embodiments, $R^{7A}$ and $R^{7B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{7A}$ and $R^{7B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{7A}$ and $R^{7B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{7A}$ and $R^{7B}$ substituents bonded to the same nitrogen atom is substituted, it is substituted with at least one substituent group. In embodiments, when the moiety formed by joining $R^{7A}$ and $R^{7B}$ substituents bonded to the same nitrogen atom is substituted, it is substituted with at least one size-limited substituent group. In embodiments, when the moiety formed by joining $R^{7A}$ and $R^{7B}$ substituents bonded to the same nitrogen atom is substituted, it is substituted with at least one lower substituent group.

In embodiments, $R^{7C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{7C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{7C}$ is substituted with a plurality of groups selected from substituent groups, size-limited substituent groups, and lower substituent groups; each substituent group, size-limited substituent group, and/or lower substituent group may optionally be different. In embodiments, when $R^{7C}$ is substituted, it is substituted with at least one substituent group. In embodiments, when $R^{7C}$ is substituted, it is substituted with at least one size-limited substituent group. In embodiments, when $R^{7C}$ is substituted, it is substituted with at least one lower substituent group.

In embodiments, $R^{7D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{7D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{7D}$ is substituted with a plurality of groups selected from substituent groups, size-limited substituent groups, and lower substituent groups; each substituent group, size-limited substituent group, and/or lower substituent group may optionally be different. In embodiments, when $R^{7D}$ is substituted, it is substituted with at least one substituent group. In embodiments, when $R^{7D}$ is substituted, it is substituted with at least one size-limited substituent group. In embodiments, when $R^{7D}$ is substituted, it is substituted with at least one lower substituent group.

In embodiments, $R^7$ is independently hydrogen. In embodiments, $R^7$ is independently halogen. In embodiments, $R^7$ is independently $-F$. In embodiments, $R^7$ is independently $-Cl$. In embodiments, $R^7$ is independently —Br. In embodiments, $R^7$ is independently —I. In embodiments, $R^7$ is independently —OH.

In embodiments, $R^7$ is independently —$OR^{7D}$. In embodiments, $R^{7D}$ is independently hydrogen. In embodiments, $R^{7D}$ is independently unsubstituted $C_1$-$C_4$ alkyl. In embodiments, $R^{7D}$ is independently unsubstituted methyl. In embodiments, $R^{7D}$ is independently unsubstituted ethyl. In embodiments, $R^{7D}$ is independently unsubstituted propyl. In embodiments, $R^{7D}$ is independently unsubstituted n-propyl. In embodiments, $R^{7D}$ is independently unsubstituted isopropyl. In embodiments, $R^{7D}$ is independently unsubstituted butyl. In embodiments, $R^{7D}$ is independently unsubstituted n-butyl. In embodiments, $R^{7D}$ is independently unsubstituted tert-butyl. In embodiments, $R^{7D}$ is independently substituted or unsubstituted aryl. In embodiments, $R^{7D}$ is independently substituted or unsubstituted phenyl.

In embodiments, $R^8$ is independently hydrogen, halogen, —$CX^8_3$, —$CHX^B$2, —$CH_2X^8$, —$OCX^8_3$, —$OCH_2X^8$, —$OCHX^8_2$, —CN, —$SO_{n8}R^{8D}$, —$SO_{v8}NR^{8A}R^{8B}$, —NHC(O)$NR^{8A}R^{8B}$, —$NR^{8C}NR^{8A}R^{8B}$, —$ONR^{8A}R^{8B}$, —NHC(O)$NR^{8C}NR^{8A}R^{8B}$, —$N(O)_{m8}$, —$NR^{8A}R^{8B}$, —$C(O)R^{8C}$, —$C(O)OR^{8C}$, —$C(O)NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{8A}$, $R^{BB}$, $R^{8C}$, and $R^{8D}$ are as described herein, including in embodiments. $X^8$ is independently —F, —Cl, —Br, or —I. The symbol n8 is independently an integer from 0 to 4. The symbols m8 and v8 are independently 1 or 2.

In embodiments, $R^8$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^8$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^8$ is substituted with a plurality of groups selected from substituent groups, size-limited substituent groups, and lower substituent groups; each substituent group, size-limited substituent group, and/or lower substituent group may optionally be different. In embodiments, when $R^8$ is substituted, it is substituted with at least one substituent group. In embodiments, when $R^8$ is substituted, it is substituted with at least one size-limited substituent group. In embodiments, when $R^8$ is substituted, it is substituted with at least one lower substituent group.

In embodiments, $R^{8A}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{8A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8A}$ is substituted with a plurality of groups selected from substituent groups, size-limited substituent groups, and lower substituent groups; each substituent group, size-limited substituent group, and/or lower substituent group may optionally be different. In embodiments, when $R^{8A}$ is substituted, it is substituted with at least one substituent group. In embodiments, when $R^{8A}$ is substituted, it is substituted with at least one size-limited substituent group. In embodiments, when $R^{8A}$ is substituted, it is substituted with at least one lower substituent group.

In embodiments, $R^{8B}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{8B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8B}$ is substituted with a plurality of groups selected from substituent groups, size-limited substituent groups, and lower substituent groups; each substituent group, size-limited substituent group, and/or lower substituent group may optionally be different. In embodiments, when $R^{8B}$ is substituted, it is substituted with at least one substituent group. In embodiments, when $R^{8B}$ is substituted, it is substituted with at least one size-limited substituent group. In embodiments, when $R^{8B}$ is substituted, it is substituted with at least one lower substituent group.

In embodiments, $R^{8A}$ and $R^{8B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{8A}$ and $R^{8B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{8A}$ and $R^{8B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{8A}$ and $R^{8B}$ substituents bonded to the same nitrogen atom is substituted, it is substituted with at least one substituent group. In embodiments, when the moiety formed by joining $R^{8A}$ and $R^{8B}$ substituents bonded to the same nitrogen atom is substituted, it is substituted with at least one size-limited substituent group. In embodiments, when the moiety formed by joining $R^{8A}$ and $R^{8B}$ substituents bonded to the same nitrogen atom is substituted, it is substituted with at least one lower substituent group.

In embodiments, $R^{8C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{8C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8C}$ is substituted with a plurality of groups selected from substituent groups, size-limited substituent groups, and lower substituent groups; each substituent group, size-limited substituent group, and/or lower substituent group may optionally be different. In embodiments, when $R^{8C}$ is substituted, it is substituted with at least one substituent group. In embodiments, when $R^{8C}$ is substituted, it is substituted with at least one size-limited substituent group. In embodiments, when $R^{8C}$ is substituted, it is substituted with at least one lower substituent group.

In embodiments, $R^{8D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $—SO_3H$, $—SO_4H$, $—SO_2NH_2$, $—NHNH_2$, $—ONH_2$, —NHC(O)$NHNH_2$, —NHC(O)$NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{8D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8D}$ is substituted with a plurality of groups selected from substituent groups, size-limited substituent groups, and lower substituent groups; each substituent group, size-limited substituent group, and/or lower substituent group may optionally be different. In embodiments, when $R^{8D}$ is substituted, it is substituted with at least one substituent group. In embodiments, when $R^{8D}$ is substituted, it is substituted with at least one size-limited substituent group. In embodiments, when $R^{8D}$ is substituted, it is substituted with at least one lower substituent group.

In embodiments, $R^8$ is independently hydrogen. In embodiments, $R^8$ is independently halogen. In embodiments, $R^8$ is independently —F. In embodiments, $R^8$ is independently —Cl. In embodiments, $R^8$ is independently —Br. In embodiments, $R^8$ is independently —I. In embodiments, $R^8$ is independently —OH.

In embodiments, $R^8$ is independently $—OR^{8D}$. In embodiments, $R^{8D}$ is independently hydrogen. In embodiments, $R^{8D}$ is independently unsubstituted $C_1$-$C_4$ alkyl. In embodiments, $R^{8D}$ is independently unsubstituted methyl. In embodiments, $R^{8D}$ is independently unsubstituted ethyl. In embodiments, $R^{8D}$ is independently unsubstituted propyl. In embodiments, $R^{8D}$ is independently unsubstituted n-propyl. In embodiments, $R^{8D}$ is independently unsubstituted isopropyl. In embodiments, $R^{8D}$ is independently unsubstituted butyl. In embodiments, $R^{8D}$ is independently unsubstituted n-butyl. In embodiments, $R^{8D}$ is independently unsubstituted tert-butyl. In embodiments, $R^{8D}$ is independently substituted or unsubstituted aryl. In embodiments, $R^{8D}$ is independently substituted or unsubstituted phenyl.

In embodiments, $R^9$ is independently hydrogen, halogen, $—CX^9_3$, $—CHX^9_2$, $—CH_2X^9$, $—OCX^9_3$, $—OCH_2X^9$, $—OCHX^9_2$, —CN, $—SO_{n9}R^{9D}$, $—SO_{v9}NR^{9A}R^{9B}$, —NHC(O)$NR^{9A}R^{9B}$, $—NR^{9C}NR^{9A}R^{9B}$, $—ONR^{9A}R^{9B}$, —NHC(O)$NR^{9C}NR^{9A}R^{9B}$, $—N(O)_{m9}$, $—NR^{9A}R^{9B}$, —C(O)$R^{9C}$, —C(O)$OR^{9C}$, —C(O)$NR^{9A}R^{9B}$, $—OR^{9D}$, $—NR^{9A}SO_2R^{9D}$, $—NR^{9A}$C(O)$R^{9C}$, $—NR^{9A}$C(O)$OR^{9C}$, $—NR^{9A}OR^{9C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{9A}$, $R^{9B}$, $R^{9C}$, and $R^{9D}$ are as described herein, including in embodiments. $X^9$ is independently —F, —Cl, —Br, or —I. The symbol n9 is independently an integer from 0 to 4. The symbols m9 and v9 are independently 1 or 2.

In embodiments, $R^9$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O)$NHNH_2$, —NHC(O)$NH_2$, $—NHSO_2H$, —NHC(O)H, —NHC(O)OH, —NHOH, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^9$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group.

In embodiments, $R^{9A}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{9A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9A}$ is substituted with a plurality of groups selected from substituent groups, size-limited substituent groups, and lower substituent groups; each substituent group, size-limited substituent group, and/or lower substituent group may optionally be different. In embodiments, when $R^{9A}$ is substituted, it is substituted with at least one substituent group. In embodiments, when $R^{9A}$ is substituted, it is substituted with at least one size-limited substituent group. In embodiments, when $R^{9A}$ is substituted, it is substituted with at least one lower substituent group.

In embodiments, $R^{9B}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{9B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9B}$ is substituted with a plurality of groups selected from substituent groups, size-limited substituent groups, and lower substituent groups; each substituent group, size-limited substituent group, and/or lower substituent group may optionally be different. In embodiments, when $R^{9B}$ is substituted, it is substituted with at least one substituent group. In embodiments, when $R^{9B}$ is substituted, it is substituted with at least one size-limited substituent group. In embodiments, when $R^{9B}$ is substituted, it is substituted with at least one lower substituent group.

In embodiments, $R^{9A}$ and $R^{9B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{9A}$ and $R^{9B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{9A}$ and $R^{9B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{9A}$ and $R^{9B}$ substituents bonded to the same nitrogen atom is substituted, it is substituted with at least one substituent group. In embodiments, when the moiety formed by joining $R^{9A}$ and $R^{9B}$ substituents bonded to the same nitrogen atom is substituted, it is substituted with at least one size-limited substituent group. In embodiments, when the moiety formed by joining $R^{9A}$ and $R^{9B}$ substituents bonded to the same nitrogen atom is substituted, it is substituted with at least one lower substituent group.

In embodiments, $R^{9C}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{9C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9C}$ is substituted with a plurality of groups selected from substituent groups, size-limited substituent groups, and lower substituent groups; each substituent group, size-limited substituent group, and/or lower substituent group may optionally be different. In embodiments, when $R^{9C}$ is substituted, it is substituted with at least one substituent group. In embodiments, when $R^{9C}$ is substituted, it is substituted with at least one size-limited substituent group. In embodiments, when $R^{9C}$ is substituted, it is substituted with at least one lower substituent group.

In embodiments, $R^{9D}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{9D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9D}$ is substituted with a plurality of groups selected from substituent groups, size-limited substituent groups, and lower substituent groups; each substituent group, size-limited substituent group, and/or lower substituent group may optionally be different. In embodiments, when $R^{9D}$ is substituted, it is substituted with at least one substituent group. In embodiments, when $R^{9D}$ is substituted, it is substituted with at least one size-limited substituent group. In embodiments, when $R^{9D}$ is substituted, it is substituted with at least one lower substituent group.

In embodiments, $R^9$ is independently hydrogen. In embodiments, $R^9$ is independently halogen. In embodiments, $R^9$ is independently —F. In embodiments, $R^9$ is independently —Cl. In embodiments, $R^9$ is independently —Br. In embodiments, $R^9$ is independently —I. In embodiments, $R^9$ is independently —OH.

In embodiments, $R^9$ is independently —$OR^{9D}$. In embodiments, $R^{9D}$ is independently hydrogen. In embodiments, $R^{9D}$ is independently unsubstituted $C_1$-$C_4$ alkyl. In embodiments, $R^{9D}$ is independently unsubstituted methyl. In embodiments, $R^{9D}$ is independently unsubstituted ethyl. In embodiments, $R^{9D}$ is independently unsubstituted propyl. In embodiments, $R^{9D}$ is independently unsubstituted n-propyl. In embodiments, $R^{9D}$ is independently unsubstituted isopropyl. In embodiments, $R^{9D}$ is independently unsubstituted butyl. In embodiments, $R^{9D}$ is independently unsubstituted n-butyl. In embodiments, $R^{9D}$ is independently unsubstituted tert-butyl. In embodiments, $R^{9D}$ is independently substituted or unsubstituted aryl. In embodiments, $R^{9D}$ is independently substituted or unsubstituted phenyl.

In embodiments, $R^{10}$ is independently hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10D}$, —$SO_{v10}NR^{10A}R^{10B}$, —$NHC(O)NR^{10A}R^{10B}$, —$NR^{10C}NR^{10A}R^{10B}$, —$ONR^{10A}R^{10B}$, —$NHC(O)NR^{10C}NR^{10A}R^{10B}$, —$N(O)_{m10}$, —$NR^{10A}R^{10B}$, —$C(O)R^{10C}$, —$C(O)OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{10A}$, $R^{10B}$, $R^{10C}$, and $R^{10D}$ are as described herein, including in embodiments. $X^{10}$ is independently —F, —Cl, —Br, or —I. The symbol n10 is independently an integer from 0 to 4. The symbols m10 and v10 are independently 1 or 2.

In embodiments, $R^{10}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, $R^{10A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{10A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10A}$ is substituted with a plurality of groups selected from substituent groups, size-limited substituent groups, and lower substituent groups; each substituent group, size-limited substituent group, and/or lower substituent group may optionally be different. In embodiments, when $R^{10A}$ is substituted, it is substituted with at least one substituent group. In embodiments, when $R^{10A}$ is substituted, it is substituted with at least one size-limited substituent group. In embodiments, when $R^{10A}$ is substituted, it is substituted with at least one lower substituent group.

In embodiments, $R^{10B}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{10B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10B}$ is substituted with a plurality of groups selected from substituent groups, size-limited substituent groups, and lower substituent groups; each substituent group, size-limited substituent group, and/or lower substituent group may optionally be different. In embodiments, when $R^{10B}$ is substituted, it is substituted with at least one substituent group. In embodiments, when $R^{10B}$ is substituted, it is substituted with at least one size-limited substituent group. In embodiments, when $R^{10B}$ is substituted, it is substituted with at least one lower substituent group.

In embodiments, $R^{10A}$ and $R^{10B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{10A}$ and $R^{10B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{10A}$ and $R^{10B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{10A}$ and $R^{10B}$ substituents bonded to the same nitrogen atom is substituted, it is substituted with at least one substituent group. In embodiments, when the moiety formed by joining $R^{10A}$ and $R^{10B}$ substituents bonded to the same nitrogen atom is substituted, it is substituted with at least one size-limited substituent group. In embodiments, when the moiety formed by joining $R^{10A}$ and $R^{10B}$ substituents bonded to the same nitrogen atom is substituted, it is substituted with at least one lower substituent group.

In embodiments, $R^{10C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{10C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10C}$ is substituted with a plurality of groups selected from substituent groups, size-limited substituent groups, and lower substituent groups; each substituent group, size-limited substituent group, and/or lower substituent group may optionally be different. In embodiments, when $R^{10C}$ is substituted, it is substituted with at least one substituent group. In embodiments, when $R^{10C}$ is substituted, it is substituted with at least one size-limited substituent group. In embodiments, when $R^{10C}$ is substituted, it is substituted with at least one lower substituent group.

In embodiments, $R^{10D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{10D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10D}$ is substituted with a plurality of groups selected from substituent groups, size-limited substituent groups, and lower substituent groups; each substituent group, size-limited substituent group, and/or lower substituent group may optionally be different. In embodiments, when $R^{10D}$ is substituted, it is substituted with at least one substituent group. In embodiments, when $R^{10D}$ is substituted, it is substituted with at least one size-limited substituent group. In embodiments, when $R^{10D}$ is substituted, it is substituted with at least one lower substituent group.

In embodiments, $R^{10}$ is independently hydrogen. In embodiments, $R^{10}$ is independently halogen. In embodiments, $R^{10}$ is independently —F. In embodiments, $R^{10}$ is independently —Cl. In embodiments, $R^{10}$ is independently —Br. In embodiments, $R^{10}$ is independently —I. In embodiments, $R^{10}$ is independently —OH.

In embodiments, $R^{10}$ is independently —$OR^{10D}$. In embodiments, $R^{10D}$ is independently hydrogen. In embodiments, $R^{10D}$ is independently unsubstituted $C_1$-$C_4$ alkyl. In embodiments, $R^{10D}$ is independently unsubstituted methyl. In embodiments, $R^{10D}$ is independently unsubstituted ethyl. In embodiments, $R^{10D}$ is independently unsubstituted propyl. In embodiments, $R^{10D}$ is independently unsubstituted n-propyl. In embodiments, $R^{10D}$ is independently unsubstituted isopropyl. In embodiments, $R^{10D}$ is independently unsubstituted butyl. In embodiments, $R^{10D}$ is independently unsubstituted n-butyl. In embodiments, $R^{10D}$ is independently unsubstituted tert-butyl. In embodiments, $R^{10D}$ is independently substituted or unsubstituted aryl. In embodiments, $R^{10D}$ is independently substituted or unsubstituted phenyl.

In embodiments, $R^{11}$ is independently hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —CN, —$SO_{n11}R^{11D}$, —$SO_{v11}NR^{11A}R^{11B}$, —$NHC(O)NR^{11A}R^{11B}$, —$NR^{11C}NR^{11A}R^{11B}$, —$ONR^{11A}R^{11B}$, —$NHC(O)NR^{11C}NR^{11A}R^{11B}$, —$N(O)_{m11}$, —$NR^{11A}R^{11B}$, —$C(O)R^{11C}$, —$C(O)OR^{11C}$, —$C(O)NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{11A}$, $R^{11B}$, $R^{11C}$, and $R^{11D}$ are as described herein, including in embodiments. $X^{11}$ is independently —F, —Cl, —Br, or —I. The symbol n11 is independently an integer from 0 to 4. The symbols m11 and v11 are independently 1 or 2.

In embodiments, $R^{11}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{11}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{11}$ is substituted with a plurality of groups selected from substituent groups, size-limited substituent groups, and lower substituent groups; each substituent group, size-limited substituent group, and/or lower substituent group may optionally be different. In embodiments, when $R^{11}$ is substituted, it is substituted with at least one substituent group. In embodiments, when $R^{11}$ is substituted, it is substituted with at least one size-limited substituent group. In embodiments, when $R^{11}$ is substituted, it is substituted with at least one lower substituent group.

In embodiments, $R^{11A}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{11A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{11A}$ is substituted with a plurality of groups selected from substituent groups, size-limited substituent groups, and lower substituent groups; each substituent group, size-limited substituent group, and/or lower substituent group may optionally be different. In embodiments, when $R^{11A}$ is substituted, it is substituted with at least one substituent group. In embodiments, when $R^{11A}$ is substituted, it is substituted with at least one size-limited substituent group. In embodiments, when $R^{11A}$ is substituted, it is substituted with at least one lower substituent group.

In embodiments, $R^{11B}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHOH, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{11B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{11B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, it is substituted with at least one substituent group. In embodiments, when $R^{1B}$ is substituted, it is substituted with at least one size-limited substituent group. In embodiments, when $R^{11B}$ is substituted, it is substituted with at least one lower substituent group.

In embodiments, $R^{11A}$ and $R^{11B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{11A}$ and $R^{11B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{11A}$ and $R^{11B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{11A}$ and $R^{11B}$ substituents bonded to the same nitrogen atom is substituted, it is substituted with at least one substituent group. In embodiments, when the moiety formed by joining $R^{11A}$ and $R^{11B}$ substituents bonded to the same nitrogen atom is substituted, it is substituted with at least one size-limited substituent group. In embodiments, when the moiety formed by joining $R^{11A}$ and $R^{11B}$ substituents bonded to the same nitrogen atom is substituted, it is substituted with at least one lower substituent group.

In embodiments, $R^{11C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHOH, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{11C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{11C}$ is substituted with a plurality of groups selected from substituent groups, size-limited substituent groups, and lower substituent groups; each substituent group, size-limited substituent group, and/or lower substituent group may optionally be different. In embodiments, when $R^{11C}$ is substituted, it is substituted with at least one substituent group. In embodiments, when $R^{11C}$ is substituted, it is substituted with at least one size-limited substituent group. In embodiments, when $R^{11C}$ is substituted, it is substituted with at least one lower substituent group.

In embodiments, $R^{11D}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{11D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{11D}$ is substituted with a plurality of groups selected from substituent groups, size-limited substituent groups, and lower substituent groups; each substituent group, size-limited substituent group, and/or lower substituent group may optionally be different. In embodiments, when $R^{11D}$ is substituted, it is substituted with at least one substituent group. In embodiments, when $R^{11D}$ is substituted, it is substituted with at least one size-limited substituent group. In embodiments, when $R^{11D}$ is substituted, it is substituted with at least one lower substituent group.

In embodiments, $R^{11}$ is independently hydrogen. In embodiments, $R^{11}$ is independently halogen. In embodiments, $R^{11}$ is independently —F. In embodiments, $R^{11}$ is independently —Cl. In embodiments, $R^{11}$ is independently —Br. In embodiments, $R^{11}$ is independently —I. In embodiments, $R^{11}$ is independently —OH.

In embodiments, $R^{11}$ is independently —$OR^{11D}$. In embodiments, $R^{11D}$ is independently hydrogen. In embodiments, $R^{11D}$ is independently unsubstituted $C_1$-$C_4$ alkyl. In embodiments, $R^{11D}$ is independently unsubstituted methyl. In embodiments, $R^{11D}$ is independently unsubstituted ethyl. In embodiments, $R^{11D}$ is independently unsubstituted propyl. In embodiments, $R^{11D}$ is independently unsubstituted n-propyl. In embodiments, $R^{11D}$ is independently unsubstituted isopropyl. In embodiments, $R^{11D}$ is independently unsubstituted butyl. In embodiments, $R^{11D}$ is independently unsubstituted n-butyl. In embodiments, $R^{11D}$ is independently unsubstituted tert-butyl. In embodiments, $R^{11D}$ is independently substituted or unsubstituted aryl. In embodiments, $R^{11D}$ is independently substituted or unsubstituted phenyl.

In embodiments, $R^{12}$ is independently hydrogen, halogen, —$CX^{12}_3$, —$CHX^{12}_2$, —$CH_2X^{12}$, —$OCX^{12}_3$, —$OCH_2X^{12}$, —$OCHX^{12}_2$, —CN, —$SO_{n12}R^{12D}$, —$SO_{v12}NR^{12A}R^{12B}$, —NHC(O)$NR^{12A}R^{12B}$, —$NR^{12C}NR^{12A}R^{12B}$, —$ONR^{12A}R^{12B}$, —NHC(O)$NR^{12C}NR^{12A}R^{12B}$, —$N(O)_{m12}$, —$NR^{12A}R^{12B}$, —C(O)$R^{12C}$, —C(O)$OR^{12C}$, —C(O)$NR^{12A}R^{12B}$, —$OR^{12D}$, —$NR^{12A}SO_2R^{12D}$, —$NR^{12A}$C(O)$R^{12C}$, —$NR^{12A}$C(O)$OR^{12C}$, —$NR^{12A}OR^{12C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{12A}$, $R^{12B}$, $R^{12C}$, and $R^{12D}$ are as described herein, including in embodiments. $X^{12}$ is independently —F, —Cl, —Br, or —I. The symbol n12 is independently an integer from 0 to 4. The symbols m12 and v12 are independently 1 or 2.

In embodiments, $R^{12}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{12}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{12}$ is substituted with a plurality of groups selected from substituent groups, size-limited substituent groups, and lower substituent groups; each substituent group, size-limited substituent group, and/or lower substituent group may optionally be different. In embodiments, when $R^{12}$ is substituted, it is substituted with at least one substituent group. In embodiments, when $R^{12}$ is substituted, it is substituted with at least one size-limited substituent group. In embodiments, when $R^{12}$ is substituted, it is substituted with at least one lower substituent group.

In embodiments, $R^{12A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{12A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{12A}$ is substituted with a plurality of groups selected from substituent groups, size-limited substituent groups, and lower substituent groups; each substituent group, size-limited substituent group, and/or lower substituent group may optionally be different. In embodiments, when $R^{12A}$ is substituted, it is substituted with at least one substituent group. In embodiments, when $R^{12A}$ is substituted, it is substituted with at least one size-limited substituent group. In embodiments, when $R^{12A}$ is substituted, it is substituted with at least one lower substituent group.

In embodiments, $R^{12B}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{12B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{12B}$ is substituted with a plurality of groups selected from substituent groups, size-limited substituent groups, and lower substituent groups; each substituent group, size-limited substituent group, and/or lower substituent group may optionally be different. In embodiments, when $R^{12B}$ is substituted, it is substituted with at least one substituent group. In embodiments, when $R^{12B}$ is substituted, it is substituted with at least one size-limited substituent group. In embodiments, when $R^{12B}$ is substituted, it is substituted with at least one lower substituent group.

In embodiments, $R^{12A}$ and $R^{12B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{12A}$ and $R^{12B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{12A}$ and $R^{12B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{12A}$ and $R^{12B}$ substituents bonded to the same nitrogen atom is substituted, it is substituted with at least one substituent group. In embodiments, when the moiety formed by joining $R^{12A}$ and $R^{12B}$ substituents bonded to the same nitrogen atom is substituted, it is substituted with at least one size-limited substituent group. In embodiments, when the moiety formed by joining $R^{12A}$ and $R^{12B}$ substituents bonded to the same nitrogen atom is substituted, it is substituted with at least one lower substituent group.

In embodiments, $R^{12C}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{12C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{12C}$ is substituted with a plurality of groups selected from substituent groups, size-limited substituent groups, and lower substituent groups; each substituent group, size-limited substituent group, and/or lower substituent group may optionally be different. In embodiments, when $R^{12C}$ is substituted, it is substituted with at least one substituent group. In embodiments, when $R^{12C}$ is substituted, it is substituted with at least one size-limited substituent group. In embodiments, when $R^{12C}$ is substituted, it is substituted with at least one lower substituent group.

In embodiments, $R^{12D}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{12D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{12D}$ is substituted with a plurality of groups selected from substituent groups, size-limited substituent groups, and lower substituent groups; each substituent group, size-limited substituent group, and/or lower substituent group may optionally be different. In embodiments, when $R^{12D}$ is substituted, it is substituted with at least one substituent group. In embodiments, when $R^{12D}$ is substituted, it is substituted with at least one size-limited substituent group. In embodiments, when $R^{12D}$ is substituted, it is substituted with at least one lower substituent group.

In embodiments, $R^{12}$ is independently hydrogen. In embodiments, $R^{12}$ is independently halogen. In embodiments, $R^{12}$ is independently —F. In embodiments, $R^{12}$ is independently —Cl. In embodiments, $R^{12}$ is independently —Br. In embodiments, $R^{12}$ is independently —I. In embodiments, $R^{12}$ is independently —OH.

In embodiments, $R^{12}$ is independently $—OR^{12D}$. In embodiments, $R^{12D}$ is independently hydrogen. In embodiments, $R^{12D}$ is independently unsubstituted $C_1$-$C_4$ alkyl. In embodiments, $R^{12D}$ is independently unsubstituted methyl. In embodiments, $R^{12D}$ is independently unsubstituted ethyl. In embodiments, $R^{12D}$ is independently unsubstituted propyl. In embodiments, $R^{12D}$ is independently unsubstituted n-propyl. In embodiments, $R^{12D}$ is independently unsubstituted isopropyl. In embodiments, $R^{12D}$ is independently unsubstituted butyl. In embodiments, $R^{12D}$ is independently unsubstituted n-butyl. In embodiments, $R^{12D}$ is independently unsubstituted tert-butyl. In embodiments, $R^{12D}$ is independently substituted or unsubstituted aryl. In embodiments, $R^{12D}$ is independently substituted or unsubstituted phenyl.

In embodiments, $R^{13}$ is independently hydrogen, halogen, $—CX^{13}_3$, $—CHX^{13}_2$, $—CH_2X^{13}$, $—OCX^{13}_3$, $—OCH_2X^{13}$, $—OCHX^{13}_2$, —CN, $—SO_{n13}R^{13D}$, $—SO_{v13}NR^{13A}R^{13B}$, $—NHC(O)NR^{13A}R^{13B}$, $—NR^{13C}NR^{13A}R^{13B}$, $—ONR^{13A}R^{13B}$, $—NHC(O)NR^{13C}NR^{13A}R^{13B}$, $—N(O)_{m13}$, $—NR^{13A}R^{13B}$, $—C(O)R^{13C}$, $—C(O)OR^{13C}$, $—C(O)NR^{13A}R^{13B}$, $—OR^{13D}$, $—NR^{13A}SO_2R^{13D}$, $—NR^{13A}C(O)R^{13C}$, $—NR^{13A}C(O)OR^{13C}$, $—NR^{13A}OR^{13C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{13A}$, $R^{13B}$, $R^{13C}$, and $R^{13D}$ are as described herein, including in embodiments. $X^{13}$ is independently —F, —Cl, —Br, or —I. The symbol n13 is independently an integer from 0 to 4. The symbols m13 and v13 are independently 1 or 2.

In embodiments, $R^{13}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{13}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{13}$ is substituted with a plurality of groups selected from substituent groups, size-limited substituent groups, and lower substituent groups; each substituent group, size-limited substituent group, and/or lower substituent group may optionally be different. In embodiments, when $R^{13}$ is substituted, it is substituted with at least one substituent group. In embodiments, when $R^{13}$ is substituted, it is substituted with at least one size-limited substituent group. In embodiments, when $R^{13}$ is substituted, it is substituted with at least one lower substituent group.

In embodiments, $R^{13A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{13A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{13A}$ is substituted with a plurality of groups selected from substituent groups, size-limited substituent groups, and lower substituent groups; each substituent group, size-limited substituent group, and/or lower substituent group may optionally be different. In embodiments, when $R^{13A}$ is substituted, it is substituted with at least one substituent group. In embodiments, when $R^{13A}$ is substituted, it is substituted with at least one size-limited substituent group. In embodiments, when $R^{13A}$ is substituted, it is substituted with at least one lower substituent group.

In embodiments, $R^{13B}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{13B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{13B}$ is substituted with a plurality of groups selected from substituent groups, size-limited substituent groups, and lower substituent groups; each substituent group, size-limited substituent group, and/or lower substituent group may optionally be different. In embodiments, when $R^{13B}$ is substituted, it is substituted with at least one substituent group. In embodiments, when $R^{13B}$ is substituted, it is substituted with at least one size-limited substituent group. In embodiments, when $R^{13B}$ is substituted, it is substituted with at least one lower substituent group.

In embodiments, $R^{13A}$ and $R^{13B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{13A}$ and $R^{13B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{13A}$ and $R^{13B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{13A}$ and $R^{13B}$ substituents bonded to the same nitrogen atom is substituted, it is substituted with at least one substituent group. In embodiments, when the moiety formed by joining $R^{13A}$ and $R^{13B}$ substituents bonded to the same nitrogen atom is substituted, it is substituted with at least one size-limited substituent group. In embodiments, when the moiety formed by joining $R^{13A}$ and $R^{13B}$ substituents bonded to the same nitrogen atom is substituted, it is substituted with at least one lower substituent group.

In embodiments, $R^{13C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{13C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{13C}$ is substituted with a plurality of groups selected from substituent groups, size-limited substituent groups, and lower substituent groups; each substituent group, size-limited substituent group, and/or lower substituent group may optionally be different. In embodiments, when $R^{13C}$ is substituted, it is substituted with at least one substituent group. In embodiments, when $R^{13C}$ is substituted, it is substituted with at least one size-limited substituent group. In embodiments, when $R^{13C}$ is substituted, it is substituted with at least one lower substituent group.

In embodiments, $R^{13D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{13D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{13D}$ is substituted with a plurality of groups selected from substituent groups, size-limited substituent groups, and lower substituent groups; each substituent group, size-limited substituent group, and/or lower substituent group may optionally be different. In embodiments, when $R^{13D}$ is substituted, it is substituted with at least one substituent group. In embodiments, when $R^{13D}$ is substituted, it is substituted with at least one size-limited substituent group. In embodiments, when $R^{13D}$ is substituted, it is substituted with at least one lower substituent group.

In embodiments, $R^{13}$ is independently hydrogen. In embodiments, $R^{13}$ is independently halogen. In embodiments, $R^{13}$ is independently —F. In embodiments, $R^{13}$ is independently —Cl. In embodiments, $R^{13}$ is independently —Br. In embodiments, $R^{13}$ is independently —I. In embodiments, $R^{13}$ is independently —OH.

In embodiments, $R^{13}$ is independently —$OR^{13D}$. In embodiments, $R^{13D}$ is independently hydrogen. In embodiments, $R^{13D}$ is independently unsubstituted $C_1$-$C_4$ alkyl. In embodiments, $R^{13D}$ is independently unsubstituted methyl. In embodiments, $R^{13D}$ is independently unsubstituted ethyl. In embodiments, $R^{13D}$ is independently unsubstituted propyl. In embodiments, $R^{13D}$ is independently unsubstituted n-propyl. In embodiments, $R^{13D}$ is independently unsubstituted isopropyl. In embodiments, $R^{13D}$ is independently unsubstituted butyl. In embodiments, $R^{13D}$ is independently unsubstituted n-butyl. In embodiments, $R^{13D}$ is independently unsubstituted tert-butyl. In embodiments, $R^{13D}$ is independently substituted or unsubstituted aryl. In embodiments, $R^{13D}$ is independently substituted or unsubstituted phenyl.

In embodiments, $R^{14}$ is independently hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —CN, —$SO_{n14}R^{14D}$, —$SO_{v14}NR^{14A}R^{14B}$, —$NHC(O)NR^{14A}R^{14B}$, —$NR^{14C}NR^{14A}R^{14B}$, —$ONR^{14A}R^{14B}$, —$NHC(O)NR^{14C}NR^{14A}R^{14B}$, —$N(O)_{m14}$, —$NR^{14A}R^{14B}$, —$C(O)R^{14C}$, —$C(O)OR^{14C}$, —$C(O)NR^{14A}R^{14B}$, —$OR^{14D}$, —$NR^{14A}SO_2R^{14D}$, —$NR^{14A}C(O)R^{14C}$, —$NR^{14A}C(O)OR^{14C}$, —$NR^{14A}OR^{14C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{14A}$, $R^{14B}$, $R^{14C}$, and $R^{14D}$ are as described herein, including in embodiments. $X^{14}$ is independently —F, —Cl, —Br, or —I. The symbol n14 is independently an integer from 0 to 4. The symbols m14 and v14 are independently 1 or 2.

In embodiments, $R^{14}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{14}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{14}$ is substituted with a plurality of groups selected from substituent groups, size-limited substituent groups, and lower substituent groups; each substituent group, size-limited substituent group, and/or lower substituent group may optionally be different. In embodiments, when $R^{14}$ is substituted, it is substituted with at least one substituent group. In embodiments, when $R^{14}$ is substituted, it is substituted with at least one size-limited substituent group. In embodiments, when $R^{14}$ is substituted, it is substituted with at least one lower substituent group.

In embodiments, $R^{14A}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{14A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{14A}$ is substituted with a plurality of groups selected from substituent groups, size-limited substituent groups, and lower substituent groups; each substituent group, size-limited substituent group, and/or lower substituent group may optionally be different. In embodiments, when $R^{14A}$ is substituted, it is substituted with at least one substituent group. In embodiments, when $R^{14A}$ is substituted, it is substituted with at least one size-limited substituent group. In embodiments, when $R^{14A}$ is substituted, it is substituted with at least one lower substituent group.

In embodiments, $R^{14B}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{14B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{14B}$ is substituted with a plurality of groups selected from substituent groups, size-limited substituent groups, and lower substituent groups; each substituent group, size-limited substituent group, and/or lower substituent group may optionally be different. In embodiments, when $R^{14B}$ is substituted, it is substituted with at least one substituent group. In embodiments, when $R^{14B}$ is substituted, it is substituted with at least one size-limited substituent group. In embodiments, when $R^{14B}$ is substituted, it is substituted with at least one lower substituent group.

In embodiments, $R^{14A}$ and $R^{14B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{14A}$ and $R^{14B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{14A}$ and $R^{14B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{14A}$ and $R^{14B}$ substituents bonded to the same nitrogen atom is substituted, it is substituted with at least one substituent group. In embodiments, when the moiety formed by joining $R^{14A}$ and $R^{14B}$ substituents bonded to the same nitrogen atom is substituted, it is substituted with at least one size-limited substituent group. In embodiments, when the moiety formed by joining $R^{14A}$ and $R^{14B}$ substituents bonded to the same nitrogen atom is substituted, it is substituted with at least one lower substituent group.

In embodiments, $R^{14C}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_5$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{14C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{14C}$ is substituted with a plurality of groups selected from substituent groups, size-limited substituent groups, and lower substituent groups; each substituent group, size-limited substituent group, and/or lower substituent group may optionally be different. In embodiments, when $R^{14C}$ is substituted, it is substituted with at least one substituent group. In embodiments, when $R^{14C}$ is substituted, it is substituted with at least one size-limited substituent group. In embodiments, when $R^{14C}$ is substituted, it is substituted with at least one lower substituent group.

In embodiments, $R^{14D}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{14D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{14D}$ is substituted with a plurality of groups selected from substituent groups, size-limited substituent groups, and lower substituent groups; each substituent group, size-limited substituent group, and/or lower substituent group may optionally be different. In embodiments, when $R^{14D}$ is substituted, it is substituted with at least one substituent group. In embodiments, when $R^{14D}$ is substituted, it is substituted with at least one size-limited substituent group. In embodiments, when $R^{14D}$ is substituted, it is substituted with at least one lower substituent group.

In embodiments, $R^{14}$ is independently hydrogen. In embodiments, $R^{14}$ is independently halogen. In embodiments, $R^{14}$ is independently —F. In embodiments, $R^{14}$ is independently —Cl. In embodiments, $R^{14}$ is independently —Br. In embodiments, $R^{14}$ is independently —I. In embodiments, $R^{14}$ is independently —OH.

In embodiments, $R^{14}$ is independently $—OR^{14D}$. In embodiments, $R^{14D}$ is independently hydrogen. In embodiments, $R^{14D}$ is independently unsubstituted $C_1$-$C_4$ alkyl. In embodiments, $R^{14D}$ is independently unsubstituted methyl. In embodiments, $R^{14D}$ is independently unsubstituted ethyl. In embodiments, $R^{14D}$ is independently unsubstituted propyl. In embodiments, $R^{14D}$ is independently unsubstituted n-propyl. In embodiments, $R^{14D}$ is independently unsubstituted isopropyl. In embodiments, $R^{14D}$ is independently unsubstituted butyl. In embodiments, $R^{14D}$ is independently unsubstituted n-butyl. In embodiments, $R^{14D}$ is independently unsubstituted tert-butyl. In embodiments, $R^{14D}$ is independently substituted or unsubstituted aryl. In embodiments, $R^{14D}$ is independently substituted or unsubstituted phenyl.

In embodiments, $R^{15}$ is independently hydrogen, halogen, $—CX^{15}_3$, $—CHX^{15}_2$, $—CH_2X^{15}$, $—OCX^{15}_3$, $—OCH_2X^{15}$, $—OCHX^{15}_2$, —CN, $—SO_{n15}R^{5D}$, $—SO_{v15}NR^{15A}R^{151B}$, $—NHC(O)NR^{15A}R^{15B}$, $—NR^{15C}NR^{15A}R^{15B}$, $—ONR^{15A}R^{15B}$, $—NHC(O)NR^{15C}NR^{15A}R^{15B}$, $—N(O)_{m15}$, $—NR^{15A}R^{15B}$, $—C(O)R^{15C}$, $—C(O)OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered). $R^{15A}$, $R^{15B}$, $R^{15C}$, and $R^{15D}$ are as described herein, including in embodiments. $X^{15}$ is independently —F, —Cl, —Br, or —I. The symbol n15 is independently an integer from 0 to 4. The symbols m15 and v15 are independently 1 or 2.

In embodiments, $R^{15}$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—SF_5$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{15}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{15}$ is substituted with a plurality of groups selected from substituent groups, size-limited substituent groups, and lower substituent groups; each substituent group, size-limited substituent group, and/or lower substituent group may optionally be different. In embodiments, when $R^{15}$ is substituted, it is substituted with at least one substituent group. In embodiments, when $R^{15}$ is substituted, it is substituted with at least one size-limited substituent group. In embodiments, when $R^{15}$ is substituted, it is substituted with at least one lower substituent group.

In embodiments, $R^{15A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{15A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{15A}$ is substituted with a plurality of groups selected from substituent groups, size-limited substituent groups, and lower substituent groups; each substituent group, size-limited substituent group, and/or lower substituent group may optionally be different. In embodiments, when $R^{15A}$ is substituted, it is substituted with at least one substituent group. In embodiments, when $R^{15A}$ is substituted, it is substituted with at least one size-limited substituent group. In embodiments, when $R^{15A}$ is substituted, it is substituted with at least one lower substituent group.

In embodiments, $R^{15B}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{15B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{15B}$ is substituted with a plurality of groups selected from substituent groups, size-limited substituent groups, and lower substituent groups; each substituent group, size-limited substituent group, and/or lower substituent group may optionally be different. In embodiments, when $R^{15B}$ is substituted, it is substituted with at least one substituent group. In embodiments, when $R^{15B}$ is substituted, it is substituted with at least one size-limited substituent group. In embodiments, when $R^{15B}$ is substituted, it is substituted with at least one lower substituent group.

In embodiments, $R^{15A}$ and $R^{15B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{15A}$ and $R^{15B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{15A}$ and $R^{15B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{15A}$ and $R^{15B}$ substituents bonded to the same nitrogen atom is substituted, it is substituted with at least one substituent group. In embodiments, when the moiety formed by joining $R^{15A}$ and $R^{15B}$ substituents bonded to the same nitrogen atom is substituted, it is substituted with at least one size-limited substituent group. In embodiments, when the moiety formed by joining $R^{15A}$ and $R^{15B}$ substituents bonded to the same nitrogen atom is substituted, it is substituted with at least one lower substituent group.

In embodiments, $R^{15C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{15C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{15C}$ is substituted with a plurality of groups selected from substituent groups, size-limited substituent groups, and lower substituent groups; each substituent group, size-limited substituent group, and/or lower substituent group may optionally be different. In embodiments, when $R^{15C}$ is substituted, it is substituted with at least one substituent group. In embodiments, when $R^{15C}$ is substituted, it is substituted with at least one size-limited substituent group. In embodiments, when $R^{15C}$ is substituted, it is substituted with at least one lower substituent group.

In embodiments, $R^{15D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{15D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{15D}$ is substituted with a plurality of groups selected from substituent groups, size-limited substituent groups, and lower substituent groups; each substituent group, size-limited substituent group, and/or lower substituent group may optionally be different. In embodiments, when $R^{15D}$ is substituted, it is substituted with at least one substituent group. In embodiments, when $R^{15D}$ is substituted, it is substituted with at least one size-limited substituent group. In embodiments, when $R^{15D}$ is substituted, it is substituted with at least one lower substituent group.

In embodiments, $R^{15}$ is independently hydrogen. In embodiments, $R^{15}$ is independently halogen. In embodiments, $R^{15}$ is independently —F. In embodiments, $R^{15}$ is independently —Cl. In embodiments, $R^{15}$ is independently —Br. In embodiments, $R^{15}$ is independently —I. In embodiments, $R^{15}$ is independently —OH.

In embodiments, $R^{15}$ is independently —$OR^{15D}$. In embodiments, $R^{15D}$ is independently hydrogen. In embodiments, $R^{15D}$ is independently unsubstituted $C_1$-$C_4$ alkyl. In embodiments, $R^{15D}$ is independently unsubstituted methyl. In embodiments, $R^{15D}$ is independently unsubstituted ethyl. In embodiments, $R^{15D}$ is independently unsubstituted propyl. In embodiments, $R^{15D}$ is independently unsubstituted n-propyl. In embodiments, $R^{15D}$ is independently unsubstituted isopropyl. In embodiments, $R^{15D}$ is independently unsubstituted butyl. In embodiments, $R^{15D}$ is independently unsubstituted n-butyl. In embodiments, $R^{15D}$ is independently unsubstituted tert-butyl. In embodiments, $R^{15D}$ is independently substituted or unsubstituted aryl. In embodiments, $R^{15D}$ is independently substituted or unsubstituted phenyl.

In embodiments, $R^1$ and $R^2$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^1$ and $R^2$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^1$ and $R^2$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^1$ and $R^2$ substituents is substituted, it is substituted with at least one substituent group. In embodiments, when the ring formed by joining $R^1$ and $R^2$ substituents is substituted, it is substituted with at least one size-limited substituent group. In embodiments, when the ring formed by joining $R^1$ and $R^2$ substituents is substituted, it is substituted with at least one lower substituent group.

In embodiments, $R^2$ and $R^3$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^2$ and $R^3$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^2$ and $R^3$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^2$ and $R^3$ substituents is substituted, it is substituted with at least one substituent group. In embodiments, when the ring formed by joining $R^2$ and $R^3$ substituents is substituted, it is substituted with at least one size-limited substituent group. In embodiments, when the ring formed by joining $R^2$ and $R^3$ substituents is substituted, it is substituted with at least one lower substituent group.

In embodiments, $R^3$ and $R^4$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^3$ and $R^4$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^3$ and $R^4$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^3$ and $R^4$ substituents is substituted, it is substituted with at least one substituent group. In embodiments, when the ring formed by joining $R^3$ and $R^4$ substituents is substituted, it is substituted with at least one size-limited substituent group. In embodiments, when the ring formed by joining $R^3$ and $R^4$ substituents is substituted, it is substituted with at least one lower substituent group.

In embodiments, $R^4$ and $R^5$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^4$ and $R^5$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^4$ and $R^5$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^4$ and $R^5$ substituents is substituted, it is substituted with at least one substituent group. In embodiments, when the ring formed by joining $R^4$ and $R^5$ substituents is substituted, it is substituted with at least one size-limited substituent group. In embodiments, when the ring formed by joining $R^4$ and $R^5$ substituents is substituted, it is substituted with at least one lower substituent group.

In embodiments, $R^6$ and $R^7$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^6$ and $R^7$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^6$ and $R^7$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^6$ and $R^7$ substituents is substituted, it is substituted with at least one substituent group. In embodiments, when the ring formed by joining $R^6$ and $R^7$ substituents is substituted, it is substituted with at least one size-limited substituent group. In embodiments, when the ring formed by joining $R^6$ and $R^7$ substituents is substituted, it is substituted with at least one lower substituent group.

In embodiments, $R^7$ and $R^8$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^7$ and $R^8$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^7$ and $R^8$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^7$ and $R^8$ substituents is substituted, it is substituted with at least one substituent group. In embodiments, when the ring formed by joining $R^7$ and $R^8$ substituents is substituted, it is substituted with at least one size-limited substituent group. In embodiments, when the ring formed by joining $R^7$ and $R^8$ substituents is substituted, it is substituted with at least one lower substituent group.

In embodiments, $R^8$ and $R^9$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^8$ and $R^9$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^8$ and $R^9$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^8$ and $R^9$ substituents is substituted, it is substituted with at least one substituent group. In embodiments, when the ring formed by joining $R^8$ and $R^9$ substituents is substituted, it is substituted with at least one size-limited substituent group. In embodiments, when the ring formed by joining $R^8$ and $R^9$ substituents is substituted, it is substituted with at least one lower substituent group.

In embodiments, $R^9$ and $R^{10}$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^9$ and $R^{10}$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^9$ and $R^{10}$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^9$ and $R^{10}$ substituents is substituted, it is substituted with at least one substituent group. In embodiments, when the ring formed by joining $R^9$ and $R^{10}$ substituents is substituted, it is substituted with at least one size-limited substituent group. In embodiments, when the ring formed by joining $R^9$ and $R^{10}$ substituents is substituted, it is substituted with at least one lower substituent group.

In embodiments, $R^{11}$ and $R^{12}$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^{11}$ and $R^{12}$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^{11}$ and $R^{12}$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^{11}$ and $R^{12}$ substituents is substituted, it is substituted with at least one substituent group. In embodiments, when the ring formed by joining $R^{11}$ and $R^{12}$ substituents is substituted, it is substituted with at least one size-limited substituent group. In embodiments, when the ring formed by joining $R^{11}$ and $R^{12}$ substituents is substituted, it is substituted with at least one lower substituent group.

In embodiments, $R^{12}$ and $R^{13}$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^{12}$ and $R^{13}$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^{12}$ and $R^{13}$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^{12}$ and $R^{13}$ substituents is substituted, it is substituted with at least one substituent group. In embodiments, when the ring formed by joining $R^{12}$ and $R^{13}$ substituents is substituted, it is substituted with at least one size-limited substituent group. In embodiments, when the ring formed by joining $R^{12}$ and $R^{13}$ substituents is substituted, it is substituted with at least one lower substituent group.

In embodiments, $R^{13}$ and $R^{14}$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^{13}$ and $R^{14}$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^{13}$ and $R^{14}$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^{13}$ and $R^{14}$ substituents is substituted, it is substituted with at least one substituent group. In embodiments, when the ring formed by joining $R^{13}$ and $R^{14}$ substituents is substituted, it is substituted with at least one size-limited substituent group. In embodiments, when the ring formed by joining $R^{13}$ and $R^{14}$ substituents is substituted, it is substituted with at least one lower substituent group.

In embodiments, $R^{14}$ and $R^{15}$ substituents may be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted ring formed by joining $R^{14}$ and $R^{15}$ substituents (e.g., substituted cycloalkyl, substituted heterocycloalkyl, substituted aryl, and/or substituted heteroaryl) is substituted with at least one substituent group, size-limited substituent group, or lower substituent group; wherein if the substituted ring formed by joining $R^{14}$ and $R^{15}$ substituents is substituted with a plurality of groups selected from substituent groups, size-limited substituent groups, and lower substituent groups; each substituent group, size-limited substituent group, and/or lower substituent group may optionally be different. In embodiments, when the ring formed by joining $R^{14}$ and $R^{15}$ substituents is substituted, it is substituted with at least one substituent group. In embodiments, when the ring formed by joining $R^{14}$ and $R^{15}$ substituents is substituted, it is substituted with at least one size-limited substituent group. In embodiments, when the ring formed by joining $R^{14}$ and $R^{15}$ substituents is substituted, it is substituted with at least one lower substituent group.

In embodiments, $R^1$ is independently —$OR^{1D}$; $R^6$ is independently —$OR^{6D}$; $R^{11}$ is independently —$OR^{11D}$; and $R^4$, $R^9$, and $R^{14}$ are each independently halogen. In embodiments, $R^1$, $R^6$, and $R^{11}$ are each independently —OH; and $R^4$, $R^9$, and $R^{14}$ are each independently —Cl.

In embodiments, $R^1$ is independently —$OR^{1D}$; $R^6$ is independently —$OR^{6D}$; and $R^4$ and $R^9$ are each independently halogen. In embodiments, $R^1$ and $R^6$ are each independently —OH; and $R^4$ and $R^9$ are each independently —Cl.

In embodiments, when $R^1$ is substituted, $R^1$ is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when $R^{1A}$ is substituted, $R^{1A}$ is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A}$, $R^{1A.1}$, $R^{1A.2}$, and $R^{1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1A}$, $R^{1A.1}$, $R^{1A.2}$, and $R^{1A.3}$, respectively.

In embodiments, when $R^{1B}$ is substituted, $R^{1B}$ is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B}$, $R^{1B.1}$, $R^{1B.2}$, and $R^{1B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1B}$, $R^{1B.1}$, $R^{1B.2}$, and $R^{1B.3}$, respectively.

In embodiments, when $R^{1A}$ and $R^{1B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A.1}$, $R^{1A.2}$, and $R^{1A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{1A.1}$, $R^{1A.2}$, and $R^{1A.3}$, respectively.

In embodiments, when $R^{1A}$ and $R^{1B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B.1}$, $R^{1B.2}$, and $R^{1B.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{1B.1}$, $R^{1B.2}$, and $R^{1B.3}$, respectively.

In embodiments, when $R^{1C}$ is substituted, $R^{1C}$ is substituted with one or more first substituent groups denoted by $R^{1C.1}$ as explained in the definitions section above in the description of “first substituent group(s)”. In embodiments, when an $R^{1C.1}$ substituent group is substituted, the $R^{1C.1}$ substituent group is substituted with one or more second substituent groups denoted by $R^{1C.2}$ as explained in the definitions section above in the description of “first substituent group(s)”. In embodiments, when an $R^{1C.2}$ substituent group is substituted, the $R^{1C.2}$ substituent group is substituted with one or more third substituent groups denoted by $R^{1C.3}$ as explained in the definitions section above in the description of “first substituent group(s)”. In the above embodiments, $R^{1C}$, $R^{1C.1}$, $R^{1C.2}$, and $R^{1C.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{1C}$, $R^{1C.1}$, $R^{1C.2}$, and $R^{1C.3}$, respectively.

In embodiments, when $R^{1D}$ is substituted, $R^{1D}$ is substituted with one or more first substituent groups denoted by $R^{1D.1}$ as explained in the definitions section above in the description of “first substituent group(s)”. In embodiments, when an $R^{1D.1}$ substituent group is substituted, the $R^{1D.1}$ substituent group is substituted with one or more second substituent groups denoted by $R^{1D.2}$ as explained in the definitions section above in the description of “first substituent group(s)”. In embodiments, when an $R^{1D.2}$ substituent group is substituted, the $R^{1D.2}$ substituent group is substituted with one or more third substituent groups denoted by $R^{1D.3}$ as explained in the definitions section above in the description of “first substituent group(s)”. In the above embodiments, $R^{1D}$, $R^{1D.1}$, $R^{1D.2}$, and $R^{1D.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{1D}$, $R^{1D.1}$, $R^{1D.2}$, and $R^{1D.3}$, respectively.

In embodiments, when $R^2$ is substituted, $R^2$ is substituted with one or more first substituent groups denoted by $R^{2.1}$ as explained in the definitions section above in the description of “first substituent group(s)”. In embodiments, when an $R^{2.1}$ substituent group is substituted, the $R^{2.1}$ substituent group is substituted with one or more second substituent groups denoted by $R^{2.2}$ as explained in the definitions section above in the description of “first substituent group(s)”. In embodiments, when an $R^{2.2}$ substituent group is substituted, the $R^{2.2}$ substituent group is substituted with one or more third substituent groups denoted by $R^{2.3}$ as explained in the definitions section above in the description of “first substituent group(s)”. In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when $R^{2A}$ is substituted, $R^{2A}$ is substituted with one or more first substituent groups denoted by $R^{2A.1}$ as explained in the definitions section above in the description of “first substituent group(s)”. In embodiments, when an $R^{2A.1}$ substituent group is substituted, the $R^{2A.1}$ substituent group is substituted with one or more second substituent groups denoted by $R^{2A.2}$ as explained in the definitions section above in the description of “first substituent group(s)”. In embodiments, when an $R^{2A.2}$ substituent group is substituted, the $R^{2A.2}$ substituent group is substituted with one or more third substituent groups denoted by $R^{2A.3}$ as explained in the definitions section above in the description of “first substituent group(s)”. In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$ and $R^{WW.3}$ correspond to $R^{2A}$, $R^{2A.1}$, $R^{2A.2}$, and $R^{2A.3}$, respectively.

In embodiments, when $R^{2B}$ is substituted, $R^{2B}$ is substituted with one or more first substituent groups denoted by $R^{2B.1}$ as explained in the definitions section above in the description of “first substituent group(s)”. In embodiments, when an $R^{2B.1}$ substituent group is substituted, the $R^{2B.1}$ substituent group is substituted with one or more second substituent groups denoted by $R^{2B.2}$ as explained in the definitions section above in the description of “first substituent group(s)”. In embodiments, when an $R^{2B.2}$ substituent group is substituted, the $R^{2B.2}$ substituent group is substituted with one or more third substituent groups denoted by $R^{2B.3}$ as explained in the definitions section above in the description of “first substituent group(s)”. In the above embodiments, $R^{2B}$, $R^{2B.1}$, $R^{2B.2}$ and $R^{2B.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2A}$ and $R^{2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{2A.1}$ as explained in the definitions section above in the description of “first substituent group(s)”. In embodiments, when an $R^{2A.1}$ substituent group is substituted, the $R^{2A.1}$ substituent group is substituted with one or more second substituent groups denoted by $R^{2A.2}$ as explained in the definitions section above in the description of “first substituent group(s)”. In embodiments, when an $R^{2A.2}$ substituent group is substituted, the $R^{2A.2}$ substituent group is substituted with one or more third substituent groups denoted by $R^{2A.3}$ as explained in the definitions section above in the description of “first substituent group(s)”. In the above embodiments, $R^{2A.1}$, $R^{2A.2}$, and $R^{2A.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{2A.1}$, $R^{2A.2}$, and $R^{2A.3}$, respectively.

In embodiments, when $R^{2A}$ and $R^{2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{2B.1}$ as explained in the definitions section above in the description of “first substituent group(s)”. In embodiments, when an $R^{2B.1}$ substituent group is substituted, the $R^{2B.1}$ substituent group is substituted with one or more second substituent groups denoted by $R^{2B.2}$ as explained in the definitions section above in the description of “first substituent group(s)”. In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B.1}$, $R^{2B.2}$, and $R^{2B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{2B.1}$, $R^{2B.2}$, and $R^{2B.3}$, respectively.

In embodiments, when $R^{2C}$ is substituted, $R^{2C}$ is substituted with one or more first substituent groups denoted by $R^{2C.1}$ as explained in the definitions section above in the description of "first substituent group(s)". In embodiments, when an $R^{2C.1}$ substituent group is substituted, the $R^{2C.1}$ substituent group is substituted with one or more second substituent groups denoted by $R^{2C.2}$ as explained in the definitions section above in the description of "first substituent group(s)". In embodiments, when an $R^{2C.2}$ substituent group is substituted, the $R^{2C.2}$ substituent group is substituted with one or more third substituent groups denoted by $R^{2C.3}$ as explained in the definitions section above in the description of "first substituent group(s)". In the above embodiments, $R^{2C}$, $R^{2C.1}$, $R^{2C.2}$, and $R^{2C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2C}$, $R^{2C.1}$, $R^{2C.2}$, and $R^{2C.3}$, respectively.

In embodiments, when $R^{2D}$ is substituted, $R^{2D}$ is substituted with one or more first substituent groups denoted by $R^{2D.1}$ as explained in the definitions section above in the description of "first substituent group(s)". In embodiments, when an $R^{2D.1}$ substituent group is substituted, the $R^{2D.1}$ substituent group is substituted with one or more second substituent groups denoted by $R^{2D.2}$ as explained in the definitions section above in the description of "first substituent group(s)". In embodiments, when an $R^{2D.2}$ substituent group is substituted, the $R^{2D.2}$ substituent group is substituted with one or more third substituent groups denoted by $R^{2D.3}$ as explained in the definitions section above in the description of "first substituent group(s)". In the above embodiments, $R^{2D}$, $R^{2D.1}$, $R^{2D.2}$, and $R^{2D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2D}$, $R^{2D.1}$, $R^{2D.2}$, and $R^{2D.3}$, respectively.

In embodiments, when $R^3$ is substituted, $R^3$ is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.2}$ substituent group is substituted, the $R^{3.2}$ substituent group is substituted with one or more third substituent groups denoted by $R^{3.3}$ as explained in the definitions section above in the description of "first substituent group(s)". In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, Respectively, as Explained in the Definitions section above in the description of "first substituent group(s)", wherein $R^{WW}$, $R^{WW.1}$, $R^{WW.2}$, and $R^{WW.3}$ correspond to $R^3$, $R^{3.1}$, $R^{3.2}$, and $R^{3.3}$, respectively.

In embodiments, when $R^{3A}$ is substituted, $R^{3A}$ is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A}$, $R^{3A.1}$, $R^{3A.2}$, and $R^{3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3A}$, $R^{3A.1}$, $R^{3A.2}$, and $R^{3A.3}$, respectively.

In embodiments, when $R^{3B}$ is substituted, $R^{3B}$ is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ as explained in the definitions section above in the description of "first substituent group(s)". In the above embodiments, $R^{3B}$, $R^{3B.1}$, $R^{3B.2}$, and $R^{3B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3B}$, $R^{3B.1}$, $R^{3B.2}$, and $R^{3B.3}$, respectively.

In embodiments, when $R^{3A}$ and $R^{3B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A.1}$, $R^{3A.2}$, and $R^{3A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{3A.1}$, $R^{3A.2}$, and $R^{3A.3}$, respectively.

In embodiments, when $R^{3A}$ and $R^{3B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ as explained in the definitions section above in the description of "first substituent group(s)". In the above embodiments, $R^{3B.1}$, $R^{3B.2}$, and $R^{3B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{3B.1}$, $R^{3B.2}$, and $R^{3B.3}$, respectively.

In embodiments, when $R^{3C}$ is substituted, $R^{3C}$ is substituted with one or more first substituent groups denoted by $R^{3C.1}$ as explained in the definitions section above in the description of "first substituent group(s)". In embodiments, when an $R^{3C.1}$ substituent group is substituted, the $R^{3C.1}$ substituent group is substituted with one or more second substituent groups denoted by $R^{3C.2}$ as explained in the definitions section above in the description of "first substituent group(s)". In embodiments, when an $R^{3C.2}$ substituent group is substituted, the $R^{3C.2}$ substituent group is substituted with one or more third substituent groups denoted by $R^{3C.3}$ as explained in the definitions section above in the description of "first substituent group(s)". In the above embodiments, $R^{3C}$, $R^{3C.1}$, $R^{3C.2}$, and $R^{3C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R_{WW}$, $R^{WW.1}$, $R^{WW.2}$ and $R^{WW.3}$ correspond to $R^{3C}$, $R^{3C.1}$, $R^{3C.2}$ and $R^{3C.3}$, respectively.

In embodiments, when $R^{3D}$ is substituted, $R^{3D}$ is substituted with one or more first substituent groups denoted by $R^{3D.1}$ as explained in the definitions section above in the description of "first substituent group(s)". In embodiments, when an $R^{3D.1}$ substituent group is substituted, the $R^{3D.1}$ substituent group is substituted with one or more second substituent groups denoted by $R^{3D.2}$ as explained in the definitions section above in the description of "first substituent group(s)". In embodiments, when an $R^{3D.2}$ substituent group is substituted, the $R^{3D.2}$ substituent group is substituted with one or more third substituent groups denoted by $R^{3D.3}$ as explained in the definitions section above in the description of "first substituent group(s)". In the above embodiments, $R^{3D}$, $R^{3D.1}$, $R^{3D.2}$, and $R^{3D.3}$ have values corresponding to the values of $R_{WW}$, $R_{WW.1}$, $R^{WW.2}$, and $R^{WW.3}$, respectively, as explained in the definitions section above in the description of "first substituent group(s)", wherein $R_{WW}$, $R_{WW.1}$, $R^{WW.2}$, and $R^{WW.3}$ correspond to $R^{3D}$, $R^{3D.1}$, $R^{3D.2}$, and $R^{3D.3}$, respectively.

In embodiments, when $R^4$ is substituted, $R^4$ is substituted with one or more first substituent groups denoted by $R^{4.1}$ as explained in the definitions section above in the description of "first substituent group(s)". In embodiments, when an $R^{4A.1}$ substituent group is substituted, the $R^{4A.1}$ substituent group is substituted with one or more second substituent groups denoted by $R^{4A.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R_{WW.1}$, $R^{WW.2}$, and $R^{WW.3}$ correspond to $R^4$, $R^{4.1}$, $R^{4.2}$, and $R^{4.3}$, respectively.

In embodiments, when $R^{4A}$ is substituted, $R^{4A}$ is substituted with one or more first substituent groups denoted by $R^{4A.1}$ as explained in the definitions section above in the description of "first substituent group(s)". In embodiments, when an $R^{4A.1}$ substituent group is substituted, the $R^{4A.1}$ substituent group is substituted with one or more second substituent groups denoted by $R^{4A.2}$ as explained in the definitions section above in the description of "first substituent group(s)". In embodiments, when an $R^{4A.2}$ substituent group is substituted, the $R^{4A.2}$ substituent group is substituted with one or more third substituent groups denoted by $R^{4A.3}$ as explained in the definitions section above in the description of "first substituent group(s)". In the above embodiments, $R^{4A}$, $R^{4A.1}$, $R^{4A.2}$, and $R^{4A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$ and $R^{WW.3}$ correspond to $R^{4A}$, $R^{4A.1}$, $R^{4A.2}$, and $R^{4A.3}$, respectively.

In embodiments, when $R^{4B}$ is substituted, $R^{4B}$ is substituted with one or more first substituent groups denoted by $R^{4B.1}$ as explained in the definitions section above in the description of "first substituent group(s)". In embodiments, when an $R^{4B.1}$ substituent group is substituted, the $R^{4B.1}$ substituent group is substituted with one or more second substituent groups denoted by $R^{4B.2}$ as explained in the definitions section above in the description of "first substituent group(s)". In embodiments, when an $R^{4B.2}$ substituent group is substituted, the $R^{4B.2}$ substituent group is substituted with one or more third substituent groups denoted by $R^{4B.3}$ as explained in the definitions section above in the description of "first substituent group(s)". In the above embodiments, $R^{4B}$, $R^{4B.1}$, $R^{4B.2}$, and $R^{4B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4B}$, $R^{4B.1}$, $R^{4B.2}$, and $R^{4B.3}$, respectively.

In embodiments, when $R^{4A}$ and $R^{4B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{4A.1}$ as explained in the definitions section above in the description of "first substituent group(s)". In embodiments, when an $R^{4A.1}$ substituent group is substituted, the $R^{4A.1}$ substituent group is substituted with one or more second substituent groups denoted by $R^{4A.2}$ as explained in the definitions section above in the description of "first substituent group(s)". In embodiments, when an $R^{4A.2}$ substituent group is substituted, the $R^{4A.2}$ substituent group is substituted with one or more third substituent groups denoted by $R^{4A.3}$ as explained in the definitions section above in the description of "first substituent group(s)". In the above embodiments, $R^{4A.1}$, $R^{4A.2}$, and $R^{4A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{4A.1}$, $R^{4A.2}$, and $R^{4A.3}$, respectively.

In embodiments, when $R^{4A}$ and $R^{4B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{4B.1}$ as explained in the definitions section above in the description of "first substituent group(s)". In embodiments, when an $R^{4B.1}$ substituent group is substituted, the $R^{4B.1}$ substituent group is substituted with one or more second substituent groups denoted by $R^{4B.2}$ as explained in the definitions section above in the description of "first substituent group(s)". In embodiments, when an $R^{4B.2}$ substituent group is substituted, the $R^{4B.2}$ substituent group is substituted with one or more third substituent groups denoted by $R^{4B.3}$ as explained in the definitions section above in the description of "first substituent group(s)". In the above embodiments, $R^{4B.1}$, $R^{4B.2}$, and $R^{4B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{4B.1}$, $R^{4B.2}$, and $R^{4B.3}$, respectively.

In embodiments, when $R^{4C}$ is substituted, $R^{4C}$ is substituted with one or more first substituent groups denoted by $R^{4C.1}$ as explained in the definitions section above in the description of "first substituent group(s)". In embodiments, when an $R^{4C.1}$ substituent group is substituted, the $R^{4C.1}$ substituent group is substituted with one or more second substituent groups denoted by $R^{4C.2}$ as explained in the definitions section above in the description of "first substituent group(s)". In embodiments, when an $R^{4C.2}$ substituent group is substituted, the $R^{4C.2}$ substituent group is substituted with one or more third substituent groups denoted by $R^{4C.3}$ as explained in the definitions section above in the description of "first substituent group(s)". In the above embodiments, $R^{4C}$, $R^{4C.1}$, $R^{4C.2}$, and $R^{4C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4C}$, $R^{4C.1}$, $R^{4C.2}$, and $R^{4C.3}$, respectively.

In embodiments, when $R^{4D}$ is substituted, $R^{4D}$ is substituted with one or more first substituent groups denoted by $R^{4D.1}$ as explained in the definitions section above in the description of "first substituent group(s)". In embodiments, when an $R^{4D.1}$ substituent group is substituted, the $R^{4D.1}$ substituent group is substituted with one or more second substituent groups denoted by $R^{4D.2}$ as explained in the definitions section above in the description of "first substituent group(s)". In embodiments, when an $R^{4D.2}$ substituent group is substituted, the $R^{4D.2}$ substituent group is substituted with one or more third substituent groups denoted by $R^{4D.3}$ as explained in the definitions section above in the description of "first substituent group(s)". In the above embodiments, $R^{4D}$, $R^{4D.1}$, $R^{4D.2}$, and $R^{4D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4D}$, $R^{4D.1}$, $R^{4D.2}$, and $R^{4D.3}$, respectively.

In embodiments, when $R^5$ is substituted, $R^5$ is substituted with one or more first substituent groups denoted by $R^{5.1}$ as explained in the definitions section above in the description of "first substituent group(s)". In embodiments, when an $R^{5.1}$ substituent group is substituted, the $R^{5.1}$ substituent group is substituted with one or more second substituent groups denoted by $R^{5.2}$ as explained in the definitions section above in the description of "first substituent group(s)". In embodiments, when an $R^{5.2}$ substituent group is substituted, the $R^{5.2}$ substituent group is substituted with one or more third substituent groups denoted by $R^{5.3}$ as explained in the definitions section above in the description of "first substituent group(s)". In the above embodiments, $R^5$, $R^{5.1}$, $R^{5.2}$, and $R^{5.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^5$, $R^{5.1}$, $R^{5.2}$, and $R^{5.3}$, respectively.

In embodiments, when $R^{5A}$ is substituted, $R^{5A}$ is substituted with one or more first substituent groups denoted by $R^{5A.1}$ as explained in the definitions section above in the description of "first substituent group(s)". In embodiments, when an $R^{5A.1}$ substituent group is substituted, the $R^{5A.1}$ substituent group is substituted with one or more second substituent groups denoted by $R^{5A.2}$ as explained in the definitions section above in the description of "first substituent group(s)". In embodiments, when an $R^{5A.2}$ substituent group is substituted, the $R^{5A.2}$ substituent group is substituted with one or more third substituent groups denoted by $R^{5A.3}$ as explained in the definitions section above in the description of "first substituent group(s)". In the above embodiments, $R^{5A}$, $R^{5A.1}$, $R^{5A.2}$, and $R^{5A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{5A}$, $R^{5A.1}$, $R^{5A.2}$, and $R^{5A.3}$, respectively.

In embodiments, when $R^{5B}$ is substituted, $R^{5B}$ is substituted with one or more first substituent groups denoted by $R^{5B.1}$ as explained in the definitions section above in the description of "first substituent group(s)". In embodiments, when an $R^{5B.1}$ substituent group is substituted, the $R^{5B.1}$ substituent group is substituted with one or more second substituent groups denoted by $R^{5B.2}$ as explained in the definitions section above in the description of "first substituent group(s)". In embodiments, when an $R^{5B.2}$ substituent group is substituted, the $R^{5B.2}$ substituent group is substituted with one or more third substituent groups denoted by $R^{5B.3}$ as explained in the definitions section above in the description of "first substituent group(s)". In the above embodiments, $R^{5B}$, $R^{5B.1}$, $R^{5B.2}$, and $R^{5B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{5B}$, $R^{5B.1}$, $R^{5B.2}$, and $R^{5B.3}$, respectively.

In embodiments, when $R^{5A}$ and $R^{5B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{5A.1}$ as explained in the definitions section above in the description of "first substituent group(s)". In embodiments, when an $R^{5A.1}$ substituent group is substituted, the $R^{5A.1}$ substituent group is substituted with one or more second substituent groups denoted by $R^{5A.2}$ as explained in the definitions section above in the description of "first substituent group(s)". In embodiments, when an $R^{5A.2}$ substituent group is substituted, the $R^{5A.2}$ substituent group is substituted with one or more third substituent groups denoted by $R^{5A.3}$ as explained in the definitions section above in the description of "first substituent group(s)". In the above embodiments, $R^{5A.1}$, $R^{5A.2}$, and $R^{5A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{5A.1}$, $R^{5A.2}$, and $R^{5A.3}$, respectively.

In embodiments, when $R^{5A}$ and $R^{5B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{5B.1}$ as explained in the definitions section above in the description of "first substituent group(s)". In embodiments, when an $R^{5B.1}$ substituent group is substituted, the $R^{5B.1}$ substituent group is substituted with one or more second substituent groups denoted by $R^{5B.2}$ as explained in the definitions section above in the description of "first substituent group(s)". In embodiments, when an $R^{5B.2}$ substituent group is substituted, the $R^{5B.2}$ substituent group is substituted with one or more third substituent groups denoted by $R^{5B.3}$ as explained in the definitions section above in the description of "first substituent group(s)". In the above embodiments, $R^{5B.1}$, $R^{5B.2}$ and $R^{5B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{5B.1}$, $R^{5B.2}$, and $R^{5B.3}$, respectively.

In embodiments, when $R^{5C}$ is substituted, $R^{5C}$ is substituted with one or more first substituent groups denoted by $R^{5C.1}$ as explained in the definitions section above in the description of "first substituent group(s)". In embodiments, when an $R^{5C.1}$ substituent group is substituted, the $R^{5C.1}$ substituent group is substituted with one or more second substituent groups denoted by $R^{5C.2}$ as explained in the definitions section above in the description of "first substituent group(s)". In embodiments, when an $R^{5C.2}$ substituent group is substituted, the $R^{5C.2}$ substituent group is substituted with one or more third substituent groups denoted by $R^{5C.3}$ as explained in the definitions section above in the description of "first substituent group(s)". In the above embodiments, $R^{5C}$, $R^{5C.1}$, $R^{5C.2}$, and $R^{5C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{5C}$, $R^{5C.1}$, $R^{5C.2}$, and $R^{5C.3}$, respectively.

In embodiments, when $R^{5D}$ is substituted, $R^{5D}$ is substituted with one or more first substituent groups denoted by $R^{5D.1}$ as explained in the definitions section above in the description of "first substituent group(s)". In embodiments, when an $R^{5D.1}$ substituent group is substituted, the $R^{5D.1}$ substituent group is substituted with one or more second substituent groups denoted by $R^{5D.2}$ as explained in the definitions section above in the description of "first substituent group(s)". In embodiments, when an $R^{5D.2}$ substituent group is substituted, the $R^{5D.2}$ substituent group is substituted with one or more third substituent groups denoted by $R^{5D.3}$ as explained in the definitions section above in the description of "first substituent group(s)". In the above embodiments, $R^{5D}$, $R^{5D.1}$, $R^{5D.2}$, and $R^{5D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{5D}$, $R^{5D.1}$, $R^{5D.2}$, and $R^{5D.3}$, respectively.

In embodiments, when $R^{6}$ is substituted, $R^{6}$ is substituted with one or more first substituent groups denoted by $R^{6.1}$ as explained in the definitions section above in the description of "first substituent group(s)". In embodiments, when an $R^{6.1}$ substituent group is substituted, the $R^{6.1}$ substituent group is substituted with one or more second substituent groups denoted by $R^{6.2}$ as explained in the definitions section above in the description of "first substituent group(s)". In embodiments, when an $R^{6.2}$ substituent group is substituted, the $R^{6.2}$ substituent group is substituted with one or more third substituent groups denoted by $R^{6.3}$ as explained in the definitions section above in the description of "first substituent group(s)". In the above embodiments, $R^{6}$, $R^{6.1}$, $R^{6.2}$, and $R^{6.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6}$, $R^{6.1}$, $R^{6.2}$, and $R^{6.3}$, respectively.

In embodiments, when $R^{6A}$ is substituted, $R^{6A}$ is substituted with one or more first substituent groups denoted by $R^{6A.1}$ as explained in the definitions section above in the description of "first substituent group(s)". In embodiments, when an $R^{6A.1}$ substituent group is substituted, the $R^{6A.1}$ substituent group is substituted with one or more second substituent groups denoted by $R^{6A.2}$ as explained in the definitions section above in the description of "first substituent group(s)". In embodiments, when an $R^{6A.2}$ substituent group is substituted, the $R^{6A.2}$ substituent group is substituted with one or more third substituent groups denoted by $R^{6A.3}$ as explained in the definitions section above in the description of "first substituent group(s)". In the above embodiments, $R^{6A}$, $R^{6A.1}$, $R^{6A.2}$, and $R^{6A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6A}$, $R^{6A.1}$, $R^{6A.2}$, and $R^{6A.3}$, respectively.

In embodiments, when $R^{6B}$ is substituted, $R^{6B}$ is substituted with one or more first substituent groups denoted by $R^{6B.1}$ as explained in the definitions section above in the description of "first substituent group(s)". In embodiments, when an $R^{6B.1}$ substituent group is substituted, the $R^{6B.1}$ substituent group is substituted with one or more second substituent groups denoted by $R^{6B.2}$ as explained in the definitions section above in the description of "first substituent group(s)". In embodiments, when an $R^{6B.2}$ substituent group is substituted, the $R^{6B.2}$ substituent group is substituted with one or more third substituent groups denoted by $R^{6B.3}$ as explained in the definitions section above in the description of "first substituent group(s)". In the above embodiments, $R^{6B}$, $R^{6B.1}$, $R^{6B.2}$, and $R^{6B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6B}$, $R^{6B.1}$, $R^{6B.2}$, and $R^{6B.3}$, respectively.

In embodiments, when $R^{6A}$ and $R^{6B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{6A.1}$ as explained in the definitions section above in the description of "first substituent group(s)". In embodiments, when an $R^{6A.1}$ substituent group is substituted, the $R^{6A.1}$ substituent group is substituted with one or more second substituent groups denoted by $R^{6A.2}$ as explained in the definitions section above in the description of "first substituent group(s)". In embodiments, when an $R^{6A.2}$ substituent group is substituted, the $R^{6A.2}$ substituent group is substituted with one or more third substituent groups denoted by $R^{6A.3}$ as explained in the definitions section above in the description of "first substituent group(s)". In the above embodiments, $R^{6A.1}$, $R^{6A.2}$, and $R^{6A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{6A.1}$, $R^{6A.2}$, and $R^{6A.3}$, respectively.

In embodiments, when $R^{6A}$ and $R^{6B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{6B.1}$ as explained in the definitions section above in the description of "first substituent group(s)". In embodiments, when an $R^{6B.1}$ substituent group is substituted, the $R^{6B.1}$ substituent group is substituted with one or more second substituent groups denoted by $R^{6B.2}$ as explained in the definitions section above in the description of "first substituent group(s)". In embodiments, when an $R^{6B.2}$ substituent group is substituted, the $R^{6B.2}$ substituent group is substituted with one or more third substituent groups denoted by $R^{6B.3}$ as explained in the definitions section above in the description of "first substituent group(s)". In the above embodiments, $R^{6B.1}$, $R^{6B.2}$, and $R^{6B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{6B.1}$, $R^{6B.2}$, and $R^{6B.3}$, respectively.

In embodiments, when $R^{6C}$ is substituted, $R^{6C}$ is substituted with one or more first substituent groups denoted by $R^{6C.1}$ as explained in the definitions section above in the description of "first substituent group(s)". In embodiments, when an $R^{6C.1}$ substituent group is substituted, the $R^{6C.1}$ substituent group is substituted with one or more second substituent groups denoted by $R^{6C.2}$ as explained in the definitions section above in the description of "first substituent group(s)". In embodiments, when an $R^{6C.2}$ substituent group is substituted, the $R^{6C.2}$ substituent group is substituted with one or more third substituent groups denoted by $R^{6C.3}$ as explained in the definitions section above in the description of "first substituent group(s)". In the above embodiments, $R^{6C}$, $R^{6C.1}$, $R^{6C.2}$, and $R^{6C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6C}$, $R^{6C.1}$, $R^{6C.2}$, and $R^{6C.3}$, respectively.

In embodiments, when $R^{6D}$ is substituted, $R^{6D}$ is substituted with one or more first substituent groups denoted by $R^{6D.1}$ as explained in the definitions section above in the description of "first substituent group(s)". In embodiments, when an $R^{6D.1}$ substituent group is substituted, the $R^{6D.1}$ substituent group is substituted with one or more second substituent groups denoted by $R^{6D.2}$ as explained in the definitions section above in the description of "first substituent group(s)". In embodiments, when an $R^{6D.2}$ substituent group is substituted, the $R^{6D.2}$ substituent group is substituted with one or more third substituent groups denoted by $R^{6D.3}$ as explained in the definitions section above in the description of "first substituent group(s)". In the above embodiments, $R^{6D}$, $R^{6D.1}$, $R^{6D.2}$, and $R^{6D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6D}$, $R^{6D.1}$, $R^{6D.2}$, and $R^{6D.3}$, respectively.

In embodiments, when $R^{7}$ is substituted, $R^{7}$ is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group(s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^{7}$, $R^{7.1}$, $R^{7.2}$, and $R^{7.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7}$, $R^{7.1}$, $R^{7.2}$, and $R^{7.3}$, respectively.

In embodiments, when $R^{7A}$ is substituted, $R^{7A}$ is substituted with one or more first substituent groups denoted by $R^{7A.1}$ as explained in the definitions section above in the description of "first substituent group(s)". In embodiments, when an $R^{7A.1}$ substituent group is substituted, the $R^{7A.1}$ substituent group is substituted with one or more second substituent groups denoted by $R^{7A.2}$ as explained in the definitions section above in the description of "first substituent group(s)". In embodiments, when an $R^{7A.2}$ substituent group is substituted, the $R^{7A.2}$ substituent group is substituted with one or more third substituent groups denoted by $R^{7A.3}$ as explained in the definitions section above in the description of "first substituent group(s)". In the above embodiments, $R^{7A}$, $R^{7A.1}$, $R^{7A.2}$, and $R^{7A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7A}$, $R^{7A.1}$, $R^{7A.2}$, and $R^{7A.3}$, respectively.

In embodiments, when $R^{7B}$ is substituted, $R^{7B}$ is substituted with one or more first substituent groups denoted by $R^{7B.1}$ as explained in the definitions section above in the description of "first substituent group(s)". In embodiments, when an $R^{7B.1}$ substituent group is substituted, the $R^{7B.1}$ substituent group is substituted with one or more second substituent groups denoted by $R^{7B.2}$ as explained in the definitions section above in the description of "first substituent group(s)". In embodiments, when an $R^{7B.2}$ substituent group is substituted, the $R^{7B.2}$ substituent group is substituted with one or more third substituent groups denoted by $R^{7B.3}$ as explained in the definitions section above in the description of "first substituent group(s)". In the above embodiments, $R^{7B}$, $R^{7B.1}$, $R^{7B.2}$, and $R^{7B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7B}$, $R^{7B.1}$, $R^{7B.2}$, and $R^{7B.3}$, respectively.

In embodiments, when $R^{7A}$ and $R^{7B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{7A.1}$ as explained in the definitions section above in the description of "first substituent group(s)". In embodiments, when an $R^{7A.1}$ substituent group is substituted, the $R^{7A.1}$ substituent group is substituted with one or more second substituent groups denoted by $R^{7A.2}$ as explained in the definitions section above in the description of "first substituent group(s)". In embodiments, when an $R^{7A.2}$ substituent group is substituted, the $R^{7A.2}$ substituent group is substituted with one or more third substituent groups denoted by $R^{7A.3}$ as explained in the definitions section above in the description of "first substituent group(s)". In the above embodiments, $R^{7A.1}$, $R^{7A.2}$, and $R^{7A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{7A.1}$, $R^{7A.2}$, and $R^{7A.3}$, respectively.

In embodiments, when $R^{7A}$ and $R^{7B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{7B.1}$ as explained in the definitions section above in the description of "first substituent group(s)". In embodiments, when an $R^{7B.1}$ substituent group is substituted, the $R^{7B.1}$ substituent group is substituted with one or more second substituent groups denoted by $R^{7B.2}$ as explained in the definitions section above in the description of "first substituent group(s)". In embodiments, when an $R^{7B.2}$ substituent group is substituted, the $R^{7B.2}$ substituent group is substituted with one or more third substituent groups denoted by $R^{7B.3}$ as explained in the definitions section above in the description of "first substituent group(s)". In the above embodiments, $R^{7B.1}$, $R^{7B.2}$, and $R^{7B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{7B.1}$, $R^{7B.2}$, and $R^{7B.3}$, respectively.

In embodiments, when $R^{7C}$ is substituted, $R^{7C}$ is substituted with one or more first substituent groups denoted by $R^{7C.1}$ as explained in the definitions section above in the description of "first substituent group(s)". In embodiments, when an $R^{7C.1}$ substituent group is substituted, the $R^{7C.1}$ substituent group is substituted with one or more second substituent groups denoted by $R^{7C.2}$ as explained in the definitions section above in the description of "first substituent group(s)". In embodiments, when an $R^{7C.2}$ substituent group is substituted, the $R^{7C.2}$ substituent group is substituted with one or more third substituent groups denoted by $R^{7C.3}$ as explained in the definitions section above in the description of "first substituent group(s)". In the above embodiments, $R^{7C}$, $R^{7C.1}$, $R^{7C.2}$, and $R^{7C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7C}$, $R^{7C.1}$, $R^{7C.2}$, and $R^{7C.3}$, respectively.

In embodiments, when $R^{7D}$ is substituted, $R^{7D}$ is substituted with one or more first substituent groups denoted by $R^{7D.1}$ as explained in the definitions section above in the description of "first substituent group(s)". In embodiments, when an $R^{7D.1}$ substituent group is substituted, the $R^{7D.1}$ substituent group is substituted with one or more second substituent groups denoted by $R^{7D.2}$ as explained in the definitions section above in the description of "first substituent group(s)". In embodiments, when an $R^{7D.2}$ substituent group is substituted, the $R^{7D.2}$ substituent group is substituted with one or more third substituent groups denoted by $R^{7D.3}$ as explained in the definitions section above in the description of "first substituent group(s)". In the above embodiments, $R^{7D}$, $R^{7D.1}$, $R^{7D.2}$, and $R^{7D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7D}$, $R^{7D.1}$, $R^{7D.2}$, and $R^{7D.3}$, respectively.

In embodiments, when $R^8$ is substituted, $R^8$ is substituted with one or more first substituent groups denoted by $R^{8.1}$ as explained in the definitions section above in the description of "first substituent group(s)". In embodiments, when an $R^{8.1}$ substituent group is substituted, the $R^{8.1}$ substituent group is substituted with one or more second substituent groups denoted by $R^{8.2}$ as explained in the definitions section above in the description of "first substituent group(s)". In embodiments, when an $R^{8.2}$ substituent group is substituted, the $R^{8.2}$ substituent group is substituted with one or more third substituent groups denoted by $R^{8.3}$ as explained in the definitions section above in the description of "first substituent group(s)". In the above embodiments, $R^8$, $R^{8.1}$, $R^{8.2}$, and $R^{8.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^8$, $R^{8.1}$, $R^{8.2}$, and $R^{8.3}$, respectively.

In embodiments, when $R^{8A}$ is substituted, $R^{8A}$ is substituted with one or more first substituent groups denoted by $R^{8A.1}$ as explained in the definitions section above in the description of "first substituent group(s)". In embodiments, when an $R^{8A.1}$ substituent group is substituted, the $R^{8A.1}$ substituent group is substituted with one or more second substituent groups denoted by $R^{8A.2}$ as explained in the definitions section above in the description of "first substituent group(s)". In embodiments, when an $R^{8A.2}$ substituent group is substituted, the $R^{8A.2}$ substituent group is substituted with one or more third substituent groups denoted by $R^{8A.3}$ as explained in the definitions section above in the description of "first substituent group(s)". In the above embodiments, $R^{8A}$, $R^{8A.1}$, $R^{8A.2}$, and $R^{8A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$ and $R^{WW.3}$ correspond to $R^{8A}$, $R^{8A.1}$, $R^{8A.2}$, and $R^{8A.3}$, respectively.

In embodiments, when $R^{8B}$ is substituted, $R^{8B}$ is substituted with one or more first substituent groups denoted by $R^{8B.1}$ as explained in the definitions section above in the description of "first substituent group(s)". In embodiments, when an $R^{8B.1}$ substituent group is substituted, the $R^{8B.1}$ substituent group is substituted with one or more second substituent groups denoted by $R^{8B.2}$ as explained in the definitions section above in the description of "first substituent group(s)". In embodiments, when an $R^{8.2}$ substituent group is substituted, the $R^{8B.2}$ substituent group is substituted with one or more third substituent groups denoted by $R^{8B.3}$ as explained in the definitions section above in the description of "first substituent group(s)". In the above embodiments, $R^{8B}$, $R^{8B.1}$, $R^{8.2}$, and $R^{8B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8B}$, $R^{8B.1}$, $R^{8B.2}$, and $R^{8B.3}$, respectively.

In embodiments, when $R^{8A}$ and $R^{8B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{8A.1}$ as explained in the definitions section above in the description of "first substituent group(s)". In embodiments, when an $R^{8A.1}$ substituent group is substituted, the $R^{8A.1}$ substituent group is substituted with one or more second substituent groups denoted by $R^{8A.2}$ as explained in the definitions section above in the description of "first substituent group(s)". In embodiments, when an $R^{8A.2}$ substituent group is substituted, the $R^{8A.2}$ substituent group is substituted with one or more third substituent groups denoted by $R^{8A.3}$ as explained in the definitions section above in the description of "first substituent group(s)". In the above embodiments, $R^{8A.1}$, $R^{8A.2}$, and $R^{8A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{8A.1}$, $R^{8A.2}$, and $R^{8A.3}$, respectively.

In embodiments, when $R^{8A}$ and $R^{8B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{8B.1}$ as explained in the definitions section above in the description of "first substituent group(s)". In embodiments, when an $R^{8B.1}$ substituent group is substituted, the $R^{8B.1}$ substituent group is substituted with one or more second substituent groups denoted by $R^{8B.2}$ as explained in the definitions section above in the description of "first substituent group(s)". In embodiments, when an $R^{8B.2}$ substituent group is substituted, the $R^{8B.2}$ substituent group is substituted with one or more third substituent groups denoted by $R^{8B.3}$ as explained in the definitions section above in the description of "first substituent group(s)". In the above embodiments, $R^{8B.1}$, $R^{8B.2}$, and $R^{8B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{8B.1}$, $R^{8B.2}$, and $R^{8B.3}$, respectively.

In embodiments, when $R^{8C}$ is substituted, $R^{8C}$ is substituted with one or more first substituent groups denoted by $R^{8C.1}$ as explained in the definitions section above in the description of "first substituent group(s)". In embodiments, when an $R^{8C.1}$ substituent group is substituted, the $R^{8C.1}$ substituent group is substituted with one or more second substituent groups denoted by $R^{8C.2}$ as explained in the definitions section above in the description of "first substituent group(s)". In embodiments, when an $R^{8C.2}$ substituent group is substituted, the $R^{8C.2}$ substituent group is substituted with one or more third substituent groups denoted by $R^{8C.3}$ as explained in the definitions section above in the description of "first substituent group(s)". In the above embodiments, $R^{8C}$, $R^{8C.1}$, $R^{8C.2}$, and $R^{8C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8C}$, $R^{8C.1}$, $R^{8C.2}$, and $R^{8C.3}$, respectively.

In embodiments, when $R^{8D}$ is substituted, $R^{8D}$ is substituted with one or more first substituent groups denoted by $R^{8D.1}$ as explained in the definitions section above in the description of "first substituent group(s)". In embodiments, when an $R^{8D.1}$ substituent group is substituted, the $R^{8D.1}$ substituent group is substituted with one or more second substituent groups denoted by $R^{8D.2}$ as explained in the definitions section above in the description of "first substituent group(s)". In embodiments, when an $R^{8D.2}$ substituent group is substituted, the $R^{8D.2}$ substituent group is substituted with one or more third substituent groups denoted by $R^{8D.3}$ as explained in the definitions section above in the description of "first substituent group(s)". In the above embodiments, $R^{8D}$, $R^{8D.1}$, $R^{8D.2}$, and $R^{8D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8D}$, $R^{8D.1}$, $R^{8D.2}$, and $R^{8D.3}$, respectively.

In embodiments, when $R^9$ is substituted, $R^9$ is substituted with one or more first substituent groups denoted by $R^{9.1}$ as explained in the definitions section above in the description of "first substituent group(s)". In embodiments, when an $R^{9.1}$ substituent group is substituted, the $R^{9.1}$ substituent group is substituted with one or more second substituent groups denoted by $R^{9.2}$ as explained in the definitions section above in the description of "first substituent group(s)". In embodiments, when an $R^{9.2}$ substituent group is substituted, the $R^{9.2}$ substituent group is substituted with one or more third substituent groups denoted by $R^{9.3}$ as explained in the definitions section above in the description of "first substituent group(s)". In the above embodiments, $R^9$, $R^{9.1}$, $R^{9.2}$, and $R^{9.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^9$, $R^{9.1}$, $R^{9.2}$, and $R^{9.3}$, respectively.

In embodiments, when $R^{9A}$ is substituted, $R^{9A}$ is substituted with one or more first substituent groups denoted by $R^{9A.1}$ as explained in the definitions section above in the description of "first substituent group(s)". In embodiments, when an $R^{9A.1}$ substituent group is substituted, the $R^{9A.1}$ substituent group is substituted with one or more second substituent groups denoted by $R^{9A.2}$ as explained in the definitions section above in the description of "first substituent group(s)". In embodiments, when an $R^{9A.2}$ substituent group is substituted, the $R^{9A.2}$ substituent group is substituted with one or more third substituent groups denoted by $R^{9A.3}$ as explained in the definitions section above in the description of "first substituent group(s)". In the above embodiments, $R^{9A}$, $R^{9A.1}$, $R^{9A.2}$, and $R^{9A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$ and $R^{WW.3}$ correspond to $R^{9A}$, $R^{9A.1}$, $R^{9A.2}$, and $R^{9A.3}$, respectively.

In embodiments, when $R^{9B}$ is substituted, $R^{9B}$ is substituted with one or more first substituent groups denoted by $R^{9B.1}$ as explained in the definitions section above in the description of "first substituent group(s)". In embodiments, when an $R^{9B.1}$ substituent group is substituted, the $R^{9B.1}$ substituent group is substituted with one or more second substituent groups denoted by $R^{9B.2}$ as explained in the definitions section above in the description of "first substituent group(s)". In embodiments, when an $R^{9B.2}$ substituent group is substituted, the $R^{9B.2}$ substituent group is substituted with one or more third substituent groups denoted by $R^{9B.3}$ as explained in the definitions section above in the description of "first substituent group(s)". In the above embodiments, $R^{9B}$, $R^{9B.1}$, $R^{9B.2}$, and $R^{9B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9B}$, $R^{9B.1}$, $R^{9B.2}$, and $R^{9B.3}$, respectively.

In embodiments, when $R^{9A}$ and $R^{9B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{9A.1}$ as explained in the definitions section above in the description of "first substituent group(s)". In embodiments, when an $R^{9A.1}$ substituent group is substituted, the $R^{9A.1}$ substituent group is substituted with one or more second substituent groups denoted by $R^{9A.2}$ as explained in the definitions section above in the description of "first substituent group(s)". In embodiments, when an $R^{9A.2}$ substituent group is substituted, the $R^{9A.2}$ substituent group is substituted with one or more third substituent groups denoted by $R^{9A.3}$ as explained in the definitions section above in the description of "first substituent group(s)". In the above embodiments, $R^{9A.1}$, $R^{9A.2}$, and $R^{9A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{9A.1}$, $R^{9A.2}$, and $R^{9A.3}$, respectively.

In embodiments, when $R^{9A}$ and $R^{9B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{9B.1}$ as explained in the definitions section above in the description of "first substituent group(s)". In embodiments, when an $R^{9B.1}$ substituent group is substituted, the $R^{9B.1}$ substituent group is substituted with one or more second substituent groups denoted by $R^{9B.2}$ as explained in the definitions section above in the description of "first substituent group(s)". In embodiments, when an $R^{9B.2}$ substituent group is substituted, the $R^{9B.2}$ substituent group is substituted with one or more third substituent groups denoted by $R^{9B.3}$ as explained in the definitions section above in the description of "first substituent group(s)". In the above embodiments, $R^{9B.1}$, $R^{9B.2}$, and $R^{9B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{9B.1}$, $R^{9B.2}$, and $R^{9B.3}$, respectively.

In embodiments, when $R^{9C}$ is substituted, $R^{9C}$ is substituted with one or more first substituent groups denoted by $R^{9C.1}$ as explained in the definitions section above in the description of "first substituent group(s)". In embodiments, when an $R^{9C.1}$ substituent group is substituted, the $R^{9C.1}$ substituent group is substituted with one or more second substituent groups denoted by $R^{9C.2}$ as explained in the definitions section above in the description of "first substituent group(s)". In embodiments, when an $R^{9C.2}$ substituent group is substituted, the $R^{9C.2}$ substituent group is substituted with one or more third substituent groups denoted by $R^{9C.3}$ as explained in the definitions section above in the description of "first substituent group(s)". In the above embodiments, $R^{9C}$, $R^{9C.1}$, $R^{9C.2}$, and $R^{9C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9C}$, $R^{9C.1}$, $R^{9C.2}$, and $R^{9C.3}$, respectively.

In embodiments, when $R^{9D}$ is substituted, $R^{9D}$ is substituted with one or more first substituent groups denoted by $R^{9D.1}$ as explained in the definitions section above in the description of "first substituent group(s)". In embodiments, when an $R^{9D.1}$ substituent group is substituted, the $R^{9D.1}$ substituent group is substituted with one or more second substituent groups denoted by $R^{9D.2}$ as explained in the definitions section above in the description of "first substituent group(s)". In embodiments, when an $R^{9D.2}$ substituent group is substituted, the $R^{9D.2}$ substituent group is substituted with one or more third substituent groups denoted by $R^{9D.3}$ as explained in the definitions section above in the description of "first substituent group(s)". In the above embodiments, $R^{9D}$, $R^{9D.1}$, $R^{9D.2}$, and $R^{9D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9D}$, $R^{9D.1}$, $R^{9D.2}$, and $R^{9D.3}$, respectively.

In embodiments, when $R^{10}$ is substituted, $R^{10}$ is substituted with one or more first substituent groups denoted by $R^{10.1}$ as explained in the definitions section above in the description of "first substituent group(s)". In embodiments, when an $R^{10.1}$ substituent group is substituted, the $R^{10.1}$ substituent group is substituted with one or more second substituent groups denoted by $R^{10.2}$ as explained in the definitions section above in the description of "first substituent group(s)". In embodiments, when an $R^{10.2}$ substituent group is substituted, the $R^{10.2}$ substituent group is substituted with one or more third substituent groups denoted by $R^{10.3}$ as explained in the definitions section above in the description of "first substituent group(s)". In the above embodiments, $R^{10}$, $R^{101}$, $R^{10.2}$, and $R^{10.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10}$, $R^{10.1}$, $R^{10.2}$, and $R^{10.3}$, respectively.

In embodiments, when $R^{10A}$ is substituted, $R^{10A}$ is substituted with one or more first substituent groups denoted by $R^{10A.1}$ as explained in the definitions section above in the description of "first substituent group(s)". In embodiments, when an $R^{10A.1}$ substituent group is substituted, the $R^{10A.1}$ substituent group is substituted with one or more second substituent groups denoted by $R^{10A.2}$ as explained in the definitions section above in the description of "first substituent group(s)". In embodiments, when an $R^{10A.2}$ substituent group is substituted, the $R^{10A.2}$ substituent group is substituted with one or more third substituent groups denoted by $R^{10A.3}$ as explained in the definitions section above in the description of "first substituent group(s)". In the above embodiments, $R^{10A}$, $R^{10A.1}$, $R^{10A.2}$, and $R^{10A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10A}$, $R^{10A.1}$, $R^{10A.2}$, and $R^{10A.3}$, respectively.

In embodiments, when $R^{10B}$ is substituted, $R^{10B}$ is substituted with one or more first substituent groups denoted by $R^{10B.1}$ as explained in the definitions section above in the description of "first substituent group(s)". In embodiments, when an $R^{10B}$ substituent group is substituted, the $R^{10B.1}$ substituent group is substituted with one or more second substituent groups denoted by $R^{10B.2}$ as explained in the definitions section above in the description of "first substituent group(s)". In embodiments, when an $R^{10B.2}$ substituent group is substituted, the $R^{10B.2}$ substituent group is substituted with one or more third substituent groups denoted by $R^{10B.3}$ as explained in the definitions section above in the description of "first substituent group(s)". In the above embodiments, $R^{10B}$, $R^{10B.1}$, $R^{10B.2}$, and $R^{10B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10B}$, $R^{10B.1}$, $R^{10B.2}$, and $R^{10B.3}$, respectively.

In embodiments, when $R^{10A}$ and $R^{10B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10A.1}$ as explained in the definitions section above in the description of "first substituent group(s)". In embodiments, when an $R^{10A.1}$ substituent group is substituted, the $R^{10A.1}$ substituent group is substituted with one or more second substituent groups denoted by $R^{10A.2}$ as explained in the definitions section above in the description of "first substituent group(s)". In embodiments, when an $R^{10A.2}$ substituent group is substituted, the $R^{10A.2}$ substituent group is substituted with one or more third substituent groups denoted by $R^{10A.3}$ as explained in the definitions section above in the description of "first substituent group(s)". In the above embodiments, $R^{10A.1}$, $R^{10A.2}$, and $R^{10A.3}$ have values corresponding to the values of $R^{WW1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10A.1}$, $R^{10A.2}$, and $R^{10A.3}$, respectively.

In embodiments, when $R^{10A}$ and $R^{10B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10B.1}$ as explained in the definitions section above in the description of "first substituent group(s)". In embodiments, when an $R^{10B.1}$ substituent group is substituted, the $R^{10B.1}$ substituent group is substituted with one or more second substituent groups denoted by $R^{10B.2}$ as explained in the definitions section above in the description of "first substituent group(s)". In embodiments, when an $R^{10B.2}$ substituent group is substituted, the $R^{10B.2}$ substituent group is substituted with one or more third substituent groups denoted by $R^{10B.3}$ as explained in the definitions section above in the description of "first substituent group(s)". In the above embodiments, $R^{10B.1}$, $R^{10B.2}$, and $R^{10B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10B.1}$, $R^{10B.2}$, and $R^{10B.3}$, respectively.

In embodiments, when $R^{10C}$ is substituted, $R^{10C}$ is substituted with one or more first substituent groups denoted by $R^{10C.1}$ as explained in the definitions section above in the description of "first substituent group(s)". In embodiments, when an $R^{10C.1}$ substituent group is substituted, the $R^{10C.1}$ substituent group is substituted with one or more second substituent groups denoted by $R^{10C.2}$ as explained in the definitions section above in the description of "first substituent group(s)". In embodiments, when an $R^{10C.2}$ substituent group is substituted, the $R^{10C.2}$ substituent group is substituted with one or more third substituent groups denoted by $R^{10C.3}$ as explained in the definitions section above in the description of "first substituent group(s)". In the above embodiments, $R^{10C}$, $R^{10C.1}$, $R^{10C.2}$ and $R^{10C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10C}$, $R^{10C.1}$, $R^{10C.2}$, and $R^{10C.3}$, respectively.

In embodiments, when $R^{10D}$ is substituted, $R^{10D}$ is substituted with one or more first substituent groups denoted by $R^{10D.1}$ as explained in the definitions section above in the description of "first substituent group(s)". In embodiments, when an $R^{10D.1}$ substituent group is substituted, the $R^{10D.1}$ substituent group is substituted with one or more second substituent groups denoted by $R^{10D.2}$ as explained in the definitions section above in the description of "first substituent group(s)". In embodiments, when an $R^{10D.2}$ substituent group is substituted, the $R^{10D.2}$ substituent group is substituted with one or more third substituent groups denoted by $R^{10D.3}$ as explained in the definitions section above in the description of "first substituent group(s)". In the above embodiments, $R^{10D}$, $R^{10D.1}$, $R^{10D.2}$ and $R^{10D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10D}$, $R^{10D.1}$, $R^{10D.2}$, and $R^{10D.3}$, respectively.

In embodiments, when $R^{11}$ is substituted, $R^{11}$ is substituted with one or more first substituent groups denoted by $R^{11.1}$ as explained in the definitions section above in the description of "first substituent group(s)". In embodiments, when an $R^{11.1}$ substituent group is substituted, the $R^{11.1}$ substituent group is substituted with one or more second substituent groups denoted by $R^{11.2}$ as explained in the definitions section above in the description of "first substituent group(s)". In embodiments, when an $R^{11.2}$ substituent group is substituted, the $R^{11.2}$ substituent group is substituted with one or more third substituent groups denoted by $R^{11.3}$ as explained in the definitions section above in the description of "first substituent group(s)". In the above embodiments, $R^{11}$, $R^{11.1}$, $R^{11.2}$, and $R^{11.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11}$, $R^{11.1}$, $R^{11.2}$, and $R^{11.3}$, respectively.

In embodiments, when $R^{11A}$ is substituted, $R^{11A}$ is substituted with one or more first substituent groups denoted by $R^{11A.1}$ as explained in the definitions section above in the description of "first substituent group(s)". In embodiments, when an $R^{11A.1}$ substituent group is substituted, the $R^{11A.1}$ substituent group is substituted with one or more second substituent groups denoted by $R^{11A.2}$ as explained in the definitions section above in the description of "first substituent group(s)". In embodiments, when an $R^{11A.2}$ substituent group is substituted, the $R^{11A.2}$ substituent group is substituted with one or more third substituent groups denoted by $R^{11A.3}$ as explained in the definitions section above in the description of "first substituent group(s)". In the above embodiments, $R^{11A}$, $R^{11A.1}$, $R^{11A.2}$ and $R^{11A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11A}$, $R^{11A.1}$, $R^{11A.2}$, and $R^{11A.3}$, respectively.

In embodiments, when $R^{11B}$ is substituted, $R^{11B}$ is substituted with one or more first substituent groups denoted by $R^{11B.1}$ as explained in the definitions section above in the description of "first substituent group(s)". In embodiments, when an $R^{11B.1}$ substituent group is substituted, the $R^{11B.1}$ substituent group is substituted with one or more second substituent groups denoted by $R^{11B.2}$ as explained in the definitions section above in the description of "first substituent group(s)". In embodiments, when an $R^{11B.2}$ substituent group is substituted, the $R^{11B.2}$ substituent group is substituted with one or more third substituent groups denoted by $R^{11B.3}$ as explained in the definitions section above in the description of "first substituent group(s)". In the above embodiments, $R^{11B}$, $R^{1B.1}$, $R^{1B.2}$, and $R^{11B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11B}$, $R^{11B.1}$, $R^{11B.2}$, and $R^{11B.3}$, respectively.

In embodiments, when $R^{11A}$ and $R^{11B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{11A.1}$ as explained in the definitions section above in the description of "first substituent group(s)". In embodiments, when an $R^{11A.1}$ substituent group is substituted, the $R^{11A.1}$ substituent group is substituted with one or more second substituent groups denoted by $R^{11A.2}$ as explained in the definitions section above in the description of "first substituent group(s)". In embodiments, when an $R^{11A.2}$ substituent group is substituted, the $R^{11A.2}$ substituent group is substituted with one or more third substituent groups denoted by $R^{11A.3}$ as explained in the definitions section above in the description of "first substituent group(s)". In the above embodiments, $R^{11A.1}$, $R^{11A.2}$ and $R^{11A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{11A.1}$, $R^{A.2}$, and $R^{11A.3}$, respectively.

In embodiments, when $R^{11A}$ and $R^{11B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{11B.1}$ as explained in the definitions section above in the description of "first substituent group(s)". In embodiments, when an $R^{11B.1}$ substituent group is substituted, the $R^{11B.1}$ substituent group is substituted with one or more second substituent groups denoted by $R^{11B.2}$ as explained in the definitions section above in the description of "first substituent group(s)". In embodiments, when an $R^{11B.2}$ substituent group is substituted, the $R^{11B.2}$ substituent group is substituted with one or more third substituent groups denoted by $R^{11B.3}$ as explained in the definitions section above in the description of "first substituent group(s)". In the above embodiments, $R^{11B.1}$, $R^{11B.2}$ and $R^{11B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{11B.1}$, $R^{11B.2}$, and $R^{11B.3}$, respectively.

In embodiments, when $R^{11C}$ is substituted, $R^{11C}$ is substituted with one or more first substituent groups denoted by $R^{11C.1}$ as explained in the definitions section above in the description of "first substituent group(s)". In embodiments, when an $R^{11C.1}$ substituent group is substituted, the $R^{11C.1}$ substituent group is substituted with one or more second substituent groups denoted by $R^{11C.2}$ as explained in the definitions section above in the description of "first substituent group(s)". In embodiments, when an $R^{11C.2}$ substituent group is substituted, the $R^{11C.2}$ substituent group is substituted with one or more third substituent groups denoted by $R^{11C.3}$ as explained in the definitions section above in the description of "first substituent group(s)". In the above embodiments, $R^{11C}$, $R^{11C.1}$, $R^{11C.2}$, and $R^{11C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11C}$, $R^{11C.1}$, $R^{11C.2}$, and $R^{11C.3}$, respectively.

In embodiments, when $R^{11D}$ is substituted, $R^{11D}$ is substituted with one or more first substituent groups denoted by $R^{11D.1}$ as explained in the definitions section above in the description of "first substituent group(s)". In embodiments, when an $R^{11D.1}$ substituent group is substituted, the $R^{11D.1}$ substituent group is substituted with one or more second substituent groups denoted by $R^{11D.2}$ as explained in the definitions section above in the description of "first substituent group(s)". In embodiments, when an $R^{11D.2}$ substituent group is substituted, the $R^{11D.2}$ substituent group is substituted with one or more third substituent groups denoted by $R^{11D.3}$ as explained in the definitions section above in the description of "first substituent group(s)". In the above embodiments, $R^{11D}$, $R^{11D.1}$, $R^{1D.2}$, and $R^{11D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11D}$, $R^{11D.1}$, $R^{11D.2}$, and $R^{11D.3}$, respectively.

In embodiments, when $R^{12}$ is substituted, $R^{12}$ is substituted with one or more first substituent groups denoted by $R^{12.1}$ as explained in the definitions section above in the description of "first substituent group(s)". In embodiments, when an $R^{12.1}$ substituent group is substituted, the $R^{12.1}$ substituent group is substituted with one or more second substituent groups denoted by $R^{12.2}$ as explained in the definitions section above in the description of "first substituent group(s)". In embodiments, when an $R^{12.2}$ substituent group is substituted, the $R^{12.2}$ substituent group is substituted with one or more third substituent groups denoted by $R^{12.3}$ as explained in the definitions section above in the description of "first substituent group(s)". In the above embodiments, $R^{12}$, $R^{12.1}$, $R^{12.2}$, and $R^{12.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12}$, $R^{12.1}$, $R^{12.2}$, and $R^{12.3}$, respectively.

In embodiments, when $R^{12A}$ is substituted, $R^{12A}$ is substituted with one or more first substituent groups denoted by $R^{12A.1}$ as explained in the definitions section above in the description of "first substituent group(s)". In embodiments, when an $R^{12A.1}$ substituent group is substituted, the $R^{12A.1}$ substituent group is substituted with one or more second substituent groups denoted by $R^{12A.2}$ as explained in the definitions section above in the description of "first substituent group(s)". In embodiments, when an $R^{12A.2}$ substituent group is substituted, the $R^{12A.2}$ substituent group is substituted with one or more third substituent groups denoted by $R^{12A.3}$ as explained in the definitions section above in the description of "first substituent group(s)". In the above embodiments, $R^{12A}$, $R^{12A.1}$, $R^{12A.2}$, and $R^{12A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12A}$, $R^{12A.1}$, $R^{12A.2}$, and $R^{12A.3}$, respectively.

In embodiments, when $R^{12B}$ is substituted, $R^{12B}$ is substituted with one or more first substituent groups denoted by $R^{12B.1}$ as explained in the definitions section above in the description of "first substituent group(s)". In embodiments, when an $R^{12B.1}$ substituent group is substituted, the $R^{12B.1}$ substituent group is substituted with one or more second substituent groups denoted by $R^{12B.2}$ as explained in the definitions section above in the description of "first substituent group(s)". In embodiments, when an $R^{12B.2}$ substituent group is substituted, the $R^{12B.2}$ substituent group is substituted with one or more third substituent groups denoted by $R^{12B.3}$ as explained in the definitions section above in the description of "first substituent group(s)". In the above embodiments, $R^{12B}$, $R^{12B.1}$, $R^{12B.2}$, and $R^{12B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12B}$, $R^{12B.1}$, $R^{12B.2}$, and $R^{12B.3}$, respectively.

In embodiments, when $R^{12A}$ and $R^{12B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{12A.1}$ as explained in the definitions section above in the description of "first substituent group(s)". In embodiments, when an $R^{12A.1}$ substituent group is substituted, the $R^{12A.1}$ substituent group is substituted with one or more second substituent groups denoted by $R^{12A.2}$ as explained in the definitions section above in the description of "first substituent group(s)". In embodiments, when an $R^{12A.2}$ substituent group is substituted, the $R^{12A.2}$ substituent group is substituted with one or more third substituent groups denoted by $R^{12A.3}$ as explained in the definitions section above in the description of "first substituent group(s)". In the above embodiments, $R^{12A.1}$, $R^{12A.2}$, and $R^{12A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{12A.1}$, $R^{12A.2}$, and $R^{12A.3}$, respectively.

In embodiments, when $R^{12A}$ and $R^{12B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{12B.1}$ as explained in the definitions section above in the description of "first substituent group(s)". In embodiments, when an $R^{12B.1}$ substituent group is substituted, the $R^{12B.1}$ substituent group is substituted with one or more second substituent groups denoted by $R^{12B.2}$ as explained in the definitions section above in the description of "first substituent group(s)". In embodiments, when an $R^{12B.2}$ substituent group is substituted, the $R^{12B.2}$ substituent group is substituted with one or more third substituent groups denoted by $R^{12B.3}$ as explained in the definitions section above in the description of "first substituent group(s)". In the above embodiments, $R^{12B.1}$, $R^{12B.2}$, and $R^{12B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{12B.1}$, $R^{12B.2}$, and $R^{12B.3}$, respectively.

In embodiments, when $R^{12C}$ is substituted, $R^{12C}$ is substituted with one or more first substituent groups denoted by $R^{12C.1}$ as explained in the definitions section above in the description of "first substituent group(s)". In embodiments, when an $R^{12C.1}$ substituent group is substituted, the $R^{12C.1}$ substituent group is substituted with one or more second substituent groups denoted by $R^{12C.2}$ as explained in the definitions section above in the description of "first substituent group(s)". In embodiments, when an $R^{12C.2}$ substituent group is substituted, the $R^{12C.2}$ substituent group is substituted with one or more third substituent groups denoted by $R^{12C.3}$ as explained in the definitions section above in the description of "first substituent group(s)". In the above embodiments, $R^{12C}$, $R^{12C.1}$, $R^{12C.2}$ and $R^{12C.3}$ have values corresponding to the values of $R_{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12C}$, $R^{12C.1}$, $R^{12C.2}$, and $R^{12C.3}$, respectively.

In embodiments, when $R^{12D}$ is substituted, $R^{12D}$ is substituted with one or more first substituent groups denoted by $R^{12D.1}$ as explained in the definitions section above in the description of "first substituent group(s)". In embodiments, when an $R^{12D.1}$ substituent group is substituted, the $R^{12D.1}$ substituent group is substituted with one or more second substituent groups denoted by $R^{12D.2}$ as explained in the definitions section above in the description of "first substituent group(s)". In embodiments, when an $R^{12D.2}$ substituent group is substituted, the $R^{12D.2}$ substituent group is substituted with one or more third substituent groups denoted by $R^{12D.3}$ as explained in the definitions section above in the description of "first substituent group(s)". In the above embodiments, $R^{12D}$, $R^{12D.1}$, $R^{12D.2}$, and $R^{12D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12D}$, $R^{12D.1}$, $R^{12D.2}$, and $R^{12D.3}$, respectively.

In embodiments, when $R^{13}$ is substituted, $R^{13}$ is substituted with one or more first substituent groups denoted by $R^{13.1}$ as explained in the definitions section above in the description of "first substituent group(s)". In embodiments, when an $R^{13.1}$ substituent group is substituted, the $R^{13.1}$ substituent group is substituted with one or more second substituent groups denoted by $R^{13.2}$ as explained in the definitions section above in the description of "first substituent group(s)". In embodiments, when an $R^{13.2}$ substituent group is substituted, the $R^{13.2}$ substituent group is substituted with one or more third substituent groups denoted by $R^{13.3}$ as explained in the definitions section above in the description of "first substituent group(s)". In the above embodiments, $R^{13}$, $R^{13.1}$, $R^{13.2}$, and $R^{13.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13}$, $R^{13.1}$, $R^{13}{}_{2}$, and $R^{13.3}$, respectively.

In embodiments, when $R^{13A}$ is substituted, $R^{13A}$ is substituted with one or more first substituent groups denoted by $R^{13A.1}$ as explained in the definitions section above in the description of "first substituent group(s)". In embodiments, when an $R^{13A.1}$ substituent group is substituted, the $R^{13A.1}$ substituent group is substituted with one or more second substituent groups denoted by $R^{13A.2}$ as explained in the definitions section above in the description of "first substituent group(s)". In embodiments, when an $R^{13A.2}$ substituent group is substituted, the $R^{13A.2}$ substituent group is substituted with one or more third substituent groups denoted by $R^{13A.3}$ as explained in the definitions section above in the description of "first substituent group(s)". In the above embodiments, $R^{13A}$, $R^{3A.1}$, $R^{13A.2}$, and $R^{13A.3}$ have values corresponding to the values of $R^{W}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13A}$, $R^{13A.1}$, $R^{13A.2}$, and $R^{13A.3}$, respectively.

In embodiments, when $R^{13B}$ is substituted, $R^{13B}$ is substituted with one or more first substituent groups denoted by $R^{13B.1}$ as explained in the definitions section above in the description of "first substituent group(s)". In embodiments, when an $R^{13B.1}$ substituent group is substituted, the $R^{13B.1}$ substituent group is substituted with one or more second substituent groups denoted by $R^{13B.2}$ as explained in the definitions section above in the description of "first substituent group(s)". In embodiments, when an $R^{13B.2}$ substituent group is substituted, the $R^{13B.2}$ substituent group is substituted with one or more third substituent groups denoted by $R^{13B.3}$ as explained in the definitions section above in the description of "first substituent group(s)". In the above embodiments, $R^{13B}$, $R^{13B.1}$, $R^{13B.2}$, and $R^{13B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13B}$, $R^{13B.1}$, $R^{13B.2}$, and $R^{13B.3}$, respectively.

In embodiments, when $R^{13A}$ and $R^{13B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{13A.1}$ as explained in the definitions section above in the description of "first substituent group(s)". In embodiments, when an $R^{13A.1}$ substituent group is substituted, the $R^{13A.1}$ substituent group is substituted with one or more second substituent groups denoted by $R^{13A.2}$ as explained in the definitions section above in the description of "first substituent group(s)". In embodiments, when an $R^{13A.2}$ substituent group is substituted, the $R^{13A.2}$ substituent group is substituted with one or more third substituent groups denoted by $R^{13A.3}$ as explained in the definitions section above in the description of "first substituent group(s)". In the above embodiments, $R^{13A.1}$, $R^{13A.2}$, and $R^{13A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{13A.1}$, $R^{13A.2}$, and $R^{13A3}$, respectively.

In embodiments, when $R^{13A}$ and $R^{13B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{13B.1}$ as explained in the definitions section above in the description of "first substituent group(s)". In embodiments, when an $R^{13B.1}$ substituent group is substituted, the $R^{13B.1}$ substituent group is substituted with one or more second substituent groups denoted by $R^{13B.2}$ as explained in the definitions section above in the description of "first substituent group(s)". In embodiments, when an $R^{13B.2}$ substituent group is substituted, the $R^{13B.2}$ substituent group is substituted with one or more third substituent groups denoted by $R^{13B.3}$ as explained in the definitions section above in the description of "first substituent group(s)". In the above embodiments, $R^{13B.1}$, $R^{13B.2}$ and $R^{13B.3}$ have values corresponding to the values of $R^{WW.1}$, $R^{WW2}$, and $R^{WW.3}$, respectively, as explained in the definitions section above in the description of "first substituent group(s)", wherein $R^{WW.1}$, $R^{WW.2}$, and $R^{WW.3}$ correspond to $R^{13B.1}$, $R^{13B.2}$, and $R^{13B.3}$, respectively.

In embodiments, when $R^{13C}$ is substituted, $R^{13C}$ is substituted with one or more first substituent groups denoted by $R^{13C.1}$ as explained in the definitions section above in the description of "first substituent group(s)". In embodiments, when an $R^{13C.1}$ substituent group is substituted, the $R^{13C.1}$ substituent group is substituted with one or more second substituent groups denoted by $R^{13C.2}$ as explained in the definitions section above in the description of "first substituent group(s)". In embodiments, when an $R^{13C.2}$ substituent group is substituted, the $R^{13C.2}$ substituent group is substituted with one or more third substituent groups denoted by $R^{13C.3}$ as explained in the definitions section above in the description of "first substituent group(s)". In the above embodiments, $R^{13C}$, $R^{13C.1}$, $R^{13C.2}$, and $R^{13C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13C}$, $R^{13C.1}$, $R^{13C.2}$, and $R^{13C.3}$, respectively.

In embodiments, when $R^{13D}$ is substituted, $R^{13D}$ is substituted with one or more first substituent groups denoted by $R^{13D.1}$ as explained in the definitions section above in the description of "first substituent group(s)". In embodiments, when an $R^{13D.1}$ substituent group is substituted, the $R^{13D.1}$ substituent group is substituted with one or more second substituent groups denoted by $R^{13D.2}$ as explained in the definitions section above in the description of "first substituent group(s)". In embodiments, when an $R^{13D.2}$ substituent group is substituted, the $R^{13D.2}$ substituent group is substituted with one or more third substituent groups denoted by $R^{13D.3}$ as explained in the definitions section above in the description of "first substituent group(s)". In the above embodiments, $R^{13D}$, $R^{13D.1}$, $R^{13D.2}$, and $R^{13D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13D}$, $R^{13D.1}$, $R^{13D.2}$, and $R^{13D.3}$, respectively.

In embodiments, when $R^{14}$ is substituted, $R^{14}$ is substituted with one or more first substituent groups denoted by $R^{14.1}$ as explained in the definitions section above in the description of "first substituent group(s)". In embodiments, when an $R^{14.1}$ substituent group is substituted, the $R^{14.1}$ substituent group is substituted with one or more second substituent groups denoted by $R^{14.2}$ as explained in the definitions section above in the description of "first substituent group(s)". In embodiments, when an $R^{14.2}$ substituent group is substituted, the $R^{14.2}$ substituent group is substituted with one or more third substituent groups denoted by $R^{14.3}$ as explained in the definitions section above in the description of "first substituent group(s)". In the above embodiments, $R^{14}$, $R^{14.1}$, $R^{14.2}$, and $R^{14.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14}$, $R^{14.1}$, $R^{14.2}$, and $R^{14.3}$, respectively.

In embodiments, when $R^{14A}$ is substituted, $R^{14A}$ is substituted with one or more first substituent groups denoted by $R^{14A.1}$ as explained in the definitions section above in the description of "first substituent group(s)". In embodiments, when an $R^{14A.1}$ substituent group is substituted, the $R^{14A.1}$ substituent group is substituted with one or more second substituent groups denoted by $R^{14A.2}$ as explained in the definitions section above in the description of "first substituent group(s)". In embodiments, when an $R^{14A.2}$ substituent group is substituted, the $R^{14A.2}$ substituent group is substituted with one or more third substituent groups denoted by $R^{14A.3}$ as explained in the definitions section above in the description of "first substituent group(s)". In the above embodiments, $R^{14A}$, $R^{14A.1}$, $R^{14A.2}$ and $R^{14A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14A}$, $R^{14A}$, $R^{14A.2}$, and $R^{14A.3}$, respectively.

In embodiments, when $R^{14B}$ is substituted, $R^{14B}$ is substituted with one or more first substituent groups denoted by $R^{14B.1}$ as explained in the definitions section above in the description of "first substituent group(s)". In embodiments, when an $R^{14B.1}$ substituent group is substituted, the $R^{14B.1}$ substituent group is substituted with one or more second substituent groups denoted by $R^{14B.2}$ as explained in the definitions section above in the description of "first substituent group(s)". In embodiments, when an $R^{14B.2}$ substituent group is substituted, the $R^{14B.2}$ substituent group is substituted with one or more third substituent groups denoted by $R^{14B.3}$ as explained in the definitions section above in the description of "first substituent group(s)". In the above embodiments, $R^{14B}$, $R^{14B.1}$, $R^{14B.2}$ and $R^{14B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14B}$, $R^{14B.1}$, $R^{14B.2}$, and $R^{14B.3}$, respectively.

In embodiments, when $R^{14A}$ and $R^{14B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{14A.1}$ as explained in the definitions section above in the description of "first substituent group(s)". In embodiments, when an $R^{14A.1}$ substituent group is substituted, the $R^{14A.1}$ substituent group is substituted with one or more second substituent groups denoted by $R^{14A.2}$ as explained in the definitions section above in the description of "first substituent group(s)". In embodiments, when an $R^{14A.2}$ substituent group is substituted, the $R^{14A.2}$ substituent group is substituted with one or more third substituent groups denoted by $R^{14A.3}$ as explained in the definitions section above in the description of "first substituent group(s)". In the above embodiments, $R^{14A.1}$, $R^{14A.2}$, and $R^{14A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{14A.1}$, $R^{14A.2}$, and $R^{14A.3}$, respectively.

In embodiments, when $R^{14A}$ and $R^{14B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{14B.1}$ as explained in the definitions section above in the description of "first substituent group(s)". In embodiments, when an $R^{14B.1}$ substituent group is substituted, the $R^{14B.1}$ substituent group is substituted with one or more second substituent groups denoted by $R^{14B.2}$ as explained in the definitions section above in the description of "first substituent group(s)". In embodiments, when an $R^{14B.2}$ substituent group is substituted, the $R^{14B.2}$ substituent group is substituted with one or more third substituent groups denoted by $R^{14B.3}$ as explained in the definitions section above in the description of "first substituent group(s)". In the above embodiments, $R^{14B.1}$, $R^{14B.2}$, and $R^{14B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{14B.1}$, $R^{14B.2}$, and $R^{14B.3}$, respectively.

In embodiments, when $R^{14C}$ is substituted, $R^{14C}$ is substituted with one or more first substituent groups denoted by $R^{14C.1}$ as explained in the definitions section above in the description of "first substituent group(s)". In embodiments, when an $R^{14C.1}$ substituent group is substituted, the $R^{14C.1}$ substituent group is substituted with one or more second substituent groups denoted by $R^{14C.2}$ as explained in the definitions section above in the description of "first substituent group(s)". In embodiments, when an $R^{14C.2}$ substituent group is substituted, the $R^{14C.2}$ substituent group is substituted with one or more third substituent groups denoted by $R^{14C.3}$ as explained in the definitions section above in the description of "first substituent group(s)". In the above embodiments, $R^{14C}$, $R^{14C.1}$, $R^{14C.2}$ and $R^{14C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14C}$, $R^{14C.1}$, $R^{14C.2}$ and $R^{14C.3}$, respectively.

In embodiments, when $R^{14D}$ is substituted, $R^{14D}$ is substituted with one or more first substituent groups denoted by $R^{14D.1}$ as explained in the definitions section above in the description of "first substituent group(s)". In embodiments, when an $R^{14D.1}$ substituent group is substituted, the $R^{14D.1}$ substituent group is substituted with one or more second substituent groups denoted by $R^{14D.2}$ as explained in the definitions section above in the description of "first substituent group(s)". In embodiments, when an $R^{14D.2}$ substituent group is substituted, the $R^{14D.2}$ substituent group is substituted with one or more third substituent groups denoted by $R^{14D.3}$ as explained in the definitions section above in the description of "first substituent group(s)". In the above embodiments, $R^{14D}$, $R^{14D.1}$, $R^{14D.2}$, and $R^{14D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14D}$, $R^{14D.1}$, $R^{14D.2}$, and $R^{14D.3}$, respectively.

In embodiments, when $R^{15}$ is substituted, $R^{15}$ is substituted with one or more first substituent groups denoted by $R^{15.1}$ as explained in the definitions section above in the description of "first substituent group(s)". In embodiments, when an $R^{15.1}$ substituent group is substituted, the $R^{15.1}$ substituent group is substituted with one or more second substituent groups denoted by $R^{15.2}$ as explained in the definitions section above in the description of "first substituent group(s)". In embodiments, when an $R^{15.2}$ substituent group is substituted, the $R^{15.2}$ substituent group is substituted with one or more third substituent groups denoted by $R^{15.3}$ as explained in the definitions section above in the description of "first substituent group(s)". In the above embodiments, $R^{15}$, $R^{15.1}$, $R^{15.2}$, and $R^{15.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15}$, $R^{151}$, $R^{15.2}$, and $R^{15.3}$, respectively.

In embodiments, when $R^{15A}$ is substituted, $R^{15A}$ is substituted with one or more first substituent groups denoted by $R^{15A.1}$ as explained in the definitions section above in the description of "first substituent group(s)". In embodiments, when an $R^{15A.1}$ substituent group is substituted, the $R^{15A.1}$ substituent group is substituted with one or more second substituent groups denoted by $R^{15A.2}$ as explained in the definitions section above in the description of "first substituent group(s)". In embodiments, when an $R^{15A.2}$ substituent group is substituted, the $R^{15A.2}$ substituent group is substituted with one or more third substituent groups denoted by $R^{15A.3}$ as explained in the definitions section above in the description of "first substituent group(s)". In the above embodiments, $R^{15A}$, $R^{15A.1}$, $R^{15A.2}$, and $R^{15A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15A}$, $R^{15A.1}$, $R^{15A.2}$, and $R^{15A.3}$ respectively.

In embodiments, when $R^{15B}$ is substituted, $R^{15B}$ is substituted with one or more first substituent groups denoted by $R^{15B.1}$ as explained in the definitions section above in the description of "first substituent group(s)". In embodiments, when an $R^{15B.1}$ substituent group is substituted, the $R^{15B.1}$ substituent group is substituted with one or more second substituent groups denoted by $R^{15B.2}$ as explained in the definitions section above in the description of "first substituent group(s)". In embodiments, when an $R^{15B.2}$ substituent group is substituted, the $R^{15B.2}$ substituent group is substituted with one or more third substituent groups denoted by $R^{15B.3}$ as explained in the definitions section above in the description of "first substituent group(s)". In the above embodiments, $R^{15B}$, $R^{15B.1}$, $R^{15B.2}$, and $R^{15B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15B}$, $R^{15B.1}$, $R^{15B.2}$, and $R^{15B.3}$, respectively.

In embodiments, when $R^{15A}$ and $R^{15B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{15A.1}$ as explained in the definitions section above in the description of "first substituent group(s)". In embodiments, when an $R^{15A.1}$ substituent group is substituted, the $R^{15A.1}$ substituent group is substituted with one or more second substituent groups denoted by $R^{15A.2}$ as explained in the definitions section above in the description of "first substituent group(s)". In embodiments, when an $R^{15A.2}$ substituent group is substituted, the $R^{15A.2}$ substituent group is substituted with one or more third substituent groups denoted by $R^{15A.3}$ as explained in the definitions section above in the description of "first substituent group(s)". In the above embodiments, $R^{15A.1}$, $R^{15A.2}$, and $R^{15A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{15A.1}$, $R^{15A.2}$, and $R^{15A.3}$, respectively.

In embodiments, when $R^{15A}$ and $R^{15B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{15B.1}$ as explained in the definitions section above in the description of "first substituent group(s)". In embodiments, when an $R^{15B.1}$ substituent group is substituted, the $R^{15B.1}$ substituent group is substituted with one or more second substituent groups denoted by $R^{15B.2}$ as explained in the definitions section above in the description of "first substituent group(s)". In embodiments, when an $R^{15B.2}$ substituent group is substituted, the $R^{15B.2}$ substituent group is substituted with one or more third substituent groups denoted by $R^{15B.3}$ as explained in the definitions section above in the description of "first substituent group(s)". In the above embodiments, $R^{15B.1}$, $R^{15B.2}$ and $R^{15B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{15B.1}$, $R^{15B.2}$, and $R^{15B.3}$, respectively.

In embodiments, when $R^{15C}$ is substituted, $R^{15C}$ is substituted with one or more first substituent groups denoted by $R^{15C.1}$ as explained in the definitions section above in the description of "first substituent group(s)". In embodiments, when an $R^{15C.1}$ substituent group is substituted, the $R^{15C.1}$ substituent group is substituted with one or more second substituent groups denoted by $R^{15C.2}$ as explained in the definitions section above in the description of "first substituent group(s)". In embodiments, when an $R^{15C.2}$ substituent group is substituted, the $R^{15C.2}$ substituent group is substituted with one or more third substituent groups denoted by $R^{15C.3}$ as explained in the definitions section above in the description of "first substituent group(s)". In the above embodiments, $R^{15C}$, $R^{15C.1}$, $R^{15C.2}$, and $R^{15C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15C}$, $R^{15C.1}$, $R^{15C.2}$, and $R^{15C.3}$, respectively.

In embodiments, when $R^{15D}$ is substituted, $R^{15D}$ is substituted with one or more first substituent groups denoted by $R^{15D.1}$ as explained in the definitions section above in the description of "first substituent group(s)". In embodiments, when an $R^{15D.1}$ substituent group is substituted, the $R^{15D.1}$ substituent group is substituted with one or more second substituent groups denoted by $R^{15D.2}$ as explained in the definitions section above in the description of "first substituent group(s)". In embodiments, when an $R^{15D.2}$ substituent group is substituted, the $R^{15D.2}$ substituent group is substituted with one or more third substituent groups denoted by $R^{15D.3}$ as explained in the definitions section above in the description of "first substituent group(s)". In the above embodiments, $R^{15D}$, $R^{15D.1}$, $R^{15D.2}$, and $R^{15D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15D}$, $R^{15D.1}$, $R^{15D.2}$, and $R^{15D.3}$, respectively.

In embodiments, when $R^1$ and $R^2$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^{1.1}$, $R^{1.2}$, and $R^{1.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{1.1}$, $R^{1.2}$, and $R^{1.3}$, respectively.

In embodiments, when $R^1$ and $R^2$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of “first substituent group(s)”. In the above embodiments, $R^{2.1}$, $R^{2.2}$, and $R^{2.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{2.1}$, $R^{2.2}$, and $R^{2.3}$, respectively.

In embodiments, when $R^2$ and $R^3$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{2.1}$ as explained in the definitions section above in the description of “first substituent group(s)”. In embodiments, when an $R^{2.1}$ substituent group is substituted, the $R^{2.1}$ substituent group is substituted with one or more second substituent groups denoted by $R^{2.2}$ as explained in the definitions section above in the description of “first substituent group(s)”. In embodiments, when an $R^{2.2}$ substituent group is substituted, the $R^{2.2}$ substituent group is substituted with one or more third substituent groups denoted by $R^{2.3}$ as explained in the definitions section above in the description of “first substituent group(s)”. In the above embodiments, $R^{2.1}$, $R^{2.2}$, and $R^{2.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{2.1}$, $R^{2.2}$, and $R^{2.3}$, respectively.

In embodiments, when $R^2$ and $R^3$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{3.1}$ as explained in the definitions section above in the description of “first substituent group(s)”. In embodiments, when an $R^{3.1}$ substituent group is substituted, the $R^{3.1}$ substituent group is substituted with one or more second substituent groups denoted by $R^{3.2}$ as explained in the definitions section above in the description of “first substituent group(s)”. In embodiments, when an $R^{3.2}$ substituent group is substituted, the $R^{3.2}$ substituent group is substituted with one or more third substituent groups denoted by $R^{3.3}$ as explained in the definitions section above in the description of “first substituent group(s)”. In the above embodiments, $R^{3.1}$, $R^{3.2}$, and $R^{3.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{3.1}$, $R^{3.2}$, and $R^{3.3}$, respectively.

In embodiments, when $R^3$ and $R^4$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{3.1}$ as explained in the definitions section above in the description of “first substituent group(s)”. In embodiments, when an $R^{3.1}$ substituent group is substituted, the $R^{3.1}$ substituent group is substituted with one or more second substituent groups denoted by $R^{3.2}$ as explained in the definitions section above in the description of “first substituent group(s)”. In embodiments, when an $R^{3.2}$ substituent group is substituted, the $R^{3.2}$ substituent group is substituted with one or more third substituent groups denoted by $R^{3.3}$ as explained in the definitions section above in the description of “first substituent group(s)”. In the above embodiments, $R^{3.1}$, $R^{3.2}$, and $R^{3.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{3.1}$, $R^{3.2}$, and $R^{3.3}$, respectively.

In embodiments, when $R^3$ and $R^4$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{4.1}$ as explained in the definitions section above in the description of “first substituent group(s)”. In embodiments, when an $R^{4.1}$ substituent group is substituted, the $R^{4.1}$ substituent group is substituted with one or more second substituent groups denoted by $R^{4.2}$ as explained in the definitions section above in the description of “first substituent group(s)”. In embodiments, when an $R^{4.2}$ substituent group is substituted, the $R^{4.2}$ substituent group is substituted with one or more third substituent groups denoted by $R^{4.3}$ as explained in the definitions section above in the description of “first substituent group(s)”. In the above embodiments, $R^{4.1}$, $R^{4.2}$, and $R^{4.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{4.1}$, $R^{4.2}$, and $R^{4.3}$, respectively.

In embodiments, when $R^4$ and $R^5$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{4.1}$ as explained in the definitions section above in the description of “first substituent group(s)”. In embodiments, when an $R^{4.1}$ substituent group is substituted, the $R^{4.1}$ substituent group is substituted with one or more second substituent groups denoted by $R^{4.2}$ as explained in the definitions section above in the description of “first substituent group(s)”. In embodiments, when an $R^{4.2}$ substituent group is substituted, the $R^{4.2}$ substituent group is substituted with one or more third substituent groups denoted by $R^{4.3}$ as explained in the definitions section above in the description of “first substituent group(s)”. In the above embodiments, $R^{4.1}$, $R^{4.2}$, and $R^{43}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{41}$, $R^{4.2}$, and $R^{4.3}$, respectively.

In embodiments, when $R^4$ and $R^5$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{5.1}$ as explained in the definitions section above in the description of “first substituent group(s)”. In embodiments, when an $R^{5.1}$ substituent group is substituted, the $R^{5.1}$ substituent group is substituted with one or more second substituent groups denoted by $R^{5.2}$ as explained in the definitions section above in the description of “first substituent group(s)”. In embodiments, when an $R^{5.2}$ substituent group is substituted, the $R^{5.2}$ substituent group is substituted with one or more third substituent groups denoted by $R^{5.3}$ as explained in the definitions section above in the description of “first substituent group(s)”. In the above embodiments, $R^{5.1}$, $R^{5.2}$, and $R^{5.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{5.1}$, $R^{5.2}$, and $R^{5.3}$, respectively.

In embodiments, when $R^6$ and $R^7$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{6.1}$ as explained in the definitions section above in the description of "first substituent group(s)". In embodiments, when an $R^{6.1}$ substituent group is substituted, the $R^{6.1}$ substituent group is substituted with one or more second substituent groups denoted by $R^{6.2}$ as explained in the definitions section above in the description of "first substituent group(s)". In embodiments, when an $R^{6.2}$ substituent group is substituted, the $R^{6.2}$ substituent group is substituted with one or more third substituent groups denoted by $R^{6.3}$ as explained in the definitions section above in the description of "first substituent group(s)". In the above embodiments, $R^{6.1}$, $R^{6.2}$, and $R^{6.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{6.1}$, $R^{6.2}$, and $R^{6.3}$, respectively.

In embodiments, when $R^6$ and $R^7$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group(s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^{7.1}$, $R^{7.2}$, and $R^{7.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{7.1}$, $R^{7.2}$, and $R^{7.3}$, respectively.

In embodiments, when $R^7$ and $R^8$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group(s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^{7.1}$, $R^{7.2}$, and $R^{7.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{7.1}$, $R^{7.2}$, and $R^{7.3}$, respectively.

In embodiments, when $R^7$ and $R^8$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{8.1}$ as explained in the definitions section above in the description of "first substituent group(s)". In embodiments, when an $R^{8.1}$ substituent group is substituted, the $R^{8.1}$ substituent group is substituted with one or more second substituent groups denoted by $R^{8.2}$ as explained in the definitions section above in the description of "first substituent group(s)". In embodiments, when an $R^{8.2}$ substituent group is substituted, the $R^{8.2}$ substituent group is substituted with one or more third substituent groups denoted by $R^{8.3}$ as explained in the definitions section above in the description of "first substituent group(s)". In the above embodiments, $R^{8.1}$, $R^{8.2}$, and $R^8_3$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{8.1}$, $R^{8.2}$, and $R^{8.3}$, respectively.

In embodiments, when $R^8$ and $R^9$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{8.1}$ as explained in the definitions section above in the description of "first substituent group(s)". In embodiments, when an $R^{8.1}$ substituent group is substituted, the $R^{8.1}$ substituent group is substituted with one or more second substituent groups denoted by $R^8_2$ as explained in the definitions section above in the description of "first substituent group(s)". In embodiments, when an $R^{8.2}$ substituent group is substituted, the $R^{8.2}$ substituent group is substituted with one or more third substituent groups denoted by $R^{8.3}$ as explained in the definitions section above in the description of "first substituent group(s)". In the above embodiments, $R^{8.1}$, $R^{8.2}$, and $R^{8.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{8.1}$, $R^{8.2}$, and $R^{8.3}$, respectively.

In embodiments, when $R^8$ and $R^9$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{9.1}$ as explained in the definitions section above in the description of "first substituent group(s)". In embodiments, when an $R^{9.1}$ substituent group is substituted, the $R^{9.1}$ substituent group is substituted with one or more second substituent groups denoted by $R^{9.2}$ as explained in the definitions section above in the description of "first substituent group(s)". In embodiments, when an $R^{9.2}$ substituent group is substituted, the $R^{9.2}$ substituent group is substituted with one or more third substituent groups denoted by $R^{9.3}$ as explained in the definitions section above in the description of "first substituent group(s)". In the above embodiments, $R^{9.1}$, $R^{9.2}$, and $R^{9.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{9.1}$, $R^{9.2}$, and $R^{9.3}$, respectively.

In embodiments, when $R^9$ and $R^{10}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{9.1}$ as explained in the definitions section above in the description of "first substituent group(s)". In embodiments, when an $R^{9.1}$ substituent group is substituted, the $R^{9.1}$ substituent group is substituted with one or more second substituent groups denoted by $R^{9.2}$ as explained in the definitions section above in the description of "first substituent group(s)". In embodiments, when an $R^{9.2}$ substituent group is substituted, the $R^{9.2}$ substituent group is substituted with one or more third substituent groups denoted by $R^{9.3}$ as explained in the definitions section above in the description of "first substituent group(s)". In the above embodiments, $R^{9.1}$, $R^{9.2}$, and $R^{9.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{9.1}$, $R^{9.2}$, and $R^{9.3}$, respectively.

In embodiments, when $R^9$ and $R^{10}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{10.1}$ as explained in the definitions section above in the description of "first substituent group(s)". In embodiments, when an $R^{10.1}$ substituent group is substituted, the $R^{10.1}$ substituent group is substituted with one or more second substituent groups denoted by $R^{10.2}$ as explained in the definitions section above in the description of "first substituent group(s)". In embodiments, when an $R^{10.2}$ substituent group is substituted, the $R^{10.2}$ substituent group is substituted with one or more third substituent groups denoted by $R^{10.3}$ as explained in the definitions section above in the description of "first substituent group(s)". In the above embodiments, $R^{10.1}$, $R^{10.2}$, and $R^{10.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.1}$, $R^{10.2}$, and $R^{10.3}$, respectively.

In embodiments, when $R^{11}$ and $R^{12}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{11.1}$ as explained in the definitions section above in the description of "first substituent group(s)". In embodiments, when an $R^{11.1}$ substituent group is substituted, the $R^{11.1}$ substituent group is substituted with one or more second substituent groups denoted by $R^{11.2}$ as explained in the definitions section above in the description of "first substituent group(s)". In embodiments, when an $R^{11.2}$ substituent group is substituted, the $R^{11.2}$ substituent group is substituted with one or more third substituent groups denoted by $R^{11.3}$ as explained in the definitions section above in the description of "first substituent group(s)". In the above embodiments, $R^{11.1}$, $R^{11.2}$, and $R^{11.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{11.1}$, $R^{11.2}$, and $R^{11.3}$, respectively.

In embodiments, when $R^{11}$ and $R^{12}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{12.1}$ as explained in the definitions section above in the description of "first substituent group(s)". In embodiments, when an $R^{12.1}$ substituent group is substituted, the $R^{12.1}$ substituent group is substituted with one or more second substituent groups denoted by $R^{12.2}$ as explained in the definitions section above in the description of "first substituent group(s)". In embodiments, when an $R^{12.2}$ substituent group is substituted, the $R^{12.2}$ substituent group is substituted with one or more third substituent groups denoted by $R^{12.3}$ as explained in the definitions section above in the description of "first substituent group(s)". In the above embodiments, $R^{12.1}$, $R^{12.2}$, and $R^{12.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{12.1}$, $R^{12.2}$, and $R^{12.3}$, respectively.

In embodiments, when $R^{12}$ and $R^{13}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{12.1}$ as explained in the definitions section above in the description of "first substituent group(s)". In embodiments, when an $R^{12.1}$ substituent group is substituted, the $R^{12.1}$ substituent group is substituted with one or more second substituent groups denoted by $R^{12.2}$ as explained in the definitions section above in the description of "first substituent group(s)". In embodiments, when an $R^{12.2}$ substituent group is substituted, the $R^{12.2}$ substituent group is substituted with one or more third substituent groups denoted by $R^{12.3}$ as explained in the definitions section above in the description of "first substituent group(s)". In the above embodiments, $R^{12.1}$, $R^{12.2}$, and $R^{12.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{12.1}$, $R^{12.2}$, and $R^{12.3}$, respectively.

In embodiments, when $R^{12}$ and $R^{13}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{13.1}$ as explained in the definitions section above in the description of "first substituent group(s)". In embodiments, when an $R^{13.1}$ substituent group is substituted, the $R^{13.1}$ substituent group is substituted with one or more second substituent groups denoted by $R^{13.2}$ as explained in the definitions section above in the description of "first substituent group(s)". In embodiments, when an $R^{13.2}$ substituent group is substituted, the $R^{13.2}$ substituent group is substituted with one or more third substituent groups denoted by $R^{13.3}$ as explained in the definitions section above in the description of "first substituent group(s)". In the above embodiments, $R^{13.1}$, $R^{13.2}$, and $R^{13.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{13.1}$, $R^{13.2}$, and $R^{13.3}$, respectively.

In embodiments, when $R^{13}$ and $R^{14}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{13.1}$ as explained in the definitions section above in the description of "first substituent group(s)". In embodiments, when an $R^{13.1}$ substituent group is substituted, the $R^{13.1}$ substituent group is substituted with one or more second substituent groups denoted by $R^{13.2}$ as explained in the definitions section above in the description of "first substituent group(s)". In embodiments, when an $R^{13.2}$ substituent group is substituted, the $R^{13.2}$ substituent group is substitutedtuted with one or more third substituent groups denoted by $R^{13.3}$ as explained in the definitions section above in the description of “first substituent group(s)”. In the above embodiments, $R^{13.1}$, $R^{13.2}$ and $R^{13.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{13.1}$, $R^{13.2}$, and $R^{13.3}$, respectively.

In embodiments, when $R^{13}$ and $R^{14}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{14.1}$ as explained in the definitions section above in the description of “first substituent group(s)”. In embodiments, when an $R^{14.1}$ substituent group is substituted, the $R^{14.1}$ substituent group is substituted with one or more second substituent groups denoted by $R^{14.2}$ as explained in the definitions section above in the description of “first substituent group(s)”. In embodiments, when an $R^{14.2}$ substituent group is substituted, the $R^{14.2}$ substituent group is substituted with one or more third substituent groups denoted by $R^{14.3}$ as explained in the definitions section above in the description of “first substituent group(s)”. In the above embodiments, $R^{14.1}$, $R^{14.2}$, and $R^{14.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{14.1}$, $R^{14.2}$, and $R^{14.3}$, respectively.

In embodiments, when $R^{14}$ and $R^{15}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{14.1}$ as explained in the definitions section above in the description of “first substituent group(s)”. In embodiments, when an $R^{14.1}$ substituent group is substituted, the $R^{14.1}$ substituent group is substituted with one or more second substituent groups denoted by $R^{14.2}$ as explained in the definitions section above in the description of “first substituent group(s)”. In embodiments, when an $R^{14.2}$ substituent group is substituted, the $R^{14.2}$ substituent group is substituted with one or more third substituent groups denoted by $R^{14.3}$ as explained in the definitions section above in the description of “first substituent group(s)”. In the above embodiments, $R^{14.1}$, $R^{14.2}$, and $R^{14.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$, and $R^{WW.3}$ correspond to $R^{14.1}$, $R^{14.2}$, and $R^{14.3}$, respectively.

In embodiments, when $R^{14}$ and $R^{15}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{15.1}$ as explained in the definitions section above in the description of “first substituent group(s)”. In embodiments, when an $R^{15.1}$ substituent group is substituted, the $R^{15.1}$ substituent group is substituted with one or more second substituent groups denoted by $R^{15.2}$ as explained in the definitions section above in the description of “first substituent group(s)”. In embodiments, when an $R^{15.2}$ substituent group is substituted, the $R^{15.2}$ substituent group is substituted with one or more third substituent groups denoted by $R^{15.3}$ as explained in the definitions section above in the description of “first substituent group(s)”. In the above embodiments, $R^{15.1}$, $R^{15.2}$, and $R^{15.3}$ have values corresponding to the values of $R^{WW.1}$, $R^{WW.2}$, and $R^{WW.3}$, respectively, as explained in the definitions section above in the description of “first substituent group(s)”, wherein $R^{WW.1}$, $R^{WW.2}$ and $R^{WW.3}$ correspond to $R^{15.1}$, $R^{15.2}$, and $R^{15.3}$, respectively.

In embodiments, the compound is

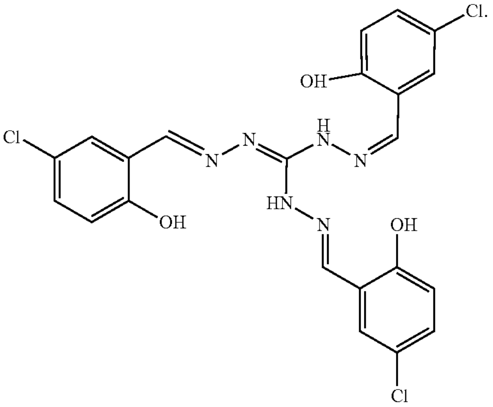 [SMILES: Oc1ccc(Cl)cc1/C=N\N/C(=N/N=C/Cc1cc(Cl)ccc1O)N/N=C/c1cc(Cl)ccc1O]

In embodiments, the compound is

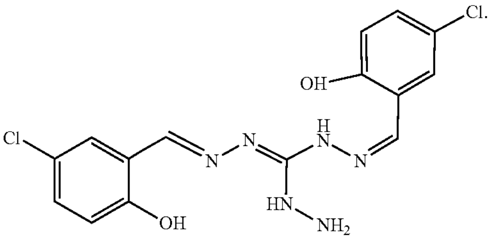 [SMILES: NN/C(=N\N=C\Cc1cc(Cl)ccc1O)N/N=C\c1cc(Cl)ccc1O]

In embodiments, the compound is

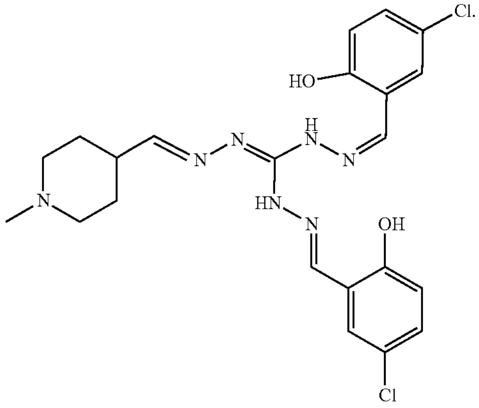 [SMILES: CN1CCC(C/C=N/N=C(/N/N=C\c2cc(Cl)ccc2O)N/N=C/c2cc(Cl)ccc2O)CC1]

In embodiments, the compound is

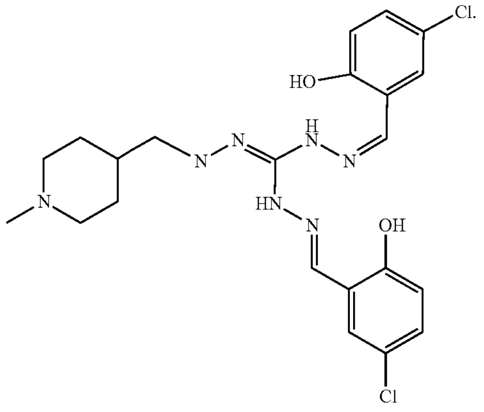 [SMILES: CN1CCC(CCN/N=C(/N/N=C\c2cc(Cl)ccc2O)N/N=C/c2cc(Cl)ccc2O)CC1]

In embodiments, the compound is

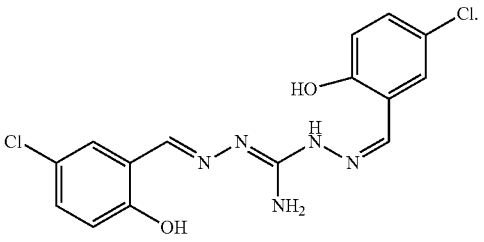 [SMILES: N/C(=N\N=C\c1cc(Cl)ccc1O)N/N=C\c1cc(Cl)ccc1O]

In embodiments, the compound is a compound described herein.

In embodiments, the compound is a compound described herein (e.g., in an aspect, embodiment, example, table, figure, or claim).

In embodiments, the compound is useful as a comparator compound. In embodiments, the comparator compound can be used to assess the activity of a test compound in an assay (e.g., an assay as described herein, for example in the examples section, figures, or tables).

In embodiments, $R^1$ is not —$OCH_3$. In embodiments, $R^4$ is not —$OCH_3$. In embodiments, $R^6$ is not —$OCH_3$. In embodiments, $R^9$ is not —$OCH_3$. In embodiments, $R^{11}$ is not —$OCH_3$. In embodiments, $R^{14}$ is not —$OCH_3$.

In embodiments, when $R^1$ is —OH, $R^4$ is not —OH. In embodiments, when $R^1$ is —OH, $R^4$ is not —$OCH_3$. In embodiments, when $R^6$ is —OH, $R^9$ is not —OH. In embodiments, when $R^6$ is —OH, $R^9$ is not —$OCH_3$. In embodiments, when $R^{11}$ is —OH, $R^{14}$ is not —OH. In embodiments, when $R^{11}$ is —OH, $R^{14}$ is not —$OCH_3$.

In embodiments, when $R^1$, $R^2$, $R^4$, and $R^5$ are each independently hydrogen, $R^3$ is not halogen. In embodiments, when $R^1$, $R^2$, $R^4$, and $R^5$ are each independently hydrogen, $R^3$ is not —Cl. In embodiments, when $R^6$, $R^7$, $R^9$, and $R^{10}$ are each independently hydrogen, $R^8$ is not halogen. In embodiments, when $R^6$, $R^7$, $R^9$, and $R^{10}$ are each independently hydrogen, $R^8$ is not —Cl. In embodiments, when $R^{11}$, $R^{12}$, $R^{14}$, and $R^{15}$ are each independently hydrogen, $R^{13}$ is not halogen. In embodiments, when $R^{11}$, $R^{12}$, $R^{14}$, and $R^{15}$ are each independently hydrogen, $R^{13}$ is not —Cl.

In embodiments, the compound is not

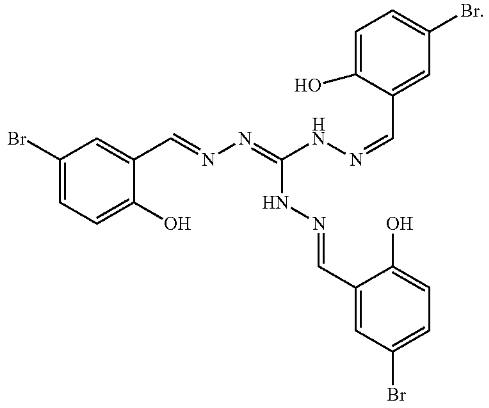 [SMILES: Oc1ccc(Br)cc1/C=N\N/C(=N/N=C/c1cc(Br)ccc1O)N/N=C/c1cc(Br)ccc1O]

In embodiments, the compound is not

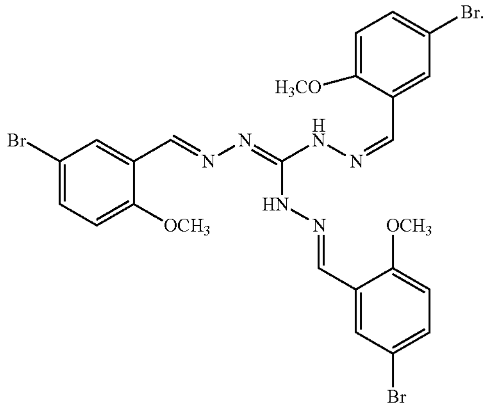 [SMILES: COc1ccc(Br)cc1/C=N\N/C(=N/N=C/c1cc(Br)ccc1OC)N/N=C/c1cc(Br)ccc1OC]

In embodiments, the compound is not

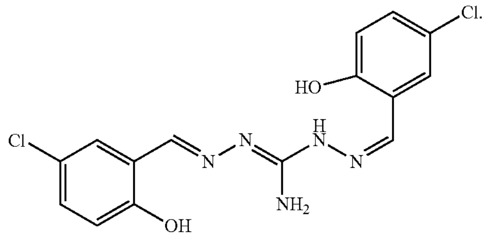 [SMILES: N/C(=N\N=C\c1cc(Cl)ccc1O)N/N=C\c1cc(Cl)ccc1O]

III. Pharmaceutical Compositions

In an aspect is provided a pharmaceutical composition including a compound described herein and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent. In embodiments, the pharmaceutical composition includes a therapeutically effective amount of a second agent. In embodiments, the second agent is an anti-cancer agent. In embodiments, the second agent is an anti-metabolic disease agent. In embodiments, the second agent is an anti-diabetic agent. In embodiments, the second agent is an anti-aging agent. In embodiments, the second agent is a longevity agent.

IV. Methods of Use

In an aspect is provided a method of treating a disease associated with a high level of IGF2BP2 in a subject in need thereof, the method including administering to the subject in need thereof a therapeutically effective amount of a compound described herein. In embodiments, the disease associated with a high level of IGF2BP2 is a cancer. In embodiments, the disease associated with a high level of IGF2BP2 is a metabolic disease. In embodiments, the disease associated with a high level of IGF2BP2 is aging.

In an aspect is provided a method of treating a cancer in a subject in need thereof, the method including administering to the subject in need thereof a therapeutically effective amount of a compound described herein.

In embodiments, the cancer is acute myeloid leukemia, colorectal cancer, liver cancer, breast cancer, lung cancer, ovarian cancer, pancreatic cancer, esophageal adenocarcinoma, endometrial adenocarcinoma, liposarcoma, glioma, glioblastoma, or gallbladder cancer. In embodiments, the cancer is acute myeloid leukemia. In embodiments, the cancer is colorectal cancer. In embodiments, the cancer is liver cancer. In embodiments, the cancer is breast cancer. In embodiments, the cancer is lung cancer. In embodiments, the cancer is ovarian cancer. In embodiments, the cancer is pancreatic cancer. In embodiments, the cancer is esophageal adenocarcinoma. In embodiments, the cancer is endometrial adenocarcinoma. In embodiments, the cancer is liposarcoma. In embodiments, the cancer is glioma. In embodiments, the cancer is glioblastoma. In embodiments, the cancer is gallbladder cancer. In embodiments, the cancer is triple negative breast cancer. In embodiments, the cancer is non-small cell lung cancer. In embodiments, the cancer is hepatocellular carcinoma. In embodiments, the cancer is neuroblastoma, glioma, glioblastoma multiforme, rhabdomyosarcoma, primary thrombocytosis, primary macroglobulinemia, or primary brain tumors.

In embodiments, the method further includes co-administering a second agent to the subject in need thereof. In embodiments, the second agent is an anti-cancer agent. In embodiments, the anti-cancer agent is cytarabine, decitabine, all-trans retinoic acid, 5-fluorouracil (5-FU), 5-azacytidine (5-Aza), cisplatin, carboplatin, oxaliplatin, irinotecan, topotecan, paclitaxel, gemcitabine, or capecitabine.

In an aspect is provided a method of treating a metabolic disorder in a subject in need thereof, the method including administering to the subject in need thereof a therapeutically effective amount of a compound described herein. In embodiments, the metabolic disorder is diabetes. In embodiments, the metabolic disorder is type 1 diabetes (T1D). In embodiments, the metabolic disorder is type 2 diabetes (T2D). In embodiments, the metabolic disorder is obesity.

In an aspect is provided a method of treating aging in a subject in need thereof, the method including administering to the subject in need thereof a therapeutically effective amount of a compound described herein.

In an aspect is provided a method of modulating (e.g., decreasing) the level of activity of IGF2BP2 in a subject in need thereof, the method including administering to the subject in need thereof an effective amount of a compound described herein. In embodiments, the method includes administering to the subject in need thereof a therapeutically effective amount of a compound described herein. In embodiments, the method of modulating is a method of decreasing the level of activity of IGF2BP2 in a subject in need thereof.

In an aspect is provided a method of decreasing the level of activity of IGF2BP2 in a cell, the method including contacting the cell with a compound described herein.

In an aspect is provided a method of treating a disease associated with a high level of IGF2BP2 in a subject in need thereof, the method including: i) determining the level of IGF2BP2 in the subject in need thereof; and ii) administering to the subject in need thereof an IGF2BP2 inhibitor, wherein the IGF2BP2 inhibitor decreases IGF2BP2 binding to RNA $N^6$-methyladenosine ($m^6A$). In embodiments, the IGF2BP2 inhibitor is a compound described herein.

In embodiments, the level of IGF2BP2 in the subject in need thereof is determined by flow cytometry, semi-quantitative polymerase chain reaction (PCR), real-time quantitative polymerase chain reaction (qPCR), western blot, high performance liquid chromatography (HPLC), mass spectrometry, enzyme-linked immunosorbent assay (ELISA), tissue arrays, histochemistry, or immunohistochemistry.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A method of treating a disease associated with a high level of IGF2BP2 in a subject in need thereof, said method comprising administering to the subject in need thereof a therapeutically effective amount of a compound having the formula (I)

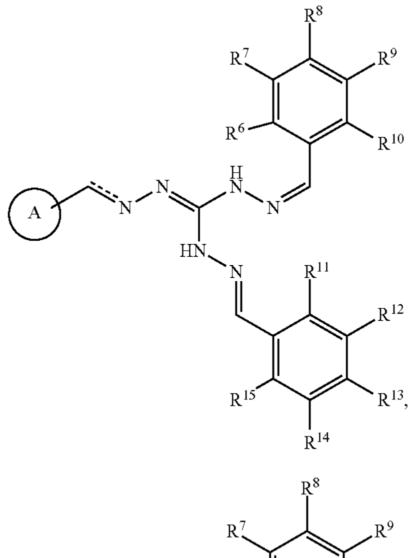

(II)

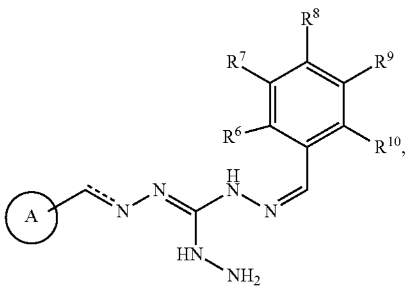

-continued (III)

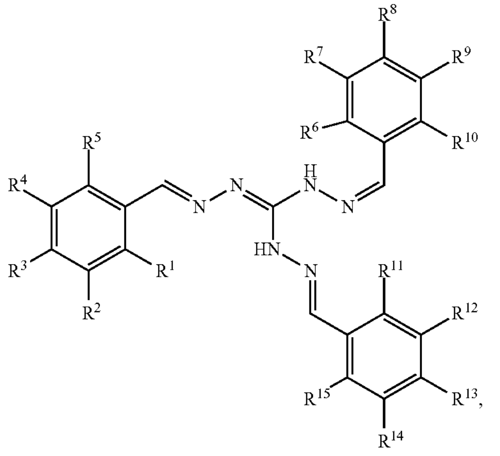

or (IV)

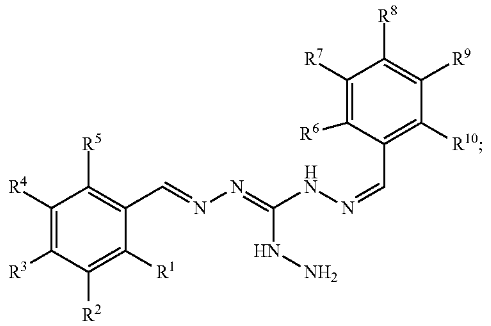

wherein

Ring A is a substituted or unsubstituted cycloalkyl, substituted or unsubstituted heterocycloalkyl, substituted or unsubstituted aryl, or substituted or unsubstituted heteroaryl;

$\overline{\cdots}$ is a single bond or a double bond;

$R^1$ is independently hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-NR^{1C}NR^{1A}R^{1B}$, $-ONR^{1A}R^{1B}$, $-NHC(O)NR^{1C}NR^{1A}R^{1B}$, $-N(O)_{m1}$, $-NR^{1A}R^{1B}$, $-C(O)R^{1C}$, $-C(O)OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-NR^{2C}NR^{2A}R^{2B}$, $-ONR^{2A}R^{2B}$, $-NHC(O)NR^{2C}NR^{2A}R^{2B}$, $-N(O)_{m2}$, $-NR^{2A}R^{2B}$, $-C(O)R^{2C}$, $-C(O)OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-NR^3CNR^{3A}R^{3B}$, $-ONR^{3A}R^{3B}$, $-NHC(O)NR^3CNR^{3A}R^{3B}$, $-N(O)_{m3}$, $-NR^{3A}R^{3B}$, $-C(O)R^{3C}$, $-C(O)OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-NR^4CNR^{4A}R^{4B}$, $-ONR^{4A}R^{4B}$, $-NHC(O)NR^4CNR^{4A}R^{4B}$, $-N(O)_{m4}$, $-NR^{4A}R^{4B}$, $-C(O)R^{4C}$, $-C(O)OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n5}R^{5D}$, $-SO_{v5}NR^{5A}R^{5B}$, $-NHC(O)NR^{5A}R^{5B}$, $-NR^{5C}NR^{5A}R^{5B}$, $-ONR^{5A}R^{5B}$, $-NHC(O)NR^{5C}NR^{5A}R^{5B}$, $-N(O)_{m5}$, $-NR^{5A}R^{5B}$, $-C(O)R^{5C}$, $-C(O)OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is independently hydrogen, halogen, $-CX^6_3$, $-CHX^6_2$, $-CH_2X^6$, $-OCX^6_3$, $-OCH_2X^6$, $-OCHX^6_2$, $-CN$, $-SO_{n6}R^{6D}$, $-SO_{v6}NR^{6A}R^{6B}$, $-NHC(O)NR^{6A}R^{6B}$, $-NR^{6C}NR^{6A}R^{6B}$, $-ONR^{6A}R^{6B}$, $-NHC(O)NR^{6C}NR^{6A}R^{6B}$, $-N(O)_{m6}$, $-NR^{6A}R^{6B}$, $-C(O)R^{6C}$, $-C(O)OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-NR^{7C}NR^{7A}R^{7B}$, $-ONR^{7A}R^{7B}$, $-NHC(O)NR^{7C}NR^{7A}R^{7B}$, $-N(O)_{m7}$, $-NR^{7A}R^{7B}$, $-C(O)R^{7C}$, $-C(O)OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is independently hydrogen, halogen, $-CX^8_3$, $-CHX^8_2$, $-CH_2X^8$, $-OCX^8_3$, $-OCH_2X^8$, —$OCHX^8_2$, —CN, —$SO_{n8}R^{8D}$, —$SO_{v8}NR^{8A}R^{8B}$, —NHC(O)$NR^{8A}R^{8B}$, —$NR^{8C}NR^{8A}R^{8B}$, —$ONR^{8A}R^{8B}$, —NHC(O)$NR^{8C}NR^{8A}R^{8B}$, —$N(O)_{m8}$, —$NR^{8A}R^{8B}$, —C(O)$R^{8C}$, —C(O)$OR^{8C}$, —C(O)$NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is independently hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9D}$, —$SO_{v9}NR^{9A}R^{9B}$, —NHC(O)$NR^{9A}R^{9B}$, —$NR^{9C}NR^{9A}R^{9B}$, —$ONR^{9A}R^{9B}$, —NHC(O)$NR^{9C}NR^{9A}R^{9B}$, —$N(O)_{m9}$, —$NR^{9A}R^{9B}$, —C(O)$R^{9C}$, —C(O)$OR^{9C}$, —C(O)$NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is independently hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10D}$, —$SO_{v10}NR^{10A}R^{10B}$, —NHC(O)$NR^{10A}R^{10B}$, —$NR^{10C}NR^{10A}R^{10B}$, —$ONR^{10A}R^{10B}$, —NHC(O)$NR^{10C}NR^{10A}R^{10B}$, —$N(O)_{m10}$, —$NR^{10A}R^{10B}$, —C(O)$R^{10C}$, —C(O)$OR^{10C}$, —C(O)$NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is independently hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —CN, —$SO_{n11}R^{11D}$, —$SO_{v11}NR^{11A}R^{11B}$, —NHC(O)$NR^{11A}R^{11B}$, —$NR^{11C}NR^{11A}R^{11B}$, —$ONR^{11A}R^{11B}$, —NHC(O)$NR^{11C}NR^{11A}R^{11B}$, —$N(O)_{m11}$, —$NR^{11A}R^{11B}$, —C(O)$R^{11C}$, —C(O)$OR^{11C}$, —C(O)$NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is independently hydrogen, halogen, —$CX^{12}_3$, —$CHX^{12}_2$, —$CH_2X^{12}$, —$OCX^{12}_3$, —$OCH_2X^{12}$, —$OCHX^{12}_2$, —CN, —$SO_{n12}R^{12D}$, —$SO_{v12}NR^{12A}R^{12B}$, —NHC(O)$NR^{12A}R^{12B}$, —$NR^{12C}NR^{12A}R^{12B}$, —$ONR^{12A}R^{12B}$, —NHC(O)$NR^{12C}NR^{12A}R^{12B}$, —$N(O)_{m12}$, —$NR^{12A}R^{12B}$, —C(O)$R^{12C}$, —C(O)$OR^{12C}$, —C(O)$NR^{12A}R^{12B}$, —$OR^{12D}$, —$NR^{12A}SO_2R^{12D}$, —$NR^{12A}C(O)R^{12C}$, —$NR^{12A}C(O)OR^{12C}$, —$NR^{12A}OR^{12C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is independently hydrogen, halogen, —$CX^{13}_3$, —$CHX^{13}_2$, —$CH_2X^{13}$, —$OCX^{13}_3$, —$OCH_2X^{13}$, —$OCHX^{13}_2$, —CN, —$SO_{n3}R^{13D}$, —$SO_{v13}NR^{13A}R^{13B}$, —NHC(O)$NR^{13A}R^{13B}$, —$NR^{13C}NR^{13A}R^{13B}$, —$ONR^{13A}R^{13B}$, —NHC(O)$NR^{13C}NR^{13A}R^{13B}$, —$N(O)_{m13}$, —$NR^{13A}R^{13B}$, —C(O)$R^{13C}$, —C(O)$OR^{13C}$, —C(O)$NR^{13A}R^{13B}$, —$OR^{13D}$, —$NR^{13A}SO_2R^{13D}$, —$NR^{13A}C(O)R^{13C}$, —$NR^{13A}C(O)OR^{13C}$, —$NR^{13A}OR^{13C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is independently hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —CN, —$SO_{n4}R^{14D}$, —$SO_{v14}NR^{14A}R^{14B}$, —NHC(O)$NR^{14A}R^{14B}$, —$NR^{14C}NR^{14A}R^{14B}$, —$ONR^{14A}R^{14B}$, —NHC(O)$NR^{14C}NR^{14A}R^{14B}$, —$N(O)_{m14}$, —$NR^{14A}R^{14B}$, —C(O)$R^{14C}$, —C(O)$OR^{14C}$, —C(O)$NR^{14A}R^{14B}$, —$OR^{14D}$, —$NR^{14A}SO_2R^{14D}$, —$NR^{14A}C(O)R^{14C}$, —$NR^{14A}C(O)OR^{14C}$, —$NR^{14A}OR^{14C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is independently hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —CN, —$SO_{n15}R_{15D}$, —$SO_{v15}NR^{15A}R^{15B}$, —NHC(O)$NR^{15A}R^{15B}$, —$NR^{15C}NR^{15A}R^{15B}$, —$ONR^{15A}R^{15B}$, —NHC(O)$NR^{15C}NR^{15A}R^{15B}$, —$N(O)_{m15}$, —$NR^{15A}R^{15B}$, —C(O)$R^{15C}$, —C(O)$OR^{15C}$, —C(O)$NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ substituents may be joined to form a substituted or unsubstituted cycloalkyl, substituted or unsubstituted heterocycloalkyl, substituted or unsubstituted aryl, or substituted or unsubstituted heteroaryl;

$R^2$ and $R^3$ substituents may be joined to form a substituted or unsubstituted cycloalkyl, substituted or unsubstituted heterocycloalkyl, substituted or unsubstituted aryl, or substituted or unsubstituted heteroaryl;

$R^3$ and $R^4$ substituents may be joined to form a substituted or unsubstituted cycloalkyl, substituted or unsubstituted heterocycloalkyl, substituted or unsubstituted aryl, or substituted or unsubstituted heteroaryl;

$R^4$ and $R^5$ substituents may be joined to form a substituted or unsubstituted cycloalkyl, substituted or unsubstituted heterocycloalkyl, substituted or unsubstituted aryl, or substituted or unsubstituted heteroaryl;

$R^6$ and $R^7$ substituents may be joined to form a substituted or unsubstituted cycloalkyl, substituted or unsubstituted heterocycloalkyl, substituted or unsubstituted aryl, or substituted or unsubstituted heteroaryl;

$R^7$ and $R^8$ substituents may be joined to form a substituted or unsubstituted cycloalkyl, substituted or unsubstituted heterocycloalkyl, substituted or unsubstituted aryl, or substituted or unsubstituted heteroaryl;

$R^8$ and $R^9$ substitutents may be joined to form a substituted or unsubstituted cycloalkyl, substituted or unsubstituted heterocycloalkyl, substituted or unsubstituted aryl, or substituted or unsubstituted heteroaryl;

$R^9$ and $R^{10}$ substitutents may be joined to form a substituted or unsubstituted cycloalkyl, substituted or unsubstituted heterocycloalkyl, substituted or unsubstituted aryl, or substituted or unsubstituted heteroaryl;

$R^{11}$ and $R^{12}$ substitutents may be joined to form a substituted or unsubstituted cycloalkyl, substituted or unsubstituted heterocycloalkyl, substituted or unsubstituted aryl, or substituted or unsubstituted heteroaryl;

$R^{12}$ and $R^{13}$ substitutents may be joined to form a substituted or unsubstituted cycloalkyl, substituted or unsubstituted heterocycloalkyl, substituted or unsubstituted aryl, or substituted or unsubstituted heteroaryl;

$R^{13}$ and $R^{14}$ substitutents may be joined to form a substituted or unsubstituted cycloalkyl, substituted or unsubstituted heterocycloalkyl, substituted or unsubstituted aryl, or substituted or unsubstituted heteroaryl;

$R^{14}$ and $R^{15}$ substitutents may be joined to form a substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, and $R^{15D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may be joined to form a substituted or unsubstituted heterocycloalkyl or substituted or unsubstituted heteroaryl; $R^{2A}$ and $R^{2B}$ substituents bonded to the same nitrogen atom may be joined to form a substituted or unsubstituted heterocycloalkyl or substituted or unsubstituted heteroaryl; $R^{3A}$ and $R^{3B}$ substituents bonded to the same nitrogen atom may be joined to form a substituted or unsubstituted heterocycloalkyl or substituted or unsubstituted heteroaryl; $R^{4A}$ and $R^{4B}$ substituents bonded to the same nitrogen atom may be joined to form a substituted or unsubstituted heterocycloalkyl or substituted or unsubstituted heteroaryl; $R^{5A}$ and $R^{5B}$ substituents bonded to the same nitrogen atom may be joined to form a substituted or unsubstituted heterocycloalkyl or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{7A}$ and $R^{7B}$ substituents bonded to the same nitrogen atom may be joined to form a substituted or unsubstituted heterocycloalkyl or substituted or unsubstituted heteroaryl; $R^{8A}$ and $R^{8B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{10A}$ and $R^{10B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{12A}$ and $R^{12B}$ substituents bonded to the same nitrogen atom may be joined to form a substituted or unsubstituted heterocycloalkyl or substituted or unsubstituted heteroaryl; $R^{13A}$ and $R^{13B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl; $R^{15A}$ and $R^{15B}$ substituents bonded to the same nitrogen atom may be joined to form a substituted or unsubstituted heterocycloalkyl or substituted or unsubstituted heteroaryl;

n1, n2, n3, n4, n5, n6, n7, n8, n9, n10, n11, n12, n13, n14, and n15 are independently an integer from 0 to 4;

m1, m2, m3, m4, m5, m6, m7, m8, m9, m10, m11, m12, m13, m14, m15, v1, v2, v3, v4, v5, v6, v7, v8, v9, v10, v11, v12, v13, v14, and v15 are independently 1 or 2; and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ are independently $-F$, $-Cl$, $-Br$, or $-I$.

Embodiment P2. The method of embodiment P1, wherein the compound has the formula (IIIa)

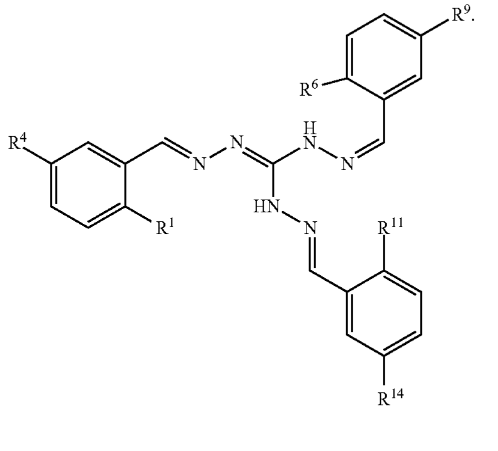

Embodiment P3. The method of embodiment P2, wherein $R^1$ is independently $-OR^{1D}$;

$R^6$ is independently $-OR^{6D}$;

$R^{11}$ is independently $-OR^{11D}$; and $R^4$, $R^9$, and $R^{14}$ are each independently halogen.

Embodiment P4. The method of embodiment P2, wherein $R^1$, $R^6$, and $R^{11}$ are each independently $-OH$; and $R^4$, $R^9$, and $R^{14}$ are each independently $-Cl$.

Embodiment P5. The method of embodiment P1, wherein the compound has the formula (IVa)

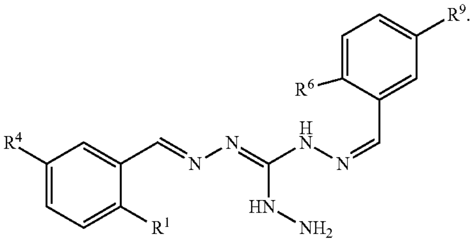

Embodiment P6. The method of embodiment P5, wherein $R^1$ is independently —$OR^{1D}$;

$R^6$ is independently —$OR^{6D}$; and $R^4$ and $R^9$ are each independently halogen.

Embodiment P7. The method of embodiment P5, wherein $R^1$ and $R^6$ are each independently —OH; and $R^4$ and $R^9$ are each independently —Cl.

Embodiment P8. The method of one of embodiments P1 to P7, wherein the disease associated with a high level of IGF2BP2 is a cancer.

Embodiment P9. The method of embodiment P8, wherein the cancer is acute myeloid leukemia, colorectal cancer, liver cancer, breast cancer, lung cancer, ovarian cancer, pancreatic cancer, esophageal adenocarcinoma, endometrial adenocarcinoma, liposarcoma, glioma, glioblastoma, or gallbladder cancer.

Embodiment P10. A compound having the formula (IIIa)

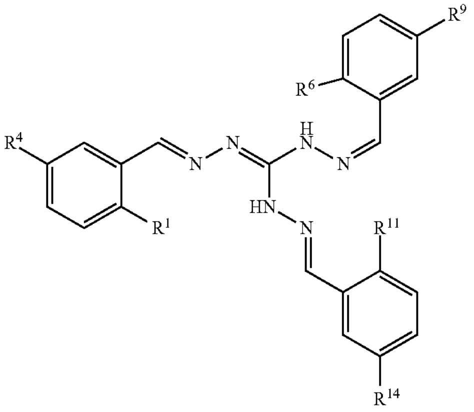

or (IVa)

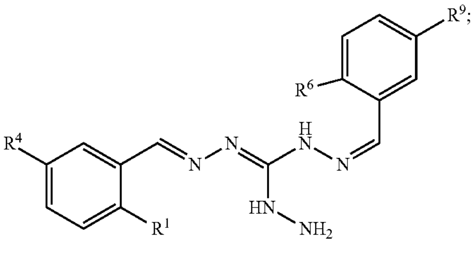

wherein $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$NR^{1C}NR^{1A}R^{1B}$, —$ONR^{1A}R^{1B}$, —$NHC(O)NR^{1C}NR^{1A}R^{1B}$, —$N(O)_{m1}$, —$NR^{1A}R^{1B}$, —$C(O)R^{1C}$, —$C(O)OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$NR^{4C}NR^{4A}R^{4B}$, —$ONR^{4A}R^{4B}$, —$NHC(O)NR^{4C}NR^{4A}R^{4B}$, —$N(O)_{m4}$, —$NR^{4A}R^{4B}$, —$C(O)R^{4C}$, —$C(O)OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}R^{6D}$—$SO_{v6}NR^{6A}R^{6B}$, —$NHC(O)NR^{6A}R^{6B}$, —$NR^{6C}NR^{6A}R^{6B}$, —$ONR^{6A}R^{6B}$, —$NHC(O)NR^{6C}NR^{6A}R^{6B}$, —$N(O)_{m6}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is independently hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9D}$, —$SO_{v9}NR^{9A}R^{9B}$, —$NHC(O)NR^{9A}R^{9B}$, —$NR^{9C}NR^{9A}R^{9B}$, —$ONR^{9A}R^{9B}$, —$NHC(O)NR^{9C}NR^{9A}R^{9B}$, —$N(O)_{m9}$, —$NR^{9A}R^{9B}$, —$C(O)R^{9C}$, —$C(O)OR^{9C}$, —$C(O)NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is independently hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —CN, —$SO_{n11}R^{11D}$, —$SO_{v11}NR^{11A}R^{11B}$, —$NHC(O)NR^{11A}R^{11B}$, —$NR^{11C}NR^{11A}R^{11B}$, —$ONR^{11A}R^{1B}$, —$NHC(O)NR^{11C}NR^{11A}R^{11B}$, —$N(O)_{m11}$, —$NR^{11A}R^{11B}$, —$C(O)R^{11C}$, —$C(O)OR^{11C}$, —$C(O)NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is independently hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —CN, —$SO_{n4}R^{14D}$, —$SO_{v14}NR^{14A}R^{14B}$, —$NHC(O)NR^{14A}R^{14B}$, —$NR^{14C}NR^{14A}R^{14B}$, —$ONR^{14A}R^{14B}$, —$NHC(O)NR^{14C}NR^{14A}R^{14B}$, —$N(O)_{m14}$, —$NR^{14A}R^{14B}$, —C(O)

$R^{14C}$, —C(O)OR$^{14C}$, —C(O)NR$^{14A}$R$^{14B}$, —OR$^{14D}$, —NR$^{14A}$SO$_2$R$^{14D}$, —NR$^{14A}$C(O)R$^{14C}$, —NR$^{14A}$C(O)OR$^{14C}$, —NR$^{14A}$OR$^{14C}$, —SF$_5$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{4A}$, $R^{4B}$, $R^{4C}$, $R^{4D}$, $R^{6A}$, $R^{6B}$, $R^{6C}$, $R^{6D}$, $R^{9A}$, $R^{9B}$, $R^{9C}$, $R^{9D}$, $R^{11A}$, $R^{11B}$, $R^{11C}$, $R^{11D}$, $R^{14A}$, $R^{14B}$, $R^{14C}$, and $R^{14D}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may be joined to form a substituted or unsubstituted heterocycloalkyl or substituted or unsubstituted heteroaryl; $R^{4A}$ and $R^{4B}$ substituents bonded to the same nitrogen atom may be joined to form a substituted or unsubstituted heterocycloalkyl or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl;

n1, n4, n6, n9, n11, and n14 are independently an integer from 0 to 4;

m1, m4, m6, m9, m11, m14, v1, v4, v6, v9, v11, and v14 are independently 1 or 2; and $X^1$, $X^4$, $X^6$, $X^9$, $X^{11}$, and $X^{14}$ are independently —F, —Cl, —Br, or —I;

wherein the compound is not

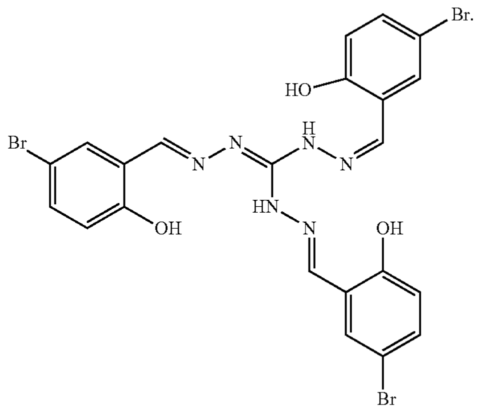 [SMILES: Oc1ccc(Br)cc1/C=N\N/C(=N/N=C/c1cc(Br)ccc1O)N/N=C/c1cc(Br)ccc1O]

Embodiment P11. The compound of embodiment P10, having the formula (IIIa)

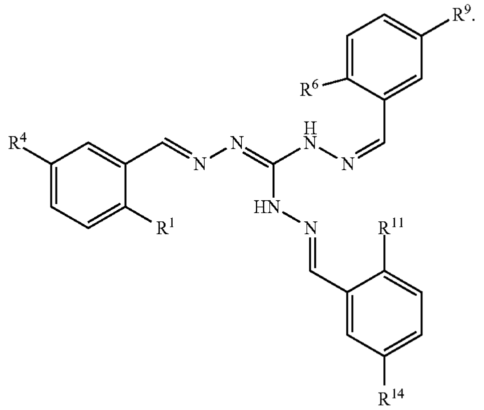

Embodiment P12. The compound of embodiment P11, wherein $R^1$ is independently —OR$^{1D}$;

$R^6$ is independently —OR$^{6D}$;

$R^{11}$ is independently —OR$^{11D}$; and $R^4$, $R^9$, and $R^{14}$ are each independently —Cl.

Embodiment P13. The compound of embodiment P11, wherein $R^1$, $R^6$, and $R^{11}$ are each independently —OH; and $R^4$, $R^9$, and $R^{14}$ are each independently —Cl.

Embodiment P14. The compound of embodiment P10, having the formula (IVa)

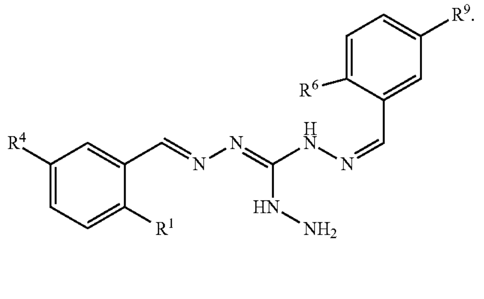

Embodiment P15. The compound of embodiment P14, wherein $R^1$ is independently $—OR^{1D}$;

$R^6$ is independently $—OR^{6D}$; and $R^4$ and $R^9$ are each independently halogen.

Embodiment P16. The compound of embodiment P14, wherein $R^1$ and $R^6$ are each independently —OH; and $R^4$ and $R^9$ are each independently —Cl.

Embodiment P17. A pharmaceutical composition comprising a compound of one of embodiments P10 to P16 and a pharmaceutically acceptable excipient.

Embodiment P18. A method of modulating the level of activity of IGF2BP2 in a subject in need thereof, the method comprising administering to the subject in need thereof an effective amount of a compound, wherein the compound has the formula (I)

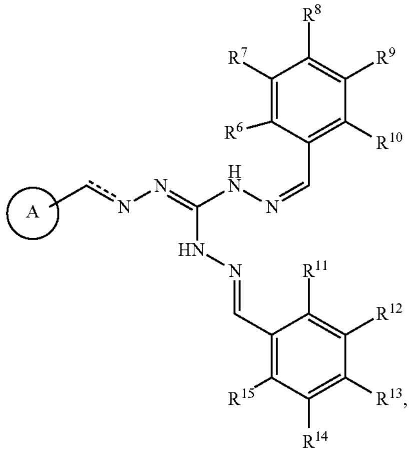

(II)

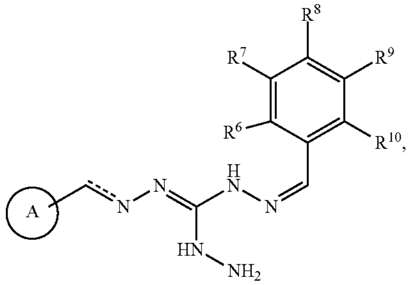

(III)

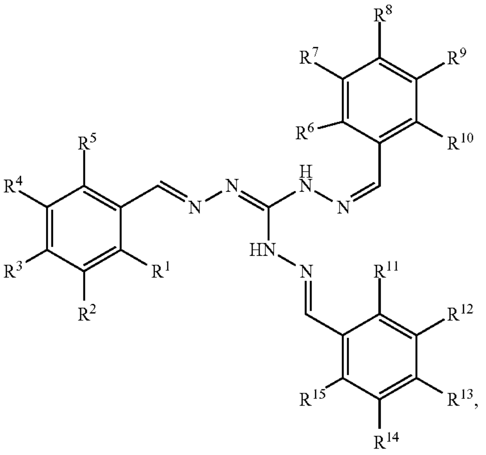

or

-continued (IV)

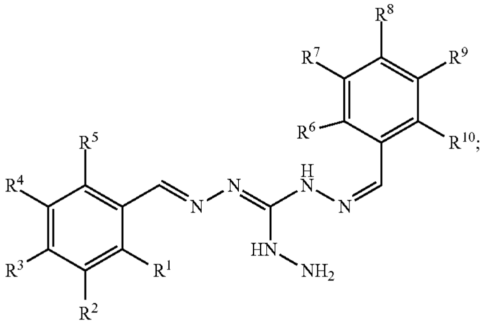

wherein

Ring A is a substituted or unsubstituted cycloalkyl, substituted or unsubstituted heterocycloalkyl, substituted or unsubstituted aryl, or substituted or unsubstituted heteroaryl;

⋰ is a single bond or a double bond;

$R^1$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NHC(O)NR^{1A}R^{1B}$, $—NR^{1C}NR^{1A}R^{1B}$, $—ONR^{1A}R^{1B}$, $—NHC(O)NR^{1C}NR^{1A}R^{1B}$, $—N(O)_{m1}$, $—NR^{1A}R^{1B}$, $—C(O)R^{1C}$, $—C(O)OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NHC(O)NR^{2A}R^{2B}$, $—NR^{2C}NR^{2A}R^{2B}$, $—ONR^{2A}R^{2B}$, $—NHC(O)NR^{2C}NR^{2A}R^{2B}$, $—N(O)_{m2}$, $—NR^{2A}R^{2B}$, $—C(O)R^{2C}$, $—C(O)OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NHC(O)NR^{3A}R^{3B}$, $—NR^3CNR^{3A}R^{3B}$, $—ONR^{3A}R^{3B}$, $—NHC(O)NR^{3C}NR^{3A}R^{3B}$, $—N(O)_{m3}$, $—NR^{3A}R^{3B}$, $—C(O)R^{3C}$, $—C(O)OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{4D}$, $—SO_{v4}NR^{4A}R^{4B}$, $—NHC(O)NR^{4A}R^{4B}$, $—NR^4CNR^{4A}R^{4B}$, $—ONR^{4A}R^{4B}$, $—NHC(O)NR^4CNR^{4A}R^{4B}$, $—N(O)_{m4}$, $—NR^{4A}R^{4B}$, $—C(O)R^{4C}$, $—C(O)OR^{4C}$, —C(O)

$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, halogen, —$CX^5_3$, —$CHX^5_2$, —$CH_2X^5$, —$OCX^5_3$, —$OCH_2X^5$, —$OCHX^5_2$, —CN, —$SO_{n5}R^{5D}$, —$SO_{v5}NR^{5A}R^{5B}$, —$NHC(O)NR^{5A}R^{5B}$, —$NR^{5C}NR^{5A}R^{5B}$, —$ONR^{5A}R^{5B}$, —$NHC(O)NR^{5C}NR^{5A}R^{5B}$, —$N(O)^{m5}$, —$NR^{5A}R^{5B}$, —$C(O)R^{5C}$, —$C(O)OR^{5C}$, —$C(O)NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}OR^{5C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}R^{6D}$, —$SO_{v6}NR^{6A}R^{6B}$, —$NHC(O)NR^{6A}R^{6B}$, —$NR^{6C}NR^{6A}R^{6B}$, —$ONR^{6A}R^{6B}$, —$NHC(O)NR^{6C}NR^{6A}R^{6B}$, —$N(O)_{m6}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —$NHC(O)NR^{7A}R^{7B}$, —$NR^{7C}NR^{7A}R^{7B}$, —$ONR^{7A}R^{7B}$, —$NHC(O)NR^{7C}NR^{7A}R^{7B}$, —$N(O)_{m7}$, —$NR^{7A}R^{7B}$, —$C(O)R^{7C}$, —$C(O)OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is independently hydrogen, halogen, —$CX^8_3$, —$CHX^8_2$, —$CH_2X^8$, —$OCX^8_3$, —$OCH_2X^8$, —$OCHX^8_2$, —CN, —$SO_{18}R^{8D}$, —$SO_{v8}NR^{8A}R^{8B}$, —$NHC(O)NR^{8A}R^{8B}$, —$NR^{8C}NR^{8A}R^{8B}$, —$ONR^{8A}R^{8B}$, —$NHC(O)NR^{8C}NR^{8A}R^{8B}$, —$N(O)_{m8}$, —$NR^{8A}R^{8B}$, —$C(O)R^{8C}$, —$C(O)OR^{8C}$, —$C(O)NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is independently hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9D}$, —$SO_{v9}NR^{9A}R^{9B}$, —$NHC(O)NR^{9A}R^{9B}$, —$NR^{9C}NR^{9A}R^{9B}$, —$ONR^{9A}R^{9B}$, —$NHC(O)NR^{9C}NR^{9A}R^{9B}$, —$N(O)_{m9}$, —$NR^{9A}R^{9B}$, —$C(O)R^{9C}$, —$C(O)OR^{9C}$, —$C(O)NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is independently hydrogen, halogen, —$CX^{10}_3$, —$CHX^{10}_2$, —$CH_2X^{10}$, —$OCX^{10}_3$, —$OCH_2X^{10}$, —$OCH^{10}_2$, —CN, —$SO_{n10}R^{10D}$, —$SO_{v10}NR^{10A}R^{10B}$, —$NHC(O)NR^{10A}R^{10B}$, —$NR^{10C}NR^{10A}R^{10B}$, —$ONR^{10A}R^{10B}$, —$NHC(O)NR^{10C}NR^{10A}R^{10B}$, —$N(O)_{m10}$, —$NR^{10A}R^{10B}$, —$C(O)R^{10C}$, —$C(O)OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is independently hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —CN, —$SO_{n11}R^{11D}$, —$SO_{v11}NR^{11A}R^{11B}$, —$NHC(O)NR^{11A}R^{11B}$, —$NR^{11C}NR^{11A}R^{11B}$, —$ONR^{11A}R^{11B}$, —$NHC(O)NR^{11C}NR^{11A}R^{11B}$, —$N(O)_{m11}$, —$NR^{11A}R^{11B}$, —$C(O)R^{11C}$, —$C(O)OR^{11C}$, —$C(O)NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is independently hydrogen, halogen, —$CX^{12}_3$, —$CHX^{12}_2$, —$CH_2X^{12}$, —$OCX^{12}_3$, —$OCH_2X^{12}$, —$OCHX^{12}_2$, —CN, —$SO_{n12}R^{12D}$, —$SO_{v12}NR^{12A}R^{12B}$, —$NHC(O)NR^{12A}R^{12B}$, —$NR^{12C}NR^{12A}R^{12B}$, —$ONR^{12A}R^{12B}$, —$NHC(O)NR^{12C}NR^{12A}R^{12B}$, —$N(O)_{m12}$, —$NR^{12A}R^{12B}$, —$C(O)R^{12C}$, —$C(O)OR^{12C}$, —$C(O)NR^{12A}R^{12B}$, —$OR^{12D}$, —$NR^{12A}SO_2R^{12D}$, —$NR^{12A}C(O)R^{12C}$, —$NR^{12A}C(O)OR^{12C}$, —$NR^{12A}OR^{12C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is independently hydrogen, halogen, —$CX^{13}_3$, —$CHX^{13}_2$, —$CH_2X^{13}$, —$OCX^{13}_3$, —$OCH_2X^{13}$, —$OCHX^{13}_2$, —CN, —$SO_{n3}R^{13D}$, —$SO_{v13}NR^{13A}R^{13B}$, —$NHC(O)NR^{13A}R^{13B}$, —$NR^{13C}NR^{13A}R^{13B}$, —$ONR^{13A}R^{13B}$, —$NHC(O)NR^{13C}NR^{13A}R^{13B}$, —$N(O)_{m13}$, —$NR^{13A}R^{13B}$, —$C(O)R^{13C}$, —$C(O)OR^{13C}$, —$C(O)NR^{13A}R^{13B}$, —$OR^{13D}$, —$NR^{13A}SO_2R^{13D}$, —$NR^{13A}C(O)R^{13C}$, —$NR^{13A}C(O)OR^{13C}$, —$NR^{13A}OR^{13C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is independently hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —CN, —$SO_{n4}R^{14D}$, —$SO_{v14}NR^{14A}R^{14B}$, —$NHC(O)NR^{14A}R^{14B}$, —$NR^{14C}NR^{14A}R^{14B}$, —$ONR^{14A}R^{14B}$, —$NHC(O)NR^{14C}NR^{14A}R^{14B}$, —$N(O)_{m14}$, —$NR^{14A}R^{14B}$, —C(O)

$R^{14C}$, —C(O)OR$^{14C}$, —C(O)NR$^{14A}$R$^{14B}$, —OR$^{14D}$, —NR$^{14A}$SO$_2$R$^{14D}$, —NR$^{14A}$C(O)R$^{14C}$, —NR$^{14A}$C(O)OR$^{14C}$, —NR$^{14A}$OR$^{14C}$, —SF$_5$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is independently hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —CN, —SO$_{n15}$R$^{15D}$, —SO$_{v15}$NR$^{15A}$R$^{15B}$, —NHC(O)NR$^{15A}$R$^{15B}$, —NR$^{15C}$NR$^{15A}$R$^{15B}$, —ONR$^{15A}$R$^{15B}$, —NHC(O)NR$^{15C}$NR$^{15A}$R$^{15B}$, —N(O)$_{m15}$, —NR$^{15A}$R$^{15B}$, —C(O)R$^{15C}$, —C(O)OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$, —SF$_5$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ substitutents may be joined to form a substituted or unsubstituted cycloalkyl, substituted or unsubstituted heterocycloalkyl, substituted or unsubstituted aryl, or substituted or unsubstituted heteroaryl;

$R^2$ and $R^3$ substitutents may be joined to form a substituted or unsubstituted cycloalkyl, substituted or unsubstituted heterocycloalkyl, substituted or unsubstituted aryl, or substituted or unsubstituted heteroaryl;

$R^3$ and $R^4$ substitutents may be joined to form a substituted or unsubstituted cycloalkyl, substituted or unsubstituted heterocycloalkyl, substituted or unsubstituted aryl, or substituted or unsubstituted heteroaryl;

$R^4$ and $R^5$ substitutents may be joined to form a substituted or unsubstituted cycloalkyl, substituted or unsubstituted heterocycloalkyl, substituted or unsubstituted aryl, or substituted or unsubstituted heteroaryl;

$R^6$ and $R^7$ substitutents may be joined to form a substituted or unsubstituted cycloalkyl, substituted or unsubstituted heterocycloalkyl, substituted or unsubstituted aryl, or substituted or unsubstituted heteroaryl;

$R^7$ and $R^8$ substitutents may be joined to form a substituted or unsubstituted cycloalkyl, substituted or unsubstituted heterocycloalkyl, substituted or unsubstituted aryl, or substituted or unsubstituted heteroaryl;

$R^8$ and $R^9$ substitutents may be joined to form a substituted or unsubstituted cycloalkyl, substituted or unsubstituted heterocycloalkyl, substituted or unsubstituted aryl, or substituted or unsubstituted heteroaryl;

$R^9$ and $R^{10}$ substitutents may be joined to form a substituted or unsubstituted cycloalkyl, substituted or unsubstituted heterocycloalkyl, substituted or unsubstituted aryl, or substituted or unsubstituted heteroaryl;

$R^{11}$ and $R^{12}$ substitutents may be joined to form a substituted or unsubstituted cycloalkyl, substituted or unsubstituted heterocycloalkyl, substituted or unsubstituted aryl, or substituted or unsubstituted heteroaryl;

$R^{12}$ and $R^{13}$ substitutents may be joined to form a substituted or unsubstituted cycloalkyl, substituted or unsubstituted heterocycloalkyl, substituted or unsubstituted aryl, or substituted or unsubstituted heteroaryl;

$R^{13}$ and $R^{14}$ substitutents may be joined to form a substituted or unsubstituted cycloalkyl, substituted or unsubstituted heterocycloalkyl, substituted or unsubstituted aryl, or substituted or unsubstituted heteroaryl;

$R^{14}$ and $R^{15}$ substitutents may be joined to form a substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{5A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{3A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, and $R^{15D}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may be joined to form a substituted or unsubstituted heterocycloalkyl or substituted or unsubstituted heteroaryl; $R^{2A}$ and $R^{2B}$ substituents bonded to the same nitrogen atom may be joined to form a substituted or unsubstituted heterocycloalkyl or substituted or unsubstituted heteroaryl; $R^{3A}$ and $R^{3B}$ substituents bonded to the same nitrogen atom may be joined to form a substituted or unsubstituted heterocycloalkyl or substituted or unsubstituted heteroaryl; $R^{4A}$ and $R^{4B}$ substituents bonded to the same nitrogen atom may be joined to form a substituted or unsubstituted heterocycloalkyl or substituted or unsubstituted heteroaryl; $R^{5A}$ and $R^{5B}$ substituents bonded to the same nitrogen atom may be joined to form a substituted or unsubstituted heterocycloalkyl or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{7A}$ and $R^{7B}$ substituents bonded to the same nitrogen atom may be joined to form a substituted or unsubstituted heterocycloalkyl or substituted or unsubstituted heteroaryl; $R^{8A}$ and $R^{8B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{10A}$ and $R^{10B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{12A}$ and $R^{12B}$ substituents bonded to the same nitrogen atom may be joined to form a substituted or unsubstituted heterocycloalkyl or substituted or unsubstituted heteroaryl; $R^{13A}$ and $R^{13B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl; $R^{15A}$ and $R^{15B}$ substituents bonded to the same nitrogen atom may be joined to form a substituted or unsubstituted heterocycloalkyl or substituted or unsubstituted heteroaryl;

n1, n2, n3, n4, n5, n6, n7, n8, n9, n10, n11, n12, n13, n14, and n15 are independently an integer from 0 to 4;

m1, m2, m3, m4, m5, m6, m7, m8, m9, m10, m11, m12, m13, m14, m15, v1, v2, v3, v4, v5, v6, v7, v8, v9, v10, v11, v12, v13, v14, and v15 are independently 1 or 2; and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ are independently —F, —Cl, —Br, or —I.

Embodiment P19. The method of embodiment P18, wherein the compound has the formula (IIIa)

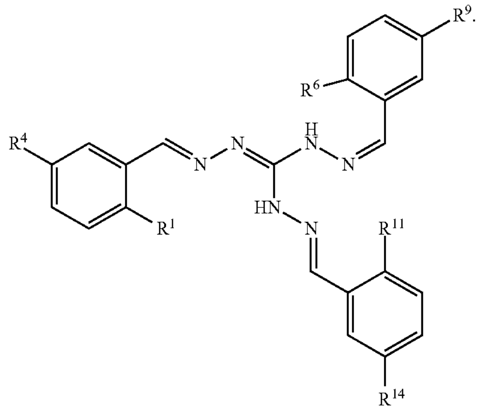

Embodiment P20. The method of embodiment P19, wherein $R^1$ is independently —$OR^{1D}$;

$R^6$ is independently —$OR^{6D}$;

$R^{11}$ is independently —$OR^{11D}$; and $R^4$, $R^9$, and $R^{14}$ are each independently halogen.

Embodiment P21. The method of embodiment P19, wherein $R^1$, $R^6$, and $R^{11}$ are each independently —OH; and $R^4$, $R^9$, and $R^{14}$ are each independently —Cl.

Embodiment P22. The method of embodiment P18, wherein the compound has the formula (IVa)

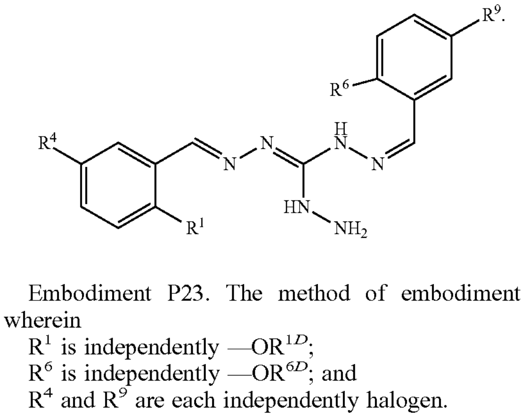

Embodiment P23. The method of embodiment P22, wherein $R^1$ is independently —$OR^{1D}$;

$R^6$ is independently —$OR^{6D}$; and $R^4$ and $R^9$ are each independently halogen.

Embodiment P24. The method of embodiment P22, wherein $R^1$ and $R^6$ are each independently —OH; and $R^4$ and $R^9$ are each independently —Cl.

Embodiment P25. A method of treating a disease associated with a high level of IGF2BP2 in a subject in need thereof, said method comprising:

i) determining the level of IGF2BP2 in the subject in need thereof, and ii) administering to the subject in need thereof an IGF2BP2 inhibitor, wherein the IGF2BP2 inhibitor decreases IGF2BP2 binding to RNA $N^6$-methyladenosine ($m^6A$).

Embodiment P26. The method of embodiment P25, wherein the IGF2BP2 inhibitor is a compound having the formula (I)

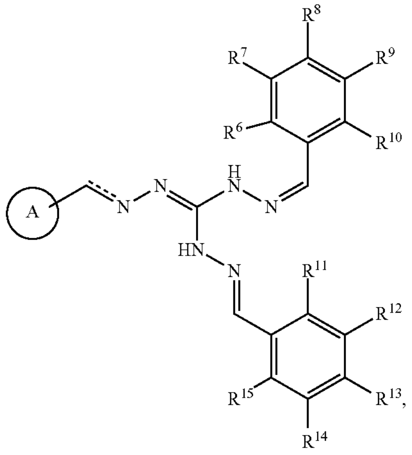

(II)

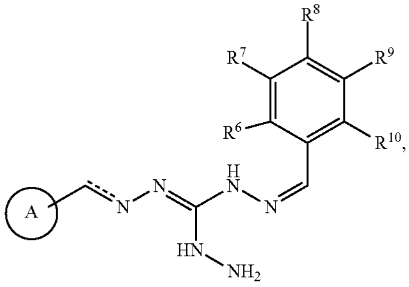

(III)

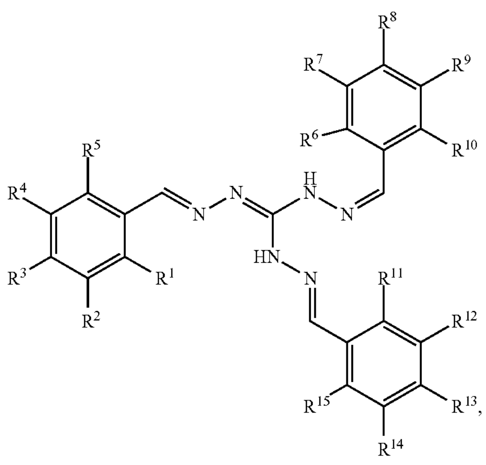

or

-continued (IV)

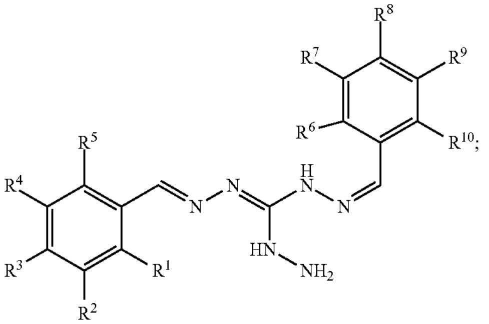

wherein

Ring A is a substituted or unsubstituted cycloalkyl, substituted or unsubstituted heterocycloalkyl, substituted or unsubstituted aryl, or substituted or unsubstituted heteroaryl;

$\cdots$ is a single bond or a double bond;

$R^1$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NHC(O)NR^{1A}R^{1B}$, $—NR^{1C}NR^{1A}R^{1B}$, $—ONR^{1A}R^{1B}$, $—NHC(O)NR^{1C}NR^{1A}R^{1B}$, $—N(O)_{m1}$, $—NR^{1A}R^{1B}$, $—C(O)R^{1C}$, $—C(O)OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NHC(O)NR^{2A}R^{2B}$, $—NR^{2C}NR^{2A}R^{2B}$, $—ONR^{2A}R^{2B}$, $—NHC(O)NR^{2C}NR^{2A}R^{2B}$, $—N(O)_{m2}$, $—NR^{2A}R^{2B}$, $—C(O)R^{2C}$, $—C(O)OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NHC(O)NR^{3A}R^{3B}$, $—NR^3CNR^{3A}R^{3B}$, $—ONR^{3A}R^{3B}$, $—NHC(O)NR^3CNR^{3A}R^{3B}$, $—N(O)_{m3}$, $—NR^{3A}R^{3B}$, $—C(O)R^{3C}$, $—C(O)OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{4D}$, $—SO_{v4}NR^{4A}R^{4B}$, $—NHC(O)NR^{4A}R^{4B}$, $—NR^4CNR^{4A}R^{4B}$, $—ONR^{4A}R^{4B}$, $—NHC(O)NR^4CNR^{4A}R^{4B}$, $—N(O)_{m4}$, $—NR^{4A}R^{4B}$, $—C(O)R^{4C}$, $—C(O)OR^{4C}$, $—C(O)NR^{4A}R^{4B}$, $—OR^{4D}$, $—NR^{4A}SO_2R^{4D}$, $—NR^{4A}C(O)R^{4C}$, $—NR^{4A}C(O)OR^{4C}$, $—NR^{4A}OR^{4C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, halogen, $—CX^5_3$, $—CHX^5_2$, $—CH_2X^5$, $—OCX^5_3$, $—OCH_2X^5$, $—OCHX^5_2$, —CN, $—SO_{n5}R^{5D}$, $—SO_{v5}NR^{5A}R^{5B}$, $—NHC(O)NR^{5A}R^{5B}$, $—NR^{5C}NR^{5A}R^{5B}$, $—ONR^{5A}R^{5B}$, $—NHC(O)NR^{5C}NR^{5A}R^{5B}$, $—N(O)_{m5}$, $—NR^{5A}R^{5B}$, $—C(O)R^{5C}$, $—C(O)OR^{5C}$, $—C(O)NR^{5A}R^{5B}$, $—OR^{5D}$, $—NR^{5A}SO_2R^{5D}$, $—NR^{5A}C(O)R^{5C}$, $—NR^{5A}C(O)OR^{5C}$, $—NR^{5A}OR^{5C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is independently hydrogen, halogen, $—CX^6_3$, $—CHX^6_2$, $—CH_2X^6$, $—OCX^6_3$, $—OCH_2X^6$, $—OCHX^6_2$, —CN, $—SO_{n6}R^{6D}$, $—SO_{v6}NR^{6A}R^{6B}$, $—NHC(O)NR^{6A}R^{6B}$, $—NR^{6C}NR^{6A}R^{6B}$, $—ONR^{6A}R^{6B}$, $—NHC(O)NR^{6C}NR^{6A}R^{6B}$, $—N(O)_{m6}$, $—NR^{6A}R^{6B}$, $—C(O)R^{6C}$, $—C(O)OR^{6C}$, $—C(O)NR^{6A}R^{6B}$, $—OR^{6D}$, $—NR^{6A}SO_2R^{6D}$, $—NR^{6A}C(O)R^{6C}$, $—NR^{6A}C(O)OR^{6C}$, $—NR^{6A}OR^{6C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently hydrogen, halogen, $—CX^7_3$, $—CHX^7_2$, $—CH_2X^7$, $—OCX^7_3$, $—OCH_2X^7$, $—OCHX^7_2$, —CN, $—SO_{n7}R^{7D}$, $—SO_{v7}NR^{7A}R^{7B}$, $—NHC(O)NR^{7A}R^{7B}$, $—NR^{7C}NR^{7A}R^{7B}$, $—ONR^{7A}R^{7B}$, $—NHC(O)NR^{7C}NR^{7A}R^{7B}$, $—N(O)_{m7}$, $—NR^{7A}R^{7B}$, $—C(O)R^{7C}$, $—C(O)OR^{7C}$, $—C(O)NR^{7A}R^{7B}$, $—OR^{7D}$, $—NR^{7A}SO_2R^{7D}$, $—NR^{7A}C(O)R^{7C}$, $—NR^{7A}C(O)OR^{7C}$, $—NR^{7A}OR^{7C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is independently hydrogen, halogen, $—CX^8_3$, $—CHX^8_2$, $—CH_2X^8$, $—OCX^8_3$, $—OCH_2X^8$, $—OCHX^8_2$, —CN, $—SO_{n8}R^{8D}$, $—SO_{v8}NR^{8A}R^{81}$, $—NHC(O)NR^{8A}R^{8B}$, $—NR^{8C}NR^{8A}R^{8B}$, $—ONR^{8A}R^{8B}$, $—NHC(O)NR^{8C}NR^{8A}R^{8B}$, $—N(O)_{m8}$, $—NR^{8A}R^{8B}$, $—C(O)R^{8C}$, $—C(O)OR^{8C}$, $—C(O)NR^{8A}R^{8B}$, $—OR^{8D}$, $—NR^{1A}SO_2R^{8D}$, $—NR^{8A}C(O)R^{8C}$, $—NR^{8A}C(O)OR^{8C}$, $—NR^{1A}OR^{8C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is independently hydrogen, halogen, $—CX^9_3$, $—CHX^9_2$, $—CH_2X^9$, $—OCX^9_3$, $—OCH_2X^9$, $—OCHX^9_2$, —CN, $—SO_{n9}R^{9D}$, $—SO_{v9}NR^{9A}R^{9B}$, $—NHC(O)NR^{9A}R^{9B}$, $—NR^{9C}NR^{9A}R^{9B}$, $—ONR^{9A}R^{9B}$, $—NHC(O)NR^{9C}NR^{9A}R^{9B}$, $—N(O)_{m9}$, $—NR^{9A}R^{9B}$, $—C(O)R^{9C}$, $—C(O)OR^{9C}$, $—C(O)NR^{9A}R^{9B}$, $—OR^{9D}$, $—NR^{9A}SO_2R^{9D}$, $—NR^{9A}C(O)R^{9C}$, $—NR^{9A}C(O)OR^{9C}$, $—NR^{9A}OR^{9C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is independently hydrogen, halogen, $-CX^{10}_3$, $-CHX^{10}_2$, $-CH_2X^{10}$, $-OCX^{10}_3$, $-OCH_2X^{10}$, $-OCHX^{10}_2$, $-CN$, $-SO_{n10}R^{10D}$, $-SO_{v10}NR^{10A}R^{10B}$, $-NHC(O)NR^{10A}R^{10B}$, $-NR^{10C}NR^{10A}R^{10B}$, $-ONR^{10A}R^{10B}$, $-NHC(O)NR^{10C}NR^{10A}R^{10B}$, $-N(O)_{m10}$, $-NR^{10A}R^{10B}$, $-C(O)R^{10C}$, $-C(O)OR^{10C}$, $-C(O)NR^{10A}R^{10B}$, $-OR^{10D}$, $-NR^{10A}SO_2R^{10D}$, $-NR^{10A}C(O)R^{10C}$, $-NR^{10A}C(O)OR^{10C}$, $-NR^{10A}OR^{10C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is independently hydrogen, halogen, $-CX^{11}_3$, $-CHX^{11}_2$, $-CH_2X^{11}$, $-OCX^{11}_3$, $-OCH_2X^{11}$, $-OCHX^{11}_2$, $-CN$, $-SO_{n11}R^{11D}$. $-SO_{v11}NR^{11A}R^{11B}$, $-NHC(O)NR^{11A}R^{11B}$, $-NR^{11C}NR^{11A}R^{11B}$, $-ONR^{11A}R^{11B}$, $-NHC(O)NR^{11C}NR^{11A}R^{11B}$, $-N(O)_{m11}$, $-NR^{11A}R^{11B}$, $-C(O)R^{11C}$, $-C(O)OR^{11C}$, $-C(O)NR^{11A}R^{11B}$, $-OR^{11D}$, $-NR^{11A}SO_2R^{11D}$, $-NR^{11A}C(O)R^{11C}$, $-NR^{11A}C(O)OR^{11C}$, $-NR^{11A}OR^{11C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is independently hydrogen, halogen, $-CX^{12}_3$, $-CHX^{12}_2$, $-CH_2X^{12}$, $-OCX^{12}_3$, $-OCH_2X^{12}$, $-OCHX^{12}_2$, $-CN$, $-SO_{n12}R^{12D}$, $-SO_{v12}NR^{12A}R^{12B}$, $-NHC(O)NR^{12A}R^{12B}$, $-NR^{12C}NR^{12A}R^{12B}$, $-ONR^{12A}R^{12B}$, $-NHC(O)NR^{12C}NR^{12A}R^{12B}$, $-N(O)_{m12}$, $-NR^{12A}R^{12B}$, $-C(O)R^{12C}$, $-C(O)OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)OR^{12C}$, $-NR^{12A}OR^{12C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is independently hydrogen, halogen, $-CX^{13}_3$, $-CHX^{13}_2$, $-CH_2X^{13}$, $-OCX^{13}_3$, $-OCH_2X^{13}$, $-OCHX^{13}_2$, $-CN$, $-SO_{n13}R^{13D}$, $-SO_{v13}NR^{13A}R^{13B}$, $-NHC(O)NR^{13A}R^{13B}$, $-NR^{13C}NR^{13A}R^{13B}$, $-ONR^{13A}R^{13B}$, $-NHC(O)NR^{13C}NR^{13A}R^{13B}$, $-N(O)_{m13}$, $-NR^{13A}R^{13B}$, $-C(O)R^{13C}$, $-C(O)OR^{13C}$, $-C(O)NR^{13A}R^{13B}$, $-OR^{13D}$, $-NR^{13A}SO_2R^{13D}$, $-NR^{13A}C(O)R^{13C}$, $-NR^{13A}C(O)OR^{13C}$, $-NR^{13A}OR^{13C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is independently hydrogen, halogen, $-CX^{14}_3$, $-CHX^{14}_2$, $-CH_2X^{14}$, $-OCX^{14}_3$, $-OCH_2X^{14}$, $-OCHX^{14}_2$, $-CN$, $-SO_{n14}R^{14D}$, $-SO_{v14}NR^{14A}R^{14B}$, $-NHC(O)NR^{14A}R^{14B}$, $-NR^{14C}NR^{14A}R^{14B}$, $-ONR^{14A}R^{14B}$, $-NHC(O)NR^{14C}NR^{14A}R^{14B}$, $-N(O)_{m14}$, $-NR^{14A}R^{14B}$, $-C(O)R^{14C}$, $-C(O)OR^{14C}$, $-C(O)NR^{14A}R^{14B}$, $-OR^{14D}$, $-NR^{14A}SO_2R^{14D}$, $-NR^{14A}C(O)R^{14C}$, $-NR^{14A}C(O)OR^{14C}$, $-NR^{14A}OR^{14C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is independently hydrogen, halogen, $-CX^{15}_3$, $-CHX^{15}_2$, $-CH_2X^{15}$, $-OCX^{15}_3$, $-OCH_2X^{15}$, $-OCHX^{15}_2$, $-CN$, $-SO_{n15}R^{15D}$, $-SO_{v15}NR^{15A}R^{15B}$, $-NHC(O)NR^{15A}R^{15B}$, $-NR^{15C}NR^{15A}R^{15B}$, $-ONR^{15A}R^{15B}$, $-NHC(O)NR^{15C}NR^{15A}R^{15B}$, $-N(O)_{m15}$, $-NR^{15A}R^{15B}$, $-C(O)R^{15C}$, $-C(O)OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)OR^{15C}$, $-NR^{15A}OR^{15C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ substituents may be joined to form a substituted or unsubstituted cycloalkyl, substituted or unsubstituted heterocycloalkyl, substituted or unsubstituted aryl, or substituted or unsubstituted heteroaryl;

$R^2$ and $R^3$ substituents may be joined to form a substituted or unsubstituted cycloalkyl, substituted or unsubstituted heterocycloalkyl, substituted or unsubstituted aryl, or substituted or unsubstituted heteroaryl;

$R^3$ and $R^4$ substituents may be joined to form a substituted or unsubstituted cycloalkyl, substituted or unsubstituted heterocycloalkyl, substituted or unsubstituted aryl, or substituted or unsubstituted heteroaryl;

$R^4$ and $R^5$ substituents may be joined to form a substituted or unsubstituted cycloalkyl, substituted or unsubstituted heterocycloalkyl, substituted or unsubstituted aryl, or substituted or unsubstituted heteroaryl;

$R^6$ and $R^7$ substituents may be joined to form a substituted or unsubstituted cycloalkyl, substituted or unsubstituted heterocycloalkyl, substituted or unsubstituted aryl, or substituted or unsubstituted heteroaryl;

$R^7$ and $R^8$ substituents may be joined to form a substituted or unsubstituted cycloalkyl, substituted or unsubstituted heterocycloalkyl, substituted or unsubstituted aryl, or substituted or unsubstituted heteroaryl;

$R^8$ and $R^9$ substituents may be joined to form a substituted or unsubstituted cycloalkyl, substituted or unsubstituted heterocycloalkyl, substituted or unsubstituted aryl, or substituted or unsubstituted heteroaryl;

$R^9$ and $R^{10}$ substituents may be joined to form a substituted or unsubstituted cycloalkyl, substituted or unsubstituted heterocycloalkyl, substituted or unsubstituted aryl, or substituted or unsubstituted heteroaryl;

$R^{11}$ and $R^{12}$ substituents may be joined to form a substituted or unsubstituted cycloalkyl, substituted or unsubstituted heterocycloalkyl, substituted or unsubstituted aryl, or substituted or unsubstituted heteroaryl;

$R^{12}$ and $R^{13}$ substituents may be joined to form a substituted or unsubstituted cycloalkyl, substituted or unsubstituted heterocycloalkyl, substituted or unsubstituted aryl, or substituted or unsubstituted heteroaryl;

$R^{13}$ and $R^{14}$ substituents may be joined to form a substituted or unsubstituted cycloalkyl, substituted or unsubstituted heterocycloalkyl, substituted or unsubstituted aryl, or substituted or unsubstituted heteroaryl;

$R^{14}$ and $R^{15}$ substitutents may be joined to form a substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{5A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, and $R^{15D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may be joined to form a substituted or unsubstituted heterocycloalkyl or substituted or unsubstituted heteroaryl; $R^{2A}$ and $R^{2B}$ substituents bonded to the same nitrogen atom may be joined to form a substituted or unsubstituted heterocycloalkyl or substituted or unsubstituted heteroaryl; $R^{3A}$ and $R^{3B}$ substituents bonded to the same nitrogen atom may be joined to form a substituted or unsubstituted heterocycloalkyl or substituted or unsubstituted heteroaryl; $R^{4A}$ and $R^{4B}$ substituents bonded to the same nitrogen atom may be joined to form a substituted or unsubstituted heterocycloalkyl or substituted or unsubstituted heteroaryl; $R^{5A}$ and $R^{5B}$ substituents bonded to the same nitrogen atom may be joined to form a substituted or unsubstituted heterocycloalkyl or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{7A}$ and $R^{7B}$ substituents bonded to the same nitrogen atom may be joined to form a substituted or unsubstituted heterocycloalkyl or substituted or unsubstituted heteroaryl; $R^{8A}$ and $R^{8B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{10A}$ and $R^{10B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{12A}$ and $R^{12B}$ substituents bonded to the same nitrogen atom may be joined to form a substituted or unsubstituted heterocycloalkyl or substituted or unsubstituted heteroaryl; $R^{13A}$ and $R^{13B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl; $R^{15A}$ and $R^{15B}$ substituents bonded to the same nitrogen atom may be joined to form a substituted or unsubstituted heterocycloalkyl or substituted or unsubstituted heteroaryl;

n1, n2, n3, n4, n5, n6, n7, n8, n9, n10, n11, n12, n13, n14, and n15 are independently an integer from 0 to 4;

m1, m2, m3, m4, m5, m6, m7, m8, m9, m10, m11, m12, m13, m14, m15, v1, v2, v3, v4, v5, v6, v7, v8, v9, v10, v11, v12, v13, v14, and v15 are independently 1 or 2; and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ are independently $-F$, $-Cl$, $-Br$, or $-I$.

Embodiment P27. The method of embodiment P26, wherein the compound has the formula (IIIa)

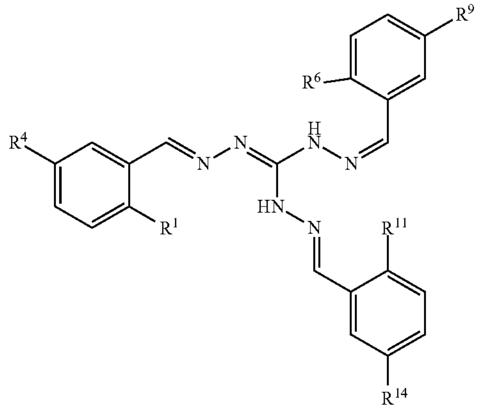

Embodiment P28. The method of embodiment P27, wherein $R^1$ is independently $-OR^1D$;

$R^6$ is independently $-OR^{6D}$;

$R^{11}$ is independently $-OR^{11D}$; and $R^4$, $R^9$, and $R^{14}$ are each independently halogen.

Embodiment P29. The method of embodiment P27, wherein $R^1$, $R^6$, and $R^{11}$ are each independently $-OH$; and $R^4$, $R^9$, and $R^{14}$ are each independently $-Cl$.

Embodiment P30. The method of embodiment P26, wherein the compound has the formula (IVa)

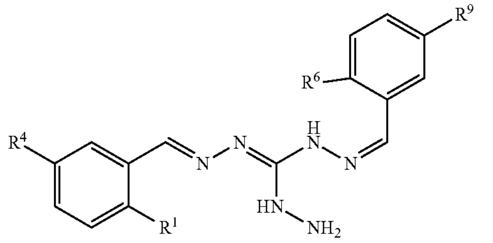

Embodiment P31. The method of embodiment P30, wherein $R^1$ is independently $-OR^{1D}$;

$R^6$ is independently $-OR^{6D}$; and $R^4$ and $R^9$ are each independently halogen.

Embodiment P32. The method of embodiment P30, wherein $R^1$ and $R^6$ are each independently —OH; and $R^4$ and $R^9$ are each independently —Cl.

EXAMPLES

Example 1: Methods and Compositions for Treating IGF2BP2-Mediated Cancers $N^6$-methyladenosine ($m^6A$) is the most abundant internal modification in messenger RNAs and affects mRNA fate in different aspects. These effects rely on the recognition of $m^6A$ by specific RNA binding proteins ($m^6A$ readers). We recently identified the insulin-like growth factor 2 mRNA-binding proteins (IGF2BP1/2/3) as $m^6A$ readers that could bind and stabilize $m^6A$-modified mRNAs. Among the three proteins in this family, IGF2BP2 is highly expressed and plays oncogenic roles in various types of cancers including colorectal cancer, hepatocellular carcinoma, breast cancer, lung cancer, gallbladder cancer, pancreatic cancer, glioblastoma, esophageal adenocarcinoma, and ovarian cancer, as well as in acute myeloid leukemia (AML). In addition, high level of IGF2BP2 expression is associated with poor prognosis in breast cancer, esophageal adenocarcinoma, gallbladder cancer, pancreatic cancer, lung cancer, ovarian cancer, liver cancer, and AML. We therefore sought to develop IGF2BP2 inhibitor-based therapeutics for the treatment of such types of cancers. Through a structure-based virtual screening following by mass spectrometry, HPLC purification, nuclear magnetic resonance and in vitro validation assays, we have successfully identified a potent small molecule compound, namely CWI1-2, which specifically binds to IGF2BP2 and prevent IGF2BP2 from binding to its mRNA targets and exhibits potent anti-cancer activities in vitro at nanomolar concentrations. CWI1-2 treatment significantly promoted apoptosis and myeloid differentiation of human AML cell lines with high-level of IGF2BP2 expression (i.e., IGF2BP2-high) in a dose-dependent manner. In addition, we showed that CWI1-2 treatment could remarkably inhibit engraftment of primary AML cells in bone marrow transplantation (BMT) recipient mice. This inhibitor is a first-in-class inhibitor that targets a RNA modification ($m^6A$) reader protein (herein IGF2BP2) and thereby suppressing expression of its oncogenic targets such as MYC oncogene.

IGF2BP2 is highly expressed and plays an oncogenic role in various cancers such as AML, colorectal cancer, hepatocellular carcinoma, breast cancer, lung cancer, gallbladder cancer, pancreatic cancer, glioblastoma, esophageal adenocarcinoma, and ovarian cancer, and that high level of IGF2BP2 is associated with poor prognosis in AML, breast cancer, gallbladder cancer, pancreatic cancer, lung cancer, ovarian cancer, liver cancer, and esophageal adenocarcinoma. Therefore, IGF2BP2 is a critical drug target.

IGF2BP2 plays an essential role in the maintenance and self-renewal of cancer stem/initiating cells. Thus, IGF2BP2 inhibitor-based therapeutics hold great potential to eradicate cancer stem/initiating cells and thereby may lead to the cure of cancer.

The identification of CWI1-2 as a potent inhibitor of IGF2BP2 that specifically inhibits binding of IGF2BP2 to its mRNA targets with $m^6A$ modification and exhibits a potent anti-cancer efficacy. CWI1-2 or an enantiomer or mixture of enantiomers thereof, or a pharmaceutically acceptable salt, solvate, hydrate, co-crystal, clathrate, or polymorph thereof, or CWI1-2 derivatives, or nanoparticle packed formula thereof is a potent inhibitor of IGF2BP2.

Using IGF2BP2 inhibitors such as CWI1-2 or its derivatives (in various formulations), alone or in combination with other therapeutic agents, to treat various types of cancers (e.g., AML, colorectal cancer, hepatocellular carcinoma, breast cancer, lung cancer, ovarian cancer, gallbladder cancer, pancreatic cancer, glioma, glioblastoma, and esophageal adenocarcinoma, etc.) in which IGF2BP2 expression is elevated than normal controls.

IGF2BP2 level may be detected at either the protein or the gene expression level.

IGF2BP2 level may serve as a biomarker for the prediction of treatment response and clinical outcome in cancer patients.

Virtual screening of library compounds and lead compound identification. NCI DTP library of approximately 260,000 compounds was screened. Screening included docking on the KH3 domain of IGF2BP2. Over 500 compounds were identified for experimental validation. NSC69557, termed CWI1, was identified as a top hit. Mass spectrometry (MS) identified CWI1 as a mixture including three major peaks: CWI1, CWI1-1, and CWI1-2. Their structures were predicted based on nuclear magnetic resonance (NMR) and MS data. The compound peaks for the predicted CWI1-1 and CWI1-2 were purified by HPLC. Through biological assays, it was determined that the fraction of the predicted CWI1-2 was the most active inhibitor of IGF2BP2. CWI1, CWI1-1, and CWI1-2 were synthesized based on the predicted structures. It was confirmed that CWI1 is less effective, CWI1-1 is effective, and CWI1-2 is much more effective, which is consistent with the data of testing the purified fractions. Thus, the structures of CWI1-1 and CWI1-2 were confirmed.

TABLE 1

| Compound structures | |
|---|---|
| 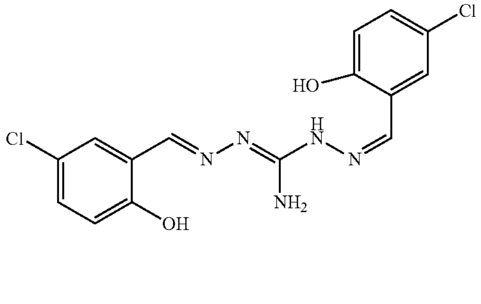 [SMILES: N/C(=N\N=C\c1cc(Cl)ccc1O)N/N=C\c1cc(Cl)ccc1O] | CWI1 (NSC 69557) |

TABLE 1-continued

| Compound structures |
|---|
| 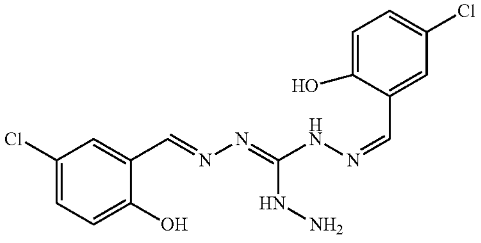 [SMILES: NN/C(=N\N=C\c1cc(Cl)ccc1O)N/N=C\c1cc(Cl)ccc1O] CWI1-1 |
| 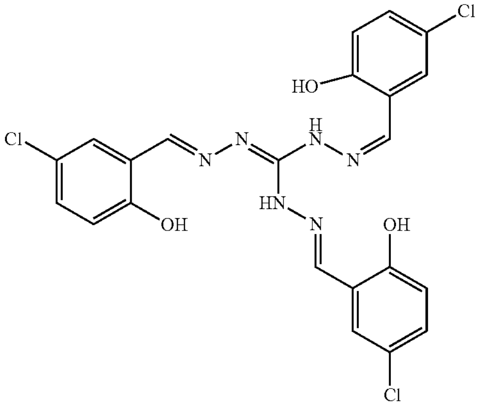 [SMILES: Oc1ccc(Cl)cc1/C=N\N/C(=N/N=C/c1cc(Cl)ccc1O)N/N=C/c1cc(Cl)ccc1O] CWI1-2 |

TABLE 1-continued

| Compound structures |
|---|
| 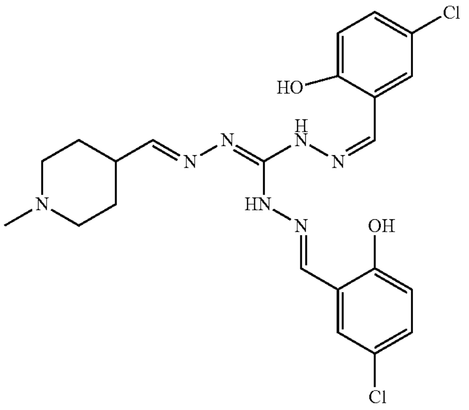 [SMILES: CN1CCC(/C=N/N=C(/N/N=C\c2cc(Cl)ccc2O)N/N=C/c2cc(Cl)ccc2O)CC1] CWI1-3 |
| 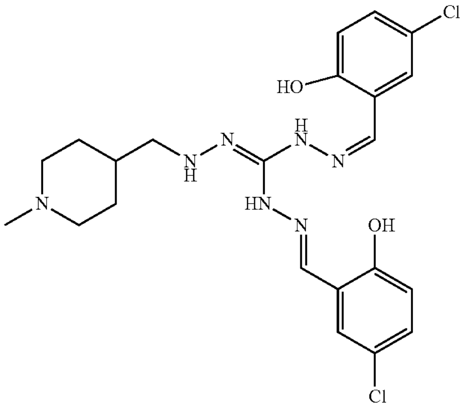 [SMILES: CN1CCC(CN/N=C(/N/N=C\c2cc(Cl)ccc2O)N/N=C/c2cc(Cl)ccc2O)CC1] CWI1-4 |

What is claimed is:

1. A method of treating a disease associated with a high level of IGF2BP2 relative to a normal control in a subject in need thereof, wherein the subject has a high level of IGF2BP2 relative to a normal control, said method comprising administering to the subject in need thereof a therapeutically effective amount of a compound having the formula (I)

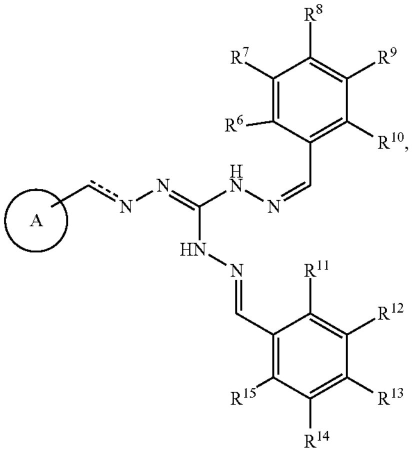

(II)

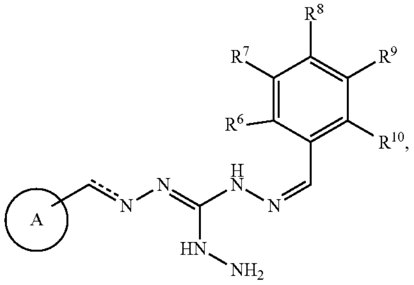

-continued (III)

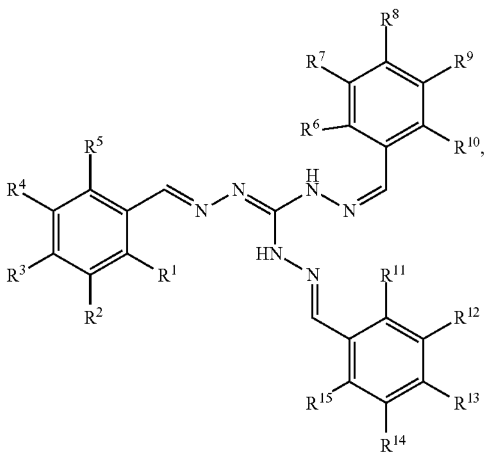

or (IV)

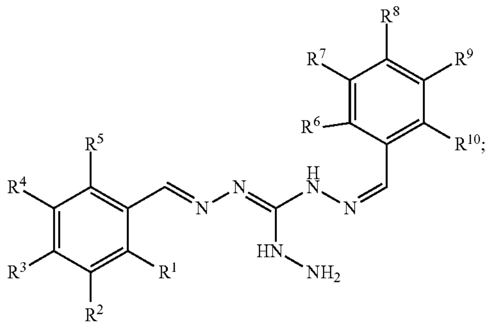

wherein

Ring A is a substituted or unsubstituted cycloalkyl, substituted or unsubstituted heterocycloalkyl, substituted or unsubstituted aryl, or substituted or unsubstituted heteroaryl;

is a single bond or a double bond;

$R^1$ is hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NHC(O)NR^{1A}R^{1B}$, $—NR^{1C}NR^{1A}R^{1B}$, $—ONR^{1A}R^{1B}$, $—NHC(O)NR^{1C}NR^{1A}R^{1B}$, $—N(O)_{m1}$, $—NR^{1A}R^{1B}$, $—C(O)R^{1C}$, $—C(O)OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^{23}$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —$NR^{2C}NR^{2A}R^{2B}$, —$ONR^{2A}R^{2B}$, —NHC(O)$NR^{2C}NR^{2A}R^{2B}$, —$N(O)_{m2}$, —$NR^{2A}R^{2B}$, —C(O)$R^{2C}$, —C(O)$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —$NR^{3C}NR^{3A}R^{3B}$, —$ONR^{3A}R^{3B}$, —NHC(O)$NR^{3C}NR^{3A}R^{3B}$, —$N(O)_{m3}$, —$NR^{3A}R^{3B}$, —C(O)$R^{3C}$, —C(O)$OR^{3C}$, —C(O)$NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —NHC(O)$NR^{4A}R^{4B}$, —$NR^{4C}NR^{4A}R^{4B}$, —$ONR^{4A}R^{4B}$, —NHC(O)$NR^{4C}NR^{4A}R^{4B}$, —$N(O)_{m4}$, —$NR^{4A}R^{4B}$, —C(O)$R^{4C}$, —C(O)$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CX^5_3$, —$CHX^5_2$, —$CH_2X^5$, —$OCX^5_3$, —$OCH_2X^5$, —$OCHX^5_2$, —CN, —$SO_{n5}R^{5D}$, —$SO_{v5}NR^{5A}R^{5B}$, —NHC(O)$NR^{5A}R^{5B}$, —$NR^{5C}NR^{5A}R^{5B}$, —$ONR^{5A}R^{5B}$, —NHC(O)$NR^{5C}NR^{5A}R^{5B}$, —$N(O)_{m5}$, —$NR^{5A}R^{5B}$, —C(O)$R^{5C}$, —C(O)$OR^{5C}$, —C(O)$NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}OR^{5C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}R^{6D}$, —$SO_{v6}NR^{6A}R^{6B}$, —NHC(O)$NR^{6A}R^{6B}$, —$NR^{6C}NR^{6A}R^{6B}$, —$ONR^{6A}R^{6B}$, —NHC(O)$NR^{6C}NR^{6A}R^{6B}$, —$N(O)_{m6}$, —$NR^{6A}R^{6B}$, —C(O)$R^{6C}$, —C(O)$OR^{6C}$, —C(O)$NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —NHC(O)$NR^{7A}R^{7B}$, —$NR^{7C}NR^{7A}R^{7B}$, —$ONR^{7A}R^{7B}$, —NHC(O)$NR^{7C}NR^{7A}R^{7B}$, —$N(O)_{m7}$, —$NR^{7A}R^{7B}$, —C(O)$R^{7C}$, —C(O)$OR^{7C}$, —C(O)$NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —$CX^8_3$, —$CHX^8_2$, —$CH_2X^8$, —$OCX^8_3$, —$OCH_2X^8$, —$OCHX^8_2$, —CN, —$SO_{n8}R^{8D}$, —$SO_{v8}NR^{8A}R^{8B}$, —NHC(O)$NR^{8A}R^{8B}$, —$NR^{8C}NR^{8A}R^{8B}$, —$ONR^{8A}R^{8B}$, —NHC(O)$NR^{8C}NR^{8A}R^{8B}$, —$N(O)_{m8}$, —$NR^{8A}R^{8B}$, —C(O)$R^{8C}$, —C(O)$OR^{8C}$, —C(O)$NR^{8A}R^{8B}$, —$OR^{8B}$, —$NR^{8A}SO_2R^{8D}$, —$NR^{8A}C(O)R^{8C}$, —$NR^{8A}C(O)OR^{8C}$, —$NR^{8A}OR^{8C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9D}$, —$SO_{v9}NR^{9A}R^{9B}$, —NHC(O)$NR^{9A}R^{9B}$, —$NR^{9C}NR^{9A}R^{9B}$, —$ONR^{9A}R^{9B}$, —NHC(O)$NR^{9C}NR^{9A}R^{9B}$, —$N(O)_{m9}$, —$NR^{9A}R^{9B}$, —C(O)$R^{9C}$, —C(O)$OR^{9C}$, —C(O)$NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10D}$, —$SO_{v10}NR^{10A}R^{10B}$, —NHC(O)$NR^{10A}R^{10B}$, —$NR^{10C}NR^{10A}R^{10B}$, —$ONR^{10A}R^{10B}$, —NHC(O)$NR^{10C}NR^{10A}R^{10B}$, —$N(O)_{m10}$, —$NR^{10A}R^{10B}$, —C(O)$R^{10C}$, —C(O)$OR^{10C}$, —C(O)$NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —CN, —$SO_{n11}R^{11D}$, —$SO_{v11}NR^{11A}R^{11B}$, —NHC(O)$NR^{11A}R^{11B}$, —$NR^{11C}NR^{11A}R^{11B}$, —$ONR^{11A}R^{11B}$, —NHC(O)$NR^{11C}NR^{11A}R^{11B}$, —$N(O)_{m11}$, —$NR^{11A}R^{11B}$, —C(O)$R^{11C}$, —C(O)$OR^{11C}$, —C(O)$NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $—CX^{12}_3$, $—CHX^{12}_2$, $—CH_2X^{12}$, $—OCX^{12}_3$, $—OCH_2X^{12}$, $—OCHX^{12}_2$, —CN, $—SO_{n12}R^{12D}$, $—SO_{v12}NR^{12A}R^{12B}$, $—NHC(O)NR^{12A}R^{12B}$, $—NR^{12C}NR^{12A}R^{12B}$, $—ONR^{12A}R^{12B}$, $—NHC(O)NR^{12C}NR^{12A}R^{12B}$, $—N(O)_{m12}$, $—NR^{12A}R^{12B}$, $—C(O)R^{12C}$, $—C(O)OR^{12C}$, $—C(O)NR^{12A}R^{12B}$, $—OR^{12D}$, $—NR^{12A}SO_2R^{12D}$, $—NR^{12A}C(O)R^{12C}$, $—NR^{12A}C(O)OR^{12C}$, $—NR^{12A}OR^{12C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, halogen, $—CX^{13}_3$, $—CHX^{13}_2$, $—CH_2X^{13}$, $—OCX^{13}_3$, $—OCH_2X^{13}$, $—OCHX^{13}_2$, —CN, $—SO_{n13}R^{13D}$, $—SO_{v13}NR^{13A}R^{13B}$, $—NHC(O)NR^{13A}R^{13B}$, $—NR^{13C}NR^{13A}R^{13B}$, $—ONR^{13A}R^{13B}$, $—NHC(O)NR^{13C}NR^{13A}R^{13B}$, $—N(O)_{m13}$, $—NR^{13A}R^{13B}$, $—C(O)R^{13C}$, $—C(O)OR^{13C}$, $—C(O)NR^{13A}R^{13B}$, $—OR^{13D}$, $—NR^{13A}SO_2R^{13D}$, $—NR^{13A}C(O)R^{13C}$, $—NR^{13A}C(O)OR^{13C}$, $—NR^{13A}OR^{13C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, $—CX^{14}_3$, $—CHX^{14}_2$, $—CH_2X^{14}$, $—OCX^{14}_3$, $—OCH_2X^{14}$, $—OCHX^{14}_2$, —CN, $—SO_{n14}R^{14D}$, $—SO_{v14}NR^{14A}R^{14B}$, $—NHC(O)NR^{14A}R^{14B}$, $—NR^{14C}NR^{14A}R^{14B}$, $—ONR^{14A}R^{14B}$, $—NHC(O)NR^{14C}NR^{14A}R^{14B}$, $—N(O)_{m14}$, $—NR^{14A}R^{14B}$, $—C(O)R^{14C}$, $—C(O)OR^{14C}$, $—C(O)NR^{14A}R^{14B}$, $—OR^{14D}$, $—NR^{14A}SO_2R^{14D}$, $—NR^{14A}C(O)R^{14C}$, $—NR^{14A}C(O)OR^{14C}$, $—NR^{14A}OR^{14C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $—CX^{15}_3$, $—CHX^{15}_2$, $—CH_2X^{15}$, $—OCX^{15}_3$, $—OCH_2X^{15}$, $—OCHX^{15}_2$, —CN, $—SO_{n15}R^{15D}$, $—SO_{v15}NR^{15A}R^{15B}$, $—NHC(O)NR^{15A}R^{15B}$, $—NR^{15C}NR^{15A}R^{15B}$, $—ONR^{15A}R^{15B}$, $—NHC(O)NR^{15C}NR^{15A}R^{15B}$, $—N(O)_{m15}$, $—NR^{15A}R^{15B}$, $—C(O)R^{15C}$, $—C(O)OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ substituents may be joined to form a substituted or unsubstituted cycloalkyl, substituted or unsubstituted heterocycloalkyl, substituted or unsubstituted aryl, or substituted or unsubstituted heteroaryl;

$R^2$ and $R^3$ substituents may be joined to form a substituted or unsubstituted cycloalkyl, substituted or unsubstituted heterocycloalkyl, substituted or unsubstituted aryl, or substituted or unsubstituted heteroaryl;

$R^3$ and $R^4$ substituents may be joined to form a substituted or unsubstituted cycloalkyl, substituted or unsubstituted heterocycloalkyl, substituted or unsubstituted aryl, or substituted or unsubstituted heteroaryl;

$R^4$ and $R^5$ substituents may be joined to form a substituted or unsubstituted cycloalkyl, substituted or unsubstituted heterocycloalkyl, substituted or unsubstituted aryl, or substituted or unsubstituted heteroaryl;

$R^6$ and $R^7$ substituents may be joined to form a substituted or unsubstituted cycloalkyl, substituted or unsubstituted heterocycloalkyl, substituted or unsubstituted aryl, or substituted or unsubstituted heteroaryl;

$R^7$ and $R^8$ substituents may be joined to form a substituted or unsubstituted cycloalkyl, substituted or unsubstituted heterocycloalkyl, substituted or unsubstituted aryl, or substituted or unsubstituted heteroaryl;

$R^8$ and $R^9$ substituents may be joined to form a substituted or unsubstituted cycloalkyl, substituted or unsubstituted heterocycloalkyl, substituted or unsubstituted aryl, or substituted or unsubstituted heteroaryl;

$R^9$ and $R^{10}$ substituents may be joined to form a substituted or unsubstituted cycloalkyl, substituted or unsubstituted heterocycloalkyl, substituted or unsubstituted aryl, or substituted or unsubstituted heteroaryl;

$R^{11}$ and $R^{12}$ substituents may be joined to form a substituted or unsubstituted cycloalkyl, substituted or unsubstituted heterocycloalkyl, substituted or unsubstituted aryl, or substituted or unsubstituted heteroaryl;

$R^{12}$ and $R^{13}$ substituents may be joined to form a substituted or unsubstituted cycloalkyl, substituted or unsubstituted heterocycloalkyl, substituted or unsubstituted aryl, or substituted or unsubstituted heteroaryl;

$R^{13}$ and $R^{14}$ substituents may be joined to form a substituted or unsubstituted cycloalkyl, substituted or unsubstituted heterocycloalkyl, substituted or unsubstituted aryl, or substituted or unsubstituted heteroaryl;

$R^{14}$ and $R^{15}$ substituents may be joined to form a substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, and $R^{15D}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may be joined to form a substituted or unsubstituted heterocycloalkyl or substituted or unsubstituted heteroaryl; $R^{2A}$ and $R^{2B}$ substituents bonded to the same nitrogen atom may be joined to form a substituted or unsubstituted heterocycloalkyl or substituted or unsubstituted heteroaryl; $R^{3A}$ and $R^{3B}$ substituents bonded to the same nitrogen atom may be joined to form a substituted or unsubstituted heterocycloalkyl or substituted or unsubstituted heteroaryl; $R^{4A}$ and $R^{4B}$ substituents bonded to the same nitrogen atom may be joined to form a substituted or unsubstituted heterocycloalkyl or substituted or unsubstituted heteroaryl; $R^{5A}$ and $R^{5B}$ substituents bonded to the same nitrogen atom may be joined to form a substituted or unsubstituted heterocycloalkyl or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{7A}$ and $R^{7B}$ substituents bonded to the same nitrogen atom may be joined to form a substituted or unsubstituted heterocycloalkyl or substituted or unsubstituted heteroaryl; $R^{8A}$ and $R^{8B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{10A}$ and $R^{11B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{12A}$ and $R^{12B}$ substituents bonded to the same nitrogen atom may be joined to form a substituted or unsubstituted heterocycloalkyl or substituted or unsubstituted heteroaryl; $R^{13A}$ and $R^{13B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl; $R^{15A}$ and $R^{15B}$ substituents bonded to the same nitrogen atom may be joined to form a substituted or unsubstituted heterocycloalkyl or substituted or unsubstituted heteroaryl;

n1, n2, n3, n4, n5, n6, n7, n8, n9, n10, n11, n12, n13, n14, and n15 are independently an integer from 0 to 4;

m1, m2, m3, m4, m5, m6, m7, m8, m9, m10, m11, m12, m13, m14, m15, v1, v2, v3, v4, v5, v6, v7, v8, v9, v10, v11, v12, v13, v14, and v15 are independently 1 or 2; and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ are independently —F, —Cl, —Br, or —I.

2. The method of claim 1, wherein the compound has the formula (IIIa)

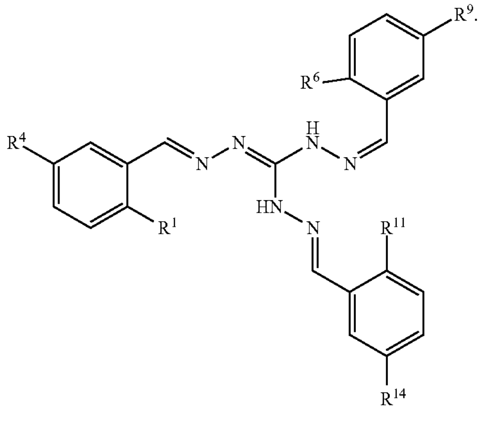

3. The method of claim 2, wherein $R^1$ is —$OR^{1D}$;

$R^6$ is —$OR^{6D}$;

$R^{11}$ is —$OR^{11D}$; and $R^4$, $R^9$, and $R^{14}$ are halogen.

4. The method of claim 2, wherein $R^1$, $R^6$, and $R^{11}$ are —OH; and $R^4$, $R^9$, and $R^{14}$ are —Cl.

5. The method of claim 1, wherein the compound has the formula (IVa)

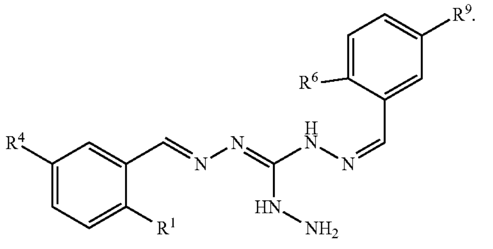

6. The method of claim 5, wherein $R^1$ is —$OR^{1D}$;

$R^6$ is —$OR^{6D}$; and $R^4$ and $R^9$ are halogen.

7. The method of claim 5, wherein $R^1$ and $R^6$ are —OH; and $R^4$ and $R^9$ are —Cl.

8. The method of claim 1, wherein the disease associated with a high level of IGF2BP2 is a cancer.

9. The method of claim 8, wherein the cancer is acute myeloid leukemia, colorectal cancer, liver cancer, breast cancer, lung cancer, ovarian cancer, pancreatic cancer, esophageal adenocarcinoma, endometrial adenocarcinoma, liposarcoma, glioma, glioblastoma, or gallbladder cancer.

10. A method of modulating the level of activity of IGF2BP2 in a subject in need thereof, wherein the subject has a high level of IGF2BP2 relative to a normal control, the method comprising administering to the subject in need thereof an effective amount of a compound, wherein the compound has the formula (I)

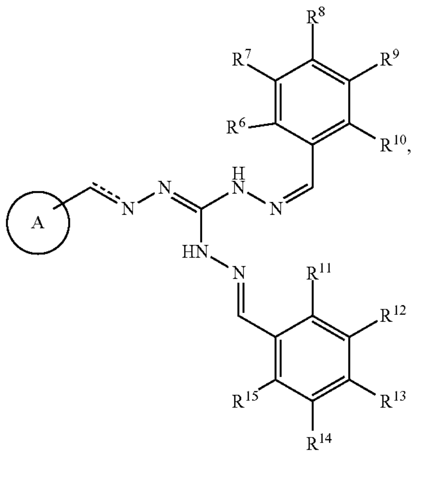

-continued (II)

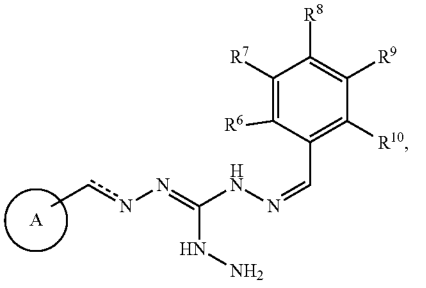

(III)

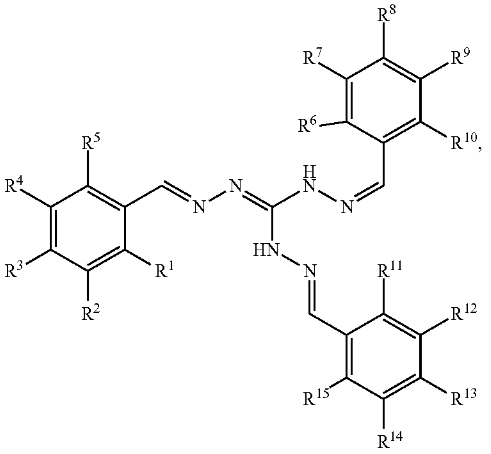

or (IV)

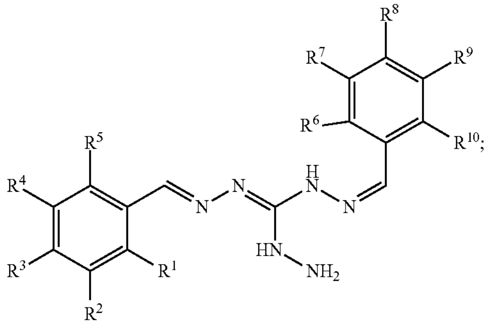

wherein

Ring A is a substituted or unsubstituted cycloalkyl, substituted or unsubstituted heterocycloalkyl, substituted or unsubstituted aryl, or substituted or unsubstituted heteroaryl;

 is a single bond or a double bond;

$R^1$ is hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NHC(O)NR^{1A}R^{1B}$, $—NR^{1C}NR^{1A}R^{1B}$, $—ONR^{1A}R^{1B}$, $—NHC(O)NR^{1C}NR^{1A}R^{1B}$, $—N(O)_{m1}$, $—NR^{1A}R^{1B}$, $—C(O)R^{1C}$, $—C(O)OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NHC(O)NR^{2A}R^{2B}$, $—NR^{2C}NR^{2A}R^{2B}$, $—ONR^{2A}R^{2B}$, $—NHC(O)NR^{2C}NR^{2A}R^{2B}$, $—N(O)_{m2}$, $—NR^{2A}R^{2B}$, $—C(O)R^{2C}$, $—C(O)OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NHC(O)NR^{3A}R^{3B}$, $—NR^{3C}NR^{3A}R^{3B}$, $—ONR^{3A}R^{3B}$, $—NHC(O)NR^{3C}NR^{3A}R^{3B}$, $—N(O)_{m3}$, $—NR^{3A}R^{3B}$, $—C(O)R^{3C}$, $—C(O)OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{4D}$, $—SO_{v4}NR^{4A}R^{4B}$, $—NHC(O)NR^{4A}R^{4B}$, $—NR^{4C}NR^{4A}R^{4B}$, $—ONR^{4A}R^{4B}$, $—NHC(O)NR^{4C}NR^{4A}R^{4B}$, $—N(O)_{m4}$, $—NR^{4A}R^{4B}$, $—C(O)R^{4C}$, $—C(O)OR^{4C}$, $—C(O)NR^{4A}R^{4B}$, $—OR^{4D}$, $—NR^{4A}SO_2R^{4D}$, $—NR^{4A}C(O)R^{4C}$, $—NR^{4A}C(O)OR^{4C}$, $—NR^{4A}OR^{4C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $—CX^5_3$, $—CHX^5_2$, $—CH_2X^5$, $—OCX^5_3$, $—OCH_2X^5$, $—OCHX^5_2$, —CN, $—SO_{n5}R^{5D}$, $—SO_{v5}NR^{5A}R^{5B}$, $—NHC(O)NR^{5A}R^{5B}$, $—NR^{5C}NR^{5A}R^{5B}$, $—ONR^{5A}R^{5B}$, $—NHC(O)NR^{5C}NR^{5A}R^{5B}$, $—N(O)_{m5}$, $—NR^{5A}R^{5B}$, $—C(O)R^{5C}$, $—C(O)OR^{5C}$, $—C(O)NR^{5A}R^{5B}$, $—OR^{5D}$, $—NR^{5A}SO_2R^{5D}$, $—NR^{5A}C(O)R^{5C}$, $—NR^{5A}C(O)OR^{5C}$, $—NR^{5A}OR^{5C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, $—CX^6_3$, $—CHX^6_2$, $—CH_2X^6$, $—OCX^6_3$, $—OCH_2X^6$, $—OCHX^6_2$, —CN, $—SO_{n6}R^{6D}$, $—SO_{v6}NR^{6A}R^{6B}$, $—NHC(O)NR^{6A}R^{6B}$, $—NR^{6C}NR^{6A}R^{6B}$, $—ONR^{6A}R^{6B}$, $—NHC(O)NR^{6C}NR^{6A}R^{6B}$, $—N(O)_{m6}$, $—NR^{6A}R^{6B}$, $—C(O)R^{6C}$, $—C(O)OR^{6C}$, $—C(O)NR^{6A}R^{6B}$, $—OR^{6D}$, $—NR^{6A}SO_2R^{6D}$, $—NR^{6A}C(O)R^{6C}$, $—NR^{6A}C(O)OR^{6C}$, $—NR^{6A}OR^{6C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $—CX^7_3$, $—CHX^7_2$, $—CH_2X^7$, $—OCX^7_3$, $—OCH_2X^7$, $—OCHX^7_2$, —CN, $—SO_{n7}R^{7D}$, $—SO_{v7}NR^{7A}R^{7B}$, $—NHC(O)NR^{7A}R^{7B}$, $—NR^{7C}N^{7A}R^{7B}$, $—ONR^{7A}R^{7B}$, —NHC(O)

$NR^{7C}NR^{7A}R^{7B}$, $—N(O)_{m7}$, $—NR^{7A}R^{7B}$, $—C(O)R^{7C}$, $—C(O)OR^{7C}$, $—C(O)NR^{7A}R^{7B}$, $—OR^{7D}$, $—NR^{7A}SO_2R^{7D}$, $—NR^{7A}C(O)R^{7C}$, $—NR^{7A}C(O)OR^{7C}$, $—NR^{7A}OR^{7C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, $—CX^8_3$, $—CHX^8_2$, $—CH_2X^8$, $—OCX^8_3$, $—OCH_2X^8$, $—OCHX^8_2$, —CN, $—SO_{n8}R^{8D}$, $—SO_{v8}NR^{8A}R^{8B}$, $—NHC(O)NR^{8A}R^{8B}$, $—NR^{8C}NR^{8A}R^{8B}$, $—ONR^{8A}R^{8B}$, $—NHC(O)NR^{8C}NR^{8A}R^{8B}$, $—N(O)_{m8}$, $—NR^{8A}R^{8B}$, $—C(O)R^{8C}$, $—C(O)OR^{8C}$, $—C(O)NR^{8A}R^{8B}$, $—OR^{8D}$, $—NR^{8A}SO_2R^{8D}$, $—NR^{8A}C(O)R^{8C}$, $—NR^{8A}C(O)OR^{8C}$, $—NR^{8A}OR^{8C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $—CX^9_3$, $—CHX^9_2$, $—CH_2X^9$, $—OCX^9_3$, $—OCH_2X^9$, $—OCHX^9_2$, —CN, $—SO_{n9}R^{9D}$, $—SO_{v9}NR^{9A}R^{9B}$, $—NHC(O)NR^{9A}R^{9B}$, $—NR^{9C}NR^{9A}R^{9B}$, $—ONR^{9A}R^{9B}$, $—NHC(O)NR^{9C}NR^{9A}R^{9B}$, $—N(O)_{m9}$, $—NR^{9A}R^{9B}$, $—C(O)R^{9C}$, $—C(O)OR^{9C}$, $—C(O)NR^{9A}R^{9B}$, $—OR^{9D}$, $—NR^{9A}SO_2R^{9D}$, $—NR^{9A}C(O)R^{9C}$, $—NR^{9A}C(O)OR^{9C}$, $—NR^{9A}OR^{9C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $—CX^{10}_3$, $—CHX^{10}_2$, $—CH_2X^{10}$, $—OCX^{10}_3$, $—OCH_2X^{10}$, $—OCHX^{10}_2$, —CN, $—SO_{n10}R^{10D}$, $—SO_{v10}NR^{10A}R^{10B}$, $—NHC(O)NR^{10A}R^{10B}$, $—NR^{10C}NR^{10A}R^{10B}$, $—ONR^{10A}R^{10B}$, $—NHC(O)NR^{10C}NR^{10A}R^{10B}$, $—N(O)_{m10}$, $—NR^{10A}R^{10B}$, $—C(O)R^{10C}$, $—C(O)OR^{10C}$, $—C(O)NR^{10A}R^{10B}$, $—OR^{10D}$, $—NR^{10A}SO_2R^{10D}$, $—NR^{10A}C(O)R^{10C}$, $—NR^{10A}C(O)OR^{10C}$, $—NR^{10A}OR^{10C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $—CX^{11}_3$, $—CHX^{11}_2$, $—CH_2X^{11}$, $—OCX^{11}_3$, $—OCH_2X^{11}$, $—OCHX^{11}_2$, —CN, $—SO_{n11}R^{11D}$, $—SO_{v11}NR^{11A}R^{11B}$, $—NHC(O)NR^{11A}R^{11B}$, $—NR^{11C}NR^{11A}R^{11B}$, $—ONR^{11A}R^{11B}$, $—NHC(O)NR^{11C}NR^{11A}R^{11B}$, $—N(O)_{m11}$, $—NR^{11A}R^{11B}$, $—C(O)R^{11C}$, $—C(O)OR^{11C}$, $—C(O)NR^{11A}R^{11B}$, $—OR^{11D}$, $—NR^{11A}SO_2R^{11D}$, $—NR^{11A}C(O)R^{11C}$, $—NR^{11A}C(O)OR^{11C}$, $—NR^{11A}OR^{11C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $—CX^{12}_3$, $—CHX^{12}_2$, $—CH_2X^{12}$, $—OCX^{12}_3$, $—OCH_2X^{12}$, $—OCHX^{12}_2$, —CN, $—SO_{n12}R^{12D}$, $—SO_{12}NR^{12A}R^{12B}$, $—NHC(O)NR^{12A}R^{12B}$, $—NR^{12C}NR^{12A}R^{12B}$, $—ONR^{12A}R^{12B}$, $—NHC(O)NR^{12C}NR^{12A}R^{12B}$, $—N(O)_{m12}$, $—NR^{12A}R^{12B}$, $—C(O)R^{12C}$, $—C(O)OR^{12C}$, $—C(O)NR^{12A}R^{12B}$, $—OR^{12D}$, $—NR^{12A}SO_2R^{12D}$, $—NR^{12A}C(O)R^{12C}$, $—NR^{12A}C(O)OR^{12C}$, $—NR^{12A}OR^{12C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, halogen, $—CX^{13}_3$, $—CHX^{13}_2$, $—CH_2X^{13}$, $—OCX^{13}_3$, $—OCH_2X^{13}$, $—OCHX^{13}_2$, —CN, $—SO_{n13}R^{13D}$, $—SO_{v13}NR^{13A}R^{13B}$, $—NHC(O)NR^{13A}R^{13B}$, $—NR^{13C}NR^{13A}R^{13B}$, $—ONR^{13A}R^{13B}$, $—NHC(O)NR^{13C}NR^{13A}R^{13B}$, $—N(O)_{m3}$, $—NR^{13A}R^{13B}$, $—C(O)R^{13C}$, $—C(O)OR^{13C}$, $—C(O)NR^{13A}R^{13B}$, $—OR^{13D}$, $—NR^{13A}SO_2R^{13D}$, $—NR^{13A}C(O)R^{13C}$, $—NR^{13A}C(O)OR^{13C}$, $—NR^{13A}OR^{13C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, $—CX^{14}_3$, $—CHX^{14}_2$, $—CH_2X^{14}$, $—OCX^{14}_3$, $—OCH_2X^{14}$, $—OCHX^{14}_2$, —CN, $—SO_{n14}R^{14D}$, $—SO_{v14}NR^{14A}R^{14B}$, $—NHC(O)NR^{14A}R^{14B}$, $—NR^{14C}NR^{14A}R^{14B}$, $—ONR^{14A}R^{14B}$, $—NHC(O)NR^{14C}NR^{14A}R^{14B}$, $—N(O)_{m14}$, $—NR^{14A}R^{14B}$, $—C(O)R^{14C}$, $—C(O)OR^{14C}$, $—C(O)NR^{14A}R^{14B}$, $—OR^{14D}$, $—NR^{14A}SO_2R^{14D}$, $—NR^{14A}C(O)R^{14C}$, $—NR^{14A}C(O)OR^{14C}$, $—NR^{14A}OR^{14C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $—CX^{15}_3$, $—CHX^{15}_2$, $—CH_2X^{15}$, $—OCX^{15}_3$, $—OCH_2X^{15}$, $—OCHX^{15}_2$, —CN, $—SO_{n15}R^{15D}$, $—SO_{v15}NR^{15A}R^{15B}$, $—NHC(O)NR^{15A}R^{15B}$, $—NR^{15C}NR^{15A}R^{15B}$, $—ONR^{15A}R^{15B}$, $—NHC(O)NR^{15C}NR^{15A}R^{15B}$, $—N(O)_{m15}$, $—NR^{15A}R^{15B}$, $—C(O)R^{15C}$, $—C(O)OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ substituents may be joined to form a substituted or unsubstituted cycloalkyl, substituted or unsubstituted heterocycloalkyl, substituted or unsubstituted aryl, or substituted or unsubstituted heteroaryl;

$R^2$ and $R^3$ substituents may be joined to form a substituted or unsubstituted cycloalkyl, substituted or unsubstituted heterocycloalkyl, substituted or unsubstituted aryl, or substituted or unsubstituted heteroaryl;

$R^3$ and $R^4$ substituents may be joined to form a substituted or unsubstituted cycloalkyl, substituted or unsubstituted heterocycloalkyl, substituted or unsubstituted aryl, or substituted or unsubstituted heteroaryl;

$R^4$ and $R^5$ substituents may be joined to form a substituted or unsubstituted cycloalkyl, substituted or unsubstituted heterocycloalkyl, substituted or unsubstituted aryl, or substituted or unsubstituted heteroaryl;

$R^6$ and $R^7$ substituents may be joined to form a substituted or unsubstituted cycloalkyl, substituted or unsubstituted heterocycloalkyl, substituted or unsubstituted aryl, or substituted or unsubstituted heteroaryl;

$R^7$ and $R^8$ substituents may be joined to form a substituted or unsubstituted cycloalkyl, substituted or unsubstituted heterocycloalkyl, substituted or unsubstituted aryl, or substituted or unsubstituted heteroaryl;

$R^1$ and $R^9$ substituents may be joined to form a substituted or unsubstituted cycloalkyl, substituted or unsubstituted heterocycloalkyl, substituted or unsubstituted aryl, or substituted or unsubstituted heteroaryl;

$R^9$ and $R^{10}$ substituents may be joined to form a substituted or unsubstituted cycloalkyl, substituted or unsubstituted heterocycloalkyl, substituted or unsubstituted aryl, or substituted or unsubstituted heteroaryl;

$R^{11}$ and $R^{12}$ substituents may be joined to form a substituted or unsubstituted cycloalkyl, substituted or unsubstituted heterocycloalkyl, substituted or unsubstituted aryl, or substituted or unsubstituted heteroaryl;

$R^{12}$ and $R^{13}$ substituents may be joined to form a substituted or unsubstituted cycloalkyl, substituted or unsubstituted heterocycloalkyl, substituted or unsubstituted aryl, or substituted or unsubstituted heteroaryl;

$R^{13}$ and $R^{14}$ substituents may be joined to form a substituted or unsubstituted cycloalkyl, substituted or unsubstituted heterocycloalkyl, substituted or unsubstituted aryl, or substituted or unsubstituted heteroaryl;

$R^{14}$ and $R^{15}$ substituents may be joined to form a substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, and $R^{15D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may be joined to form a substituted or unsubstituted heterocycloalkyl or substituted or unsubstituted heteroaryl; $R^{2A}$ and $R^{2B}$ substituents bonded to the same nitrogen atom may be joined to form a substituted or unsubstituted heterocycloalkyl or substituted or unsubstituted heteroaryl; $R^{3A}$ and $R^{3B}$ substituents bonded to the same nitrogen atom may be joined to form a substituted or unsubstituted heterocycloalkyl or substituted or unsubstituted heteroaryl; $R^{4A}$ and $R^{4B}$ substituents bonded to the same nitrogen atom may be joined to form a substituted or unsubstituted heterocycloalkyl or substituted or unsubstituted heteroaryl; $R^{5A}$ and $R^{5B}$ substituents bonded to the same nitrogen atom may be joined to form a substituted or unsubstituted heterocycloalkyl or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{7A}$ and $R^{7B}$ substituents bonded to the same nitrogen atom may be joined to form a substituted or unsubstituted heterocycloalkyl or substituted or unsubstituted heteroaryl; $R^{8A}$ and $R^{8B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{10A}$ and $R^{10B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{12A}$ and $R^{12B}$ substituents bonded to the same nitrogen atom may be joined to form a substituted or unsubstituted heterocycloalkyl or substituted or unsubstituted heteroaryl; $R^{13A}$ and $R^{13B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl; $R^{15A}$ and $R^{15B}$ substituents bonded to the same nitrogen atom may be joined to form a substituted or unsubstituted heterocycloalkyl or substituted or unsubstituted heteroaryl;

n1, n2, n3, n4, n5, n6, n7, n8, n9, n10, n11, n12, n13, n14, and n15 are independently an integer from 0 to 4;

m1, m2, m3, m4, m5, m6, m7, m8, m9, m10, m11, m12, m13, m14, m15, v1, v2, v3, v4, v5, v6, v7, v8, v9, v10, v11, v12, v13, v14, and v15 are independently 1 or 2; and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ are independently —F, —Cl, —Br, or —I.

11. A method of treating a disease associated with a high level of IGF2BP2 relative to a normal control in a subject in need thereof, said method comprising:

i) determining the level of IGF2BP2 in the subject in need thereof; and ii) administering to the subject in need thereof an IGF2BP2 inhibitor, wherein the IGF2BP2 inhibitor decreases IGF2BP2 binding to RNA $N^6$-methyladenosine ($m^6A$);

wherein the IGF2BP2 inhibitor is a compound having the formula (I)

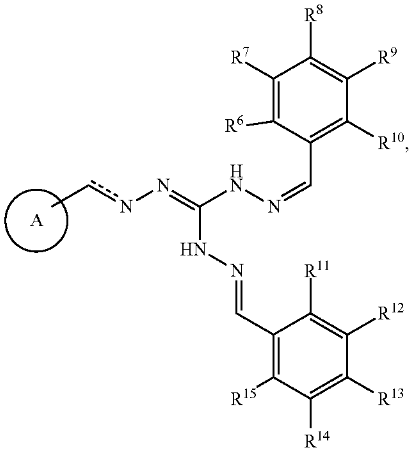

(II)

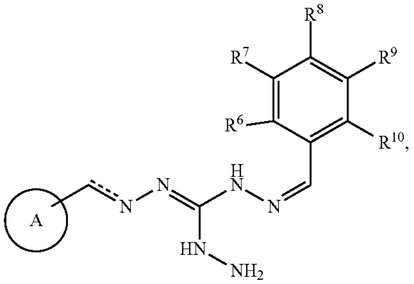

(III)

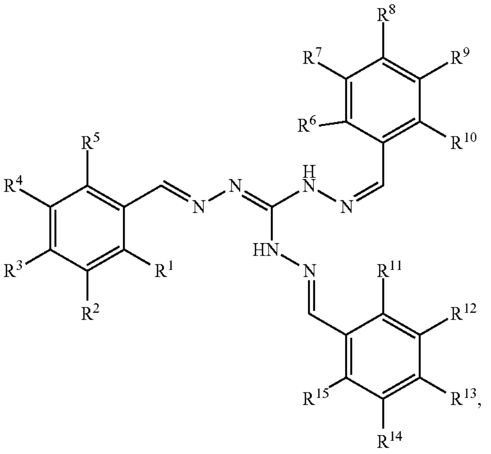

or (IV)

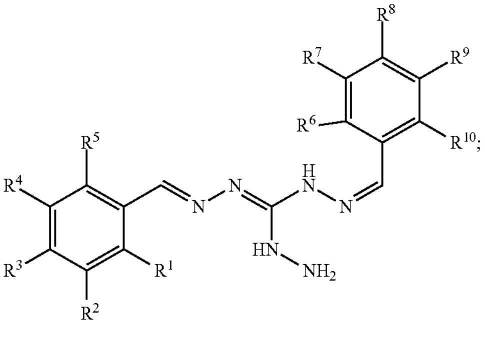

wherein

Ring A is a substituted or unsubstituted cycloalkyl, substituted or unsubstituted heterocycloalkyl, substituted or unsubstituted aryl, or substituted or unsubstituted heteroaryl;

 is a single bond or a double bond;

$R^1$ is hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-NR^{1C}NR^{1A}R^{1B}$, $-ONR^{1A}R^{1B}$, $-NHC(O)NR^{1C}NR^{1A}R^{1B}$, $-N(O)_{m1}$, $-NR^{1A}R^{1B}$, $-C(O)R^{1C}$, $-C(O)OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-NR^{2C}NR^{2A}R^{2B}$, $-ONR^{2A}R^{2B}$, $-NHC(O)NR^{2C}NR^{2A}R^{2B}$, $-N(O)_{m2}$, $-NR^{2A}R^{2B}$, $-C(O)R^{2C}$, $-C(O)OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-NR^{3C}NR^{3A}R^{3B}$, $-ONR^{3A}R^{3B}$, $-NHC(O)NR^{3C}NR^{3A}R^{3B}$, $-N(O)_{m3}$, $-NR^{3A}R^{3B}$, $-C(O)R^{3C}$, $-C(O)OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-NR^{4C}NR^{4A}R^{4B}$, $-ONR^{4A}R^{4B}$, $-NHC(O)NR^{4C}NR^{4A}R^{4B}$, $-N(O)_{m4}$, $-NR^{4A}R^{4B}$, $-C(O)R^{4C}$, $-C(O)OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n5}R^{5D}$, $-SO_{v5}NR^{5A}R^{5B}$, $-NHC(O)NR^{5A}R^{5B}$, $-NR^{5C}NR^{5A}R^{5B}$, $-ONR^{5A}R^{5B}$, $-NHC(O)NR^{5C}NR^{5A}R^{5B}$, $-N(O)_{m5}$, $-NR^{5A}R^{5B}$, $-C(O)R^{5C}$, $-C(O)OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, $—CX^6_3$, $—CHX^6_2$, $—CH_2X^6$, $—OCX^6_3$, $—OCH_2X^6$, $—OCHX^6_2$, —CN, $—SO_{n6}R^{6D}$, $—SO_{v6}NR^{6A}R^{6B}$, $—NHC(O)NR^{6A}R^{6B}$, $—NR^{6C}NR^{6A}R^{6B}$, $—ONR^{6A}R^{6B}$, $—NHC(O)NR^{6C}NR^{6A}R^{6B}$, $—N(O)_{m6}$, $—NR^{6A}R^{6B}$, $—C(O)R^{6C}$, $—C(O)OR^{6C}$, $—C(O)NR^{6A}R^{6B}$, $—OR^{6D}$, $—NR^{6A}SO_2R^{6D}$, $—NR^{6A}C(O)R^{6C}$, $—NR^{6A}C(O)OR^{6C}$, $—NR^{6A}OR^{6C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $—CX^7_3$, $—CHX^7_2$, $—CH_2X^7$, $—OCX^7_3$, $—OCH_2X^7$, $—OCHX^7_2$, —CN, $—SO_{n7}R^{7D}$, $—SO_{v7}NR^{7A}R^{7B}$, $—NHC(O)NR^{7A}R^{7B}$, $—NR^{7C}NR^{7A}R^{7B}$, $—ONR^{7A}R^{7B}$, $—NHC(O)NR^{7C}NR^{7A}R^{7B}$, $—N(O)_{m7}$, $—NR^{7A}R^{7B}$, $—C(O)R^{7C}$, $—C(O)OR^{7C}$, $—C(O)NR^{7A}R^{7B}$, $—OR^{7D}$, $—NR^{7A}SO_2R^{7D}$, $—NR^{7A}C(O)R^{7C}$, $—NR^{7A}C(O)OR^{7C}$, $—NR^{7A}OR^{7C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, $—CX^8_3$, $—CHX^8_2$, $—CH_2X^8$, $—OCX^8_3$, $—OCH_2X^8$, $—OCHX^8_2$, —CN, $—SO_{n8}R^{8D}$, $—SO_{v8}NR^{8A}R^{8B}$, $—NHC(O)NR^{8A}R^{8B}$, $—NR^{8C}NR^{8A}R^{8B}$, $—ONR^{8A}R^{8B}$, $—NHC(O)NR^{8C}NR^{8A}R^{8B}$, $—N(O)_{m8}$, $—NR^{8A}R^{8B}$, $—C(O)R^{8C}$, $—C(O)OR^{8C}$, $—C(O)NR^{8A}R^{8B}$, $—OR^{8D}$, $—NR^{8A}SO_2R^{8D}$, $—NR^{8A}C(O)R^{8C}$, $—NR^{8A}C(O)OR^{8C}$, $—NR^{8A}OR^{8C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $—CX^9_3$, $—CHX^9_2$, $—CH_2X^9$, $—OCX^9_3$, $—OCH_2X^9$, $—OCHX^9_2$, —CN, $—SO_{n9}R^{9D}$, $—SO_{v9}NR^{9A}R^{9B}$, $—NHC(O)NR^{9A}R^{9B}$, $—NR^{9C}NR^{9A}R^{9B}$, $—ONR^{9A}R^{9B}$, $—NHC(O)NR^{9C}NR^{9A}R^{9B}$, $—N(O)_{m9}$, $—NR^{9A}R^{9B}$, $—C(O)R^{9C}$, $—C(O)OR^{9C}$, $—C(O)NR^{9A}R^{9B}$, $—OR^{9D}$, $—NR^{9A}SO_2R^{9D}$, $—NR^{9A}C(O)R^{9C}$, $—NR^{9A}C(O)OR^{9C}$, $—NR^{9A}OR^{9C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $—CX^{10}_3$, $—CHX^{10}_2$, $—CH_2X^{10}$, $—OCX^{10}_3$, $—OCH_2X^{10}$, $—OCHX^{10}_2$, —CN, $—SO_{n10}R^{10D}$, $—SO_{v10}NR^{10A}R^{10B}$, $—NHC(O)NR^{10A}R^{10B}$, $—NR^{10C}NR^{10A}R^{10B}$, $—ONR^{10A}R^{10B}$, $—NHC(O)NR^{10C}NR^{10A}R^{10B}$, $—N(O)_{m10}$, $—NR^{1A}R^{10B}$, $—C(O)R^{10C}$, $—C(O)OR^{10C}$, $—C(O)NR^{10A}R^{10B}$, $—OR^{10D}$, $—NR^{10A}SO_2R^{10D}$, $—NR^{10A}C(O)R^{10C}$, $—NR^{10A}C(O)OR^{10C}$, $—NR^{10A}OR^{10C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $—CX^{11}_3$, $—CHX^{11}_2$, $—CH_2X^{11}$, $—OCX^{11}_3$, $—OCH_2X^{11}$, $—OCHX^{11}_2$, —CN, $—SO_{n11}R^{11D}$, $—SO_{v11}NR^{11A}R^{11B}$, $—NHC(O)NR^{11A}R^{11B}$, $—NR^{11C}NR^{11A}R^{11B}$, $—ONR^{11A}R^{11B}$, $—NHC(O)NR^{11C}NR^{11A}R^{11B}$, $—N(O)_{m11}$, $—NR^{11A}R^{11B}$, $—C(O)R^{11C}$, $—C(O)OR^{11C}$, $—C(O)NR^{11A}R^{11B}$, $—OR^{11D}$, $—NR^{11A}SO_2R^{11D}$, $—NR^{11A}C(O)R^{11C}$, $—NR^{11A}C(O)OR^{11C}$, $—NR^{11A}OR^{11C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $—CX^{12}_3$, $—CHX^{12}_2$, $—CH_2X^{12}$, $—OCX^{12}_3$, $—OCH_2X^{12}$, $—OCHX^{12}_2$, —CN, $—SO_{n12}R^{12D}$, $—SO_{v12}NR^{12A}R^{12B}$, $—NHC(O)NR^{12A}R^{12B}$, $—NR^{12C}NR^{12A}R^{12B}$, $—ONR^{12A}R^{12B}$, $—NHC(O)NR^{12C}NR^{12A}R^{12B}$, $—N(O)_{m12}$, $—NR^{12A}R^{12B}$, $—C(O)R^{12C}$, $—C(O)OR^{12C}$, $—C(O)NR^{12A}R^{12B}$, $—OR^{12D}$, $—NR^{12A}SO_2R^{12D}$, $—NR^{12A}C(O)R^{12C}$, $—NR^{12A}C(O)OR^{12C}$, $—NR^{12A}OR^{12C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, halogen, $—CX^{13}_3$, $—CHX^{13}_2$, $—CH_2X^{13}$, $—OCX^{13}_3$, $—OCH_2X^{13}$, $—OCHX^{13}_2$, —CN, $—SO_{n13}R^{13D}$, $—SO_{v13}NR^{13A}R^{13B}$, $—NHC(O)NR^{13A}R^{13B}$, $—NR^{13C}NR^{13A}R^{13B}$, $—ONR^{13A}R^{13B}$, $—NHC(O)NR^{13C}NR^{13A}R^{13B}$, $—N(O)_{m13}$, $—NR^{13A}R^{13B}$, $—C(O)R^{13C}$, $—C(O)OR^{13C}$, $—C(O)NR^{13A}R^{13B}$, $—OR^{13D}$, $—NR^{13A}SO_2R^{13D}$, $—NR^{13A}C(O)R^{13C}$, $—NR^{13A}C(O)OR^{13C}$, $—NR^{13A}OR^{13C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, $—CX^{14}_3$, $—CHX^{14}_2$, $—CH_2X^{14}$, $—OCX^{14}_3$, $—OCH_2X^{14}$, $—OCHX^{14}_2$, —CN, $—SO_{n14}R^{14D}$, $—SO_{v14}NR^{14A}R^{14B}$, $—NHC(O)NR^{14A}R^{14B}$, $—NR^{14C}NR^{14A}R^{14B}$, $—ONR^{14A}R^{14B}$, $—NHC(O)NR^{14C}NR^{14A}R^{14B}$, $—N(O)_{m14}$, $—NR^{14A}R^{14B}$, $—C(O)R^{14C}$, $—C(O)OR^{14C}$, $—C(O)NR^{14A}R^{14B}$, $—OR^{14D}$, $—NR^{14A}SO_2R^{14D}$, $—NR^{14A}C(O)R^{14C}$, $—NR^{14A}C(O)OR^{14C}$, $—NR^{14A}OR^{14C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $—CX^{15}_3$, $—CHX^{15}_2$, $—CH_2X^{15}$, $—OCX^{15}_3$, $—OCH_2X^{15}$, $—OCHX^{15}_2$, —CN, $—SO_{n15}R^{15D}$, $—SO_{v15}NR^{15A}R^{15B}$, $—NHC(O)NR^{15A}R^{15B}$, $—NR^{15C}NR^{15A}R^{15B}$, $—ONR^{15A}R^{15B}$, $—NHC(O)NR^{15C}NR^{15A}R^{15B}$, $—N(O)_{m15}$, $—NR^{15A}R^{15B}$, $—C(O)R^{15C}$, $—C(O)OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—SF_5$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ substituents may be joined to form a substituted or unsubstituted cycloalkyl, substituted or unsubstituted heterocycloalkyl, substituted or unsubstituted aryl, or substituted or unsubstituted heteroaryl;

$R^2$ and $R^3$ substituents may be joined to form a substituted or unsubstituted cycloalkyl, substituted or unsubstituted heterocycloalkyl, substituted or unsubstituted aryl, or substituted or unsubstituted heteroaryl;

$R^3$ and $R^4$ substituents may be joined to form a substituted or unsubstituted cycloalkyl, substituted or unsubstituted heterocycloalkyl, substituted or unsubstituted aryl, or substituted or unsubstituted heteroaryl;

$R^4$ and $R^5$ substituents may be joined to form a substituted or unsubstituted cycloalkyl, substituted or unsubstituted heterocycloalkyl, substituted or unsubstituted aryl, or substituted or unsubstituted heteroaryl;

$R^6$ and $R^7$ substituents may be joined to form a substituted or unsubstituted cycloalkyl, substituted or unsubstituted heterocycloalkyl, substituted or unsubstituted aryl, or substituted or unsubstituted heteroaryl;

$R^7$ and $R^8$ substituents may be joined to form a substituted or unsubstituted cycloalkyl, substituted or unsubstituted heterocycloalkyl, substituted or unsubstituted aryl, or substituted or unsubstituted heteroaryl;

$R^8$ and $R^9$ substituents may be joined to form a substituted or unsubstituted cycloalkyl, substituted or unsubstituted heterocycloalkyl, substituted or unsubstituted aryl, or substituted or unsubstituted heteroaryl;

$R^9$ and $R^{10}$ substituents may be joined to form a substituted or unsubstituted cycloalkyl, substituted or unsubstituted heterocycloalkyl, substituted or unsubstituted aryl, or substituted or unsubstituted heteroaryl;

$R^{11}$ and $R^{12}$ substituents may be joined to form a substituted or unsubstituted cycloalkyl, substituted or unsubstituted heterocycloalkyl, substituted or unsubstituted aryl, or substituted or unsubstituted heteroaryl;

$R^{12}$ and $R^{13}$ substituents may be joined to form a substituted or unsubstituted cycloalkyl, substituted or unsubstituted heterocycloalkyl, substituted or unsubstituted aryl, or substituted or unsubstituted heteroaryl;

$R^{13}$ and $R^{14}$ substituents may be joined to form a substituted or unsubstituted cycloalkyl, substituted or unsubstituted heterocycloalkyl, substituted or unsubstituted aryl, or substituted or unsubstituted heteroaryl;

$R^{14}$ and $R^{15}$ substituents may be joined to form a substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, and $R^{15D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may be joined to form a substituted or unsubstituted heterocycloalkyl or substituted or unsubstituted heteroaryl; $R^{2A}$ and $R^{2B}$ substituents bonded to the same nitrogen atom may be joined to form a substituted or unsubstituted heterocycloalkyl or substituted or unsubstituted heteroaryl; $R^{3A}$ and $R^{3B}$ substituents bonded to the same nitrogen atom may be joined to form a substituted or unsubstituted heterocycloalkyl or substituted or unsubstituted heteroaryl; $R^{4A}$ and $R^{4B}$ substituents bonded to the same nitrogen atom may be joined to form a substituted or unsubstituted heterocycloalkyl or substituted or unsubstituted heteroaryl; $R^{5A}$ and $R^{5B}$ substituents bonded to the same nitrogen atom may be joined to form a substituted or unsubstituted heterocycloalkyl or substituted or unsubstituted heteroaryl; $R^{6A}$ and $R^{6B}$ substituents bonded to the same nitrogen atom may be joined to form a substituted or unsubstituted heterocycloalkyl or substituted or unsubstituted heteroaryl; $R^{7A}$ and $R^{7B}$ B substituents bonded to the same nitrogen atom may be joined to form a substituted or unsubstituted heterocycloalkyl or substituted or unsubstituted heteroaryl; $R^{8A}$ and $R^{8B}$ substituents bonded to the same nitrogen atom may be joined to form a substituted or unsubstituted heterocycloalkyl or substituted or unsubstituted heteroaryl; $R^{9A}$ and $R^{9B}$ substituents bonded to the same nitrogen atom may be joined to form a substituted or unsubstituted heterocycloalkyl or substituted or unsubstituted heteroaryl; $R^{10A}$ and $R^{11B}$ substituents bonded to the same nitrogen atom may be joined to form a substituted or unsubstituted heterocycloalkyl or substituted or unsubstituted heteroaryl; $R^{11A}$ and $R^{11B}$ substituents bonded to the same nitrogen atom may be joined to form a substituted or unsubstituted heterocycloalkyl or substituted or unsubstituted heteroaryl; $R^{12A}$ and $R^{12B}$ substituents bonded to the same nitrogen atom may be joined to form a substituted or unsubstituted heterocycloalkyl or substituted or unsubstituted heteroaryl; $R^{13A}$ and $R^{13B}$ substituents bonded to the same nitrogen atom may be joined to form a substituted or unsubstituted heterocycloalkyl or substituted or unsubstituted heteroaryl; $R^{14A}$ and $R^{14B}$ substituents bonded to the same nitrogen atom may be joined to form a substituted or unsubstituted heterocycloalkyl or substituted or unsubstituted heteroaryl; $R^{15A}$ and $R^{15B}$ substituents bonded to the same nitrogen atom may be joined to form a substituted or unsubstituted heterocycloalkyl or substituted or unsubstituted heteroaryl;

n1, n2, n3, n4, n5, n6, n7, n8, n9, n10, n11, n12, n13, n14, and n15 are independently an integer from 0 to 4;

m1, m2, m3, m4, m5, m6, m7, m8, m9, m10, m11, m12, m13, m14, m15, v1, v2, v3, v4, v5, v6, v7, v8, v9, v10, v11, v12, v13, v14, and v15 are independently 1 or 2; and $X^1$, $X^2$, $X^3$, $X^4$, $X^5$, $X^6$, $X^7$, $X^8$, $X^9$, $X^{10}$, $X^{11}$, $X^{12}$, $X^3$, $X^{14}$, and $X^{15}$ are independently —F, —Cl, —Br, or —I.

12. The method of claim 10, wherein the compound has the formula (IIIa)

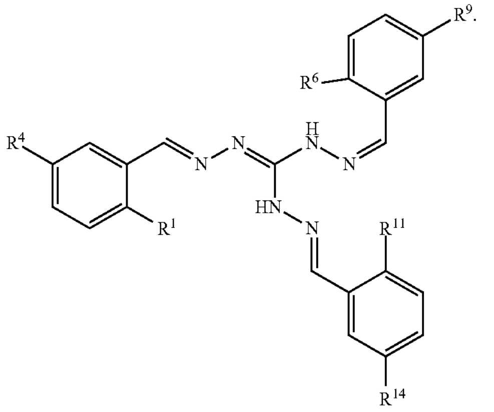

13. The method of claim 12, wherein $R^1$ is independently —$OR^{1D}$;

$R^6$ is independently —$OR^{6D}$;

$R^{11}$ is independently —$OR^{11D}$; and $R^4$, $R^9$, and $R^{14}$ are each independently halogen.

14. The method of claim 12, wherein $R^1$, $R^6$, and $R^{11}$ are each independently —OH; and $R^4$, $R^9$, and $R^{14}$ are each independently —Cl.

15. The method of claim 11, wherein the compound has the formula (IIIa)

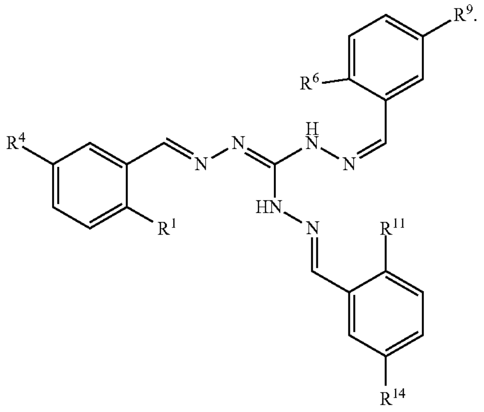

16. The method of claim 15, wherein $R^1$ is independently —$OR^{1D}$;

$R^6$ is independently —$OR^{6D}$;

$R^{11}$ is independently —$OR^{11D}$; and $R^4$, $R^9$, and $R^{14}$ are each independently halogen.

17. The method of claim 15, wherein $R^1$, $R^6$, and $R^{11}$ are each independently —OH; and $R^4$, $R^9$, and $R^{14}$ are each independently —Cl.

* * * * *

SEQUENCE LISTING

```
<160> NUMBER OF SEQ ID NOS: 1

<210> SEQ ID NO 1
<211> LENGTH: 599
<212> TYPE: PRT
<213> ORGANISM: Artificial Sequence
<220> FEATURE:
<223> OTHER INFORMATION: Synthetic polypeptide

<400> SEQUENCE: 1

Met Met Asn Lys Leu Tyr Ile Gly Asn Leu Ser Pro Ala Val Thr Ala
1               5                   10                  15

Asp Asp Leu Arg Gln Leu Phe Gly Asp Arg Lys Leu Pro Leu Ala Gly
            20                  25                  30

Gln Val Leu Leu Lys Ser Gly Tyr Ala Phe Val Asp Tyr Pro Asp Gln
        35                  40                  45

Asn Trp Ala Ile Arg Ala Ile Glu Thr Leu Ser Gly Lys Val Glu Leu
    50                  55                  60

His Gly Lys Ile Met Glu Val Asp Tyr Ser Val Ser Lys Lys Leu Arg
65                  70                  75                  80

Ser Arg Lys Ile Gln Ile Arg Asn Ile Pro Pro His Leu Gln Trp Glu
                85                  90                  95

Val Leu Asp Gly Leu Leu Ala Gln Tyr Gly Thr Val Glu Asn Val Glu
            100                 105                 110
```

```
Gln Val Asn Thr Asp Thr Glu Thr Ala Val Val Asn Val Thr Tyr Ala
        115                 120                 125

Thr Arg Glu Glu Ala Lys Ile Ala Met Glu Lys Leu Ser Gly His Gln
    130                 135                 140

Phe Glu Asn Tyr Ser Phe Lys Ile Ser Tyr Ile Pro Asp Glu Glu Val
145                 150                 155                 160

Ser Ser Pro Ser Pro Pro Gln Arg Ala Gln Arg Gly Asp His Ser Ser
                165                 170                 175

Arg Glu Gln Gly His Ala Pro Gly Gly Thr Ser Gln Ala Arg Gln Ile
            180                 185                 190

Asp Phe Pro Leu Arg Ile Leu Val Pro Thr Gln Phe Val Gly Ala Ile
        195                 200                 205

Ile Gly Lys Glu Gly Leu Thr Ile Lys Asn Ile Thr Lys Gln Thr Gln
    210                 215                 220

Ser Arg Val Asp Ile His Arg Lys Glu Asn Ser Gly Ala Ala Glu Lys
225                 230                 235                 240

Pro Val Thr Ile His Ala Thr Pro Glu Gly Thr Ser Glu Ala Cys Arg
                245                 250                 255

Met Ile Leu Glu Ile Met Gln Lys Glu Ala Asp Glu Thr Lys Leu Ala
            260                 265                 270

Glu Glu Ile Pro Leu Lys Ile Leu Ala His Asn Gly Leu Val Gly Arg
        275                 280                 285

Leu Ile Gly Lys Glu Gly Arg Asn Leu Lys Lys Ile Glu His Glu Thr
    290                 295                 300

Gly Thr Lys Ile Thr Ile Ser Ser Leu Gln Asp Leu Ser Ile Tyr Asn
305                 310                 315                 320

Pro Glu Arg Thr Ile Thr Val Lys Gly Thr Val Glu Ala Cys Ala Ser
                325                 330                 335

Ala Glu Ile Glu Ile Met Lys Lys Leu Arg Glu Ala Phe Glu Asn Asp
            340                 345                 350

Met Leu Ala Val Asn Gln Gln Ala Asn Leu Ile Pro Gly Leu Asn Leu
        355                 360                 365

Ser Ala Leu Gly Ile Phe Ser Thr Gly Leu Ser Val Leu Ser Pro Pro
    370                 375                 380

Ala Gly Pro Arg Gly Ala Pro Pro Ala Ala Pro Tyr His Pro Phe Thr
385                 390                 395                 400

Thr His Ser Gly Tyr Phe Ser Ser Leu Tyr Pro His His Gln Phe Gly
                405                 410                 415

Pro Phe Pro His His His Ser Tyr Pro Glu Gln Glu Ile Val Asn Leu
            420                 425                 430

Phe Ile Pro Thr Gln Ala Val Gly Ala Ile Ile Gly Lys Lys Gly Ala
        435                 440                 445

His Ile Lys Gln Leu Ala Arg Phe Ala Gly Ala Ser Ile Lys Ile Ala
    450                 455                 460

Pro Ala Glu Gly Pro Asp Val Ser Glu Arg Met Val Ile Ile Thr Gly
465                 470                 475                 480

Pro Pro Glu Ala Gln Phe Lys Ala Gln Gly Arg Ile Phe Gly Lys Leu
                485                 490                 495

Lys Glu Glu Asn Phe Phe Asn Pro Lys Glu Glu Val Lys Leu Glu Ala
            500                 505                 510

His Ile Arg Val Pro Ser Ser Thr Ala Gly Arg Val Ile Gly Lys Gly
        515                 520                 525

Gly Lys Thr Val Asn Glu Leu Gln Asn Leu Thr Ser Ala Glu Val Ile
```

-continued

```
    530                 535                 540

Val Pro Arg Asp Gln Thr Pro Asp Glu Asn Glu Glu Val Ile Val Arg
545                 550                 555                 560

Ile Ile Gly His Phe Phe Ala Ser Gln Thr Ala Gln Arg Lys Ile Arg
                565                 570                 575

Glu Ile Val Gln Gln Val Lys Gln Gln Glu Gln Lys Tyr Pro Gln Gly
            580                 585                 590

Val Ala Ser Gln Arg Ser Lys
        595
```